United States Patent
Thon et al.

(10) Patent No.: US 12,403,161 B2
(45) Date of Patent: Sep. 2, 2025

(54) COMPOSITIONS FOR DRUG DELIVERY AND METHODS OF USE THEREOF

(71) Applicant: Stellular Bio, Inc., Watertown, MA (US)

(72) Inventors: Jonathan N. Thon, Watertown, MA (US); Brad Dykstra, Watertown, MA (US); Brenden William Smith, Watertown, MA (US)

(73) Assignee: Stellular Bio, Inc., Watertown, MA (US)

( * ) Notice: Subject to any disclaimer, the term of this patent is extended or adjusted under 35 U.S.C. 154(b) by 1209 days.

(21) Appl. No.: 16/973,688

(22) PCT Filed: Jun. 29, 2019

(86) PCT No.: PCT/US2019/040021
§ 371 (c)(1),
(2) Date: Dec. 9, 2020

(87) PCT Pub. No.: WO2020/006539
PCT Pub. Date: Jan. 2, 2020

(65) Prior Publication Data
US 2021/0252070 A1  Aug. 19, 2021

Related U.S. Application Data

(60) Provisional application No. 62/692,277, filed on Jun. 29, 2018.

(51) Int. Cl.
*A61K 35/19* (2015.01)
*A61K 9/127* (2025.01)
(Continued)

(52) U.S. Cl.
CPC .............. *A61K 35/19* (2013.01); *A61K 9/127* (2013.01); *A61K 9/1271* (2013.01);
(Continued)

(58) Field of Classification Search
CPC ...... A61K 35/19; A61K 9/127; A61K 9/1271; A61K 47/6901; A61K 9/5068;
(Continued)

(56) References Cited

U.S. PATENT DOCUMENTS

| | | |
|---|---|---|
| 5,292,524 A | 3/1994 | Male et al. |
| 5,521,290 A | 5/1996 | Sivam et al. |

(Continued)

FOREIGN PATENT DOCUMENTS

| | | |
|---|---|---|
| WO | 2006050330 A1 | 5/2006 |
| WO | 2008121027 A1 | 10/2008 |

(Continued)

OTHER PUBLICATIONS

Eicke et al. Transfus Med Hemother 2017;44 (suppl 1):2-87, V03-2. (Year: 2017).*

(Continued)

*Primary Examiner* — Mark L Shibuya
(74) *Attorney, Agent, or Firm* — Greenberg Traurig, LLP; Roman Fayerberg; George Banis

(57) ABSTRACT

Methods for producing megakaryocytes and platelets derived from inducible pluripotent stem cells and comprising a therapeutic agent are provided. The present disclosure further provides methods and compositions for loading a platelet or a megakaryocyte with a therapeutic agent and for genetically modifying a platelet or a megakaryocyte to express an agent.

20 Claims, 105 Drawing Sheets

(51) Int. Cl.
*A61K 9/1271* (2025.01)
*A61K 47/69* (2017.01)
*C12N 5/074* (2010.01)
*C12N 5/078* (2010.01)

(52) U.S. Cl.
CPC ........ *A61K 47/6901* (2017.08); *C12N 5/0607* (2013.01); *C12N 5/0644* (2013.01); *C12N 5/0696* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2303* (2013.01); *C12N 2501/2306* (2013.01); *C12N 2501/26* (2013.01); *C12N 2501/415* (2013.01); *C12N 2501/91* (2013.01); *C12N 2506/03* (2013.01); *C12N 2506/45* (2013.01); *C12N 2513/00* (2013.01); *C12N 2533/52* (2013.01)

(58) Field of Classification Search
CPC ............ A61K 31/704; A61K 2039/505; A61K 38/00; C12N 5/0607; C12N 5/0644; C12N 5/0696; C12N 2501/115; C12N 2501/125; C12N 2501/145; C12N 2501/155; C12N 2501/165; C12N 2501/2303; C12N 2501/2306; C12N 2501/26; C12N 2501/415; C12N 2501/91; C12N 2506/03; C12N 2506/45; C12N 2513/00; C12N 2533/52; C12N 2501/2309; C12N 2510/00; C12N 2533/54; C07K 2317/92; C07K 16/2818; C07K 16/2827
See application file for complete search history.

(56) References Cited

U.S. PATENT DOCUMENTS

| | | | |
|---|---|---|---|
| 5,605,689 A | 2/1997 | Ammann |
| 5,733,254 A | 3/1998 | Jones et al. |
| 5,811,301 A | 9/1998 | Cameron |
| 6,225,119 B1 | 5/2001 | Qasba et al. |
| 6,589,759 B1 | 7/2003 | Loscalzo et al. |
| 6,723,497 B2 | 4/2004 | Wolkers et al. |
| 7,494,807 B2 | 2/2009 | Nakorn et al. |
| 7,794,707 B2 | 9/2010 | Penninger et al. |
| 7,939,063 B2 | 5/2011 | Cines et al. |
| 8,137,970 B2 | 3/2012 | Jhon et al. |
| 8,263,556 B2 | 9/2012 | Du Clos et al. |
| 8,372,642 B2 | 2/2013 | Rajesh et al. |
| 8,535,943 B2 | 9/2013 | Nakano et al. |
| 8,546,141 B2 | 10/2013 | Nakauchi et al. |
| 8,557,580 B2 | 10/2013 | Daigh et al. |
| 8,741,905 B2 | 6/2014 | Wagner et al. |
| 8,835,163 B2 | 9/2014 | Zhao et al. |
| 8,889,645 B2 | 11/2014 | Layzer et al. |
| 9,012,221 B2 | 4/2015 | Baruch et al. |
| 9,200,254 B2 | 12/2015 | Eto et al. |
| 9,259,443 B2 | 2/2016 | Poncz et al. |
| 9,574,178 B2 | 2/2017 | Mitchell et al. |
| 9,574,179 B2 | 2/2017 | Yu et al. |
| 9,738,906 B2 | 8/2017 | Eto et al. |
| 9,763,984 B2 | 9/2017 | Feng et al. |
| 9,795,965 B2 | 10/2017 | Italiano et al. |
| 9,803,164 B2 | 10/2017 | Mitchell |
| 9,909,102 B2 | 3/2018 | Baruch et al. |
| 9,982,034 B2 | 5/2018 | Wilcox et al. |
| 9,988,602 B2 | 6/2018 | Lanza et al. |
| 9,988,603 B2 | 6/2018 | Li et al. |
| 9,993,503 B2 | 6/2018 | Feng et al. |
| 10,100,282 B2 | 10/2018 | Rajesh et al. |
| 10,294,291 B2 | 5/2019 | Wilcox et al. |
| 10,307,462 B2 | 6/2019 | Ben Yehuda et al. |
| 10,426,799 B2 | 10/2019 | Feng et al. |
| 10,538,738 B2 | 1/2020 | Papoutsakis et al. |
| 10,604,738 B2 | 3/2020 | Pedersen et al. |
| 10,669,529 B2 | 6/2020 | Nakahata et al. |
| 10,729,730 B2 | 8/2020 | Zhao |
| 10,869,898 B2 | 12/2020 | Mata-Fink et al. |
| 10,894,065 B2 | 1/2021 | Feng et al. |
| 12,060,576 B2 * | 8/2024 | Thon ................... C12N 5/0075 |
| 2002/0009500 A1 | 1/2002 | Wolkers et al. |
| 2002/0141992 A1 | 10/2002 | Nieswandt |
| 2002/0176804 A1 | 11/2002 | Strand et al. |
| 2005/0074426 A1 | 4/2005 | Corti et al. |
| 2005/0086710 A1 | 4/2005 | Peluso et al. |
| 2005/0252892 A1 | 11/2005 | Newman et al. |
| 2006/0099198 A1 | 5/2006 | Thomson et al. |
| 2006/0153813 A1 | 7/2006 | Quesenberry |
| 2007/0077246 A1 | 4/2007 | Koenig et al. |
| 2007/0077654 A1 | 4/2007 | Thomson et al. |
| 2007/0141656 A1 | 6/2007 | Mapes et al. |
| 2007/0243608 A1 | 10/2007 | Kyba et al. |
| 2008/0268535 A1 | 10/2008 | Jhon et al. |
| 2009/0232834 A1 | 9/2009 | Al-Harbi et al. |
| 2010/0063070 A1 | 3/2010 | Raud |
| 2010/0248361 A1 | 9/2010 | Lasky et al. |
| 2011/0039333 A1 | 2/2011 | Kahn et al. |
| 2011/0086424 A1 | 4/2011 | Lanza et al. |
| 2011/0243813 A1 | 10/2011 | Jackinsky et al. |
| 2012/0238020 A1 | 9/2012 | Mitchell et al. |
| 2012/0282228 A1 | 11/2012 | Bhasin |
| 2012/0301438 A1 | 11/2012 | Cheng |
| 2012/0315338 A1 | 12/2012 | Li et al. |
| 2013/0052662 A1 | 2/2013 | Barnes et al. |
| 2013/0061961 A1 | 3/2013 | Rapp et al. |
| 2013/0210141 A1 | 8/2013 | Rajesh et al. |
| 2014/0037600 A1 | 2/2014 | Yu et al. |
| 2014/0099359 A1 | 4/2014 | SenGupta et al. |
| 2014/0127815 A1 | 5/2014 | Eto et al. |
| 2014/0205582 A1 | 7/2014 | Karsunky et al. |
| 2014/0227780 A1 | 8/2014 | Nishino et al. |
| 2014/0271590 A1 | 9/2014 | Feng et al. |
| 2014/0273211 A1 | 9/2014 | Slukvin et al. |
| 2015/0111296 A1 | 4/2015 | Pedersen et al. |
| 2015/0203819 A1 | 7/2015 | Murphy et al. |
| 2015/0275176 A1 | 10/2015 | Kobayashi et al. |
| 2015/0313944 A1 | 11/2015 | Feng et al. |
| 2015/0335682 A1 | 11/2015 | Murphy et al. |
| 2015/0361453 A1 | 12/2015 | Gresele et al. |
| 2016/0002586 A1 | 1/2016 | Mitchell |
| 2016/0002599 A1 | 1/2016 | Eto |
| 2016/0022736 A1 * | 1/2016 | Feng ..................... A61P 17/02 435/372 |
| 2016/0139124 A1 | 5/2016 | Newman et al. |
| 2016/0168540 A1 | 6/2016 | Hirata et al. |
| 2016/0177265 A1 | 6/2016 | Matsubara et al. |
| 2016/0209331 A1 | 7/2016 | Babic et al. |
| 2016/0272941 A1 | 9/2016 | Baruch et al. |
| 2016/0324897 A1 | 11/2016 | Ingber et al. |
| 2017/0121682 A1 | 5/2017 | Mitchell et al. |
| 2017/0130195 A1 | 5/2017 | Im et al. |
| 2017/0183616 A1 | 6/2017 | Thon et al. |
| 2018/0016597 A1 | 1/2018 | Eto et al. |
| 2018/0030415 A1 | 2/2018 | Nguyen et al. |
| 2018/0044634 A1 | 2/2018 | Dohda et al. |
| 2018/0055891 A1 | 3/2018 | Zhao |
| 2018/0135020 A1 | 5/2018 | Zhao |
| 2018/0161379 A1 | 6/2018 | Peterson et al. |
| 2018/0201889 A1 | 7/2018 | Sharei et al. |
| 2018/0237797 A1 | 8/2018 | Loh |
| 2018/0258395 A1 | 9/2018 | Shigemori et al. |
| 2018/0282697 A1 | 10/2018 | Hirose et al. |
| 2018/0318352 A1 | 11/2018 | Shigemori et al. |
| 2018/0318353 A1 | 11/2018 | Feng et al. |
| 2018/0334652 A1 | 11/2018 | Thon |
| 2019/0032015 A1 | 1/2019 | Eto et al. |
| 2019/0048317 A1 | 2/2019 | Eto et al. |
| 2019/0144823 A1 | 5/2019 | Slukvin et al. |
| 2019/0160103 A1 | 5/2019 | Garbin |
| 2019/0169566 A1 | 6/2019 | Gevaert et al. |
| 2019/0269732 A1 | 9/2019 | Matsubara et al. |
| 2019/0290686 A1 | 9/2019 | Wickham et al. |

(56) References Cited

U.S. PATENT DOCUMENTS

| | | |
|---|---|---|
| 2019/0290696 A1 | 9/2019 | DeMiroschedji |
| 2019/0376034 A1 | 12/2019 | Kahvejian et al. |
| 2020/0010809 A1 | 1/2020 | Wamhoff et al. |
| 2020/0017812 A1 | 1/2020 | Thon |
| 2020/0023011 A1 | 1/2020 | Feng et al. |
| 2020/0138868 A1 | 5/2020 | Thon et al. |
| 2020/0255804 A1 | 8/2020 | Pedersen et al. |
| 2021/0000750 A1 | 1/2021 | Gu et al. |
| 2021/0054336 A1* | 2/2021 | Thon .................... C12N 5/0644 |
| 2021/0299180 A1 | 9/2021 | Hett et al. |
| 2021/0299181 A1 | 9/2021 | Hett et al. |
| 2021/0371824 A1* | 12/2021 | Blasczyk ............. C12N 5/0644 |
| 2022/0143095 A1 | 5/2022 | Hett et al. |
| 2023/0174939 A1 | 6/2023 | Falb et al. |
| 2023/0183646 A1 | 6/2023 | Peters et al. |
| 2025/0027046 A1 | 1/2025 | Thon et al. |

FOREIGN PATENT DOCUMENTS

| | | | |
|---|---|---|---|
| WO | 2009002811 A1 | 12/2008 | |
| WO | 2009137629 A1 | 11/2009 | |
| WO | 2010099539 A1 | 9/2010 | |
| WO | 2012112690 A2 | 8/2012 | |
| WO | 2014100779 A1 | 6/2014 | |
| WO | 2014138485 A1 | 9/2014 | |
| WO | 2015179301 A1 | 11/2015 | |
| WO | 2016141137 A1 | 9/2016 | |
| WO | 2016160860 A1 | 10/2016 | |
| WO | 2017013262 A1 | 1/2017 | |
| WO | 2017070337 A1 | 4/2017 | |
| WO | 2017211906 A1 | 12/2017 | |
| WO | 2018053010 A1 | 3/2018 | |
| WO | 2018164040 A1 | 9/2018 | |
| WO | 2018165308 A1 | 9/2018 | |
| WO | 2018202881 A1 | 11/2018 | |
| WO | WO-2018202900 A1 * | 11/2018 | ............. C12N 11/10 |
| WO | 2018227286 A1 | 12/2018 | |
| WO | 2019009364 A1 | 1/2019 | |
| WO | 2019028192 A1 | 2/2019 | |
| WO | 2019089826 A1 | 5/2019 | |
| WO | 2019094614 A1 | 5/2019 | |
| WO | 2019126818 A1 | 6/2019 | |
| WO | 2019136318 A1 | 7/2019 | |
| WO | 2019136318 A2 | 7/2019 | |
| WO | 2019161192 A1 | 8/2019 | |
| WO | 2020006539 A1 | 1/2020 | |
| WO | 2020014175 A1 | 1/2020 | |
| WO | 2021195496 A2 | 9/2021 | |
| WO | 2021231990 A2 | 11/2021 | |

OTHER PUBLICATIONS

Baigger, J Cell Mol Med. Sep. 22, 2018, 22(9), 4545-4549, Electronic Publication Date: Jun. 12, 2018. (Year: 2018).*
Aatonen et al., "Isolation and Characterization of Platelet-Derived Extracellular Vesicles", Journal of Extracellular Vesicles, vol. 3, No. 1, p. 24692, Jan. 1, 2013.
Alshehri et al., "Fibrin Activates GPVI in Human and Mouse Platelets", Blood, vol. 126, No. 13, pp. 1601-1608, Sep. 24, 2015.
Hansen et al., "Human-Induced Pluripotent Stem Cell-Derived Blood Products: State of the Art and Future Directions", FEBS Letters, vol. 593, pp. 3288-3303, 2019.
Ito et al., "Turbulence Activates Platelet Biogenesis to Enable Clinical Scale Ex Vivo Production", Cell, vol. 174, No. 3, pp. 636-648, Jul. 26, 2018.
Orban et al., "Functional Comparison of Induced Pluripotent Stem Cell- and Blood-Derived GPIIbIIIa Deficient Platelets", PLoS One, vol. 20, No. 1, p. e0115978, Jan. 21, 2015.
Sullenbarger et al., "Prolonged Continuos in Vitro Human Platelet Production Using Three-Dimensional Scaffolds", Experimental Hematology, vol. 37, No. 1, pp. 101-110, Jan. 1, 2009.
Preliminary Rejection Report (South Korea); Dated: Sep. 22, 2022.
Title: "Progress and challenges in large-scale expansion of human pluripotent stem cells"; By: Christina Kropp; Dated: Oct. 25, 2016.
Title: "Application of small molecule CHIR99021 leads to the loss of hemangioblast progenitor and increased hematopoiesis of human pluripotent stem cells"; By: Yekaterina Galat; Date: May 29, 2018.
Dege et al., "Directed Differentiation of Primitive and Definitive Hematopoietic Progenitors from Human Pluripotent Stem Cells," Journal of Visualized Experiments, Nov. 1, 2017, vol. 129, e55196, pp. 1-9.
Fujimoto et al., "Production of functional platelets by differentiated embryonic stem (ES) cells in vitro," Blood, Dec. 1, 2003, vol. 102, No. 12, pp. 4044-4051.
Galat et al., "Cytokine-free directed differentiation of human pluripotent stem cells efficiently produces hemogenic endothelium with lymphoid potential," Stem Cell Research & Therapy, Mar. 17, 2017, vol. 8, Article No. 67, pp. 1-11.
Hong et al., "Transfection of Human Platelets with Short Interfering RNA," Clinical and Translational Science, Jun. 27, 2011, vol. 4, Iss. 3, pp. 180-182.
Khan, Kishwar Hayat, "Gene Transfer Technologies and their Applications: Roles in Human Diseases," Asian Journal of Experimental Biological Science, 2010, vol. 1, Iss. 1, pp. 208-218.
Mangin et al., "Thrombin overcomes the thrombosis defect associated with platelet GPVI/FcRγ deficiency," Blood, Jun. 1, 2006, vol. 107, No. 11, pp. 4346-4353.
Ohmori et al., "Efficient expression of a transgene in platelets using simian immunodeficiency virus-based vector harboring glycoprotein Ibα promoter: in vivo model for platelet-targeting gene therapy," The FASEB Journal, 2006, vol. 20, pp. E769-E779.
Pascreau et al., "Elevated thrombin generation in patients with congenital disorder of glycosylation and combined coagulation factor deficiencies," Journal of Thrombosis and Haemostasis, Jul. 4, 2019, vol. 17, Iss. 11, pp. 1798-1807.
Tozawa et al., "Megakaryocytes and platelets from a novel human adipose tissue-derived mesenchymal stem cell line," Blood, Feb. 14, 2019, vol. 133, No. 7, pp. 633-643.
Wang et al., "Scalable Production of Human Erythrocytes from Induced Pluripotent Stem Cells," bioRxiv, Apr. 23, 2016, pp. 1-31.
Wells, D. J., "Gene Therapy Progress and Prospects: Electroporation and other physical methods," Gene Therapy, Aug. 5, 2004, vol. 11, pp. 1363-1369.
Wilhelm et al., "Analysis of nanoparticle delivery to tumours," Nature Reviews Materials, May 2016, vol. 1, Article No. 16014, pp. 1-12.
International Search Report in corresponding International Patent Application No. PCT/US19/40021, mailed Sep. 10, 2019 (4 pages).
Eisenstein et al., "Nature Biotechnology's Academic Spinouts of 2019", Nature Biotechnology, vol. 38, pp. 546-558, May 2020.
Andrade et al., "Biotech-Educated Platelets: Beyond Tissue Regeneration 2.0," International Journal of Molecular Sciences, vol. 21, Iss. 17, Article No. 6061, pp. 1-14, Aug. 23, 2020.
Escolar et al., "Modifications in Accessibility of Membrane Glycoproteins, Binding of Specific Ligands and Coagulation Factor V During the Activation of Platelets in Blood Emerging from Bleeding Time Wounds", American Journal of Hematology, vol. 60, pp. 260-267 (1999).
Fujiyama et al., "Development of an Ex Vivo Xenogeneic Bone Environment Producing Human Platelet-Like Cells," PLoS One, vol. 15, No. 4, e0230507, pp. 1-12, Apr. 7, 2020.
Kailashiya et al., "Engineered Human Platelet-Derived Microparticles as Natural Vectors for Targeted Drug Delivery" Oncotarget, vol. 10, No. 56, pp. 5835-5846 (2019).
Pick et al., "Generation of Megakaryocytic Progenitors from Human Embryonic Stem Cells in a Feeder and Serum-Free Medium" PLOS One, vol. 8, No. 2, pp. 1-11, Feb. 2013.
Thon et al., "Platelet Bioreactor: Accelerated Evolution of Design and Manufacture" Platelets, vol. 28, No. 5, pp. 472-477.
Zaldivia et al., "Platelet-Derived Microvesicles in Cardiovascular Diseases" Frontiers in Cardiovascular Medicine, vol. 4, Article 74, pp. 1-13, Nov. 2017.
Amit et al., "Dynamic Suspension Culture for Scalable Expansion of Undifferentiated Human Pluripotent Stem Cells," Nature Protocols, vol. 6, No. 5., pp. 572-579, Apr. 2011.

(56) References Cited

OTHER PUBLICATIONS

Everts, "Autologous Platelet-Rich Plasma and Mesenchymal Stem Cells for the Treatment of Chronic Wounds" pp. 149-180. IntechOpen, Nov. 5, 2018.

Feng et al., "Scalable Generation of Universal Platelets from Human Induced Pluripotent Stem Cells," Stem Cell Reports, vol. 3, No. 5, pp. 817-831, Nov. 11, 2014.

Lam et al. "Improved human pluripotentstem cell attachment and spreading on xeno-free laminin-521-coated microcarriers results in efficient growth in agitated cultures," BioResearch open access, vol. 4, No. 1, pp. 242-257, Apr. 1, 2015.

Macauley et al.,"Canonical Wnt Signaling in Megakaryocytes Regulates Proplatelet Formation," Blood, vol. 121, No. 1, pp. 188-196, Jan. 3, 2013.

Mariani et al. "Platelet Concentrates in Musculoskeletal Medicine" International Journal of Molecular Sciences, vol. 21, No. 4, pp. 1-43, Feb. 16, 2020.

Moreau et al. "Large-scale production of megakaryocytes from human pluripotent stem cells by chemically defined forward programming," Nature Communications, vol. 7, No. 1, p. 11208, Apr. 7, 2016.

Baigger et al., "Large-Scale Production of Induced Pluripotent Stem Cells-Derived Megakaryocytes in Bioreactors" Transfus. Med. Hemother. Vol. 44, Supplement 1, pp. 5-6, Article No. V03-2, 2017.

Baigger et al., "Towards the Manufacture of Megakaryocytes and Platelets for Clinical Application" Transfus. Med. Hemother. vol. 44, pp. 165-173, 2017.

Borger et al., "Generation of HLA-Universal iPSC-Derived Megakaryocytes and Platelets for Survival under Refractoriness Conditions" Mol. Med. vol. 22, pp. 274-285, 2016.

Hirata et al., "Selective Inhibition of ADAM17 Efficiently Mediates Glycoprotein Ib[alpha] Retention During Expertech Vivo Generation of Human Induced Pluripotent Stem Cell-Derived Platelets" Stem Cells Translational Medicine, vol. 6, No. 3, pp. 720-730, Mar. 1, 2017.

Kronke et al., "Lenalidomide Induces Ubiquitination and Degradation of CK1a in del(5q) MDS" Nature, vol. 523, No. 7559, pp. 183-188, Jul. 1, 2015.

Lambert et al., "Challenges and Promises for the Development of Donor-Independent Platelet Transfusions" Blood, American Society of Hematology, US, vol. 121, No. 17, pp. 3319-3324, Jan. 15, 2013.

Liu et al., "Efficient Generation of Megakaryocytes from Human Induced Pluripotent Stem Cells Using Food and Drug Administration-Approved Pharmacological Reagents" Stem Cells Translational Medicine, vol. 4, No. 4, pp. 309-319, Apr. 1, 2015.

Sarkar et al., "Drug Delivery Using Platelet Cancer Cell Interaction" Pharmaceutical Research, vol. 30, No. 11, pp. 2785-2794, Jun. 6, 2013.

Solomon et al., "Current Perspectives on the Use of Ancillary Materials for the Manufacture of Cellular Therapies" Cytotherapy, vol. 18, Iss. 1, pp. 1-12, Jan. 31, 2016.

Sullivan et al., "High-Level Transgene Expression in Induced Pluripotent Stem Cell-Derived Megakaryocytes: Correction of Glanzmann Thrombasthenia" Blood, vol. 123, No. 5, pp. 753-757, 2014.

International Search Report in International Application No. PCT/US2019/040021 mailed Sep. 10, 2019.

Freshney, "Culture Vessels and Substrates" Chapter 7 In Culture of Animal Cells, pp. 89-98, 2010.

\* cited by examiner

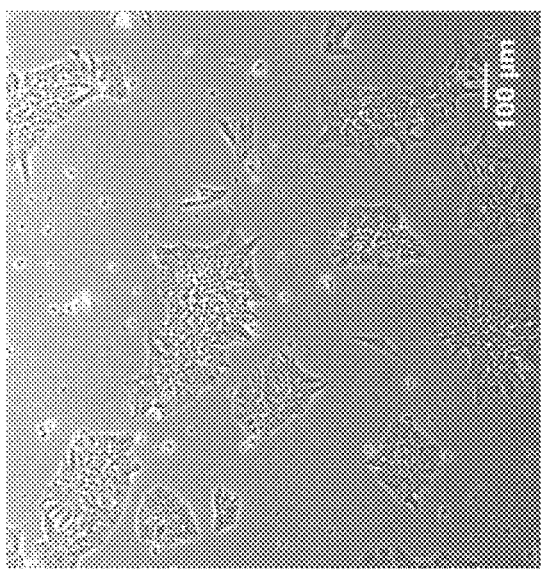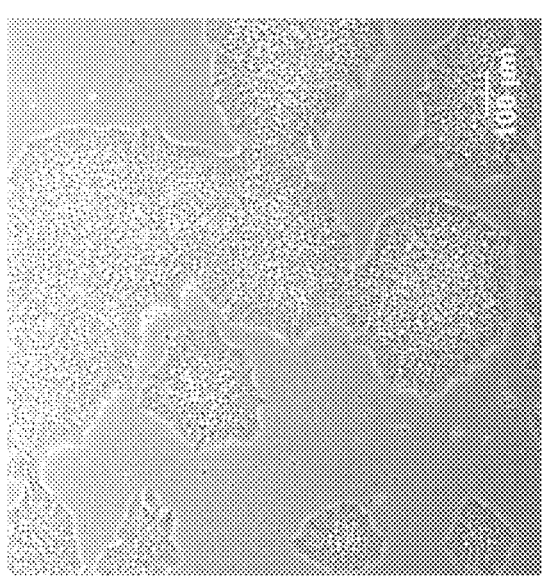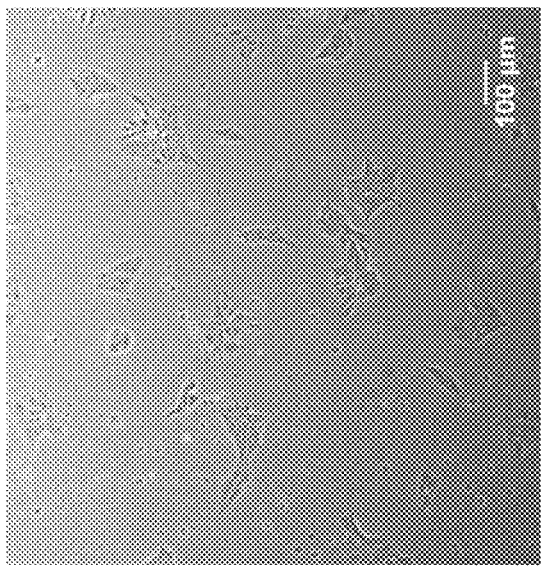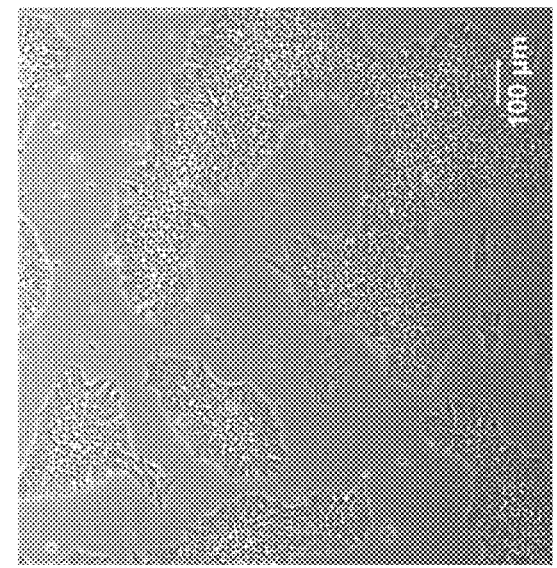
FIG. 8A Essential 8 (Gibco A15170-01): Day 1, Day 2, Day 3, Day 4

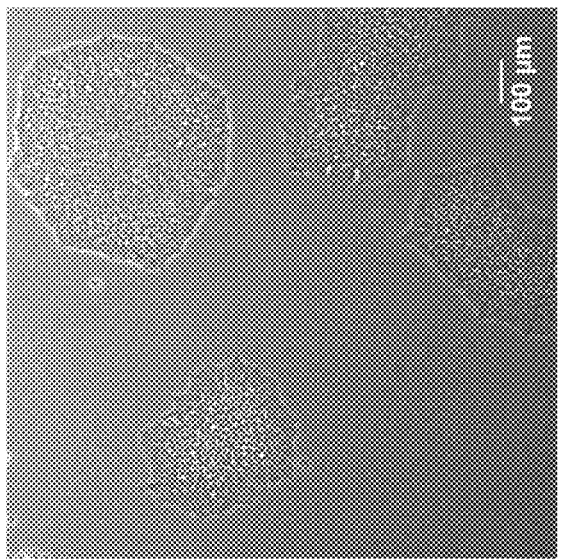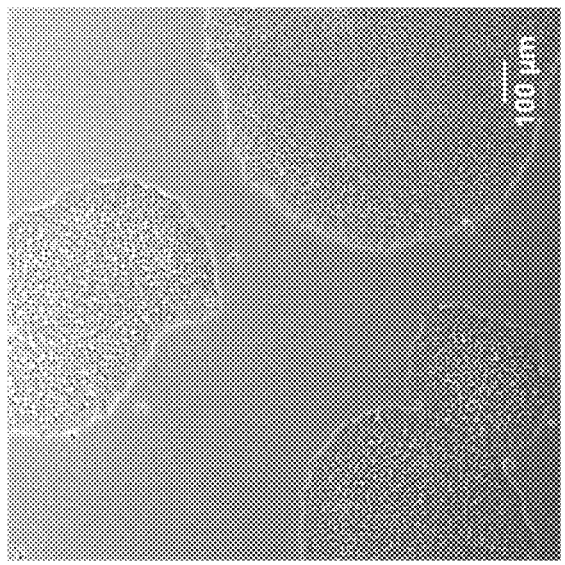
Day 1　　　　　　　　　　　　Day 2
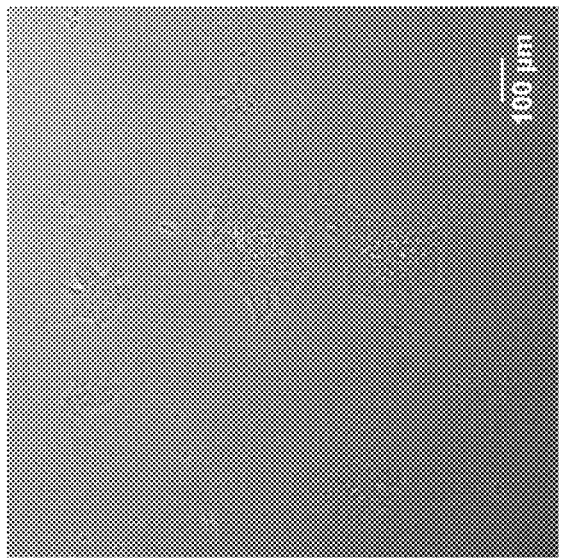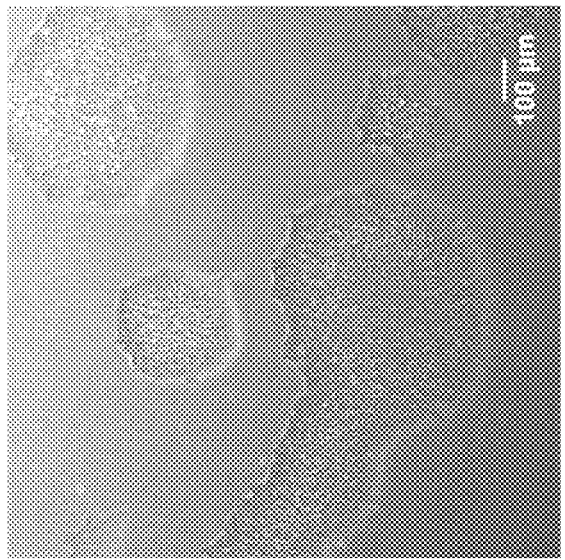
Day 3　　　　　　　　　　　　Day 4
FIG. 8B
StemFlex
(Gibco A33494-01)

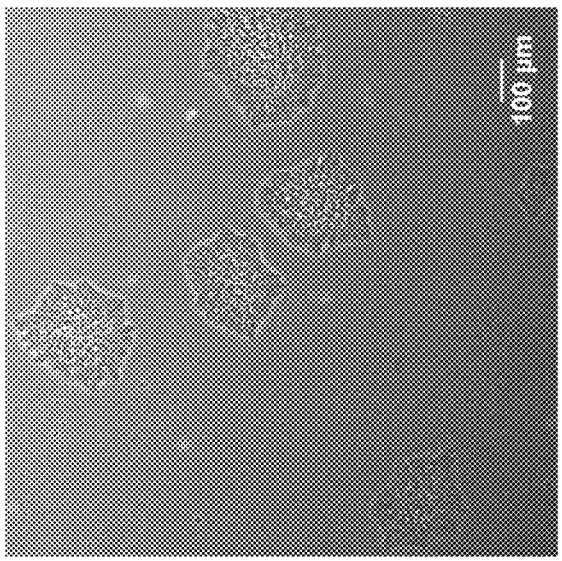
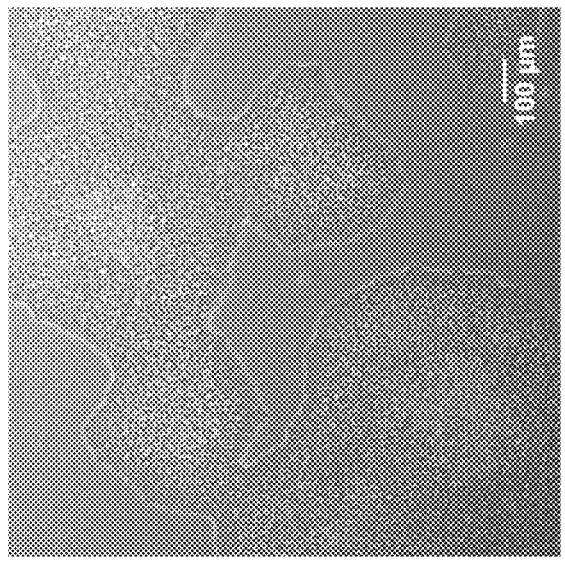
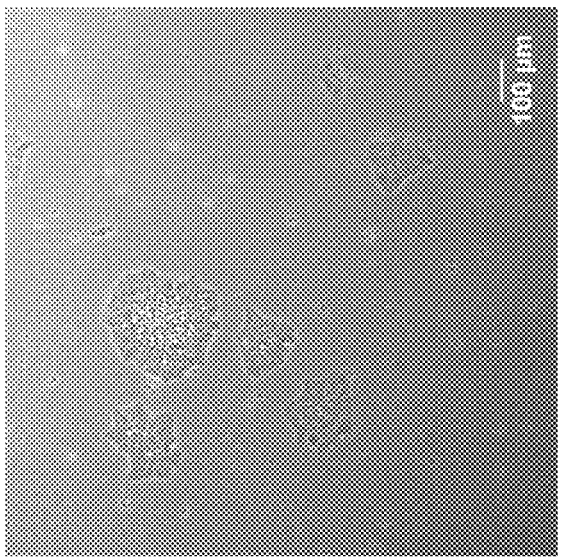
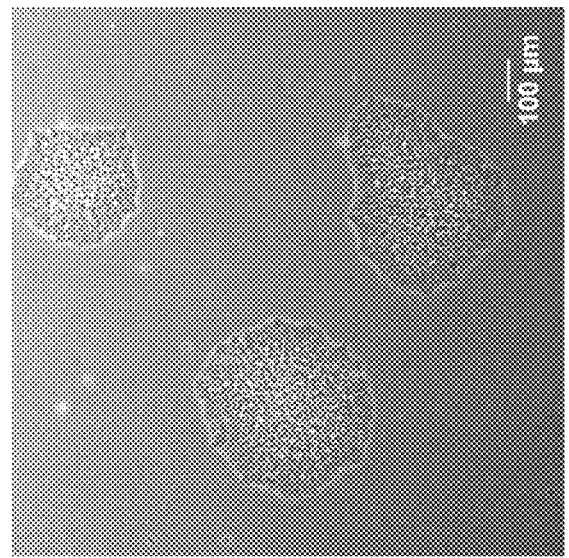
FIG. 8C
NutriStem hPSC XF
(Biological Industries)

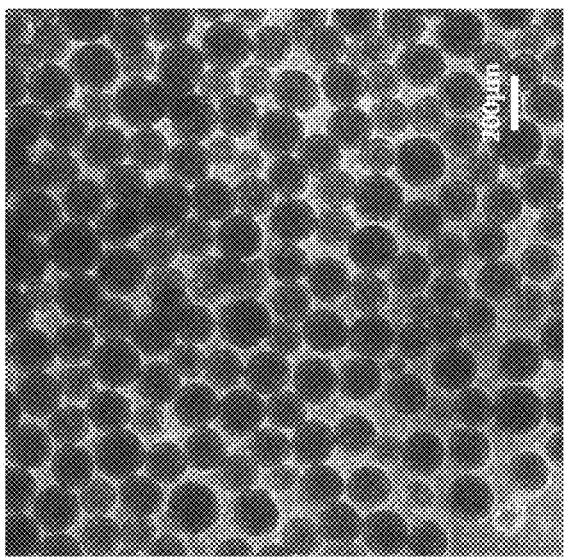
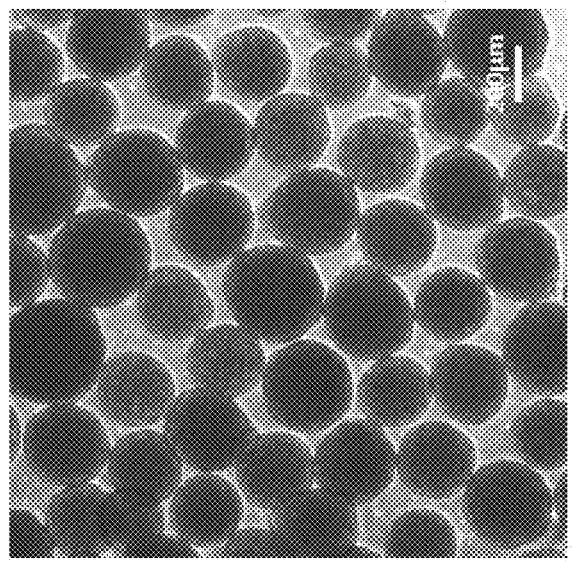
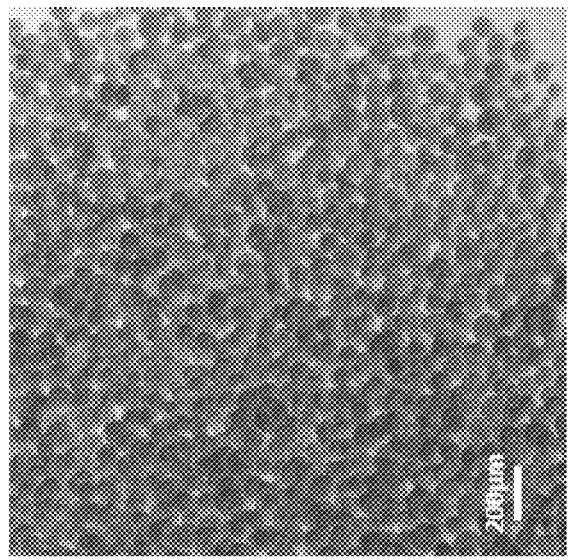
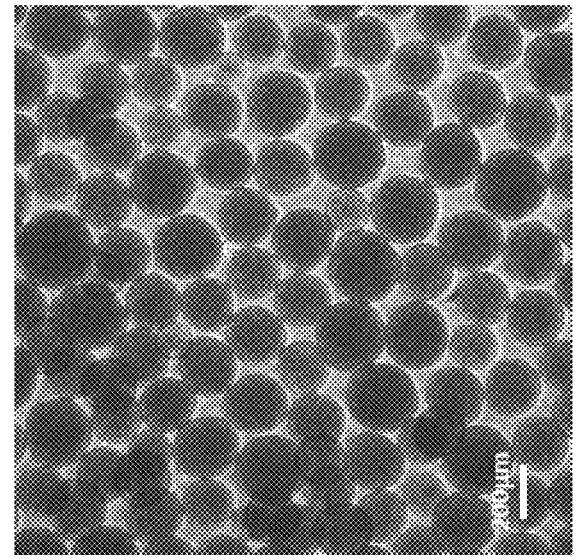
FIG. 11A

4th passage

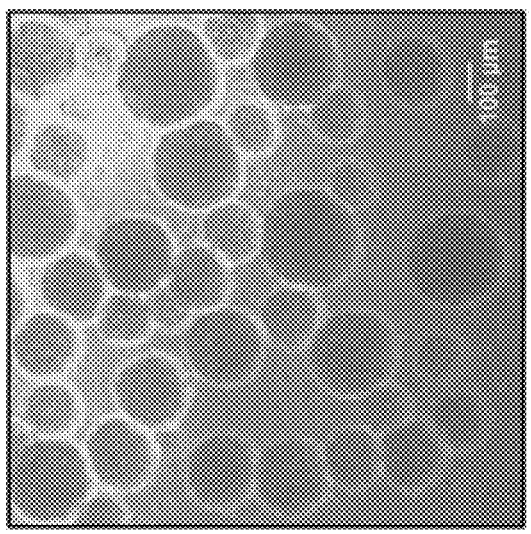
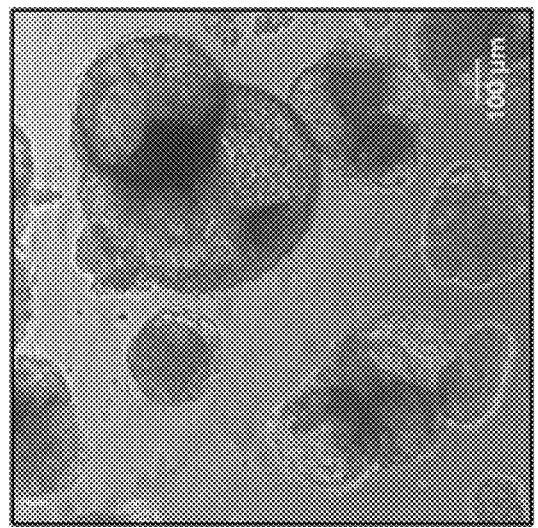
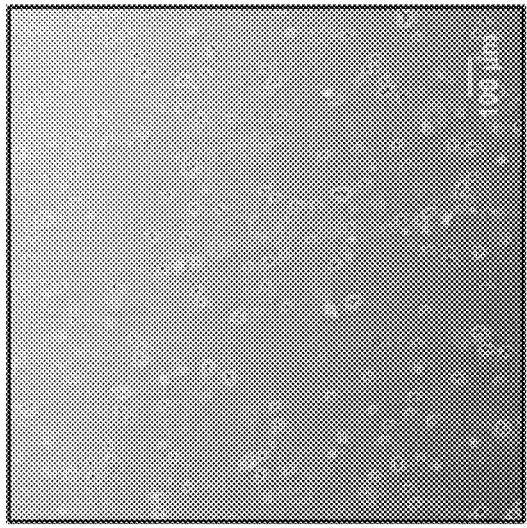
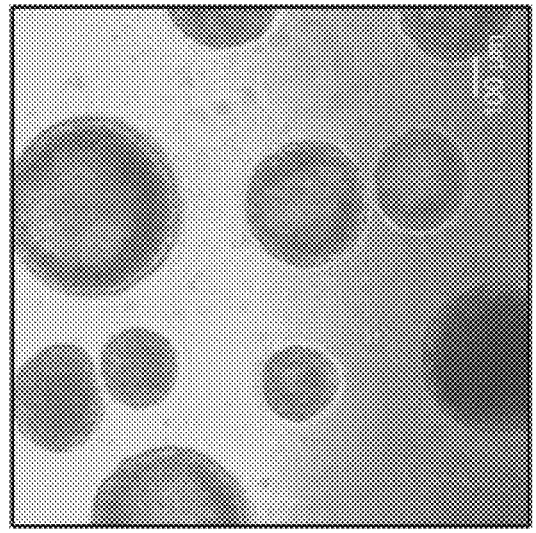
FIG. 22A

FIG. 23A
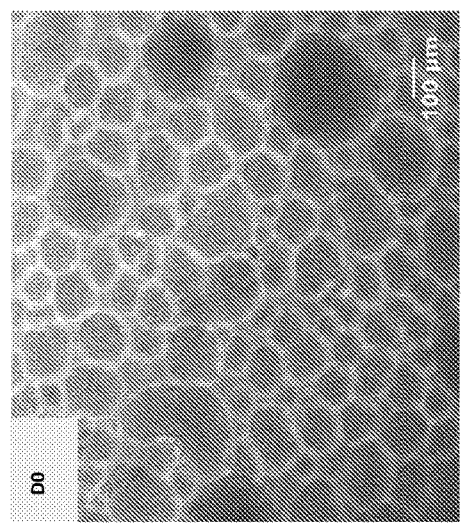
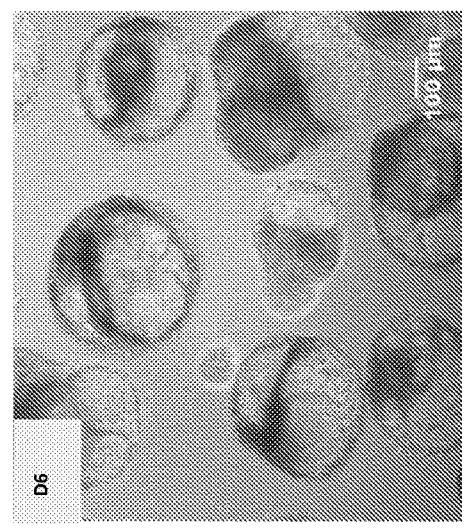
FIG. 23B
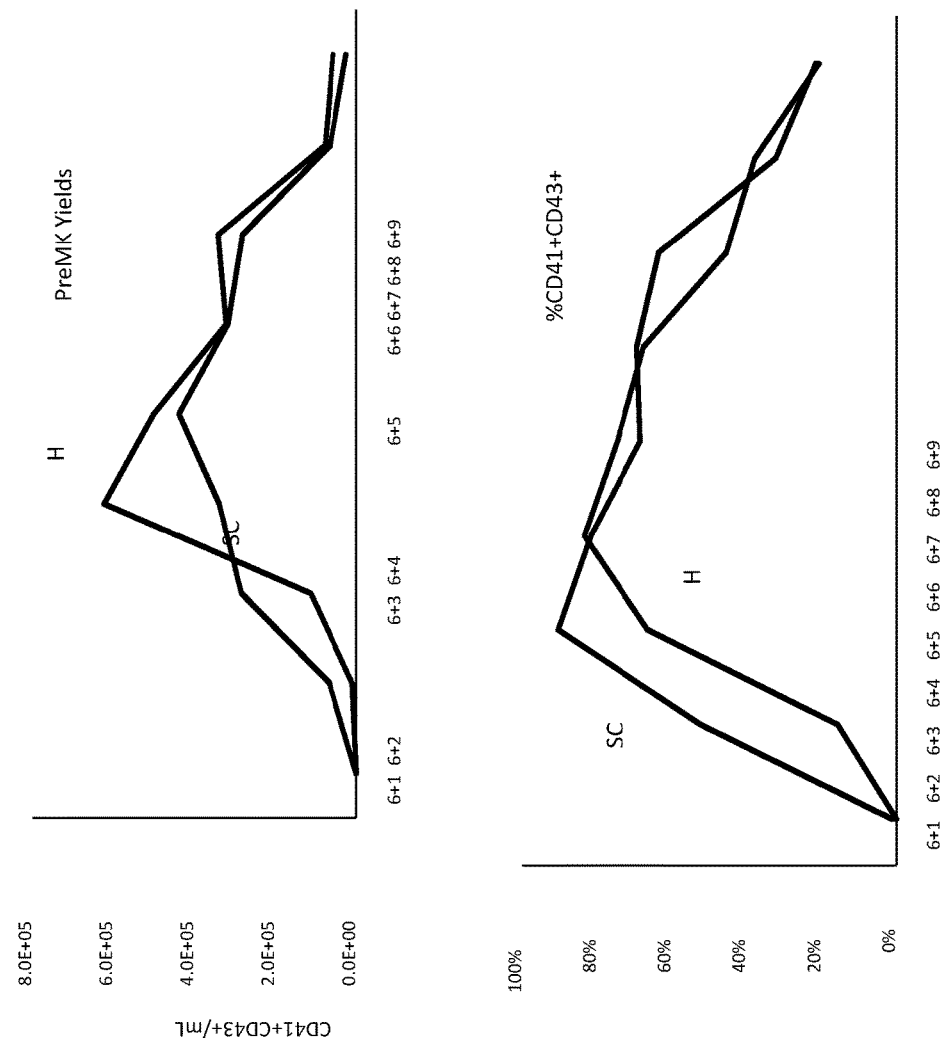

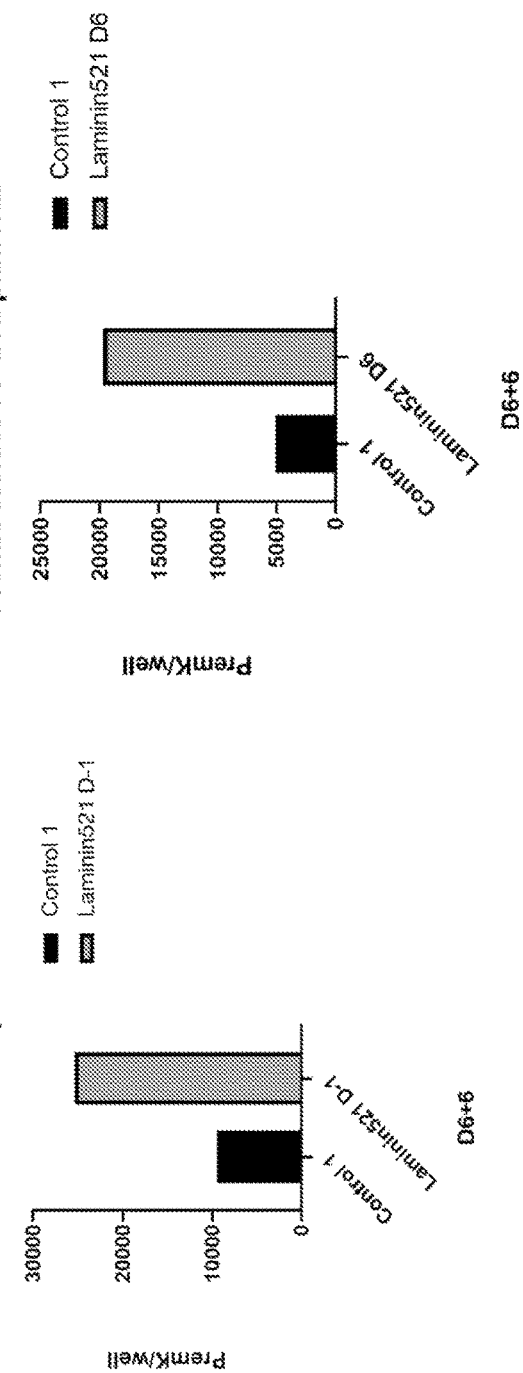
FIG. 27A
FIG. 27B
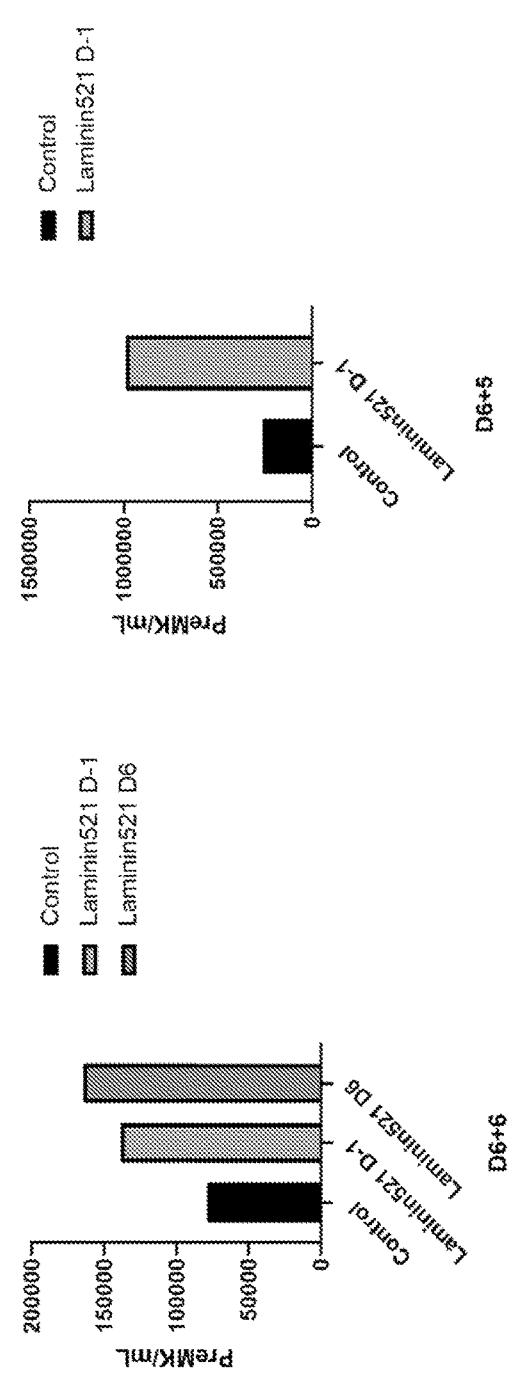
FIG. 27C
FIG. 27D

FIG. 28D
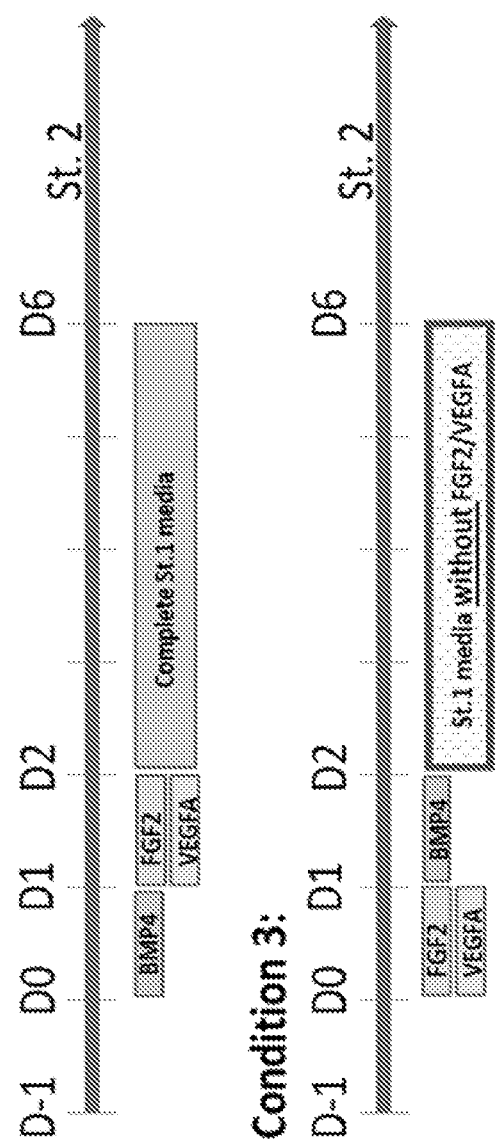
FIG. 28C
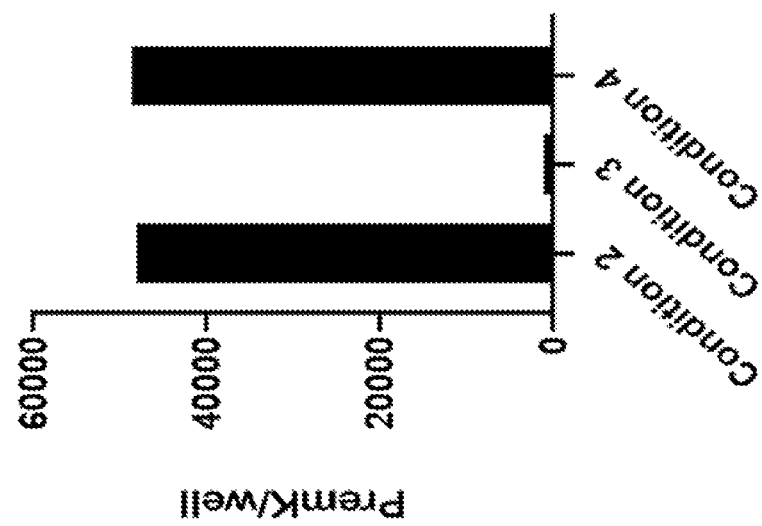
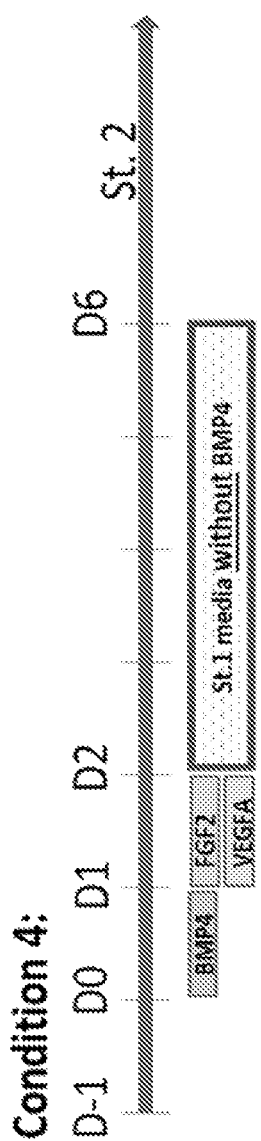

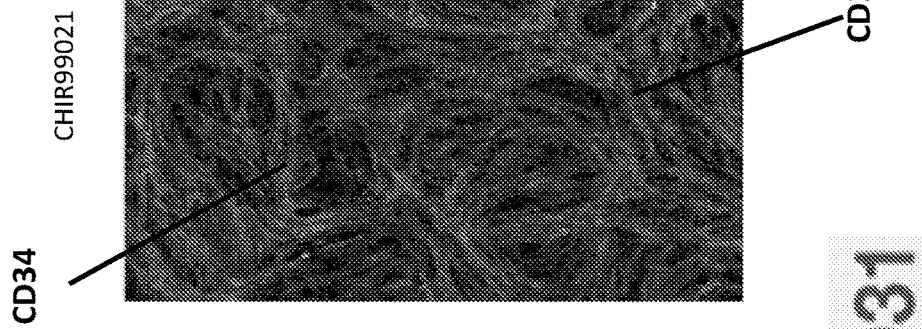
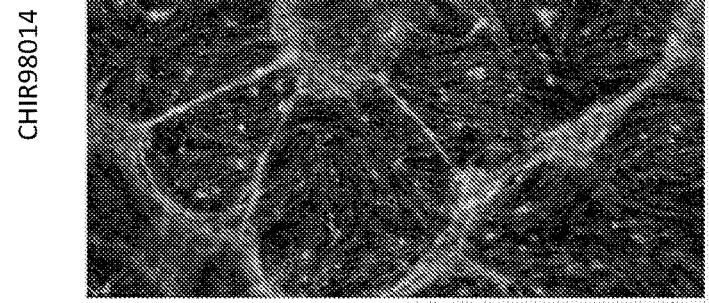
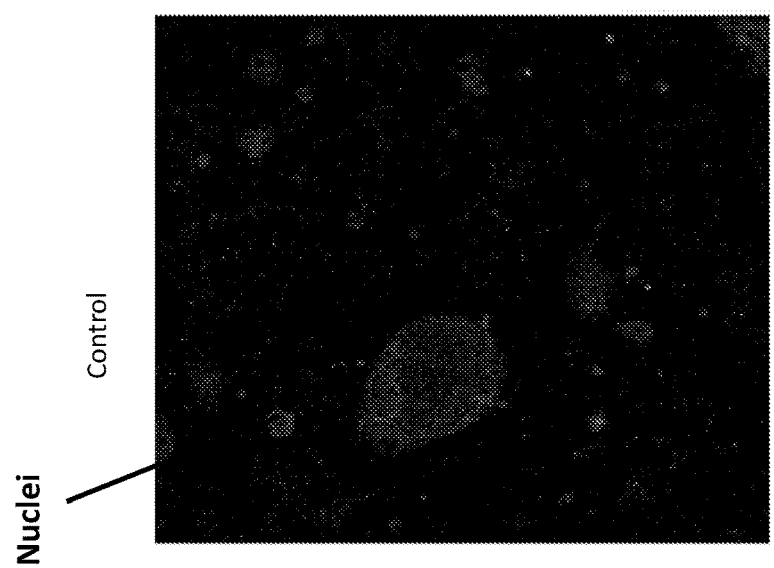

FIG. 30B
CHIR98014
CD14
CD41
CD43
FIG. 30A
Control
Nuclei
Nuclei CD41 CD43 CD14
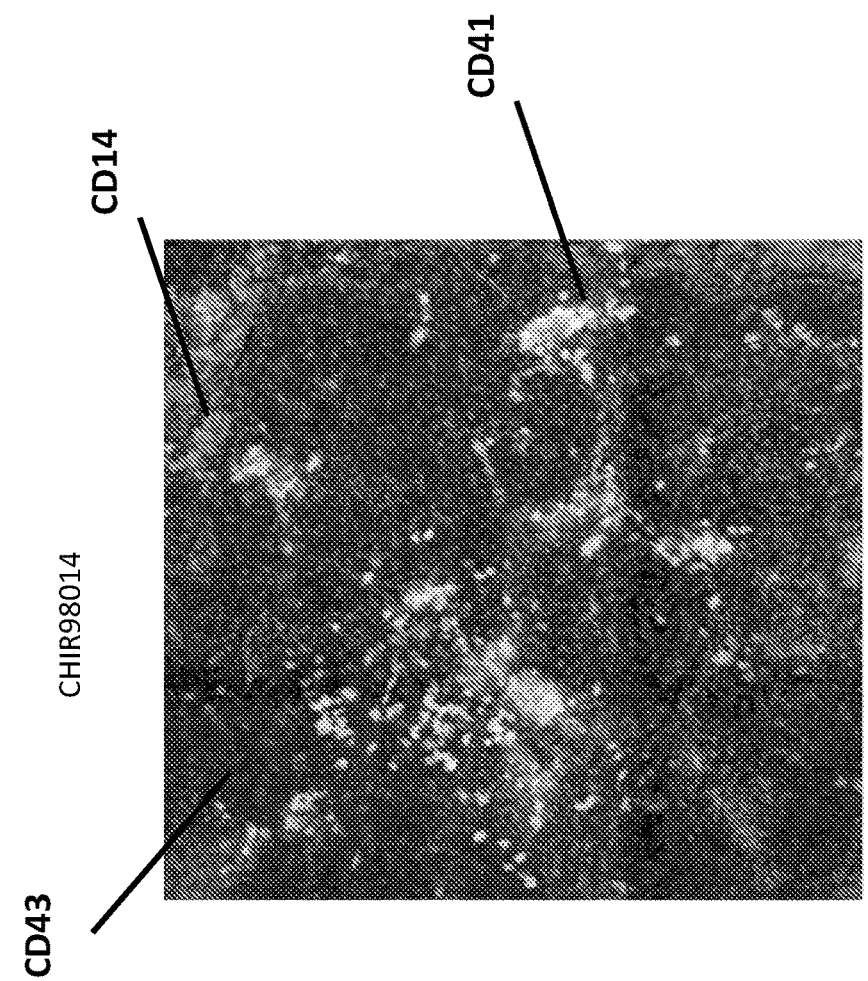
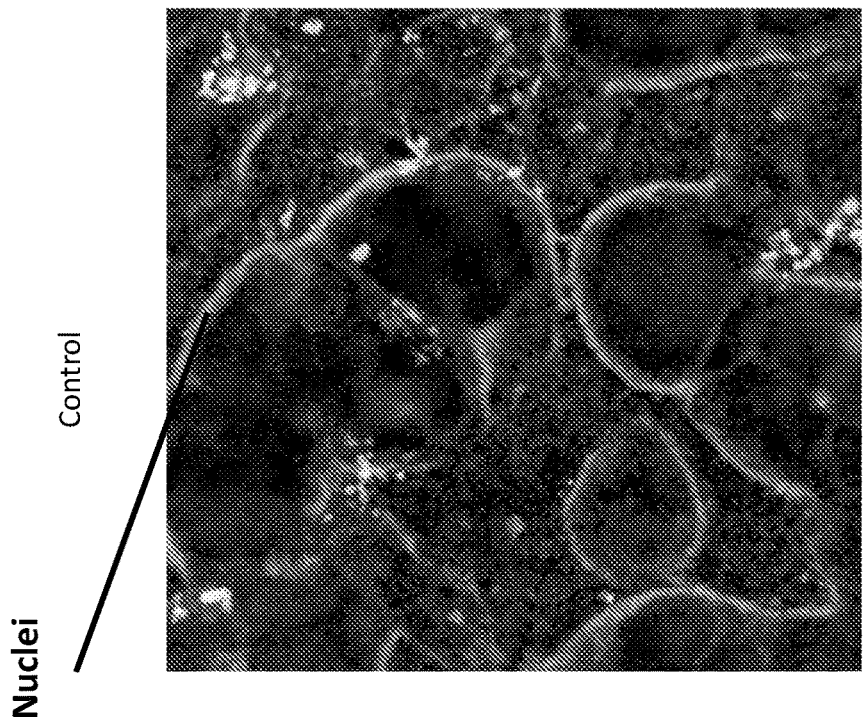

FIG. 31
Day 3
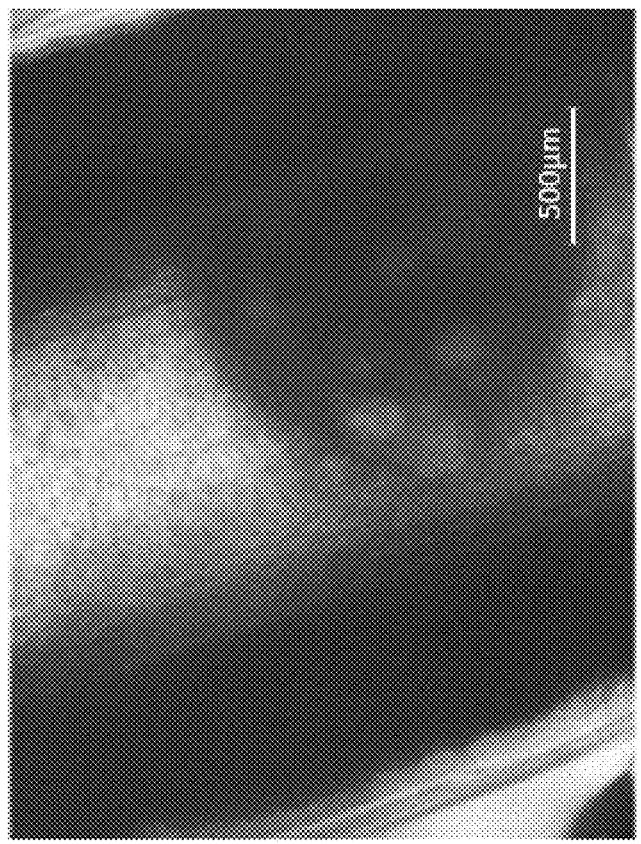
Day 6

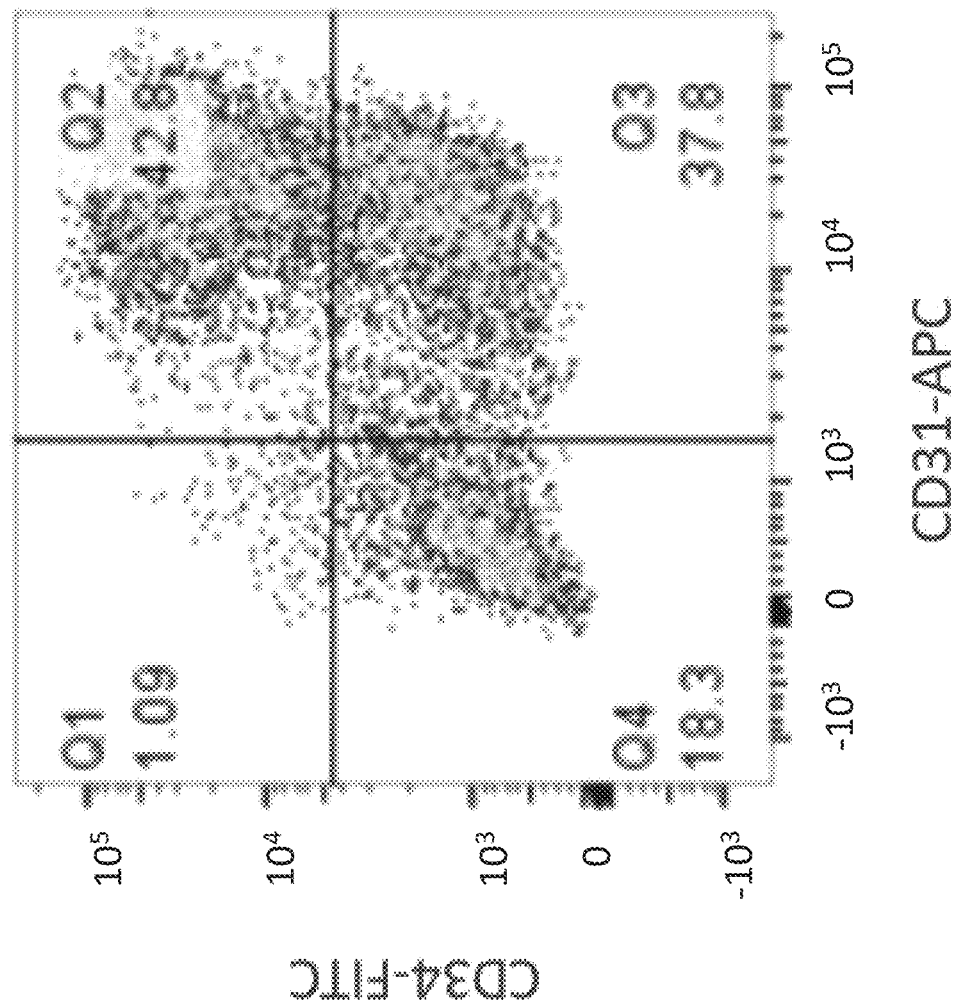

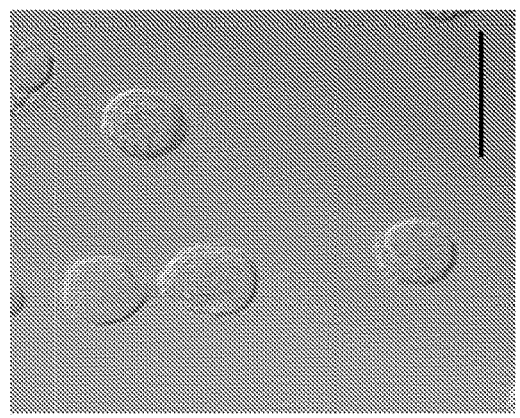
FIG. 34D Phase Contrast
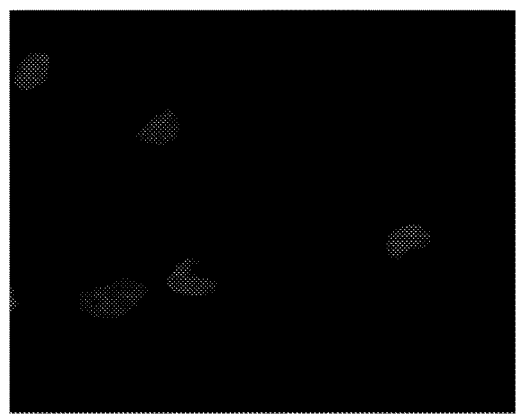
FIG. 34C Merge
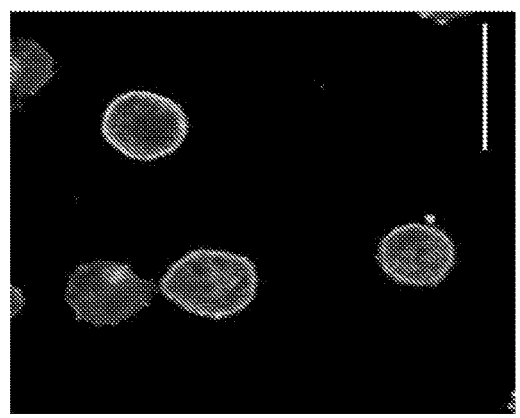
FIG. 34B Nuclei
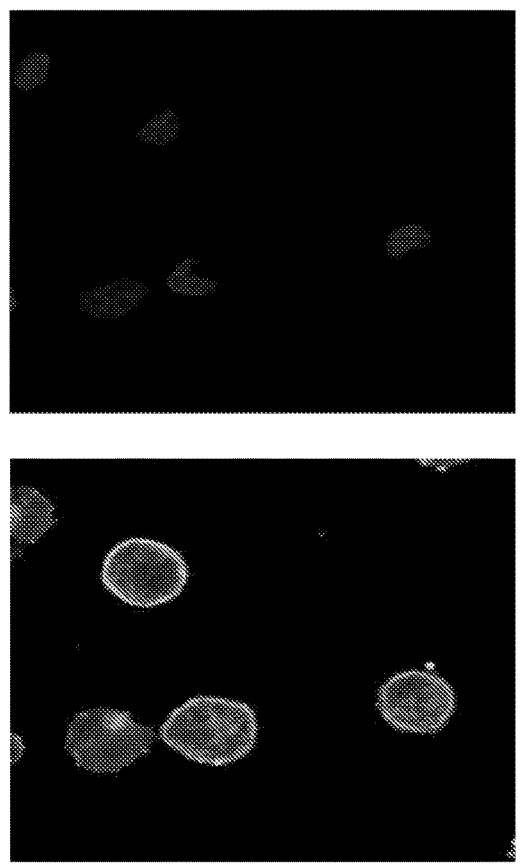
FIG. 34A β-Tubulin
Scale bar = 25μm

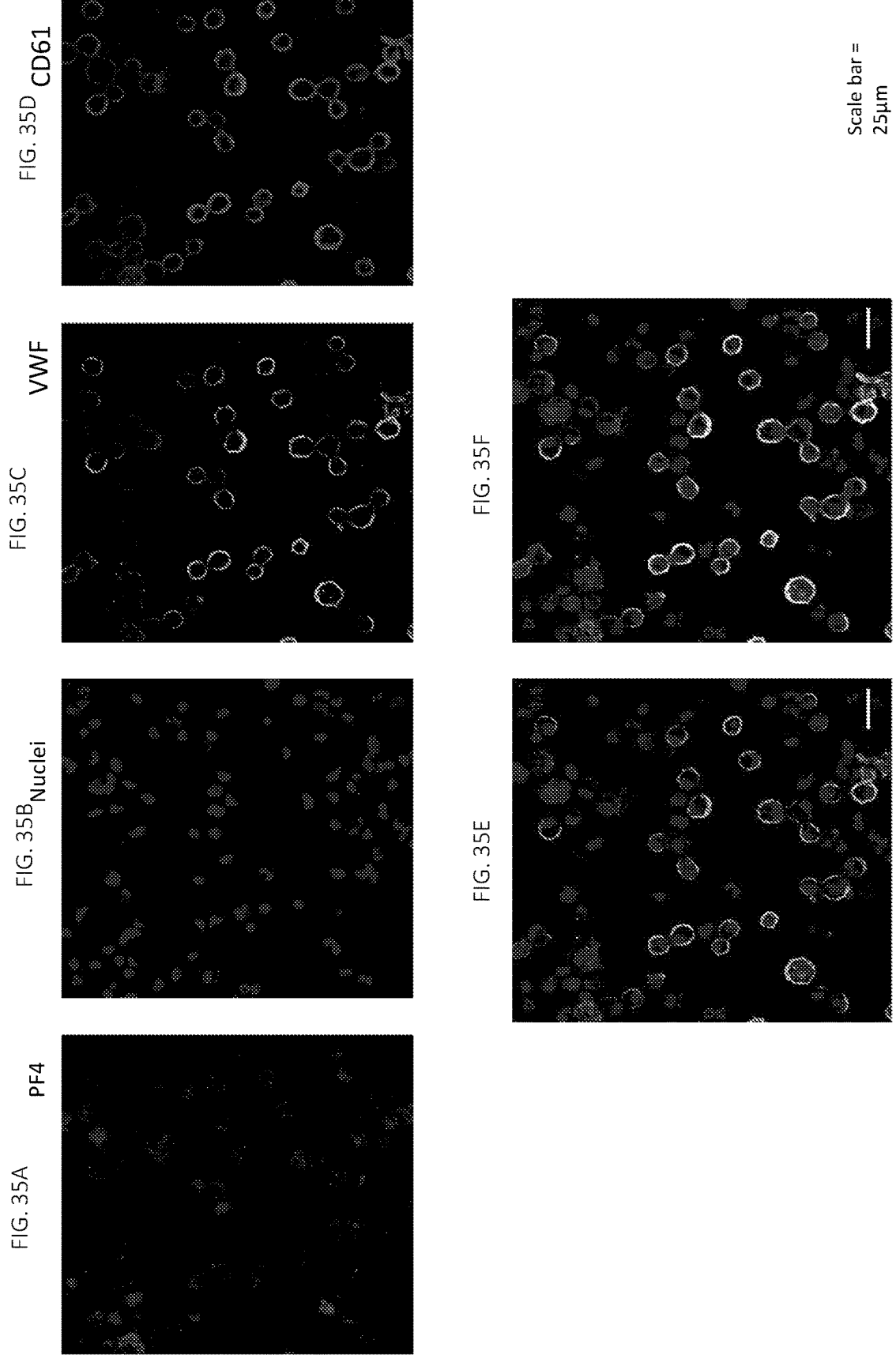

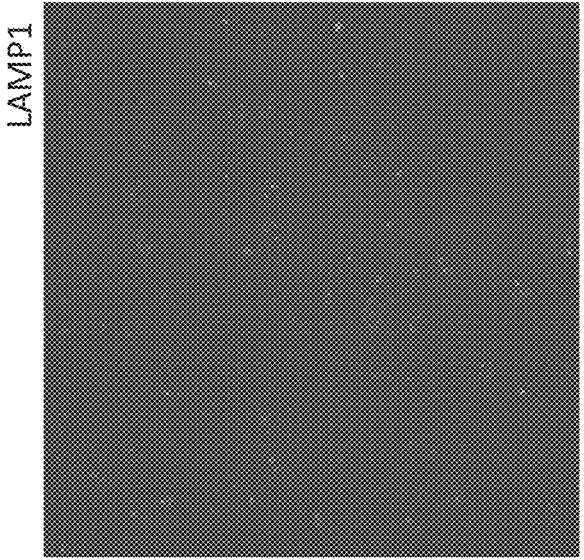
FIG. 36C Serotonin
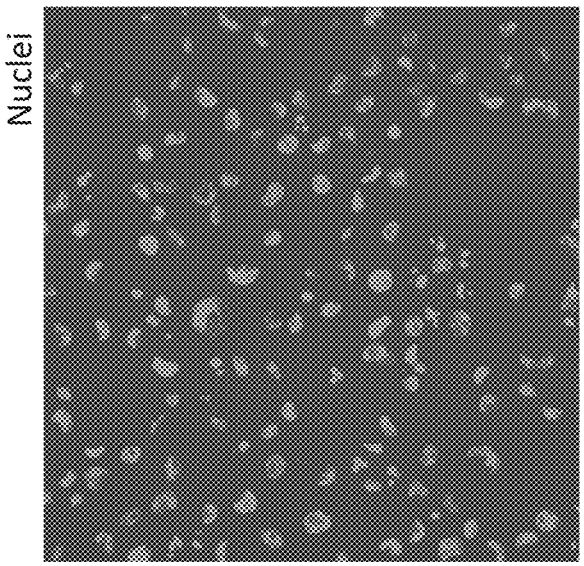
FIG. 36B Nuclei
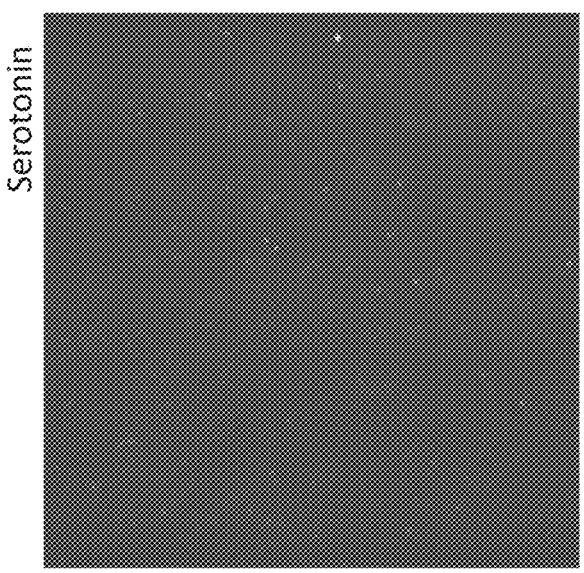
FIG. 36A LAMP1

CD61

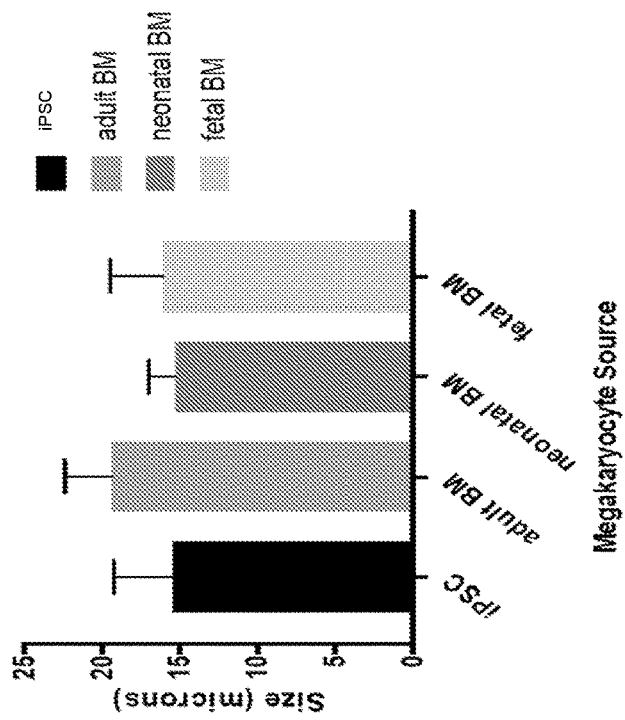
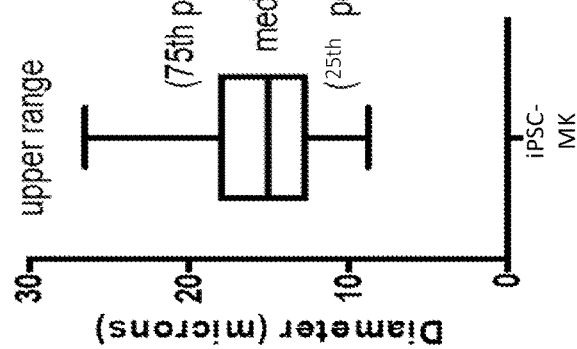
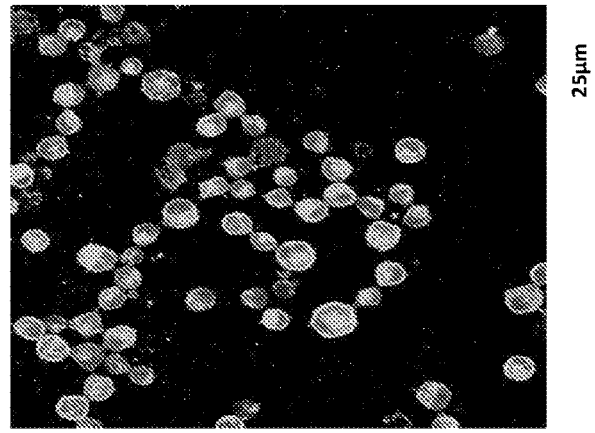
FIG. 40A
β1-Tubulin
FIG. 40B
Size distribution
FIG. 40C
Comparison with other sources
*Sola-Visner et al., Pediatr Res. 2007. 61:479-484
**Ma et al., Eur J Haematol. 1996. 57:121-127

*Sola-Visner et al., Pediatr Res. 2007. 61:479-484
**Ma et al., Eur J Haematol. 1996. 57:121-127

FIG. 44B
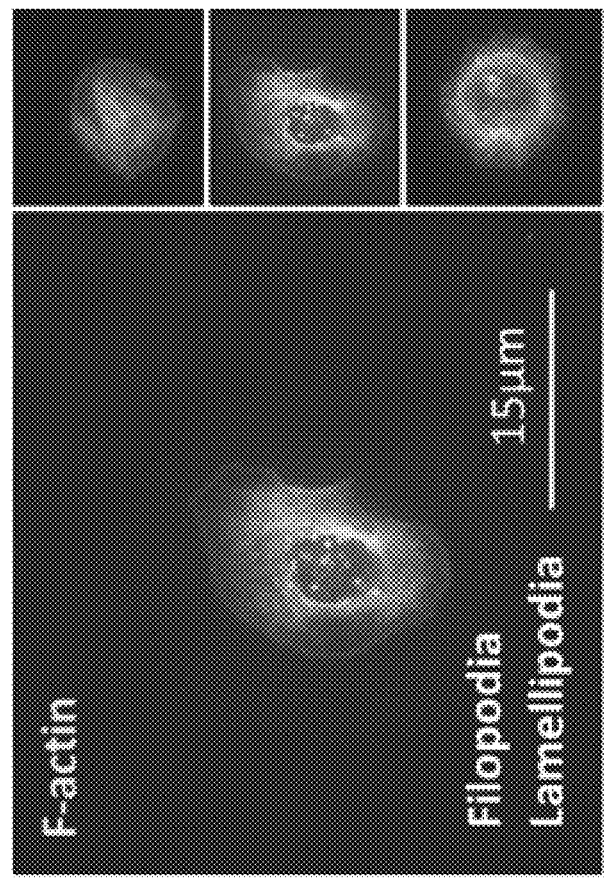
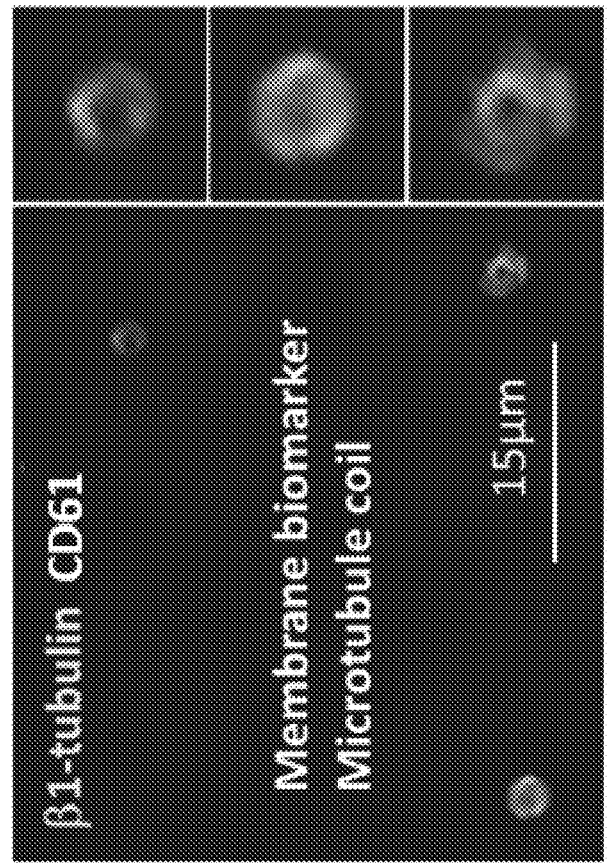

Forward vs Side Scatter

CD61 Expression

*GPVI Expression*

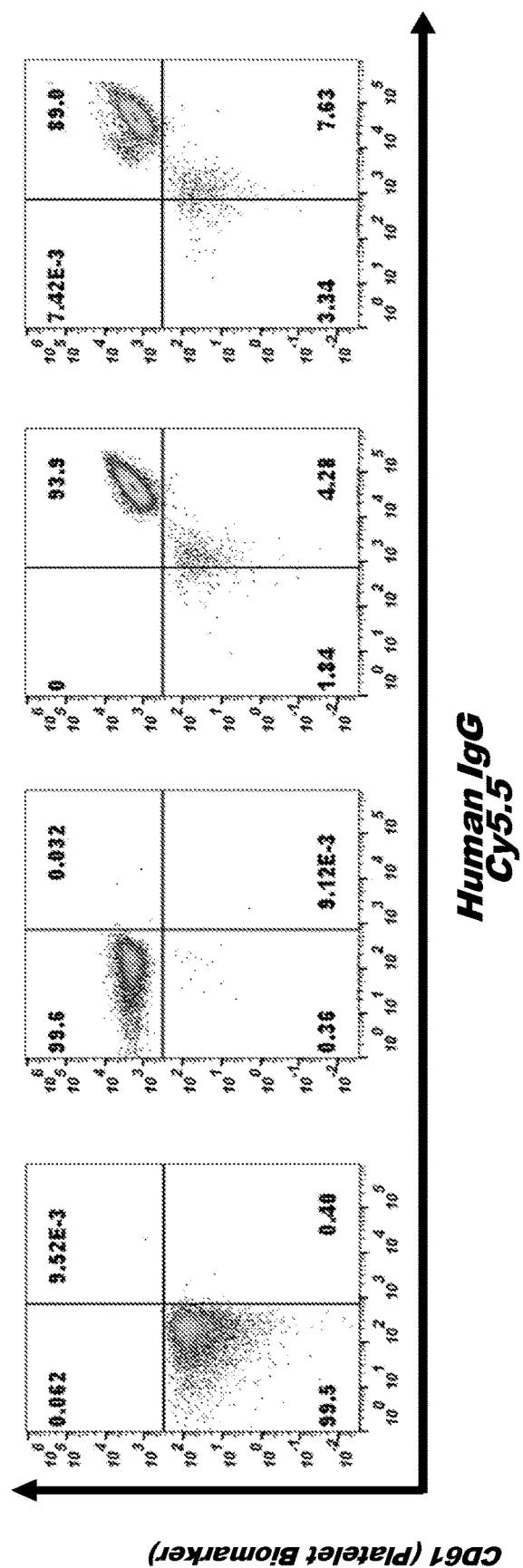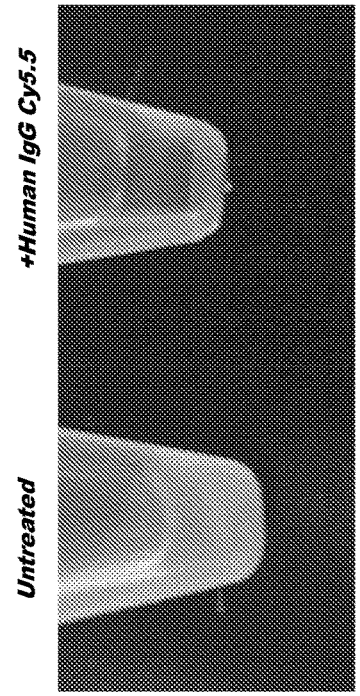
FIG. 49A  FIG. 49B  FIG. 49C  FIG. 49D
FIG. 49E

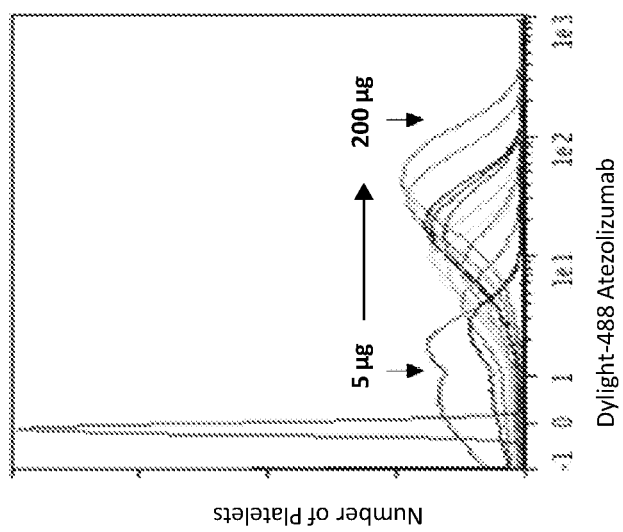
FIG. 49I
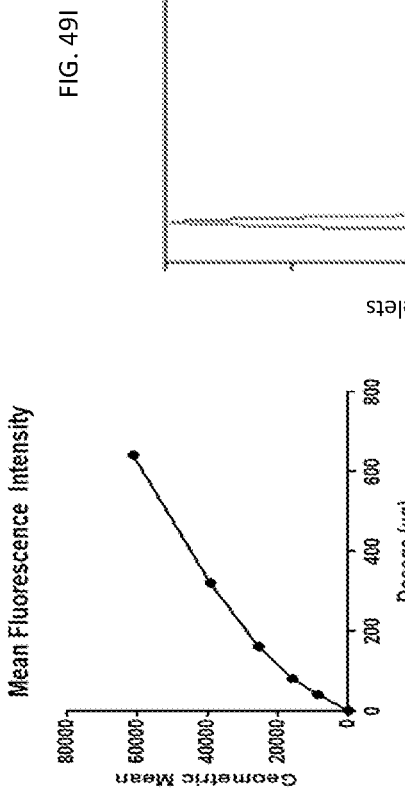
FIG. 49G
FIG. 49H
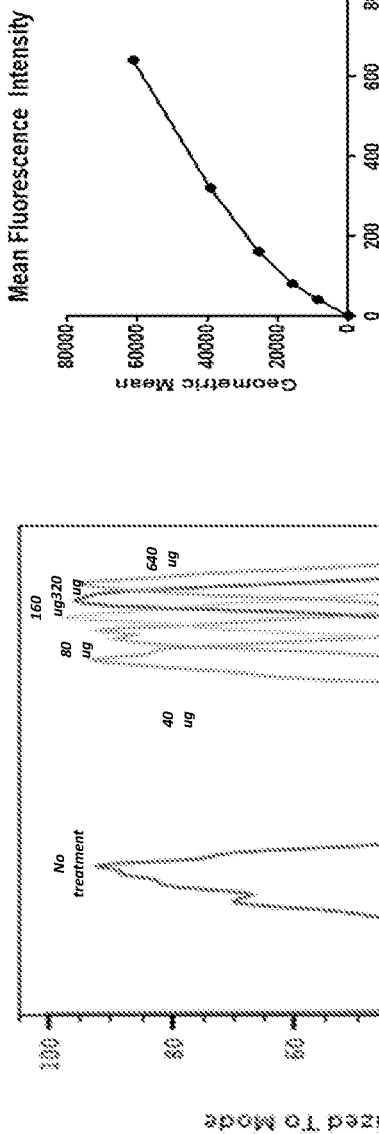
FIG. 49F

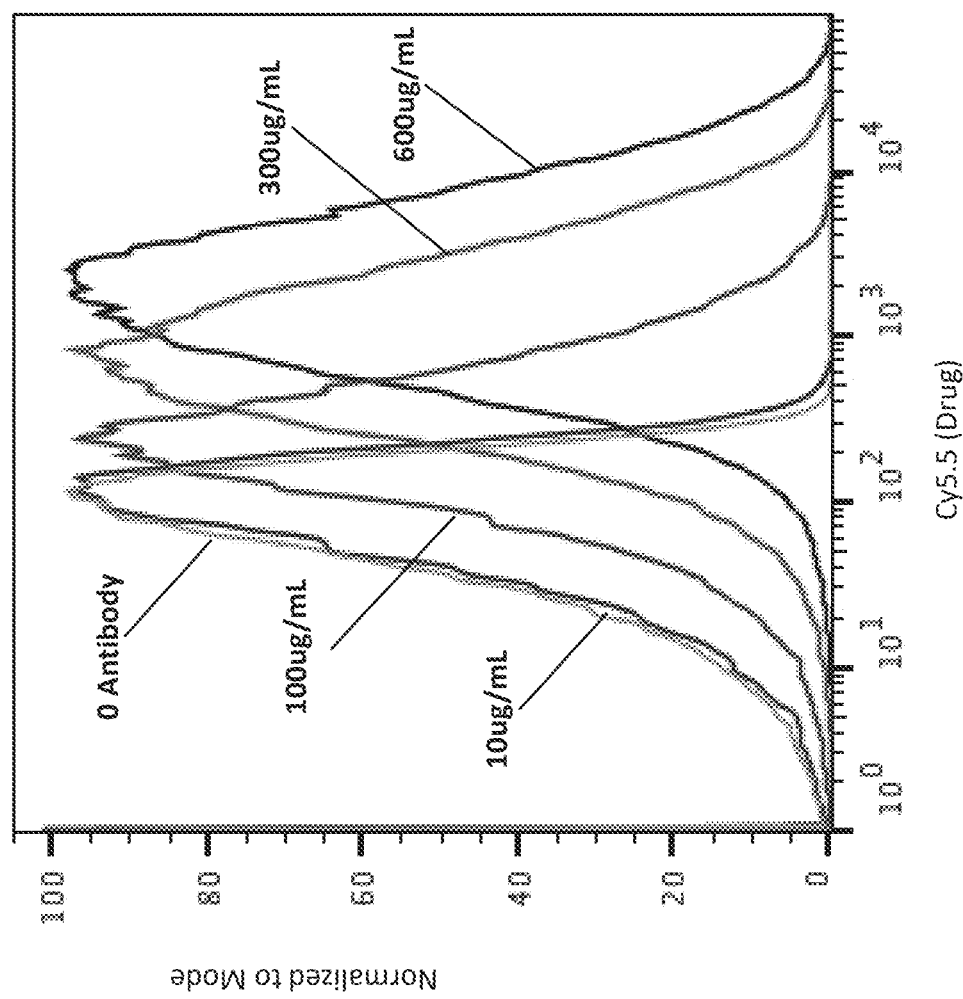

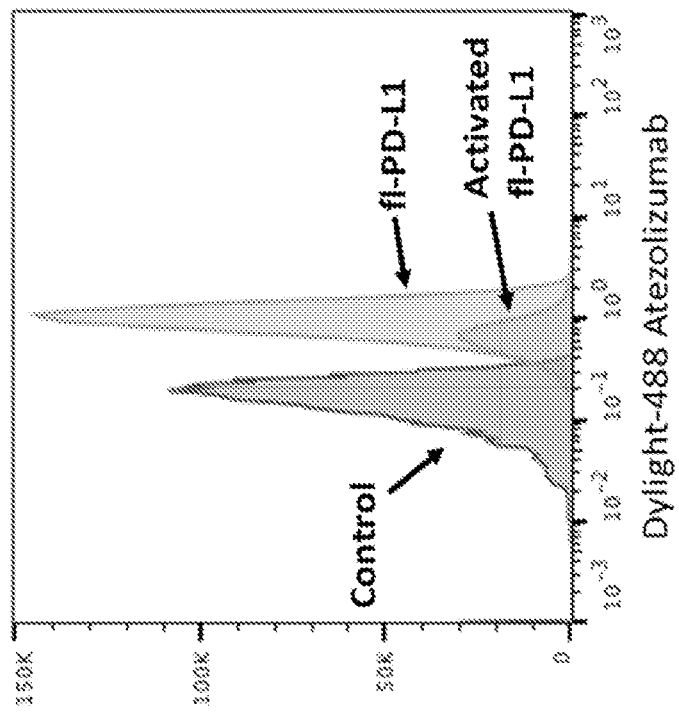
FIG. 53B
FIG. 53A
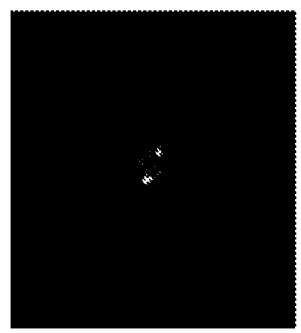
FIG. 53D
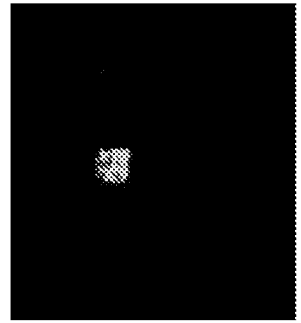
FIG. 53C

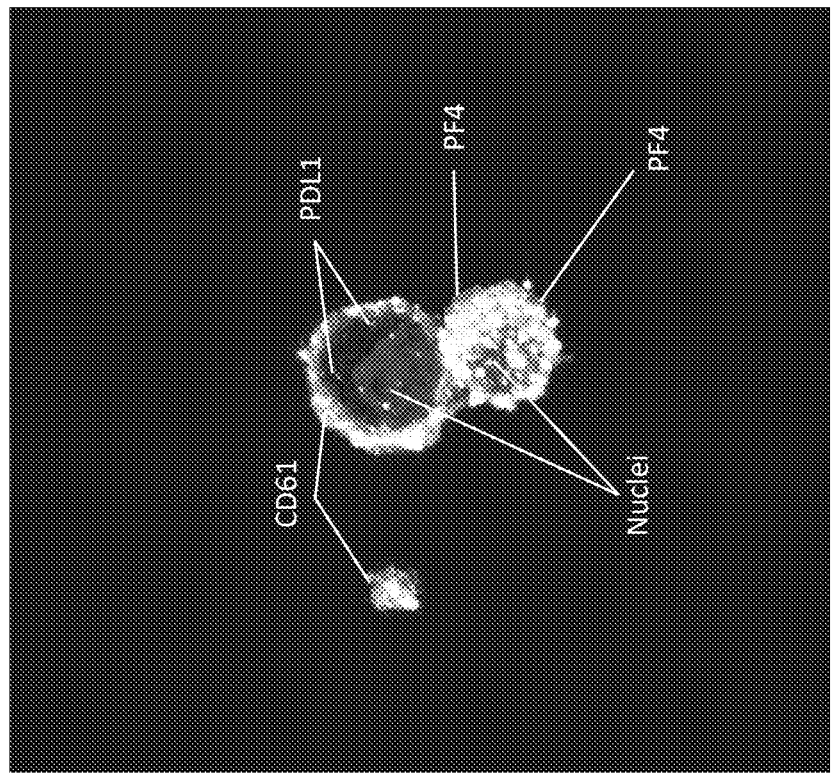
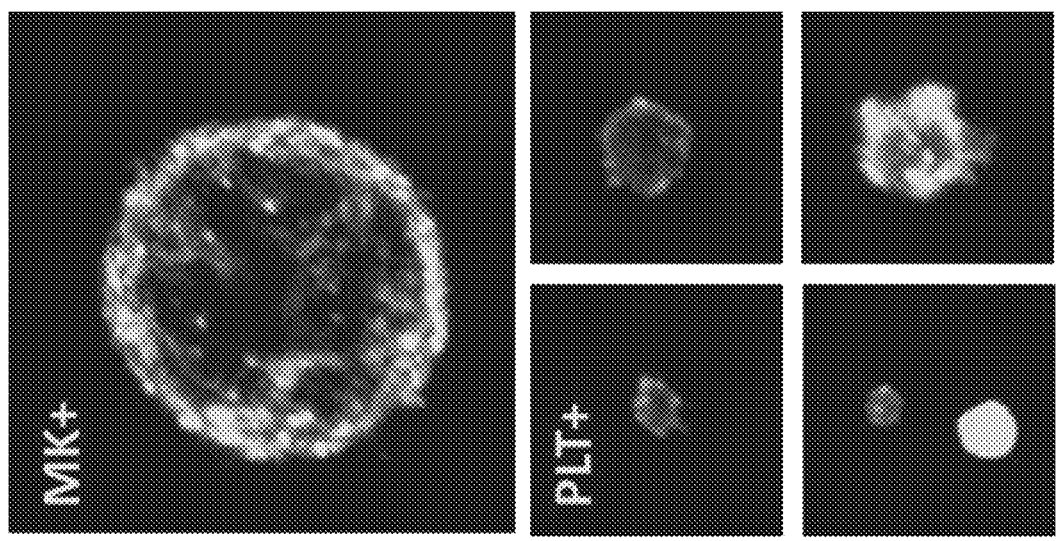

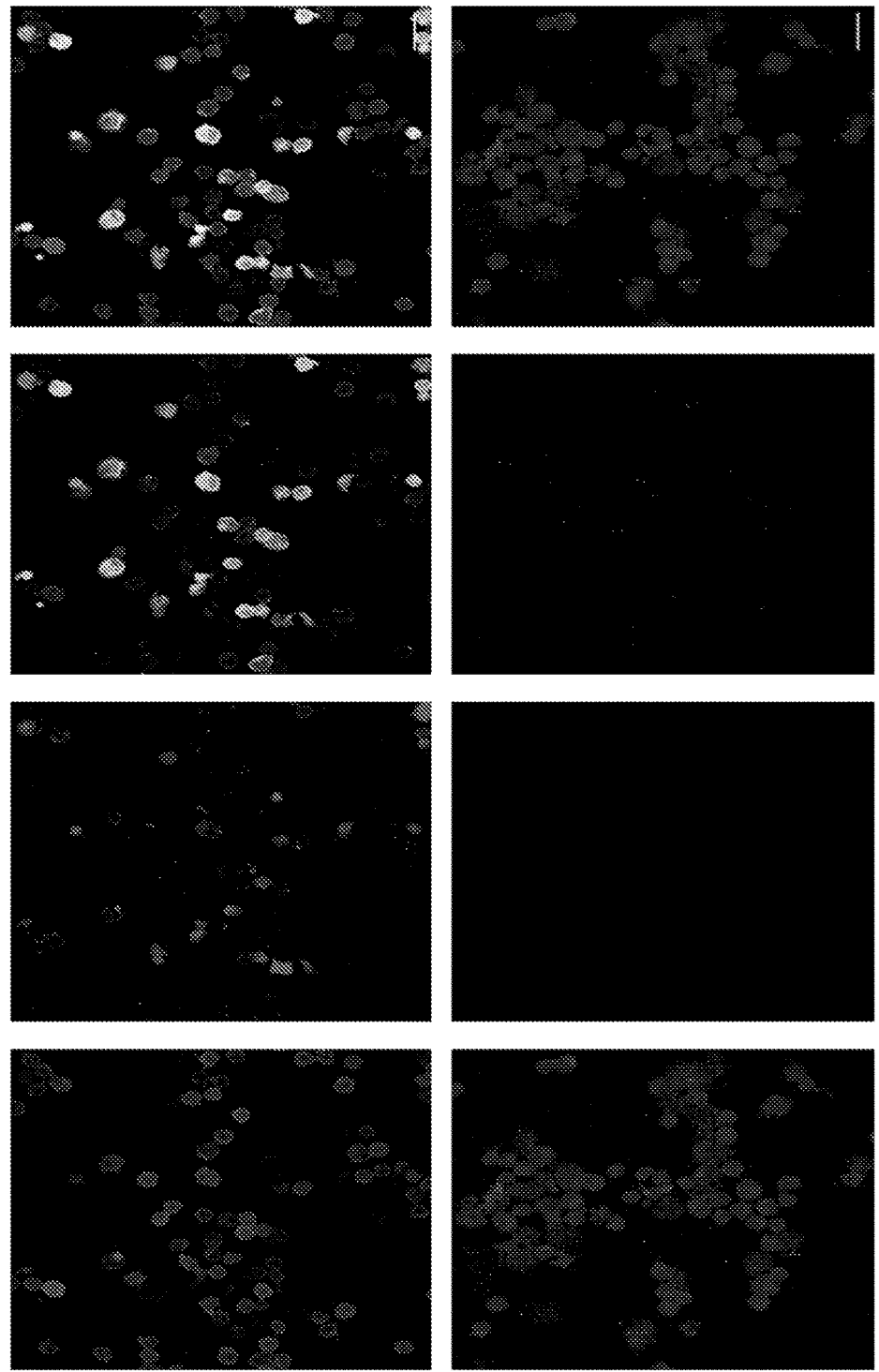

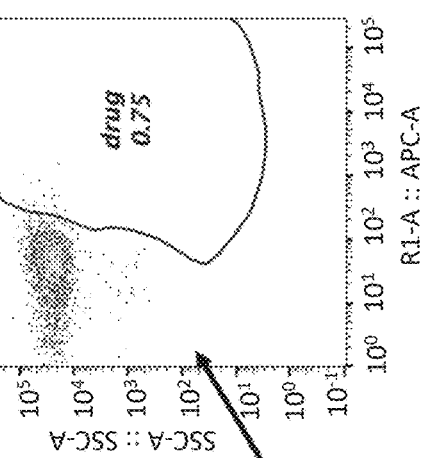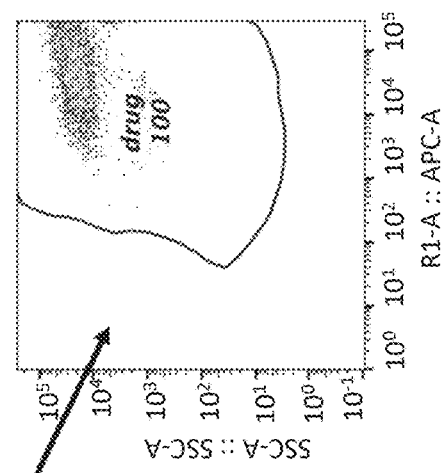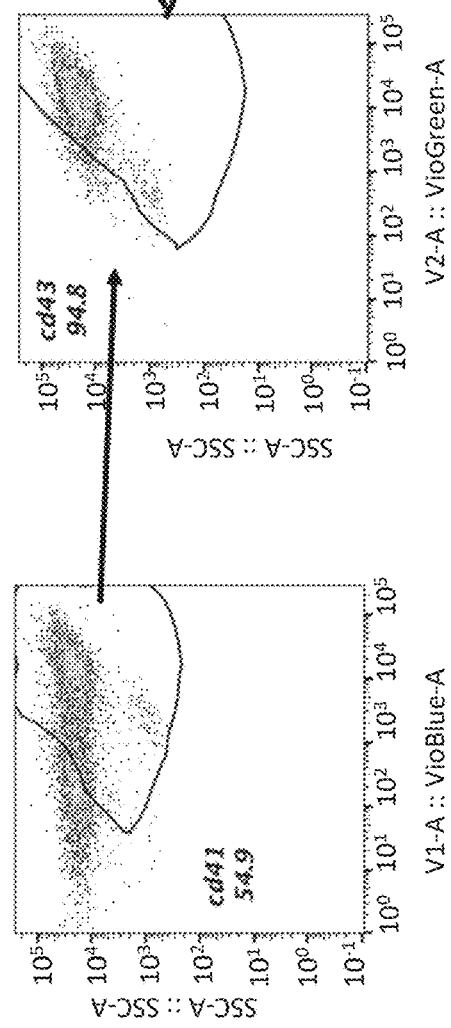

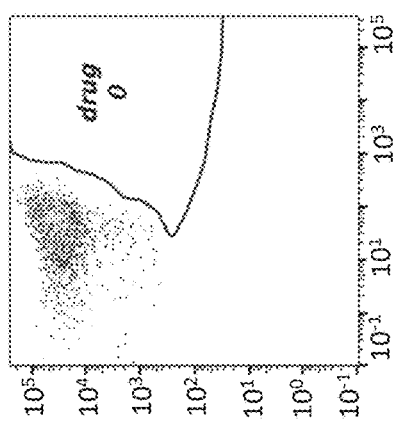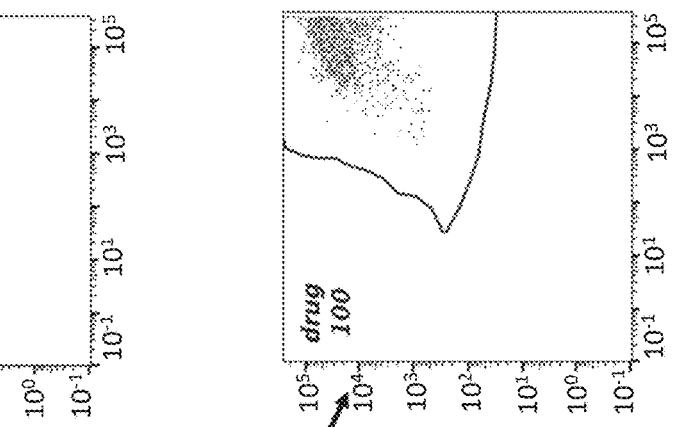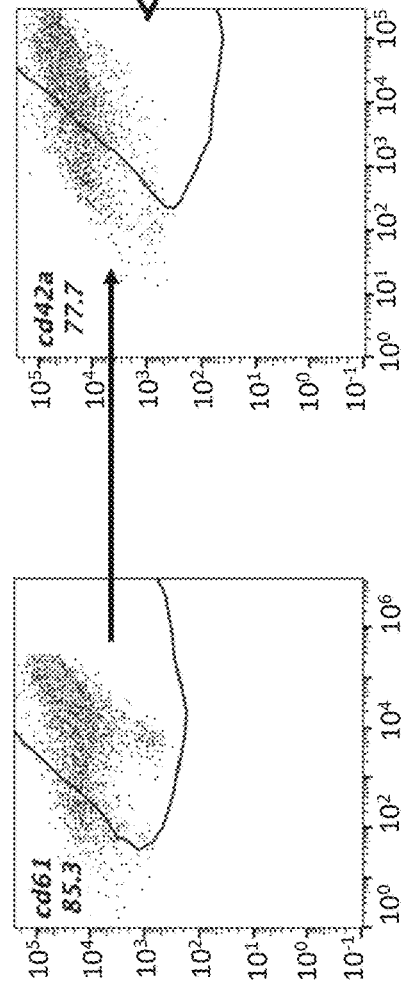
FIG. 59A FIG. 59B FIG. 59C FIG. 59D

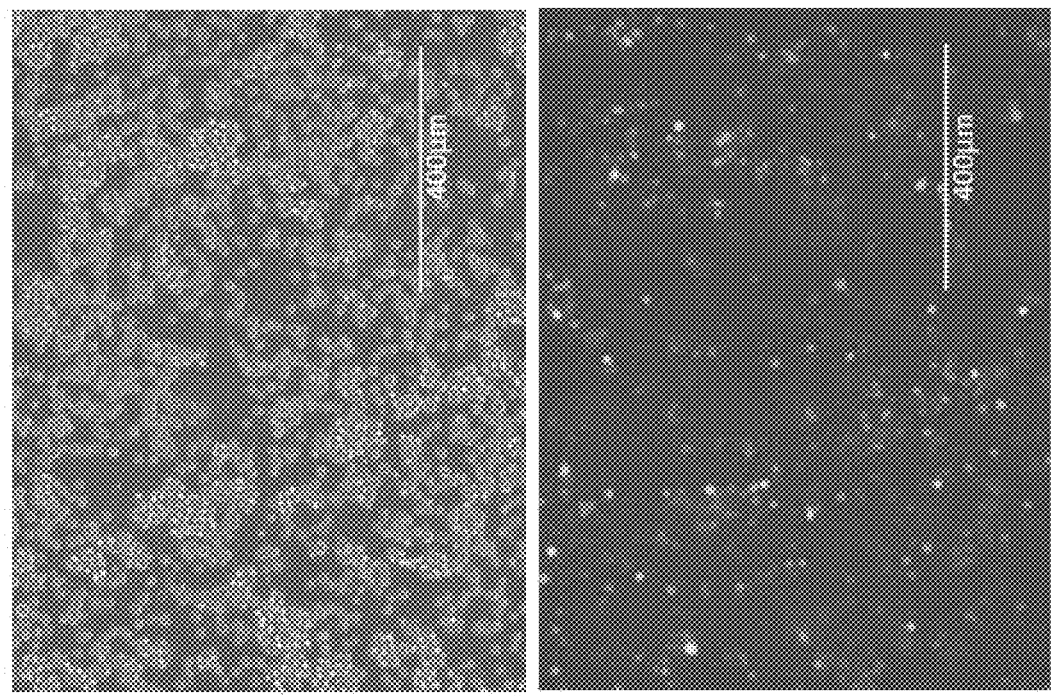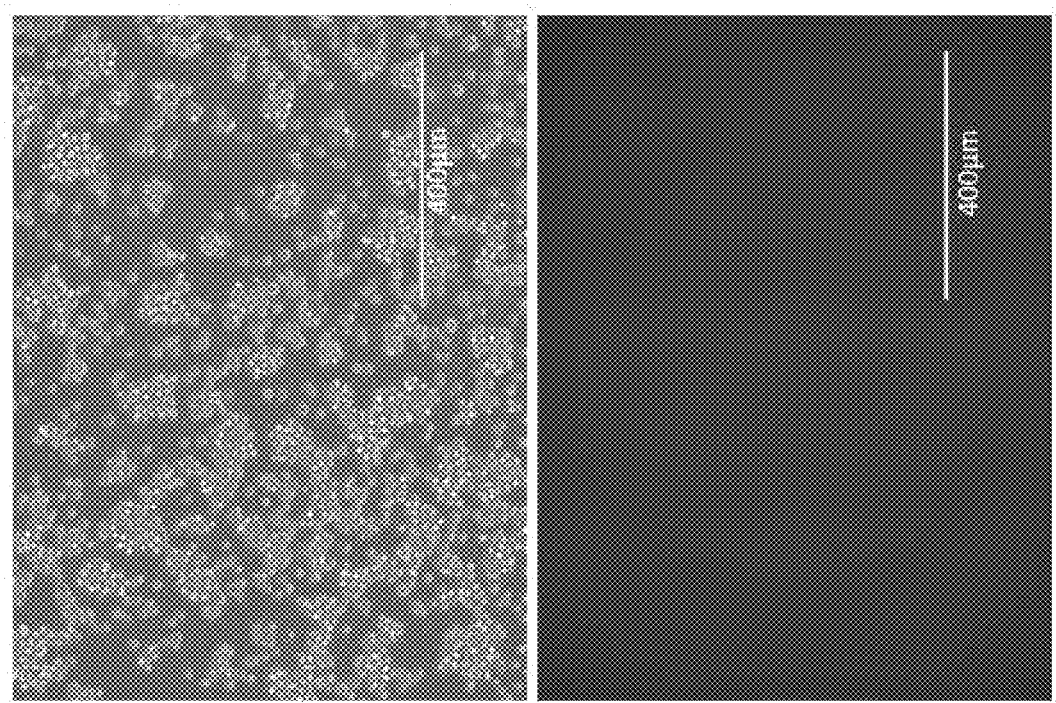
FIG. 61

COMPOSITIONS FOR DRUG DELIVERY AND METHODS OF USE THEREOF

RELATED APPLICATIONS

This application is a U.S. national phase application of PCT International Patent Application No. PCT/US2019/040021, filed on Jun. 29, 2019, which claims the benefit of and priority to U.S. Provisional Application Ser. No. 62/692,277, filed on Jun. 29, 2018, the entirety of each of which is hereby incorporated herein by reference.

STATEMENT OF GOVERNMENT SUPPORT

This work was supported by the following grant from the National Institutes of Health, Grant Nos: 1R44HL131050-01, 1R43AI125134-01A1, and 1SB1HL137591-01. The Government has certain rights in the invention.

FIELD

This disclosure relates to compositions of, methods for producing and method of using modified megakaryocytic progenitors, megakaryocytes, proplatelets, preplatelets and platelets for drug delivery.

BACKGROUND

Platelets are blood cells responsible for clot formation and blood vessel repair at sites of active bleeding. Physiologically, platelets are produced in the bone marrow by parent cells called megakaryocytes (MKs), which comprise <0.1% of cells in the bone marrow. Mature MK sit outside sinusoidal blood vessels in the bone marrow and extend long structures called proplatelets into the circulation. Proplatelets function as the assembly lines for platelet production, and sequentially release platelets from their ends.

Platelets are currently derived entirely from human volunteer donors, and shortages are common. Wide functional variability between donor platelets limit transfusion effectiveness. Mounting platelet demand exceeds current supply by ~20%, and limited platelet unit inventory is rapidly depleted in emergencies.

Efficient delivery of therapeutic drugs to target sites is desirable to maximize therapeutic efficacy and minimize side effects. Although various nanoparticle-based approaches have been advanced to improve the tissue-targeted delivery of small molecules due to their enhanced permeability and retention (EPR) effects, nanoparticle approaches have not been successful in packaging protein-based therapeutics such as coagulation factors or Ab drugs due to their larger size. Further, less than ~1% of injected nanoparticles accumulate in most targeted sites, and adverse immune responses against some components (e.g. PEG) of nano-formulations can compromise the efficacy upon repeated injections (Wilhelm Sea. Analysis of nanoparticle delivery to tumors. Nat Rev Mater. 2016; 1:16014). New methods that leverage existing physiological processes to further enhance the tissue-targeted drug delivery, particularly for protein-based therapeutics, are urgently needed.

Methods are needed for on-demand platelet production of well-defined platelet units to meet current and projected platelet need, as well as for production of new vehicles for drug delivery.

SUMMARY

In some aspects, the present disclosure is directed to compositions and methods of use of iPSCs-derived preMKs, MKs, proplatelets, preplatelets and platelets for drug delivery.

In some aspects, there is provided a method for producing induced pluripotent stem cell (iPSC)-derived cells comprising a therapeutic agent, the method comprising: differentiating the pluripotent cells in a first culture medium into hemogenic endothelial cells; differentiating the hemogenic endothelial cells in a second culture medium into megakaryocytic progenitors; differentiating the megakaryocytic progenitors into mature megakaryoctyes; differentiating the mature megakaryocytes under conditions sufficient to produce a platelet, wherein one the platelet, megakaryocyte, or megakaryocytic progenitor or combinations thereof comprises a therapeutic agent.

In some embodiments, the megakaryocytes are CD42b+, CD61+, and DNA+. In some embodiments, the platelets may be one or more of CD61+, DRAQ-, Calcein AM+, CD42a+, and CD62P+ in an activated state. The platelets may not express GPVI.

The platelet, megakaryocyte, or megakaryocytic progenitors may be loaded with the therapeutic agent, for example, by receptor-mediated loading, passive loading, or covalent conjugation. The passive loading may include incubating the therapeutic agent with a cellular suspension comprising the platelet, megakaryocyte, or megakaryocytic progenitor. The covalent conjugation may comprises thiolation of membrane proteins and sulfhydryl-reactive crosslinkers, alkyne reactive azides, high affinity binders, and antibody docking to membrane bound epitopes. The covalent conjugation may comprise reacting amines present in the therapeutic agent with succinimidyl 4-(N-maleimidomethyl)cyclohexane-1-carboxylate (SMCC).

The therapeutic agent may be a chemokine, a cytokine, a growth factor, a polypeptide, anti-angiogenic agent, a polynucleotide, or a small molecule. The anti-angiogenic agent may be doxorubicin, vincristine, irinotecan, or paclitaxel. The may be atezolizumab, ipilimumab, bevacizumab, cetuximab, or trastuzumab. The small molecule may be aripiprazole, esomeprazole, or rosuvastatin. The growth factor may be a platelet derived growth factor isoform (PDGF-AA, -AB and -BB), transforming growth factor-b (TGF-b), insulin-like growth factor-1 (IGF-1), brain derived neurotrophic factor (BDNF), vascular endothelial growth factor (VEGF), epidermal growth factor (EGF), basic fibroblast growth factor (bFGF or FGF-2), hepatocyte growth factor (HGF), connective tissue growth factor (CTGF), bone morphogenetic protein 2, -4 or -6 (BMP-2, -4, -6), von Willebrand Factor, keratinocyte growth factor, FVII, FVIII, FIX, epidermal growth factor, or hair growth factor. The cytokine may be Interleukin 1-beta, Interleukin 2, or Interleukin 12.

In some aspects, there is provided a IPSCc-derived cell, such as preMKs, MKs, proplatelets, preplatelets or platelets, comprising a therapeutic agent. In some embodiments, such cells may be loaded or conjugated with the therapeutic agent. In some embodiments, such cells may be genetically engineered to express the therapeutic agent. There is also provided a composition comprising a a IPSCc-derived cell, such as preMKs, MKs, proplatelets, preplatelets or platelets, comprising a therapeutic agent. In some embodiments, there is a method of treating a subject comprising administering a therapeutically effective amount of a composition comprising a a IPSCc-derived cell, such as preMKs, MKs, proplatelets, preplatelets or platelets, comprising a therapeutic agent.

BRIEF DESCRIPTION OF THE DRAWINGS

The present disclosure will be described in the detailed description which follows, in reference to the noted plurality of drawings by way of non-limiting examples of exemplary embodiments, in which like reference numerals represent similar parts throughout the several views of the drawings, and wherein:

FIGS. 8A-8C depict expansion of inducible pluripotent stem cells (iPSCs) on recombinant vitronectin using various growth medias. FIG. 8A shows iPSC growth in Essential 8 media. FIG. 8B shows iPSC growth in StemFlex media. FIG. 8C shows iPSC growth in Nutristem XF media.

FIG. 9A shows pluripotency marker data from iPSCs expanded in Essential 8 media. FIG. 9B shows pluripotency marker data from iPSCs expanded in StemFlex media. FIG. 9C shows pluripotency marker data from iPSCs expanded in Nutristem XF media.

FIG. 10A is a graph showing the growth reproducibility of the high-efficiency single cell passaging technique, using a standardized plating density of $2 \times 10^4$ cells/cm$^2$. P2, P4, and P5 denote passage 2, passage 4, and passage 5. FIG. 10B is an image of thawed cells after cryogenic freezing, depicting uniform undifferentiated morphology. FIG. 10C is a FACS analysis demonstrating >99% co-expression of the SSEA-5 and TRA-1-60 cell surface markers of pluripotent cells prepared using the high-efficiency single cell passaging technique.

FIG. 11A-11C depict the expansion of iPSCs in self-aggregating spheroid cultures in a 3D stir tank (matrix free). FIG. 11A shows microscope images of iPSC spheroids over time in culture. FIG. 11B depicts the increase in cell density in iPSC spheroid cultures over time. FIG. 11C depicts the average iPSC spheroid size overtime in 3D culture.

FIG. 12A shows pluripotency marker data for iPSCs after a single 7-day expansion in a 3D stir tank. FIG. 12B shows pluripotency data for iPSCs after 4 consecutive 6-7 days expansions in a 3D stir tank.

FIG. 13A depicts a portion of a 2D colony of iPSCs grown on vitronectin. FIG. 13B depicts a spheroid of iPSCs grown in 3D stirred conditions (matrix free).

FIG. 16A depicts representative flow cytometric analysis of iPSC-derived cells at day 6 of differentiation. Hemogenic endothelial cells are identified via cell surface expression of CD31 and CD34. FIG. 16B depicts the average and range of Stage 1 (day 6) differentiation efficiencies over 41 independent iPSC directed differentiations.

FIG. 17A shows a Stage 2 culture at day 6+6, with the hemogenic endothelial (HE) monolayer in the background, and megakaryocytic progenitors (preMKs) being released from the monolayer into suspension (indicated by arrow). FIG. 17B shows flow cytometric analysis of Stage 2 suspension cells, identifying the CD43+ hematopoietic progenitor cells. FIG. 17C shows flow cytometric analysis of the CD43+ hematopoietic cells, identifying the CD43+CD41+CD14−megakaryocytic progenitors (preMKs). Contaminating CD43+CD14+ myeloid progenitors are also identified in this analysis.

FIG. 18A depicts the average daily purity (i.e. % CD41+CD43+CD14− of viable suspension cells) of released preMKs over 10 days of Stage 2. FIG. 18B depicts the median, quartiles, and ranges of the contaminating myeloid progenitors (i.e. % CD43+CD14+ of viable suspension cells) over 10 days of Stage 2. All cultures were initiated with iPSCs on Collagen IV matrix in a 2D vessel. Data represents 41 independent differentiations.

FIG. 19A depicts the average daily yields of released preMKs (i.e. viable CD41+CD43+CD14−) per 6-well equivalent (i.e. 2 ml of media, 9.5 cm$^2$ surface area) during Stage 2 directed differentiation cultures initated with iPSCs. FIG. 19B depicts the cumulative yields of released preMKs (i.e. viable CD41+CD43+CD14−) per 6-well equivalent (i.e. 2 ml of media, 9.5 cm$^2$ surface area) between day 6+4 and 6+8 of Stage 2 directed differentiation cultures initiated with iPSCs. Each dot represents an independent iPSC directed differentiation culture on Collagen IV matrix in a 2D culture vessel.

FIG. 20A depicts iPSC-derived megakaryocytic progenitors at Day 1 of Stage 3 (top panel: high magnification; bottom panel:low magnification). FIG. 20B depicts maturing megakaryocytes at Day 2 of Stage 3 (top panel: high magnification; bottom panel: low magnification). FIG. 20C depicts mature megakaryocytes at Day 4 of Stage 3 (top panel: high magnification; bottom panel: low magnification). FIG. 20D illustrates spontaneous proplatelet formation from mature iPSC-derived MKs after 4 days of Stage 3 culture. The arrows indicate proplatelets. 50 µm scale bar applies to all figures.

FIG. 21A identifies the CD61+(megakaryocytic) fraction of Stage 3 cells. FIG. 21B shows flow cytometric analysis of the CD61+ megakaryocytic cells, identifying the CD42a+ CD42b+ mature MKs. Apoptotic CD42a+CD42b− cells can also be identified in this analysis. FIG. 21C depicts the subset breakdown of a representative Stage 3 culture. Non-MKs are CD61−, immature MKs are CD61+CD42a− CD42b−, apoptotic MKs are CD61+CD42a+CD42b−, and mature MKs are CD61+CD42a+CD42b+.

FIG. 22A and FIG. 22B depict Stage 0 and Stage 1 differentiation initiated with self-aggregating spheroids of iPSCs. FIG. 22A depicts a series of micrographs, starting with single cell dissociated iPSCs at day −1, self-aggregated iPSC spheroids at day 0, partially differentiated spheroids at day 3, and fully differentiated spheroids containing hemogenic endothelial cells at day 6. FIG. 22B depicts day 6 flow cytometric data showing successful CD31+CD34+ hemogenic endothelial differentiation using this approach.

FIGS. 23A and 23B show that cultures expanded and harvested using the single cell iPSC passaging approach could self-aggregate into 3D spheroids and differentiate effectively to preMK+ cells using our 3D suspension differentiation methodology in 6-well ultra-low adherent plates. FIG. 23A depicts images of single cell expanded cultures aggregated (D0) and differentiated (D6) toward hemogenic endothelia. FIG. 23B depicts preMK+ production during Stage 2 with single-cell passaged iPSCs (SC) compared to historical EDTA-passaged iPSCs cultures (H).

FIG. 24A depicts self-aggregated iPSC-derived spheroids at day 6+4 during Stage 2 of directed differentiation, with preMKs released (indicated by arrow) from the spheroids into suspension. "HE" refers to hemogenic endothelial monolayer. FIG. 24B depicts flow cytometric analysis of the harvested suspension cells, staining for the preMK markers CD41 and CD43. FIGS. 24C and 24D compare historical 2D data with data from 2 different 3D systems, an ultra-low adherent vessel on an orbital shaker, and a spinner flask. FIG. 24C depicts the preMK purity over time in Stage 2. FIG. 24D depicts the preMK yields over time in Stage 2.

FIG. 25A depicts representative flow cytometric analysis from Day 3 Stage 3 cultures, identifying the CD61+(megakaryocytic) fraction of Stage 3 cells, followed by identification of the CD42a+CD42b+ mature MKs. Apoptotic CD42a+CD42b− cells can also be identified in this analysis. FIG. 25B depicts the subset breakdown of a representative Stage 3 culture. Non-MKs are CD61−, immature MKs are CD61+CD42a−CD42b−, apoptotic MKs are CD61+CD42a+CD42b−, and mature MKs are CD61+CD42a+CD42b+. FIG. 25C shows how the mature MK fraction within Stage 3 cultures at day 3 compares between 2D (matrix-dependent) and 3D (matrix-independent) approaches.

FIGS. 27A-27D D depict increased preMK yields upon soluble Laminin 521 addition in two related 3D differentiation platforms. FIG. 27A depicts preMK counts per well at Day 6+6 of Stage 2 with or without Laminin521 addition during iPSC aggregation (Day −1) in StemFlex in a non-agitated ultra-low adherent U-bottom 96-well plate. FIG. 27B depicts preMK counts per well at Day 6+6 of Stage 2 with or without Laminin521 addition during Stage 1 to Stage 2 transition (Day 6) in a non-agitated ultra-low adherent U-bottom 96-well plate. FIG. 27C depicts preMK counts per ml at Day 6+6 of Stage 2 with or without Laminin521 addition during iPSC aggregation in StemFlex (Day −1) or during Stage 1 to Stage 2 transition (Day 6) in an ultra-low adherent 6-well plate on an orbital shaker. FIG. 27D depicts preMK counts per ml at Day 6+5 of Stage 2 with or without Laminin521 addition during single-cell passaged iPSC aggregation (Day −1) in NutriStem in a non-agitated ultra-low adherent U-bottom 96-well plate.

FIGS. 28A-28D depict experiments performed to adjust the order and timing of the addition of the Stage 1 media factors BMP4, bFGF and VEGFA. FIG. 28A is a schematic representation of the Stage 1 conditions tested in Experiment A. FIG. 28B depicts the Stage 2 premK yields observed at day 6+4 of the cultures described in panel A. FIG. 28C is a schematic representation of the Stage 1 conditions tested in Experiment B. FIG. 28D depicts the Stage 2 preMK yields observed in the cultures described in panel C. The data in this figure suggests that Stage 1 of differentiation can proceed effectively using BMP4 alone for 24 hours, followed by bFGF and VEGFA for 5 days, before transitioning to Stage 2 of differentiation.

FIGS. 29A-29C depict immunofluorescence microscopy images of Day 6 Stage I cultures on Laminin 521. FIG. 29A depicts a control culture without WNT agonist. FIG. 29B depicts a culture where 0.6 µM of the WNT agonist CHIR98014 was added to the differentiation culture for the first 48 hours of Stage 1. FIG. 29C depicts a culture where 6 µM of the WNT agonist CHIR99021 was added to the differentiation culture for the first 48 hours of Stage 1.

FIGS. 30A and 30B depict immunofluorescence microscopy images of Day 6+4 Stage 2 cultures on Laminin 521. FIG. 27A depicts a control culture without WNT agonist. FIG. 27B depicts a culture where 0.6 µM of the WNT agonist CHIR98014 was added to the first 48 hours of Stage 1.

FIG. 31 depicts Stage 1 differentiation of iPSCs on Laminin521 coated Rachig rings at day 3 and day 6. The scale bar represents 500 µm.

FIGS. 33A-33C depict flow cytometric data from stages of iPSC differentiation proceeding efficiently on Rachig ring substrate. FIG. 33A depicts Stage 1 at day 6, with flow cytometric staining for the hemogenic endothelial markers CD31 and CD34. FIG. 33B depicts Stage 2 at day 6+2, with flow cytometric staining for the megakaryocytic progenitor markers CD43 and CD41. FIG. 33C depicts Stage 3 at Day 6+3+3, with flow cytometric staining for CD61 and CD42b.

FIGS. 34A-34D depict iPSC-derived immunostained megakaryocytes. FIG. 34A is a micrograph showing megakaryocytes immunostained for the megakaryocyte-specific protein β1-tubulin. FIG. 34B is a micrograph showing the megakaryocytes nuclei visualized by nucleic acid staining. FIG. 34C is a micrograph showing a merged image of FIGS. 34A and 34B. FIG. 34D is a phase contrast image of the immunostained megakaryocytes. Scale bar represents 25 μm for each figure.

FIGS. 35A-35F depict immunostained iPSC-derived megakaryocytes. FIG. 35A is a micrograph showing iPSC-derived megakaryocytes immunostained for the α-granule specific protein Platelet Factor 4 (PF4). FIG. 35B is a micrograph showing iPSC-derived megakaryocytes with immunostained nuclei. FIG. 35C is a micrograph showing iPSC-derived megakaryocytes immunostained for the α-granule specific protein Von Willebrand Factor (VWF). FIG. 35D is a micrograph showing iPSC-derived megakaryocytes immunostained for the megakaryocyte-specific cell surface marker CD61. FIG. 35E is a micrograph showing the overlaid images of FIGS. 35A, 35B, and 35C. FIG. 35F is a micrograph showing the overlaid images of FIGS. 35A, 35B, and 35D. Scale bar represents 25 μm for each figure.

FIGS. 36A-36F depict immunostained iPSC-derived megakaryocytes. FIG. 36A is a micrograph showing iPSC-derived megakaryocytes immunostained for the Dense Granule specific protein LAMP1. FIG. 36B is a micrograph showing iPSC-derived megakaryocytes with immunostained nuclei. FIG. 36C is a micrograph showing iPSC-derived megakaryocytes immunostained for the Dense Granule specific protein serotonin. FIG. 36D is a micrograph showing iPSC-derived megakaryocytes immunostained for the megakaryocyte-specific cell surface marker CD61. FIG. 36E is a micrograph showing the overlaid images of FIGS. 36A, 36B, and 36C. FIG. 36F is a micrograph showing the overlaid images of FIGS. 36A, 36B, and 36D. Scale bar represents 25 μm for each figure.

FIG. 37A is an electron microscopy image showing a iPSC-derived megakaryocyte producing microparticles (see arrows for examples). FIG. 37B is an electron microscopy image showing a iPSC-derived megakaryocyte and multivesicular bodies (arrows; magnified in inset). FIG. 37C is an electron microscopy image showing a iPSC-derived megakaryocyte, characterized by multi-lobed nuclei, glycogen granules, alpha-granules, and an invaginated membrane system. FIG. 37D is an electron microscopy image showing the endoplasmic reticulum and mitochondria of a iPSC-derived megakaryocyte.

FIG. 38A illustrates the relative gene expression of Oct4, a pluripotency-associated gene, in iPSCs, Day 6 cells (end of Stage 1), Days 6+4 and 6+5 (Stage 2), and Days 6+5+1 through 6+5+4 (Stage 3). FIG. 38B illustrates the relative gene expression of NFE2, a transcription factor critical for megakaryocyte maturation, in iPSCs, Day 6 cells (end of Stage 1), Days 6+4 and 6+5 (Stage 2), and Days 6+5+1 through 6+5+4 (Stage 3).

FIGS. 40A-40C provide size distributions of iPSC derived megakaryocytes. FIG. 40A depicts a representative example of β1-Tubulin staining of iPSC derived megakaryocytes, which were utilized to collect size measurements of iPSC-MKs and compare with MKs from other sources. FIG. 40B depicts the size distribution of iPSC derived megakaryocytes, including the median, quartiles, and range. FIG. 40C compares the size distribution data of iPSC derived MKs with megakaryocytes from various bone marrow sources.

FIG. 41A depicts a representative example of DNA ploidy measurements performed on iPSC derived megakaryocytes. FIG. 41B compares the DNA ploidy measurements of iPSC-MKs with MKs from other sources.

FIG. 43A depicts flow cytometric analysis of anucleate and nucleated cells (upper, left). Nucleated cells contained a large number of $CD41^+CD42^+$ megakaryocytes (upper, right). Anucleate cells positive for $CD41^+$, $CD42^+$, and Calcein AM were assessed using flow cytometry and platelets were gated by size (1-5 microns). FIG. 43B is a graph depicting cumulative yield of $CD41^+CD42^+$ Calcein $AM^+$ platelet-sized particles per well during Stage 3 of the directed differentiation protocol described herein.

FIG. 44A and FIG. 44B depict resting and activated platelets. FIG. 44A includes images of platelets harvested from megakaryocyte culture assessed by electron microscopy. FIG. 44B includes micrographs showing that β1-tubulin coils and CD61 expression are characteristic features of resting platelets and that lamellipodia and filopodia characteristic of activated platelets as revealed by F-actin staining.

FIG. 46A shows FSC vs SSC parameters that reveal similar size (FSC) and granularity (SSC) characteristics between hiPSC platelets and donor-derived, human platelets. FIG. 46B shows an abundance of CD61 expression on both hiPSC platelets as well as donor-derived, human platelets. FIG. 46C demonstrates that the CD61+ hiPSC platelet population is mostly devoid of GPVI on its cell surface, whereas donor-derived, human platelets are almost exclusively positive for GPVI.

FIG. 48A shows human donor platelets (shown by dark circular areas within the dotted enclosure) incorporated into a thrombus after the laser injury had occurred and by a proximal infusion of the platelets near the injury site. FIG. 48B shows human iPSC-derived platelets (dark circular areas within the dotted enclosure) incorporated into a thrombus using the identical laser injury model.

FIGS. 49A-49I depict antibody loading on donor-derived, human washed platelets. FIG. 49A shows the isotype antibody signal that defines the gating strategy in this figure. FIG. 49B shows that, when stained exclusively for CD61, donor-derived, human washed platelets are almost exclusively CD61+. FIG. 49C shows the expression of both CD61 and Cy5.5 conjugated to human IgG antibody after co-incubation in a platelet suspension. FIG. 49D shows the co-expression of CD61 and Cy5.5 conjugated to human IgG antibody in the antibody loaded donor-derived, human platelets after a wash with phosphate buffered saline (PBS), centrifugation, and resuspension of the IgG loaded, donor-derived, human platelets. FIG. 49E is a photograph of the platelet pellets with and without human IgG Cy5.5 loaded by co-incubation of the antibody with a platelet suspension. The Cy5.5 dye is visible to the naked eye. FIG. 49F shows a dose-dependent increase of human IgG Cy5.5 incorporation into human washed platelets. FIG. 49G is a line graph that plots the geometric mean of the fluorescent signal shown in FIG. 49F. FIG. 49H shows the quantitation of the encapsulated human IgG in donor-derived, human platelets by microplate reader measurements of human IgG Cy5.5 signal from platelet lysates and calculated from standard curves generated from free Cy5.5 dye. FIG. 49I shows a similar dose-dependent escalation in antibody loading of donor-derived, human platelets using a Dylight-498 conjugated version of the FDA approved antibody drug Atezolizumab.

FIG. 50A includes representative micrographs visualizing the uptake of Atezolizumab with AlexaFluor 488 anti-human IgG in addition to appropriate controls (IgG only). FIG. 50B includes micrographs captured at a higher magnification to demonstrate the subcellular and internalization of atezolizumab in human donor platelets.

FIG. 51A is a flow cytometry histogram plot that shows a dose-dependent increase in antibody signal with increasing amounts of Ipilimumab in a reaction vessel with a platelet suspension. FIG. 51B is an immunofluorescence micrograph showing Ipilimumab both in and on the human iPSC-derived platelets as observed with antibody stains for CD61 (surface marker) and platelet factor 4, or PF4, a granule marker.

FIGS. 52A-52F describe passive drug loading in CD34+ mobilized peripheral blood-derived platelets. FIG. 52A is a flow cytometry dot plot that displays cells as events plotted by forward scatter (size) vs side scatter (granularity). FIG. 52B is a flow cytometry dot plot showing roughly 90% CD61+ cell population among the CD34+ mobilized peripheral blood-derived platelets. FIG. 52C is a flow cytometry histogram plot showing a dose-dependent increase in Cy5.5 conjugated Ipilimumab bound to CD34+ mobilized peripheral blood-derived platelets. FIG. 52D is a line graph that plots the mean fluorescence intensity (calculated as geometric mean) of the dose-dependent increase in Cy5.5 conjugated Ipilimumab plotted by the picograms (pg) of Ipilimumab added to a platelet suspension (per platelet). FIG. 52E is a bar graph that is a quantitation of the bound Ipilimumab to CD34+ mobilized peripheral blood-derived platelets. FIG. 52F includes micrographs showing the distribution of Ipilimumab in CD61+ and PF4 (platelet factor 4)+ platelets.

FIGS. 53A-53D show uptake and release of Atezolizumab by platelets upon thrombin activation. FIG. 53A and FIG. 53B are histograms of flow cytometry analysis showing uptake/release upon activation using thrombin of Atezolizumab or Ipilimumab by platelets. FIG. 53C is a representative micrograph of an atezolizumab (25 µg/ml) of a resting platelet. FIG. 53D is a representative micrograph of an atezolizumab loaded and activated platelet.

FIGS. 54A-54E illustrate covalent conjugation of human IgG1 in washed human platelets. FIG. 54A provides an example of modifying surface proteins on the membrane of platelets by converting primary amines to reactive sulfhydryls. FIG. 54B provides an example of linking maleimide to a protein. FIG. 54C provides an example of reacting the maleimide-linked protein to platelets with exposed sulfhydryl groups to form a thioether linkage. FIG. 54D is a flow cytometry histogram plot that shows an increase in IgG conjugation to a donor-derived, human washed platelet preparation at a fixed concentration but reacted to platelets that were exposed to increasing doses of Traut's reagent, making the surface more reactive. FIG. 54E is a flow cytometry histogram that shows a fixed amount of IgG conjugation to donor-derived, human washed platelets in the absence of maleimide (SMCC) linkage to the IgG, thus lowering the affinity of the antibody to the reactive sulfhydryls on the platelet membrane.

FIG. 55A shows that the human iPSC-derived platelets are >89% CD61+, confirming their expression of a platelet-specific surface marker. FIG. 55B is a flow cytometry histogram plot showing the efficient covalent conjugation that occurs when Ipilimumab is reacted to SMCC (maleimide) and platelets are treated with Traut's reagent to facilitate the covalent linkage (red trace). FIG. 55C is a micrograph that shows the staining pattern of Ipilimumab in relation to CD61 and PF4 on a resting, human iPSC-derived platelet.

FIGS. 56A-56C demonstrate megakaryocyte passive loading. FIG. 56A shows iPSC-derived megakaryocytes and platelets incubated in the presence of daylight 488-labeled atezolizumab (i.e., anti-PDL1). Cells were counter labeled with CD61 to demonstrate mature megakaryocytes. FIG. 56B shows subcellular localization of Dylight 488 atezolizumab in megakaryocytes and platelets. FIG. 56C further demonstrates subcellular localization into platelet factor-4 stained alpha-granules.

FIGS. 57A-57D demonstrate biologic drug loading in human iPSC-derived pre-megakaryocytes. FIG. 57A shows CD61 staining in this population to positively identify them as preMKs. FIG. 57B shows fibrinogen uptake, which stains the alpha granules. FIG. 57C shows the signal from a secondary antibody detecting Ipilimumab uptake. FIG. 57D is a merged image that demonstrates cells with colocalization of both surface (CD61) and granular (fibrinogen) stains with the observed Ipilimumab uptake.

FIGS. 58A-58D demonstrate covalent conjugation of Ipilimumab to pre-megakaryocytes. FIG. 58A shows CD41 expression of cells at the end of Stage 2 that identify them as pre-megakaryocytes by flow cytometry. FIG. 58B shows CD43+CD41+ cells that further characterize them as pre-megakaryocytes by flow cytometry. FIG. 58C is a flow cytometry dot plot in the untreated condition, with detection (secondary) antibody included. FIG. 58D is a flow cytometry dot plot that shows robust expression of Ipilimumab as related to the control.

FIGS. 59A-59D demonstrate covalent conjugation of Ipilimumab to human iPSC-derived megakaryocytes. FIG. 59A is a flow cytometry dot plot that demonstrates robust expression of CD61 as part of gating strategy to identify megakaryocytes. FIG. 59B is a flow cytometry dot plot that shows the CD42a+CD61+ population in these cultures, further refining the gating strategy to identify megakaryocytes. FIG. 59C is a flow cytometry dot plot in the untreated condition, with detection (secondary) antibody included. FIG. 59D is a flow cytometry dot plot that demonstrates efficient loading of Ipilimumab as opposed to the control.

FIG. 60A is a flow cytometry histogram plot showing retention of doxorubicin in the washed platelets after multiple wash steps. FIG. 60B is a flow cytometry histogram plot showing doxorubicin detected in platelets after co-incubation for various time points in a mini-dialysis cassette using constant agitation on an orbital shaker at room temperature.

FIG. 61 includes micrographs showing mock transduced preMKs and preMKs transduced with lentiviral vector comprising a nucleic acid molecule encoding an EF1alpha promoter driving expression ZsGreen fluorescent protein.

FIG. 62A includes brightfield and fluorescent micrographs of platelet cells derived from mock transduced pre-megakaryoctyes and platelets derived from premegakaryoctyes transduced with a lentiviral vector encoding an EF1alpha promoter driving expression ZsGreen fluorescent protein with Polybrene (*Lenti*(+)Poly). FIG. 62B includes flow cytometry data showing CD61+ platelets obtained from mock transduced megakaryocytes and megakaryocytes transduced with a lentiviral vector encoding an EF1alpha promoter driving expression ZsGreen fluorescent protein with Polybrene. FIG. 62C is a flow cytometry histogram plot that further illustrates the ZsGreen signal detected in the lentivirus transduced condition as opposed to the mock transduction control.

FIG. 63A is an image of a platelet bioreactor. FIG. 63B is a cross sectional view of a platelet bioreactor. FIG. 63C is a top view of a platelet bioreactor. FIG. 63D is a schematic of a platelet bioreactor.

Figure 1:
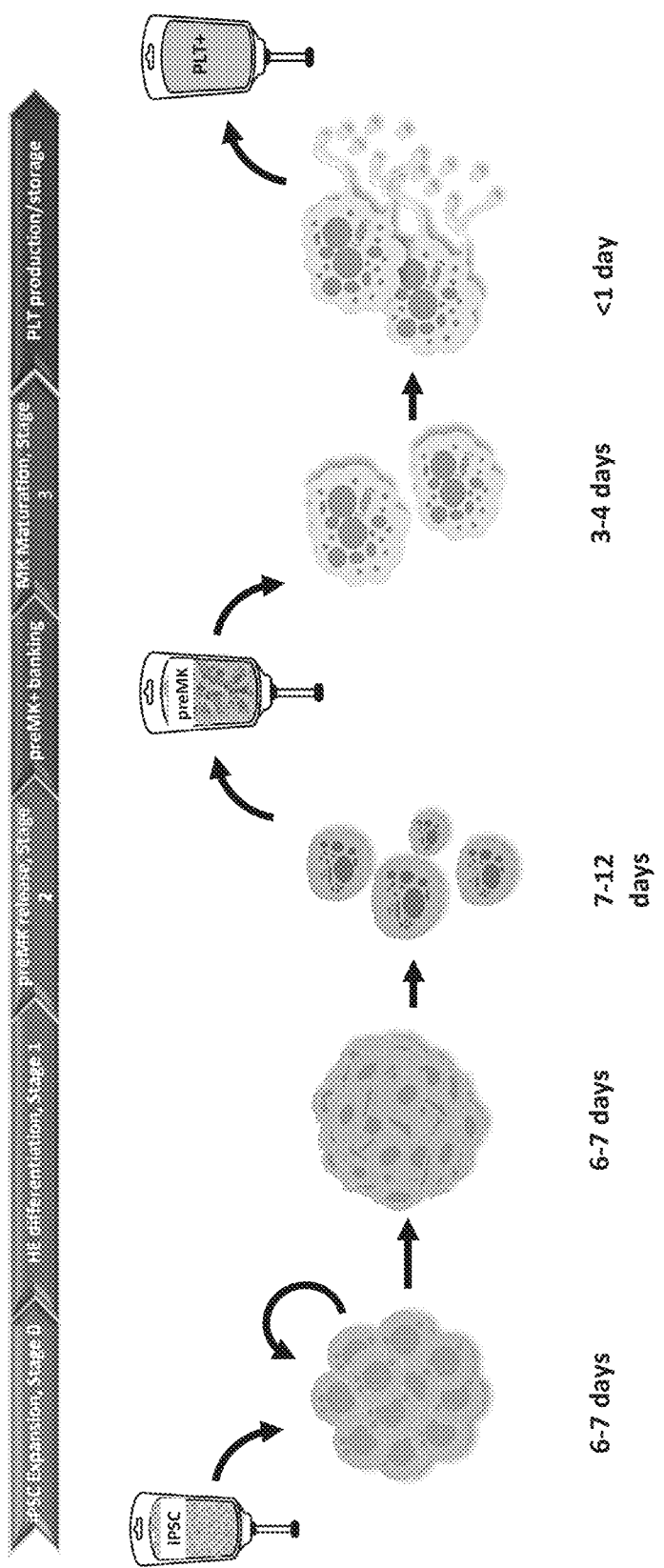
FIG. 1 shows an overall schematic for scalable differentiation of megakaryocytic progenitors (preMKs), megakaryocytes (MK), and platelets (PLT) from a iPSC line.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Definitions

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The terms "agent," "therapeutic agent," "therapeutic composition," "drug," or "therapeutic" can be used interchangeably and are meant to include any small molecule chemical compound, antibody, nucleic acid molecule, or polypeptide, or fragments thereof.

The term "antibody," as used herein, refers to an immunoglobulin molecule which specifically binds with an antigen. The term "antibody fragment" refers to a portion of an intact antibody and refers to the antigenic determining variable regions of an intact antibody.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

By "cellular composition" is meant any composition comprising one or more isolated cells.

By "cell survival" is meant cell viability.

As used herein, "clinical grade" is meant to refer to a cell or cell line derived or obtained using current Good Manufacturing Practice (GMP), which permits its clinical use in humans. GMP is a quality assurance system used in the pharmaceutical industry to ensure that the end product meets preset specifications. GMP covers both manufacturing and testing of the final product. It requires traceability of raw materials and also that production follows validated standard operating procedures (SOPs).

By "detectable levels" is meant that the amount of an analyte is sufficient for detection using methods routinely used to carry out such an analysis.

"Detect" refers to identifying the presence, absence or amount of the object to be detected.

The term "covalent conjugation" refers to using a chemical linker that reacts with specific chemical groups on the molecule to be conjugated. In some embodiments, covalent conjugation of a therapeutic composition to another molecule or compound is achieved by reacting amines on the therapeutic composition with the linker succinimidyl 4-(N-maleimidomethyl)cyclohexane-1-carboxylate (SMCC).

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include any disease or injury that results in a reduction in cell number or biological function, including ischemic injury, such as stroke, myocardial infarction, or any other ischemic event that causes tissue damage, peripheral vascular disease, wounds, burns, fractures, blunt trauma, arthritis, and inflammatory diseases.

By "effective amount" is meant the amount of an agent required to produce an intended effect.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the present disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the present disclosure that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the present disclosure. An isolated polypeptide of the present disclosure may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "hemogenic endothelial cell" as used herein refers to cells capable of differentiating to give rise to hematopoietic cell types or endothelial cell types, and which may optionally be derived from pluripotent stem cells. Hemogenic endothelial cells are normally adherent to extracellular matrix protein and/or to other hemogenic endothelial cells, and can be characterized by the expression of the markers CD31 and CD34.

By "marker" is meant any protein or other epitope having an alteration in expression level or activity that is associated with a characteristic or condition.

The term "megakaryocyte" (MK) as used herein refers to a large (e.g., diameter ≥10 μm), polyploid hematopoietic cell with the propensity to generate proplatelets and/or platelets. One morphological characteristic of mature megakaryocytes is the development of a large, multi-lobed nucleus. Mature megakaryocytes can stop proliferating, but continue to increase their DNA content through endomitosis, with a parallel increase in cell size.

The term "megakaryocytic progenitor" (preMK), as used herein, refers to a mononuclear hematopoietic cell that is committed to the megakaryocyte lineage and is a precursor to mature megakaryocytes. Megakaryocytic progenitors are normally found in (but not limited to) bone marrow and other hematopoietic locations, but can also be generated from pluripotent stem cells, such as by further differentiation of hemogenic endothelial cells that were themselves derived from pluripotent stem cells.

The term "microparticle" refers to a very small (<1 micron) phospholipid vesicle shed from a megakaryocyte or other cell. Microparticles may contain genetic material such as RNA, and express the extracellular markers of their parental cells. Megakaryocyte- and platelet-derived microparticles may have a role in multiple pathways, including hemostasis and inflammation.

By "passive drug loading" is meant the uptake of a therapeutic composition by a cell (e.g., a platelet or progenitor thereof) without conjugation or mechanical or chemical disruption or modification of the cell. For example, liposomal delivery systems can be used for passive drug loading.

The term "platelet" refers to a cell with a diameter of 1-3 microns with no nucleus but does contain RNA. Internally, it contains alpha and dense granules, which contain such factors as P-selectin and serotonin, respectively. Platelets also have an open canalicular system, which refer to channels that are a pathway for the transport of extracellular material into the cell and the release of material from granules to the extracellular environment. They primarily function in the regulation of hemostasis by participating in blood clotting but also have been shown to have a role in inflammation.

The term "preplatelet" refers to a cell with a diameter of 3-10 microns with no nucleus but with RNA. Preplatelets are otherwise morphologically and ultra-structurally similar to platelets and constitute an intermediate cell stage produced by megakaryocytes that break apart through cytoskeletal rearrangement to form individual platelets.

The term "proplatelet" refers to cytosolic extensions from megakaryocytes or just released from megakaryocytes. Proplatelets break apart through cytoskeletal rearrangement to form individual preplatelets and platelets.

The term "pluripotent stem cell" includes embryonic stem cells, embryo-derived stem cells, and induced pluripotent stem cells and other stem cells having the capacity to form cells from all three germ layers of the body, regardless of the method by which the pluripotent stem cells are derived. Pluripotent stem cells are defined functionally as stem cells that can have one or more of the following characteristics: (a) be capable of inducing teratomas when transplanted in immunodeficient (SCID) mice; (b) be capable of differentiating to cell types of all three germ layers (e.g., can differentiate to ectodermal, mesodermal, and endodermal cell types); or (c) express one or more markers of embryonic stem cells (e.g., express Oct 4, alkaline phosphatase. SSEA-3 surface antigen, SSEA-4 surface antigen, SSEA-5 surface antigen, Nanog, TRA-1-60, TRA-1-81, SOX2, REX1, etc.).

The term "induced pluripotent stem cells" (iPS cells or iPSCs) refers to a type of pluripotent stem cell generated by reprogramming a somatic cell by expressing a combination of reprogramming factors. The iPSCs can be generated using fetal, postnatal, newborn, juvenile, or adult somatic cells. Factors that can be used to reprogram somatic cells to pluripotent stem cells include, for example, a combination of Oct 4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In certain embodiments, at least two, three, or four reprogramming factors are expressed in a somatic cell to reprogram the somatic cell.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration of at least 10%, 25%, 50%, 75%, or 100%.

By "reducing cell death" is meant reducing the propensity or probability that a cell will die. Cell death can be apoptotic, necrotic, or by any other means.

By "reduced level" is meant that the amount of an analyte in a sample is lower than the amount of the analyte in a corresponding control sample.

By "reference" is meant a standard or control condition.

By "specifically binds" is meant a compound or antibody that recognizes and binds a polypeptide of the present disclosure, but which does not substantially recognize and bind other molecules in a sample, for example, a biological sample, which naturally includes a polypeptide of the present disclosure.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The present disclosure is directed to compositions and methods for producing megakaryocytic progenitors (preMKs), megakaryocytes (MKs), proplatelets, preplatelets or platelets from stem cells, such as, pluripotent stem cells, for example, clinical-grade human induced pluripotent stem cells. The methods enable the continued production of preMKs, MKs, proplatelets, preplatelets or platelets from hemogenic endothelial cells. The preMKs, MKs, proplatelets, preplatelets and platelets derived by the instant methods can be distinguished by one or more of the following: their size range, ploidy profile, biomarker expression, gene expression, granule composition, and growth factor, cytokine and chemokine composition or combinations thereof. The present disclosure is further directed to compositions and methods of use of such preMKs, MKs, proplatelets, preplatelets and platelets for drug delivery.

Unique to megakaryocytes and platelets are the presence of secretory granules wherein multiple proteins promoting clot formation (clotting factors) and tissue repair (cytokine, chemokine, and growth factors) are naturally sequestered. Megakaryocyte and platelet granule exocytosis plays a critical role in thrombosis, immune-system modulation, and tissue regeneration. Upon contact-activation at sites of bone marrow damage or vascular injury, megakaryocytes and platelets can selectively release the contents of their secretory granules to trigger a localized therapeutic response. Platelets will also naturally accumulate at sites of cancer, wherein they selectively adhere to tumors (wounds that never heal), hiding them from the immune system and contributing pro-angiogenic factors such as VEGF, and anti-inflammatory cytokines such as TGF-β through their granules that contribute to angiogenesis and tumor metastasis.

Megakaryocytes and platelets can be loaded or genetically engineered to express molecules (for example, within their granules) to produce 'designer cells' that can specifically be applied for expression of coagulation factors, cytokines, chemokines, growth factors, and drugs. These modified cells can be manipulated to be more or less sensitive and responsive to agonists and improve or inhibit clotting time even under conditions that normally cause cell dysfunction or impair coagulation. Likewise, molecules can be directly conjugated on their surface or packaged into secretory granules, which can be leveraged to improve cell specificity to target tissue and carry molecules to therapeutic targets to improve their specificity. In some embodiments, nanoparticles coated with platelet membranes may be used instead of whole platelets.

The present disclosure provides methods and systems for manufacturing of a large number of megakaryocytic progenitors, megakaryocytes, proplatelets, preplatelets, or platelets under cGMP conditions for clinical use and expressing and/or loading of drugs in these cell types for targeting to therapeutic target and selective release.

Aspects of the present disclosure relate to a scalable, cGMP-compliant stem cell-based process that enables the rapid generation of functional megakaryocytes and platelets. In some aspects of the present disclosure the cGMP-compliant human PSC line can be engineered to conditionally express specific drugs at the megakaryocyte (immediate cellular progenitor) level or the platelet level. For example, megakaryocytes and platelets generated according to the process of the present disclosure can be directed to package drugs into secretory granules as part of normal megakaryocytes or platelet production. Resulting "designer" modified megakaryocytes and platelets can consequently contain the desired drugs, which can be delivered through normal circulation to the targeted sites of injury or disease, avoiding the direct systemic exposure from intravascular transfusion of these factors to the body, and reducing non-specific risks of microaggregate/clot formation and immunogenicity.

Aspects of the present disclosure are directed to compositions comprising the presently disclosed megakaryocytic progenitor, megakaryocytes, proplatelets, preplatelets or platelets derived from iPSCs as a vehicle for drug delivery.

According to some aspects of the present disclosure, methods for producing the instant megakaryocytic progenitor, megakaryocytes, proplatelets, preplatelets or platelets from pluripotent stem cells (such as, for example, clinical-grade hiPSCs) are disclosed. These methods enable the continued production of megakaryocytic progenitors from hemogenic endothelial cells for extended time frames up to 1 week or more can be subsequently differentiated into mature megakaryocytes. These iPSC-derived megakaryocytes can be distinguished by their size range, ploidy profile, biomarker expression, and growth factor, cytokine and chemokine composition or combinations thereof.

In some embodiments, MKs and platelets can be derived from pluripotent stem cells, including but not limited to, embryonic stem cells (ESCs) (e.g. human embryonic stem cells) and induced pluripotent stem cell (iPSCs) (e.g. human induced pluripotent stem cells). ESCs are pluripotent stem cells derived from the inner cell mass of an early-stage preimplantation embryo called a blastocyst. iPSCs are a type of pluripotent stem cell that can be generated from adult cells by inducing timed expression of particular transcription factors. iPSCs can be expanded and maintained in culture indefinitely and engineered to produce MKs and platelets.

In some embodiments, MKs and platelets can also be derived from hematopoietic stem cells, including but not limited, to $CD34^+$ umbilical cord blood stem cells (UCB cells) (e.g. human $CD34^+$ umbilical cord blood stem cells), $CD34^+$ mobilized peripheral blood cells (MPB cells) (e.g. $CD34^+$ human mobilized peripheral blood), or $CD34^+$ bone marrow cells. UCB cells are multipotent stem cells derived from blood that remains in the placenta and the attached umbilical cord after childbirth. MPB cells are multipotent stem cells derived from volunteers whose stem cells are mobilized into the bloodstream by administration of G-CSF or similar agent.

In some embodiments, MKs and platelets can be derived from other stem cell types, including but not limited to mesenchymal stem cells (MSC) (such as, adipose-derived mesenchymal stem cells (AdMSC)) or mesenchymal stem from other sources.

AdMSCs are derived from white adipose tissue, which is derived from the mesoderm during embryonic development and is present in every mammalian species, located throughout the body. Due to their wide availability and ability to differentiate into other tissue types of the mesoderm-including bone, cartilage, muscle, and adipose-ASCs may serve a wide variety of applications.

In the present disclosure, the stem cell cultures can be maintained independently of embryonic fibroblast feeder cells and/or animal serum. In some embodiments, serum-free, feeder-cell free alternatives can be utilized in the instant methods.

The present disclosure provides methods for producing megakaryocytic progenitors (preMKs) and megakaryocytes (MKs) from stem cells.

In some embodiments, the present disclosure provides a method for megakaryocyte production comprising: expanding pluripotent stem cells under low adherent or non-adherent conditions and under agitation wherein expanded pluripotent stem cells form self-aggregating spheroids; differentiating the pluripotent cells in a first culture medium into hemogenic endothelial cells; differentiating the hemogenic endothelial cells in a second culture medium into megakaryocytic progenitors. The differentiating of the pluripotent cells into hemogenic endothelial cells can be carried out under adherent conditions on a matrix. In some embodiments, the differentiating of the pluripotent cells into hemogenic endothelial cells is carried out under low-adherent or non-adherent conditions to enable the hemogenic endothelial cells to self-aggregate.

In some embodiments, the present disclosure provides a method for megakaryocyte production comprising: differentiating pluripotent cells in a first culture medium into hemogenic endothelial cells; and differentiating the hemogenic endothelial cells in a second culture medium into megakaryocytic progenitors, wherein at least one of the differentiating the pluripotent cells and the differentiating the hemogenic endothelial cells is carried out on a matrix coated 3-dimensional structure. The 3-dimensional structure can be a microcarrier or a microcarrier.

In some embodiments, the present disclosure provides a method for megakaryocyte production comprising: differentiating pluripotent cells in a first culture medium into hemogenic endothelial cells; and differentiating the hemogenic endothelial cells in a second culture medium into megakaryocytic progenitors, wherein at least one of the differentiating the pluripotent cells and the differentiating the hemogenic endothelial cells is carried out under low-adherent or non-adherent conditions to enable the cells to self-aggregate.

The present disclosure further provides methods for producing platelets from MKs.

Methods of Production

Figure 2:
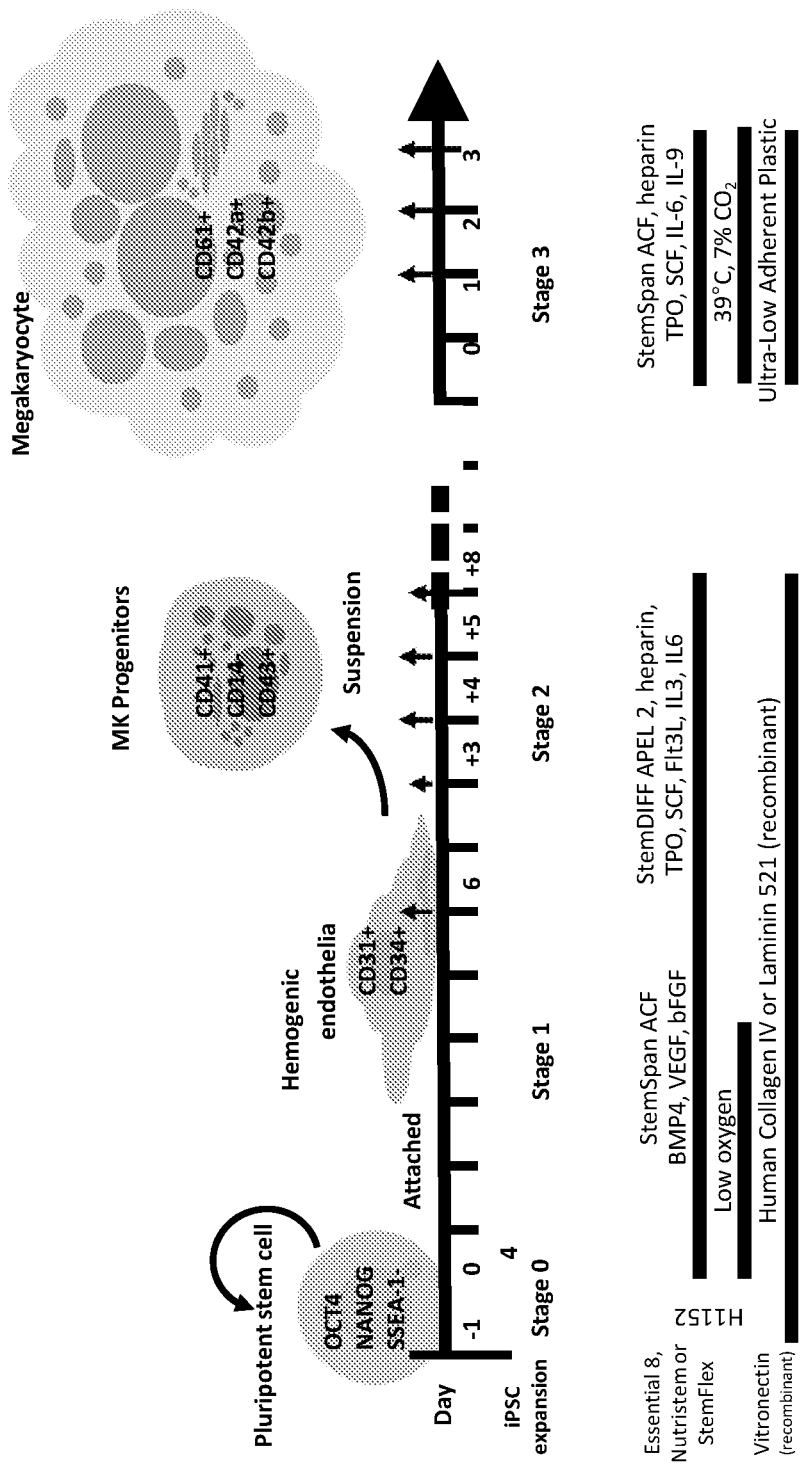
FIG. 2 depicts exemplary directed differentiation protocol of a pluripotent stem cell into a megakaryocyte in a 2D, matrix-dependent system such as a cell culture plate or flask.
Figure 3:
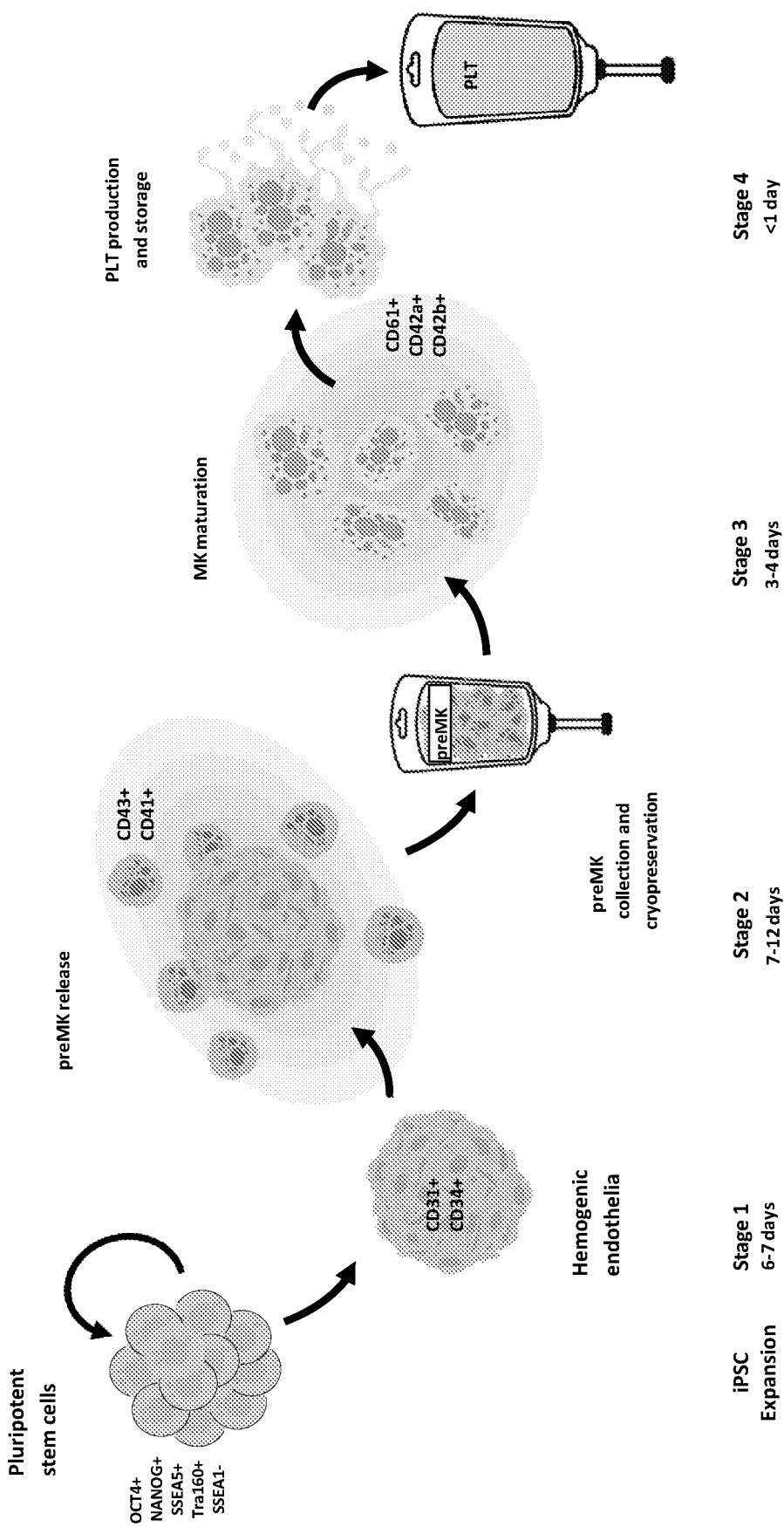
FIG. 3 is a schematic of an exemplary 3D, matrix independent method of directed differentiation using self-aggregating iPSC-derived spheroids in a stir tank.

FIG. 1 shows an overall schematic for scalable differentiation of megakaryocytic progenitors (preMKs), megakaryocytes (MK), and platelets (PLT) from one or more pluripotent stem cells. However, it should be noted that while the instant processes are described in connection with pluripotent stem cells, in various embodiments, pluripotent stem cells may be substituted or supplemented with other types of stem cells. In some embodiments, two-dimensional (2D) cultures are used to generate progenitors, megakaryocytes, and platelets, as shown in FIG. 2. Other embodiments disclosed herein describe a process that utilizes a three-dimensional culture to produce the desired cells as shown in FIG. 3.

Stage 0: Expansion of Human Induced Pluripotent Stem Cells and Preparation for Differentiation
Matrix-Dependent Expansion Cultures For matrix-dependent expansion cultures, clinical grade pluripotent stem cells (PSCs) can be expanded as colonies by culturing without feeder cells on a supportive matrix in a pluripotent stem cell culture medium. The supportive matrix can be a 2-dimensional surface or a 3-dimensional structure that enables cell attachment. In some embodiments, the clinical grade human induced pluripotent stem cells can be human induced pluripotent stem cells (iPSCs), but other types of pluripotent stem cells, such as embryonic stem cells, or other stem cells can be used.

In some embodiments, the supportive matrix can be, by way of a non-limiting example, tissue-culture treated plastic, recombinant vitronectin, recombinant laminin, Matrigel, Geltrex, or any combinations of the foregoing. In some embodiments, the pluripotent stem cell culture medium can be, for example, but not limited to, Essential 8 medium (ThermoFisher), StemFlex medium (Thermofisher), NutriStem medium (Biological Industries), or other medium able to support the maintenance and growth of pluripotent cells known in the art. In some embodiments, the cells can be cultured to reach confluency. In some embodiments, the cells can be cultured to reach from 30% to 90% % confluency. In some embodiments, the cells are cultured to reach up to 60%, up to 65%, up to 70%, up to 75% confluency. For example, the cells are cultured to reach about 70% confluency. Upon reaching a predetermined maximum percent confluency, the cells are harvested. In some embodiments, the cells can be harvested as clumps by dissociation using from 0.1 mM to 5 mM EDTA or similar chelating agent or reagent. For example, the cells can be harvested using about 0.5 mM EDTA. In some embodiments, the cells can be harvested as single cells, such as, for example, by dissociation with proteolytic enzymes, collagenolytic enzymes, or combinations thereof. For example, the cells can be harvested as single cells by dissociation with, for example, recombinant trypsin such as TrypLE™, or Accutase™. For maintenance/expansion of PSCs, the harvested cells can be resuspended in pluripotent stem cell culture medium.

A high-efficiency single cell passaging technique can be used to support scaled expansion of undifferentiated hiPSC cultures. The same methodology is intended for cell banking and scaled hiPSC seed-trains leading to pre-MK manufacturing. The approach provides rapid expansion for overall manufacturing capacity, undifferentiated pluripotent cultures with capacity to produce pre-MK, and uniformity of harvest yields and culture performance in a system compatible with cGMP manufacturing and clinical entry. Briefly, a single cell iPSC suspension is generated using one or more cell-dissociation enzymes (such as, for example, TrypLE (Thermo Fisher), followed by plating at a defined density in a feeder free culture medium (for example, NutriStem hPSC XF (Biological Industries). In some embodiments, the culture medium may be further supplemented, such as, for example, with a ROCK inhibitor and a one or more growth factors. In some embodiments, the cultures are plated at a density between $5\times10^3$ cells/cm$^2$ and $5\times10^4$ cells/cm$^2$ for 3-day or 4-day culture interval. For example, in some embodiments, cultures are plated at a density of about $5\times10^3$, cells/cm$^2$ about $1\times10^4$ cells/cm$^2$, about $2\times10^4$ cells/cm$^2$, about $3\times10^4$ cells/cm$^2$, about $4\times10^4$ cells/cm$^2$, or about $5\times10^4$ cells/cm$^2$, for a 3-day or 4-day culture interval, or $2\times10^4$ cells/cm$^2$ for a 3-day culture interval. In some embodiments, cultures are plated at a density of about $1\times10^4$ cells/cm$^2$ for a 4-day culture interval or about $2\times10^4$ cells/cm$^2$ for a 3-day culture interval. In some embodiments, cell attachment to untreated surfaces can be mediated by human serum. In some embodiments, 18-22 hours post-plating, cultures can be fed with a feeder-free culture medium, without supplementation. Cultures can be passaged at 3- or 4-day intervals, achieving predictable and consistent harvest yields over multiple passages.

Matrix-Independent 3D Expansion Cultures

Figure 4:
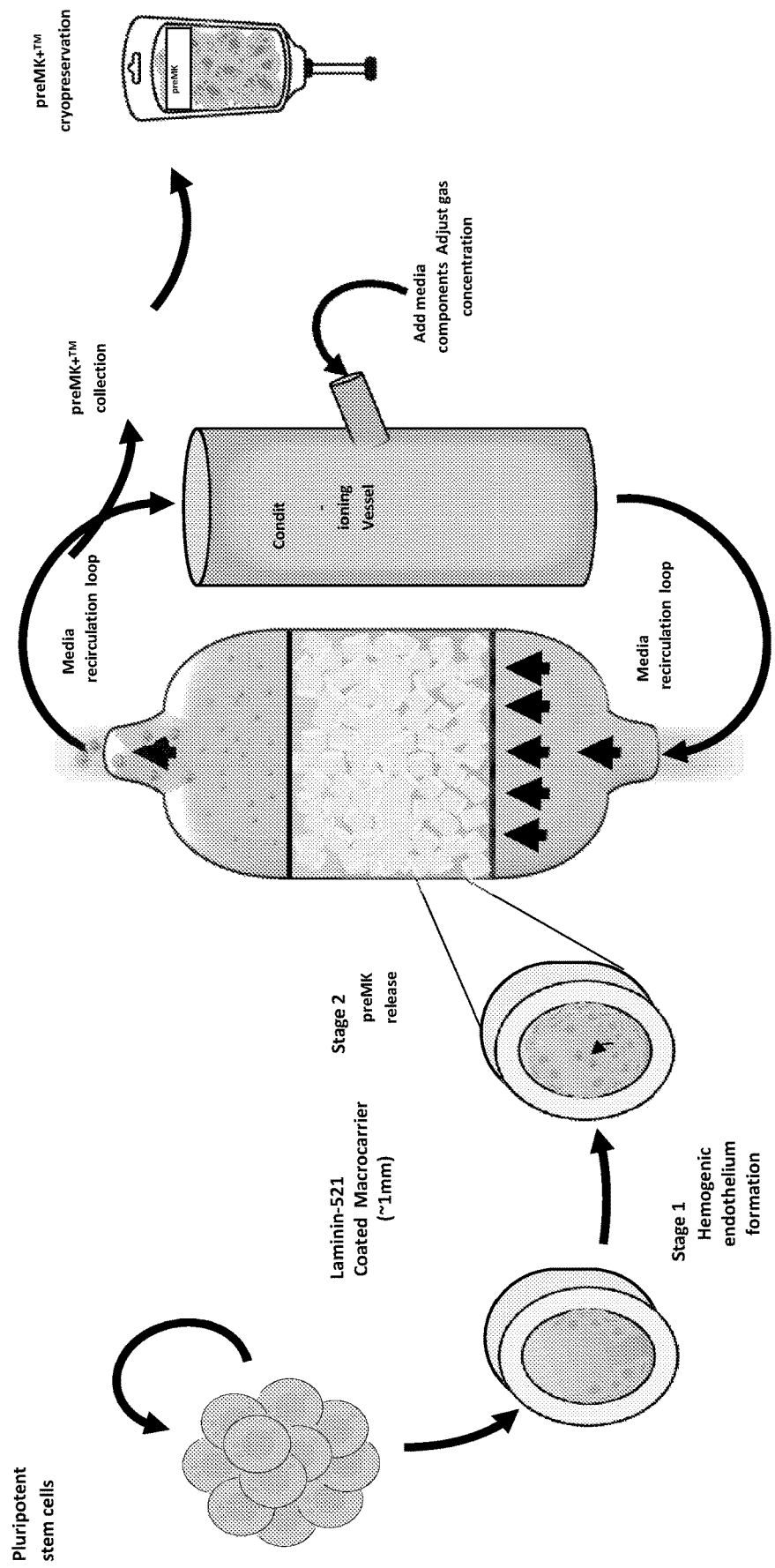
FIG. 4 is a schematic that depicts exemplary directed differentiation protocol of iPSC into megakaryocytic progenitors using a packed bed bioreactor strategy, a 3D, matrix dependent method. In the embodiment described here, Laminin 521 coated Raschig rings made of PTFE are used as macrocarriers to compose the packed bed.

FIGS. 3 and 4 present schematic overviews directed differentiation of preMK cells using 3D matrices. For matrix-independent 3D expansion cultures, clinical grade PSCs can be expanded as self-aggregating spheroids. In some embodiments, this can be achieved by seeding single cells at a density from about 0.1 to about 1.5 million per ml. For example, in some embodiments, single cells can be seeded at 0.5 million per ml.

The cells can be subjected to continuous motion by slow stirring or gentle shaking in low-adherent or non-adherent conditions in a pluripotent stem cell culture medium. In some embodiments, feeder free, serum free medium can be used. The pluripotent stem cell culture medium can be, for example, but not limited to, Essential 8 medium (ThermoFisher), StemFlex medium (Thermofisher), NutriStem medium (Biological Industries), or other similar medium able to support the maintenance and growth of pluripotent cells known in the art. In some embodiments, the culture medium can be supplemented with Rock inhibitor (e.g. H1152). In some embodiments, the medium may include an epidermal growth family member, for example, Heregulin-beta-1. In some embodiments, Heregulin-beta-1 medium is used for less than 24 hours (e.g., 18-22 hours). In some embodiments, the PSC spheroids are cultured until reaching an overall cell density of from about 3 to about 10 million cells/ml and/or attain a median spheroid size of about 150 to about 350 μm, for approximately 5-7 days. In some embodiments, the PSC spheroids are cultured until reaching an overall cell density of 5 million cells/ml. In some embodiments, the PSC spheroids are cultured until the cells attain a median spheroid size of about 250 μm. The culturing step may last for 3, 4, 5, 6, 7, or 8 days. When applicable, PSCs can be harvested as single cells by dissociation with proteolytic enzymes, collagenolytic enzymes, or combinations thereof. For example, the cells can be harvested as single cells by dissociation with, but not limited to trypsin, recombinant trypsin such as TrypLE™, Accutase™, or similar reagent known in the art. In some embodiments, the single cells are used to initiate another 3D expansion culture and/or directed differentiation culture.

Preparation for Differentiation

In some embodiments, to prepare for differentiation, PSC aggregates can be generated by partial dissociation of PSC colonies from matrix-dependent 2D cultures, by partial dissociation of PSC spheroids from matrix-independent 3D cultures, or by self-aggregation of single PSCs generated by any method known in the art. In some embodiments, prior to initiation of differentiation, these aggregates can be generated in a pluripotent stem cell culture medium, for example, but not limited to, Essential 8 medium (ThermoFisher), StemFlex medium (Thermofisher), or NutriStem medium (Biological Industries). In some embodiments, the medium may include a ROCK inhibitor, such as, for example, but not limited to, Y27632, H1152, or combination thereof. In some embodiments, the medium may include soluble Laminin, for example, recombinant Laminin 521. In some embodiments, the medium may include an epidermal growth family member, for example, Heregulin-beta-1. In some embodiments, Heregulin-beta-1 medium is used for less than 24 hours (e.g., 18-22 hours). In some embodiments, the cells can be cultured for between 0 and 72 hours at 37° C., 5% $CO_2$, 20% $O_2$ prior to initiation of differentiation.

For matrix-dependent differentiation cultures, the aggregates can be allowed to attach to a surface. In some embodiments, the step of attachment may be allowed to proceed for about 24 hours, although any time between 1 hour and 24 hours or longer may be used. In some embodiments, the surface can be pre-coated with collagen, laminin, or any other extracellular matrix protein. In some embodiments, human collagen IV can be used for coating the surface. In some embodiments, the matrix-coated surface can be 2D (for example, the bottom of a plastic dish or flask). In some embodiments, the matrix-coated surface can be 3D (for example, smooth or textured spherical microcarriers, or macrocarriers, such as, Rauchig rings). The cells on the 3D matrix coated surfaces can then be cultured with or without continuous motion. For example, the cells can be cultured under ultra-low-adherent static conditions, in roller bottles, spinner flasks, stir tank bioreactors, vertical wheel bioreactors, packed bed bioreactors, or fluidized bed systems.

For matrix-independent differentiation cultures, the aggregates can be subjected to continuous motion by slow stirring or gentle shaking in a low-adherent vessel, such as, but not restricted to, plates or flasks on an orbital shaker, spinner flasks, roller bottles, vertical wheel bioreactors, or stir tank bioreactors). The cells can be transitioned into Stage 1 of differentiation after between 0 and 72 hours, for example after about 24 hours.

Stage 1. Generation of Hemogenic Endothelial Cells

In Stage 1, prepared PSC aggregates can be differentiated into hemogenic endothelial cells. Briefly, some or all of the pluripotent stem cell culture medium is removed and replaced with Stage 1 differentiation medium. In some embodiments, the Stage 1 differentiation medium can be an animal-component free medium (ACF) comprising StemSpan™-ACF (STEMCELL Technologies, Cat. No. 09855) as basal medium, supplemented with one or more growth factors, including, for example, bone morphogenic protein 4 (BMP4), basic fibroblast growth factor (bFGF), and vascular endothelial growth factor (VEGF). In some embodiments, the basal medium is supplemented with between 1 and 200 ng/ml of one or more each of BMP4 (for example, at 50 ng/ml), bFGF (for example, at 50 ng/ml), and VEGF (for example, at 50 ng/ml). In some embodiments, the Stage 1 medium can be further supplemented with a WNT agonist (such as CHIR98014 or CHIR99021), a Laminin (such as recombinant Laminin 521), or any combination thereof. In some embodiments, cells can be incubated for between 2 and 6 days in low oxygen conditions (for example, 37° C., 5% $CO_2$, 5% $O_2$), followed by between 2 and 6 days in normoxia (37° C., 5% $CO_2$, 20% $O_2$). In some embodiments, BMP4 can be added for the first 6-48 hours (e.g., 24 hours) and can be dispensable for the remainder of Stage 1 (FIG. 28). In some embodiments, VEGF and bFGF can be dispensable for the first 6-48 hours (e.g., 24 hours) of Stage 1, and added thereafter (FIG. 28). In some embodiments, daily full media exchanges can be performed throughout Stage 1 by removal of spent media and replacement with fresh Stage 1 media. In some embodiments, partial media exchanges can be performed, with 10-99% of the spent media removed and replaced with equivalent volumes of fresh Stage 1 media. In some embodiments, additional volumes of fresh media can be added with the net effect of increasing the total volume of the culture. In some embodiments, specific media components are spiked into the culture in lieu of replacement or addition of fresh Stage 1 media.

Figure 15:
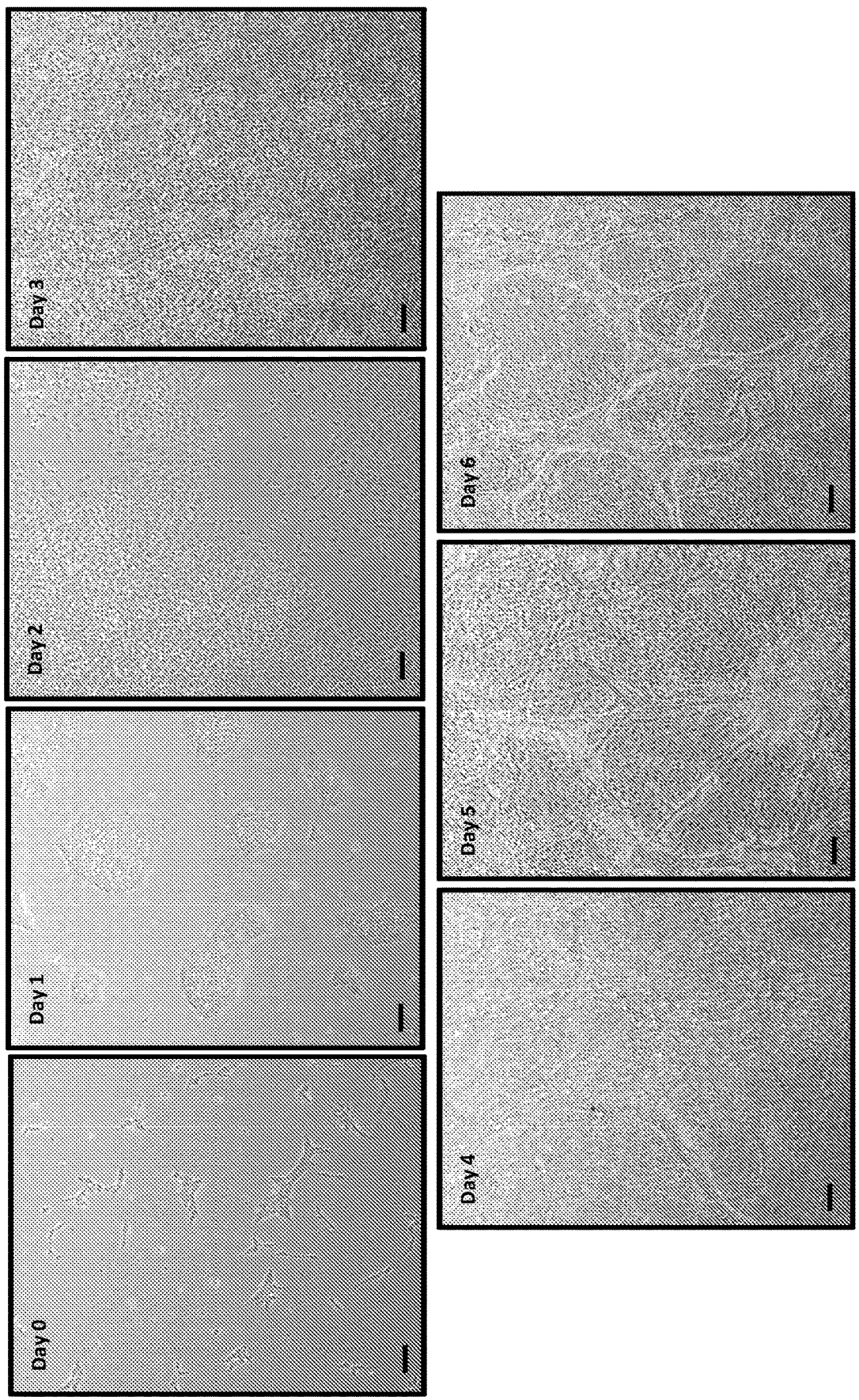
FIG. 15 depicts the morphological changes that occur over 6 days of Stage 1 differentiation of iPSC to hemogenic endothelium on Collagen IV matrix in a 2D culture vessel. The scale bar represents 100 μm.

In 2D matrix-dependent cultures, by day 2, the morphology of the colonies changes to scattered elongated cell clusters (FIG. 15). By day 5-6, a confluent adherent layer of hemogenic endothelial cells is observed, with some three-dimensional structure within the adherent cell layer (FIG. 2, FIG. 15). In matrix-independent 3D cultures, Stage 1 can proceed in matrix-independent 3D cultures where self-aggregated spheroids can be subjected to continuous motion by slow stirring or gentle shaking in a low-adherent vessel, such as, but not restricted to, plates or flasks on an orbital shaker, spinner flasks, roller bottles, vertical wheel bioreactors, or stir tank bioreactors). In matrix-independent 3D cultures, the spheroids grow larger, darker, and less uniform as Stage 1 progresses (FIG. 15). Approximately 6 days after initiation of Stage 1 differentiation, differentiation to hemogenic endothelium is complete. In some embodiments, differentiation can be deemed complete when a confluent adherent layer of hemogenic endothelial cells is observed, with some three-dimensional structure within the adherent cell layer. In some embodiments, differentiation can be assessed by expression of markers of hemogenic endothelium such as CD31 and CD34. In some embodiments, the hemogenic endothelial cells can also express CD309 and CD144 or CD309, CD144, CD140a and CD235a.

Stage 2. Generation of Detached Megakaryocytic Progenitors (preMKs) from Hemogenic Endothelial Cells In some embodiments, initiation of megakaryocytic progenitor (Stage 2) differentiation can be performed following between 4 and 8 days of Stage 1. Briefly, some or all of the Stage 1 medium is removed and replaced with a volume of Stage 2 medium, such as, for example, STEMdiff™ APEL™2 basal medium (STEMCELL Technologies, Cat. No. 05275). Such Stage 2 medium can be supplemented with 1 and 200 ng/ml of each of one or more of Stem Cell Factor (SCF) (for example, at 25 ng/ml), Thrombopoietin (TPO) (for example, at 25 ng/ml), Fms-related tyrosine kinase 3 ligand (Flt3-L) (for example, at 25 ng/ml), Interleukin-3 (IL-3) (for example, at 10 ng/ml), Interleukin-6 (IL-6) (for example, at 10 ng/ml), and Heparin (for example, at 5 Units/ml). In some embodiments, the Stage 2 medium can be further supplemented with UM171, UM729, SR-1, SU6656, Laminin (such as recombinant Laminin 521), or any combinations thereof.

Cells are then incubated for at least 3 and up to 12 or more days at 37° C., 5% $CO_2$, 20% $O_2$. For example, the cells can be incubated for 3, 4, 5, 6, 7, 8, 9, 10, 11, 12, 13, 14, 15, 16, 17 days. In some embodiments, daily partial media exchanges can be performed, with 10-99% of the spent media removed and replaced with equivalent volumes of fresh Stage 2 media. In some embodiments, additional volumes of fresh media can be added with the net effect of increasing the total volume of the culture. In some embodiments, specific media components can be spiked into the culture in lieu of replacement or addition of fresh Stage 1 media.

Figure 17A:
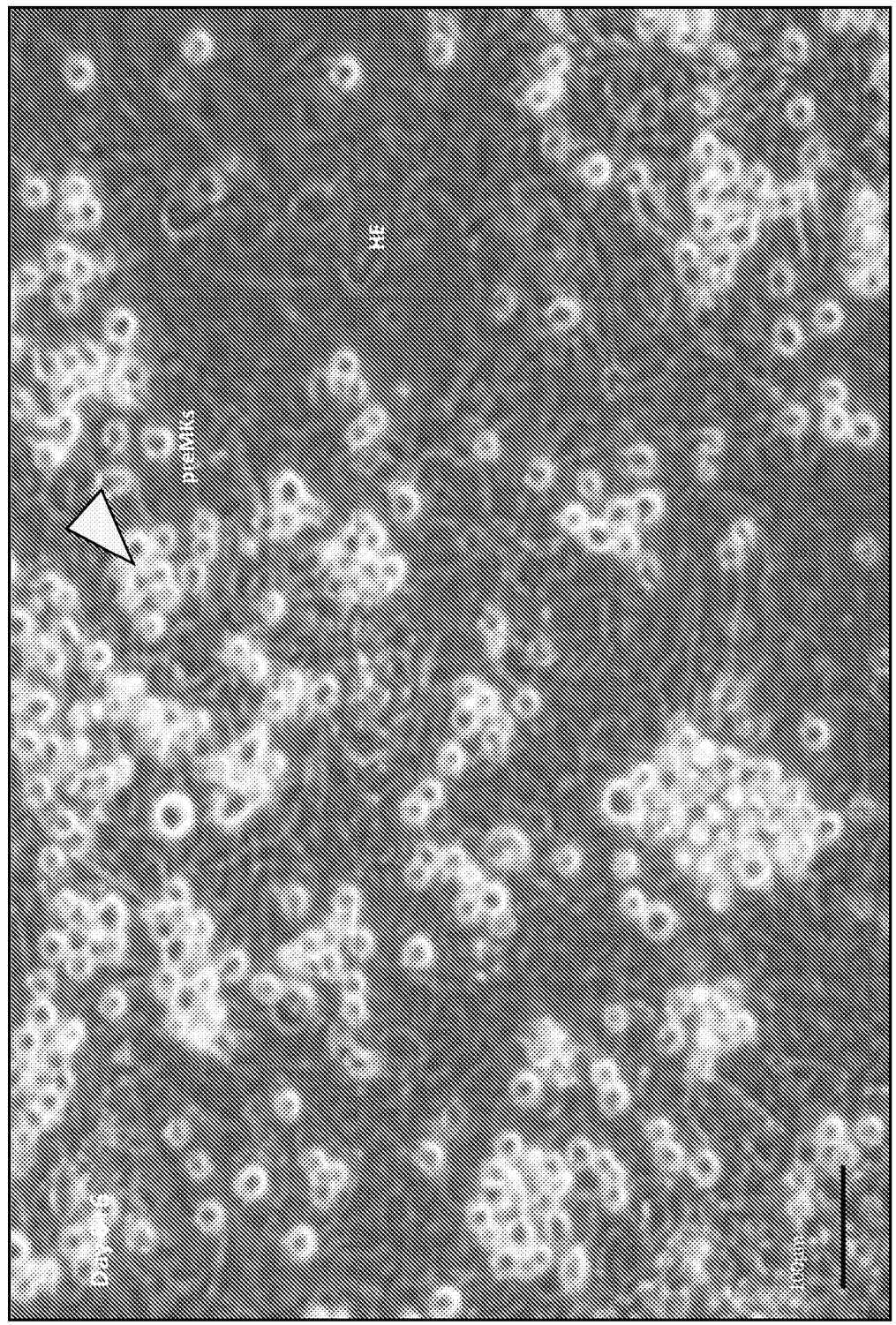
FIGS. 17A-17C depict representative Stage 2 data from iPSC differentiation cultures.
Figure 17C:
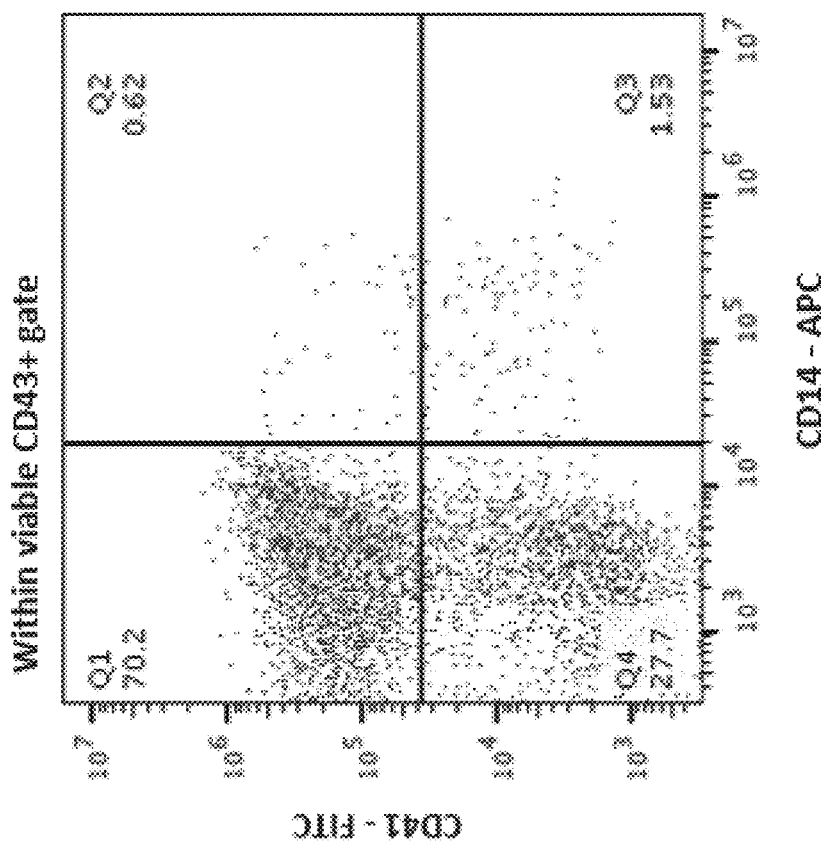
Figure 17B:
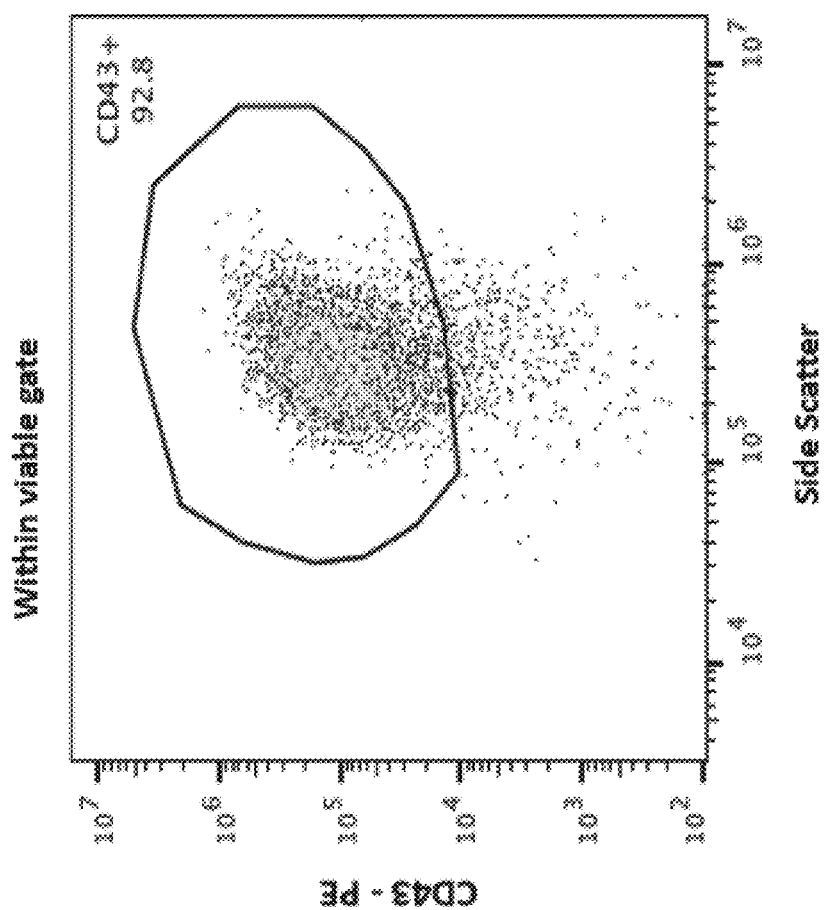
Figure 24A:
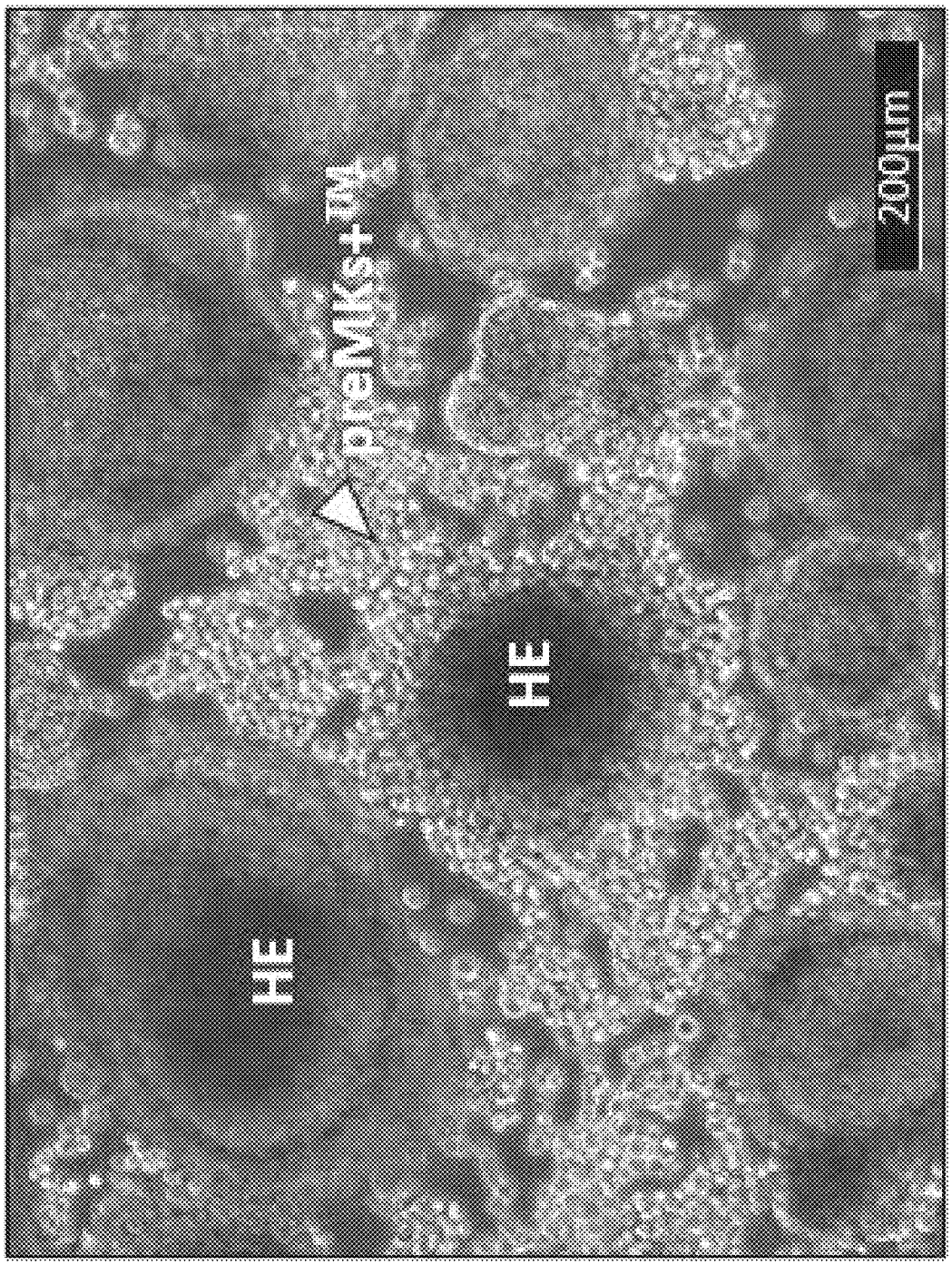
FIGS. 24A-24D describe Stage 2 in a directed differentiation initiated with self-aggregating spheroids of iPSCs.
Figure 24B:
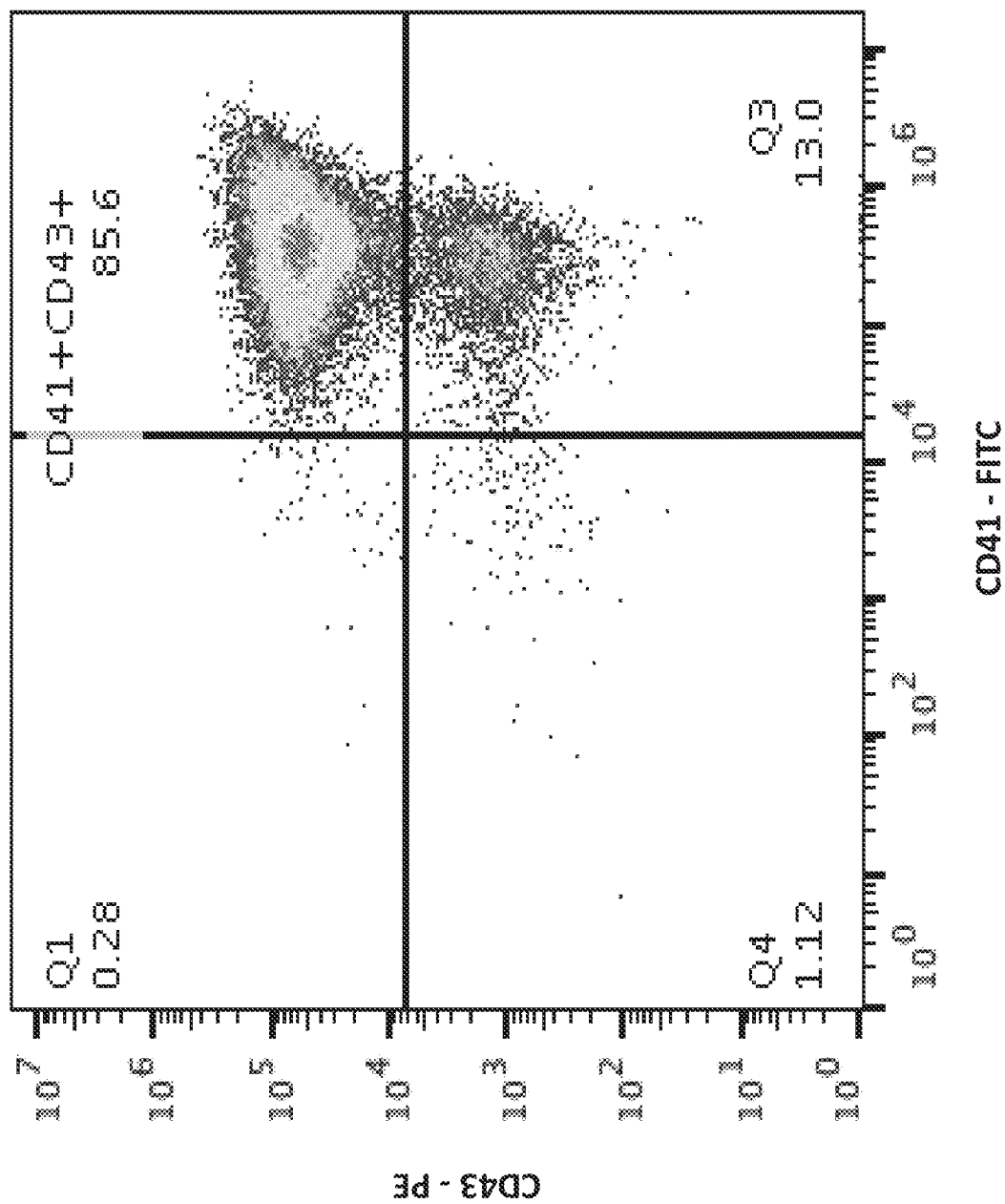

Within 1-2 days after initiation of Stage 2, small, round, refractile cells appear within the adherent hemogenic endothelial cells and are eventually released into the supernatant (FIG. 17A, FIG. 24A). These released cells can contain preMKs, as defined by cell surface expression of CD43 and CD41 and lacking expression of CD14 (FIG. 17B, 17C, 24B). In 2D cultures, floating and weakly attached Stage 2 cells that appear on top of the adherent cell layer can be harvested at regular intervals by gentle rinsing and collection of the medium. In 3D cultures, released Stage 2 cells can be harvested in a manner that allows the aggregates to settle to the bottom of the vessel (for example, by pausing agitation). The medium along with the released suspension cells can then be collected. Other exemplary methods for harvesting the released cells can include, for example leveraging the size and density differences between the aggregates and the released single cells. Thereafter, a half-media change can be initiated by adding half the original volume of fresh Stage 2 medium on top of the rinsed adherent cell layer or 3D aggregates. In some embodiments, proportions other than half are used for the media exchange. An aliquot of the collected cells in medium can be removed for viable cell enumeration and biomarker analysis by flow cytometry. The remainder of the cells can then be concentrated by centrifugation, counter-centrifugal elutriation, acoustic separation, or any other related technology. Following concentration, the media change can be completed by adding back half the original volume of conditioned media to the adherent cell layer or 3D aggregates. In some embodiments, additional volumes of fresh media can be added with the net effect of increasing the total volume of the culture. In some embodiments, specific media components can be spiked into the culture in lieu of replacement or addition of fresh Stage 2 media. The remainder of the supernatant is discarded and the preMK-containing cell pellet can be stored at −180° C. in Cryostor 10 cryopreservation media, or transitioned directly into Stage 3. In some embodiments, the preMK-containing cells can be collected over a 2- to 7-day period (e.g. 3 days) and additionally cultured in Stage 2 medium or other medium in a separate vessel. Once the final harvest is complete, the preMK-containing cells can be pooled together and stored at −180° C. in Cryostor 10 cryopreservation media (e.g. Cryostor 10), or transitioned directly into Stage 3.

Stage 3. Generation of Mature Megakaryocytes (MK) from Megakaryocytic Progenitors In some embodiments, differentiation of mature megakaryocytes can be initiated using PSC-derived preMKs, generated as described above. Fresh or thawed megakaryocytic progenitors can be seeded onto a non-adherent surface in Stage 3 medium, comprising, for example, StemSpan™-ACF. Non-adherent surfaces refer to surfaces such that the majority of cells are not intended to stick or cling to such surfaces, but instead remain mostly in suspension. For example, such surface can be made of "ultra-low adherence plastic" or may not be coated with extracellular matrix proteins to prevent or minimize adhesion of cells to the surface. In some embodiments the Stage 3 medium can be supplemented with between 0 and 200 ng/ml each of one or more of TPO (for example, at 25 ng/ml), SCF (for example, at 25 ng/ml), IL-6 (for example, at 10 ng/ml), IL-9 (for example, at 10 ng/ml), Heparin (for example, at 5 units/ml), and Rock inhibitor (e.g., Y27632 at 5 µM). In some embodiments, the Stage 3 medium can also be supplemented with UM171, UM729, SR-1, SU6656, or any combinations thereof.

Cells can then be incubated at between 37° C. and 40° C. (for example, 39° C.), between 5 and 20% $CO_2$ (for example, 7%-10%), and between 5 and 20% $O_2$ for up to 5 days. In some embodiments, partial daily media exchanges are performed, with 10-95% of the spent media removed and replaced with equivalent volumes of fresh Stage 3 media. In some embodiments, the non-adherent surface is an ultra-low-adherent plate or flask. In some embodiments, the non-adherent surface is a gas permeable membrane (such as the G-Rex®). In some embodiments, the non-adherent surface is a cell culture bag or vessel with gentle agitation. In either case, preMKs (either freshly harvested from Stage 2 culture, or thawed from cryopreserved stocks) are suspended in Stage 3 media at a density of 0.1-10 million per ml, and introduced into the vessel. For example, the preMKs can be at density of 1 to 1.5 million per ml, of 1 to 2 million per ml, of 1 to 3 million per ml, of 1 to 4 million per ml, of 2 to 5 million per ml, of 2 to 6 million per ml, of 3 to 7 million per ml, of 3 to 8 million per ml, of 5 to 9 million per ml, or of 8 to 10 million per ml. In some embodiments, the preMKs can be at a density of 0.1 to 1.5 million per ml, 0.2 to 1.5 million per ml, 0.3 to 1.5 million per ml, 0.4 to 1.5 million per ml, 0.5 to 1.5 million per ml, 0.6 to 1.5 million per ml, 0.7 to 1.5 million per ml, 0.8 to 1.5 million per ml, or 0.9 to 1.5 million per ml. The cells are cultured for a total of 1-5 days (for example, 3 days) to enable differentiation into mature MKs. In some embodiments, daily half media exchanges are performed, with 10-95% of the spent media removed and replaced with equivalent volumes of fresh Stage 3 media. At the end of the Stage 3 cultures, the resulting cells are increased in size and ploidy, and exhibit a host of features indicative of mature megakaryocytes (as for example, shown in FIGS. 34 to 42 and described below).

Figure 20D:
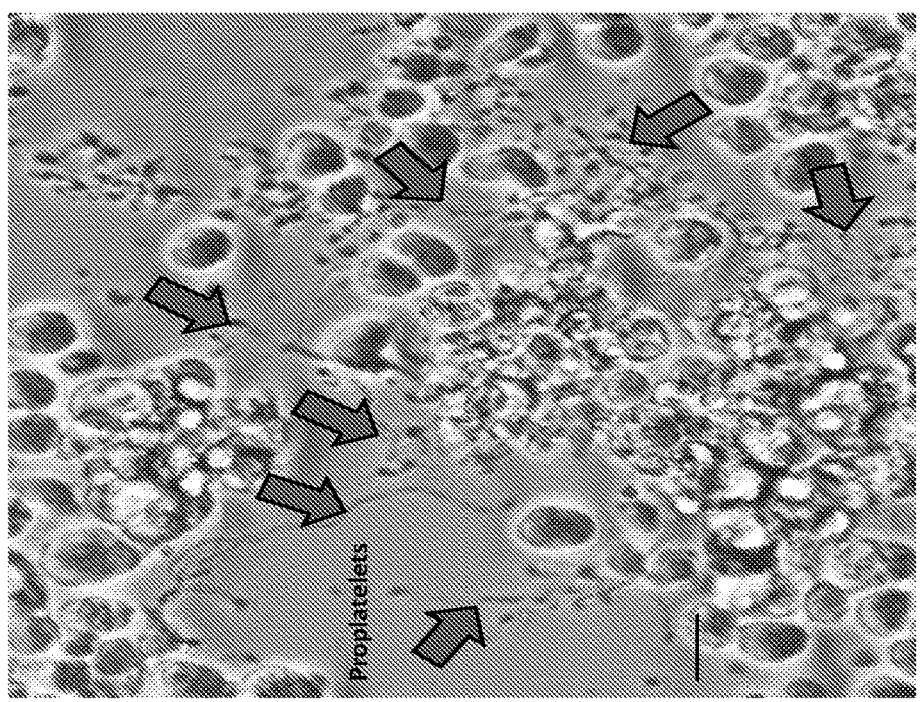
FIGS. 20A-20D depict MK differentiation and proplatelet production in Stage 3.
Figure 20C:
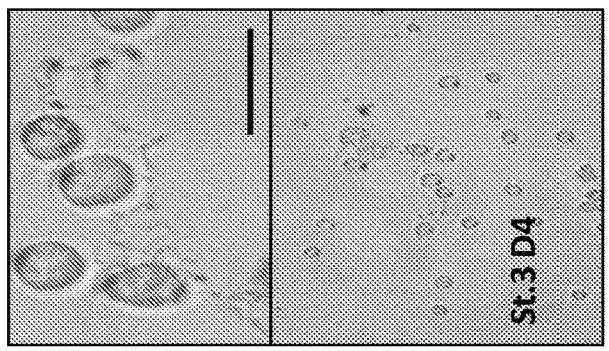
Figure 20B:
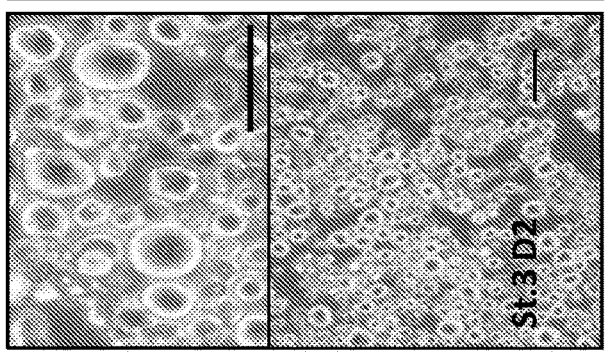
Figure 20A:
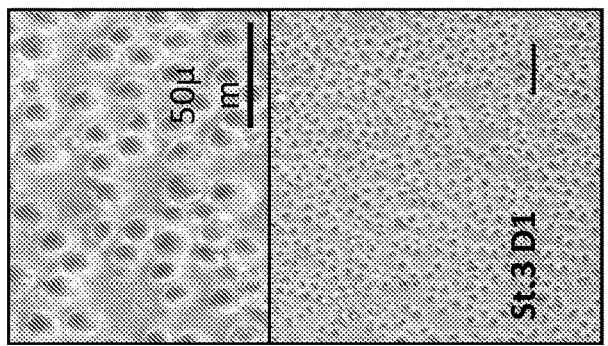
Figure 21B:
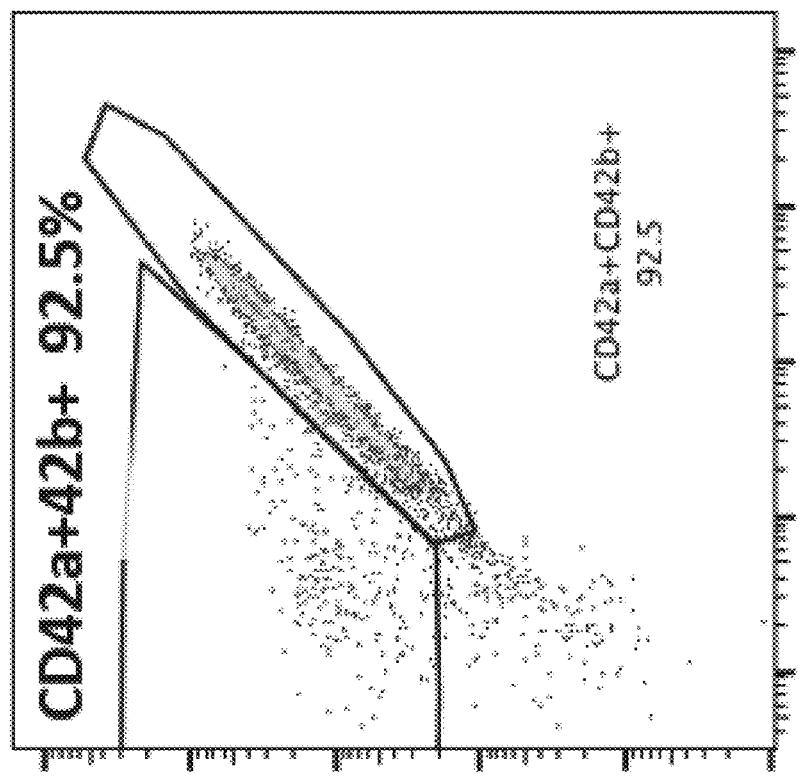
FIGS. 21A-21C depict representative flow cytometric analysis from Day 3 Stage 3 cultures initiated from iPSCs.

In some embodiments, during Stage 3, the megakaryocytic progenitors differentiate into mature MKs within several days. In some embodiments, cells that are initially uniformly small, round, and refractile (FIG. 20A) begin to increase in size and ploidy by day 2-4 (FIGS. 20B, 20C). Simultaneously, proplatelet-producing MKs can be readily observed (FIG. 20D). By 3-4 days of Stage 3, the proportion of CD61+(megakaryocytic lineage) cells co-expressing the mature MK markers CD42a and CD42b increases dramatically and can reach levels above 90% (FIG. 21B). In some embodiments, the mature MKs in the Stage 3 culture can be induced to produce proplatelets by adjusting the concentrations of heparin and Rock inhibitor for the final 1-24 hours (for example, 5 hours) of Stage 3. This effect could be utilized as a readout of proplatelet forming ability, and/or could be utilized to synchronize and increase platelet generation in the context of a platelet bioreactor or other system designed for platelet production. For example, in some embodiments, Stage 3 differentiation is performed in a millifluidic bioreactor, such as that described in PCT/US18/21354, the contents of which are incorporated herein by reference in their entirety.

Stage 4. Platelet and Preplatelet Production from Mature Megakaryocytes

Figure 44A:
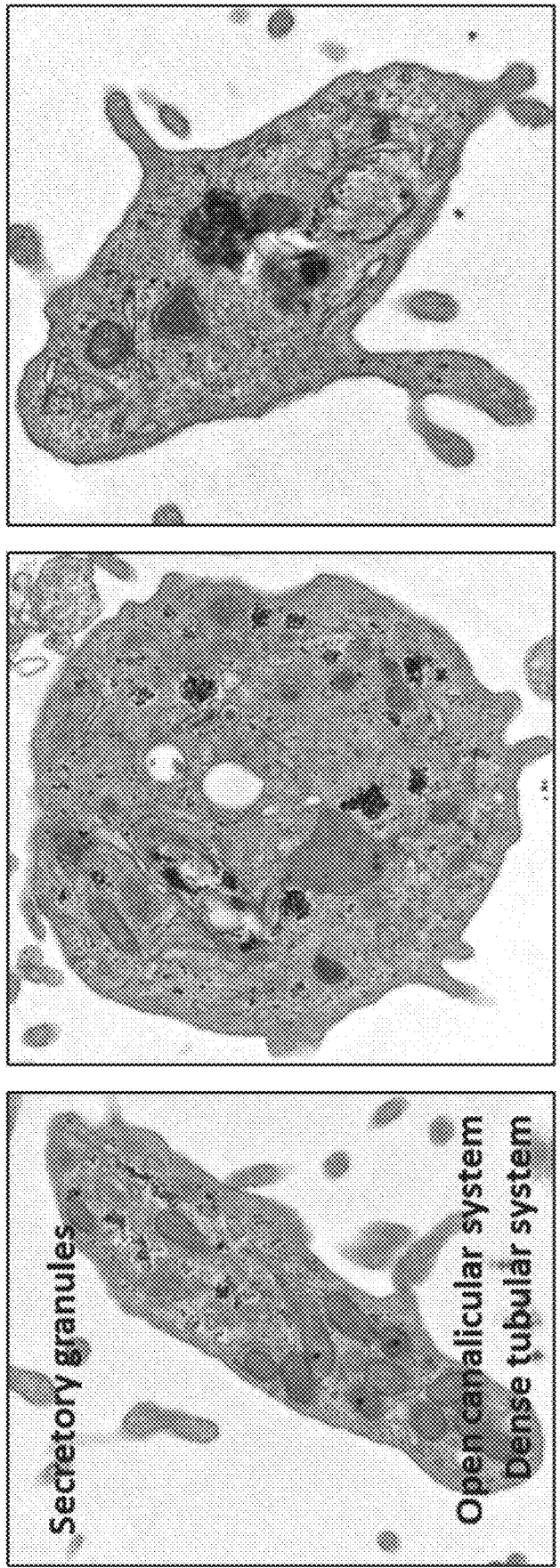

After Stage 3, platelets are produced by mature MKs into the culture medium. These platelets can be harvested, quantified, and assessed by flow cytometry, electron microscopy, and fluorescence microscopy, confirming their identity as bona fide platelets (FIGS. 44A and 44B). In some embodiments, the platelets are released after 4-5 days.

Platelets and preplatelets are produced from iPSC-derived megakaryocytes, in some iterations, by subjecting the MKs to shear stresses. In some embodiments, this can be achieved by seeding mature megakaryocytes into a millifluidic bioreactor. (FIGS. 63A-65). Various non-limiting embodiments of a suitable bioreactor are described in U.S. Pat. No. 9,795,965; US2017/0183616; US2018/0334652; WO2018165308, incorporated herein by reference in their entireties.

Figure 45:
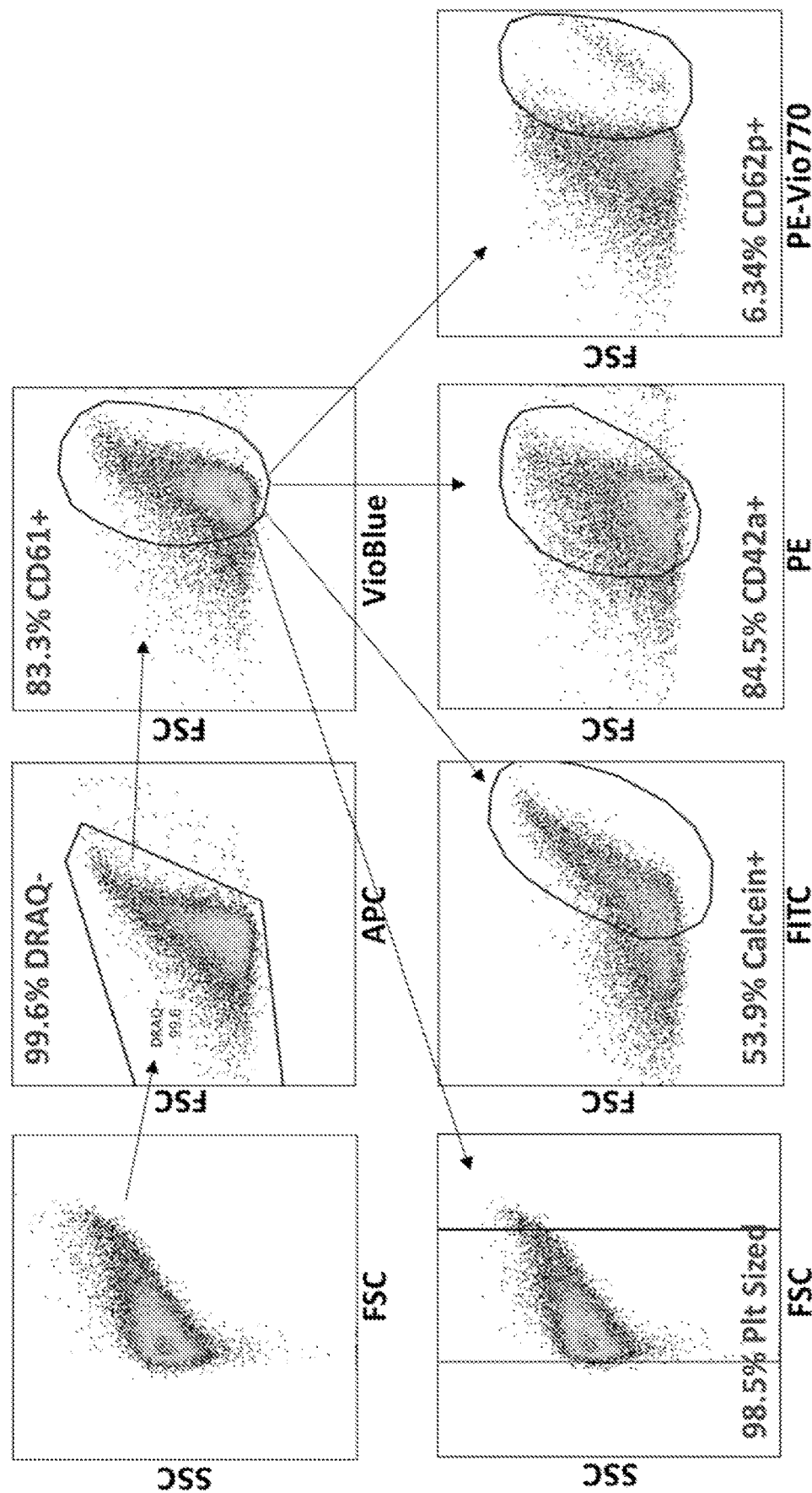
FIG. 45 is a full panel of immunophenotyping characterization of platelets derived from human iPSCs. The uppermost right panel demonstrates the forward scatter vs side scatter profile of the cells. These cells are then gated on DRAQ- (middle, top panel), demonstrating a lack of genomic material and CD61 (right, top panel), a platelet surface marker, before being assessed for multiple parameters. Gated cells were reassessed for forward scatter vs side scatter parameters (left, lower panel). They were also stained with Calcein AM to assess viability (second, lower panel). Gated cells were also probed for CD42a expression (third, lower panel) to further probe for common platelet surface markers. They were also stained for CD62P (right, lower panel), an indicator of activation, providing evidence that these platelets were in a resting state.
Figure 46A:
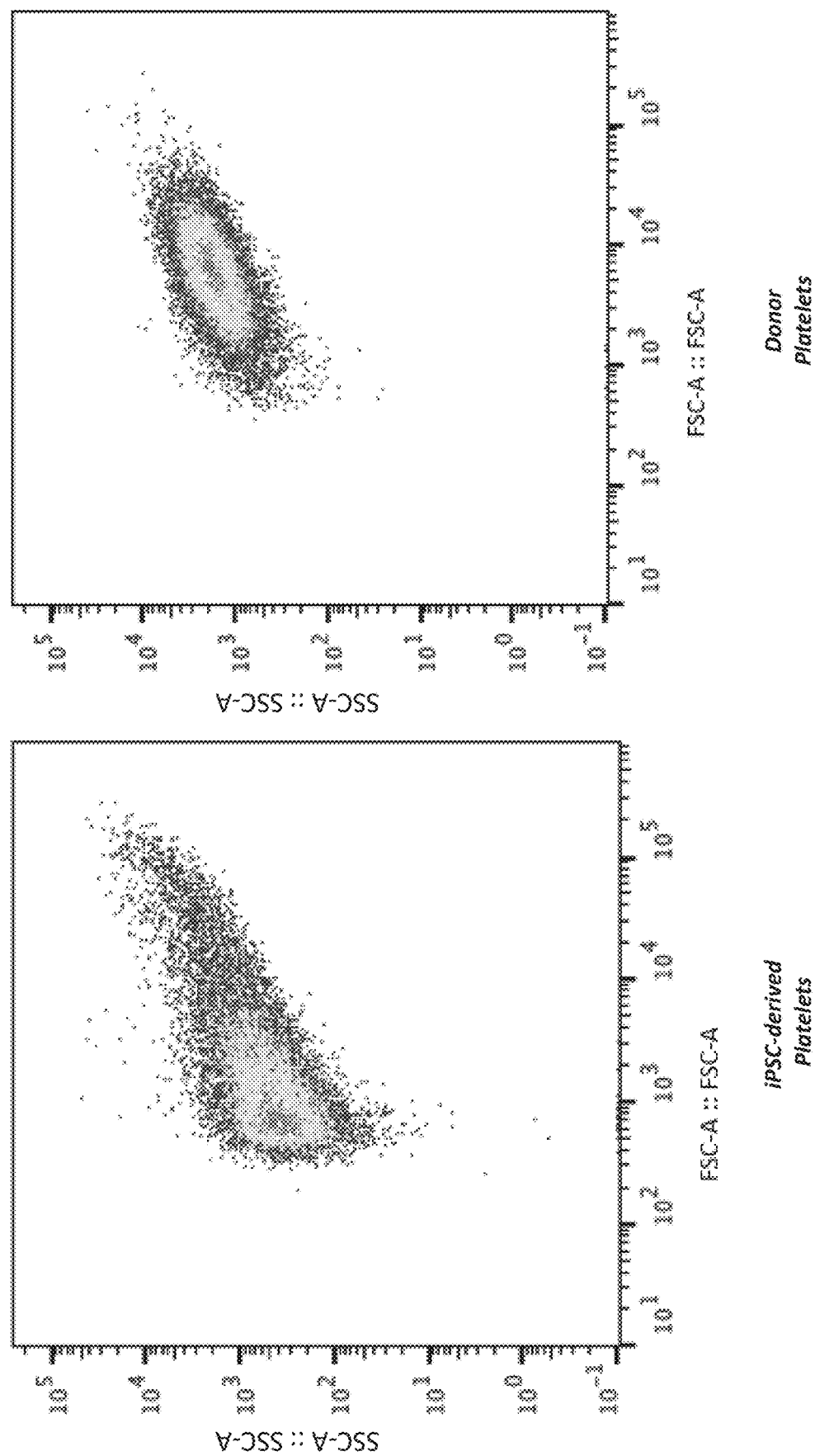
FIGS. 46A-46C depicts the relative lack of glycoprotein VI (GPVI) on the hiPSC platelet population versus those derived from human whole blood.
Figure 46B:
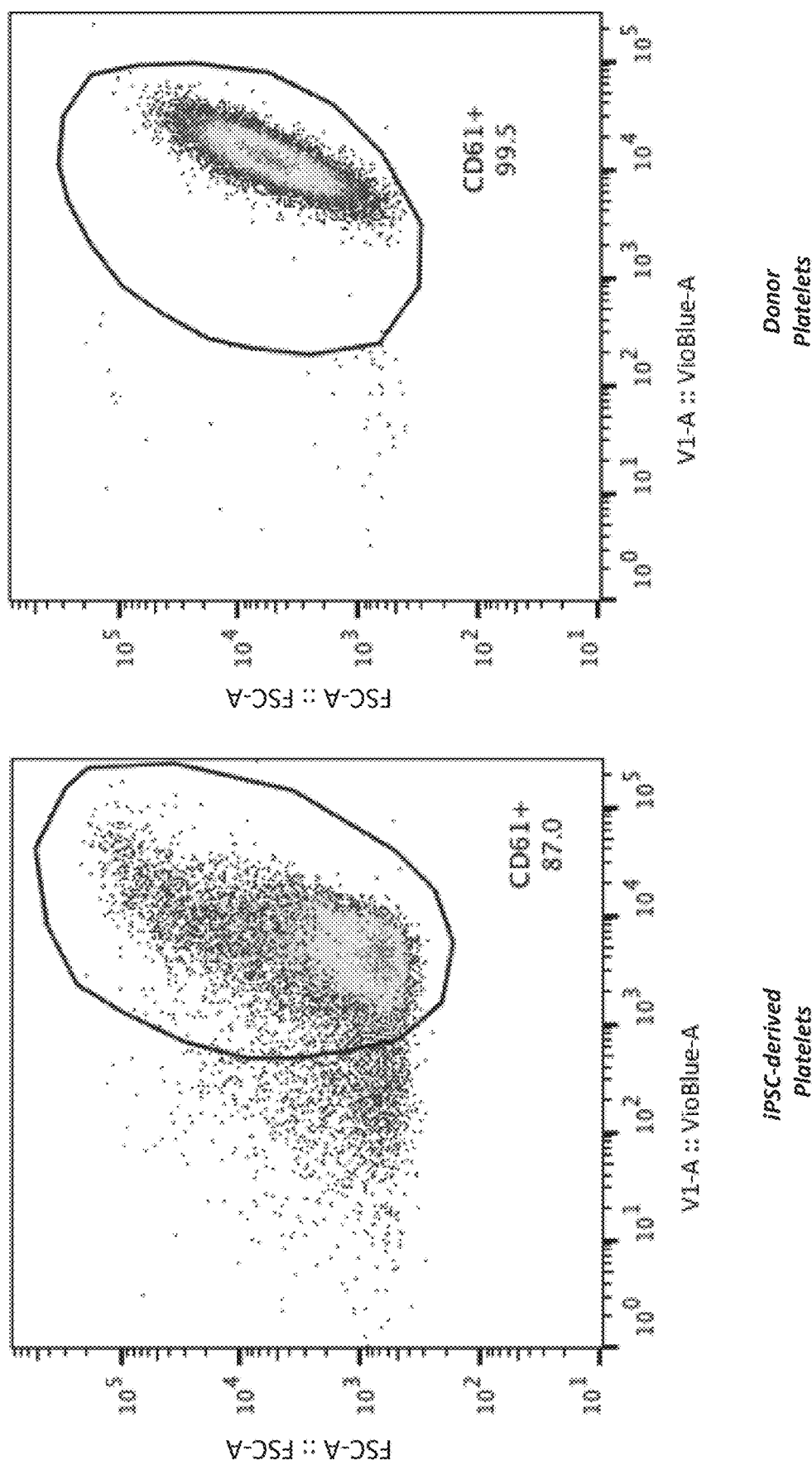
Figure 46C:
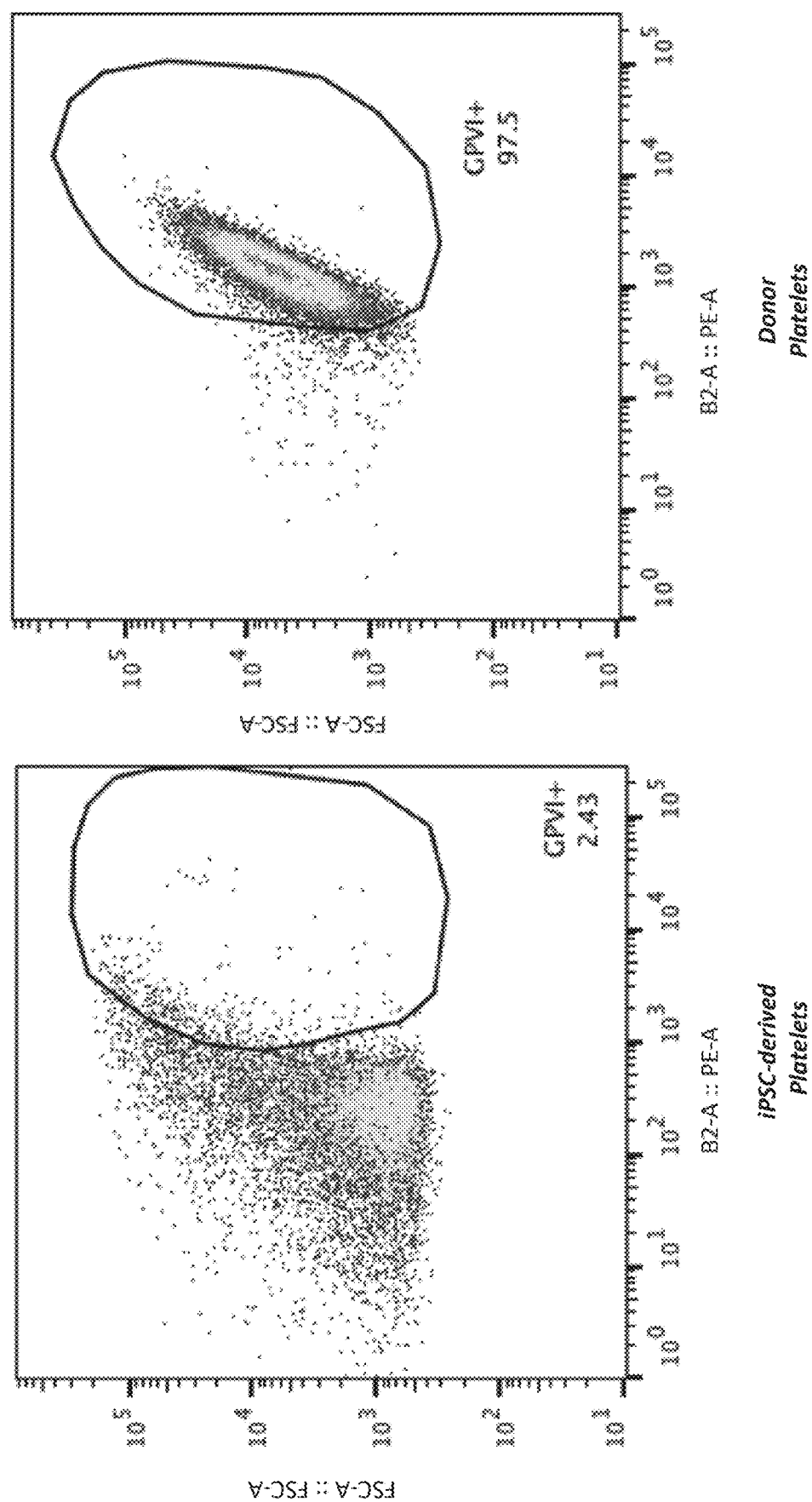
Figure 47:
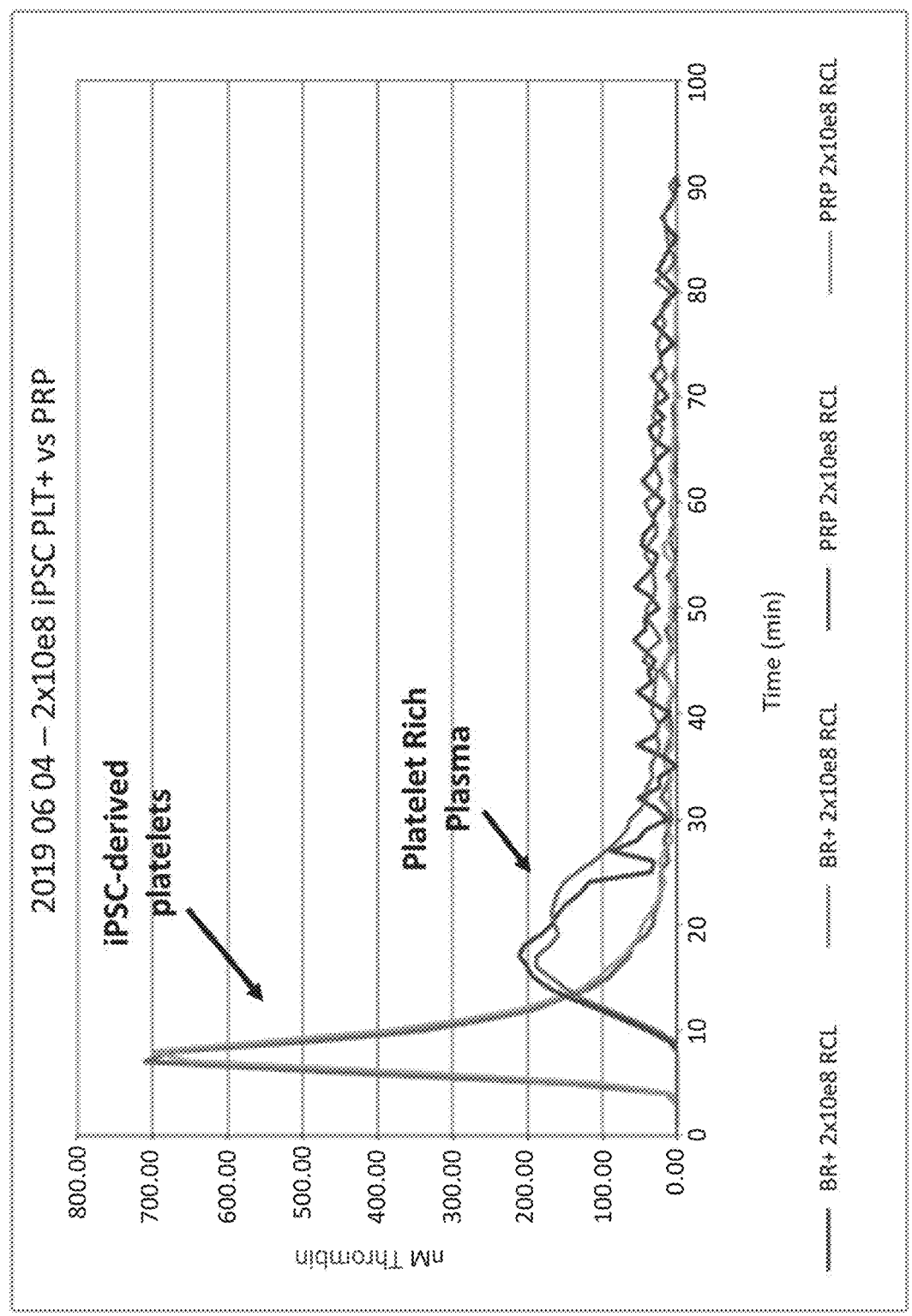
FIG. 47 is a graph of the thrombin generation by human iPSC derived platelets in aqueous buffer and primary platelets in plasma when treated with recombinant human tissue factor over time.
Figure 48B:
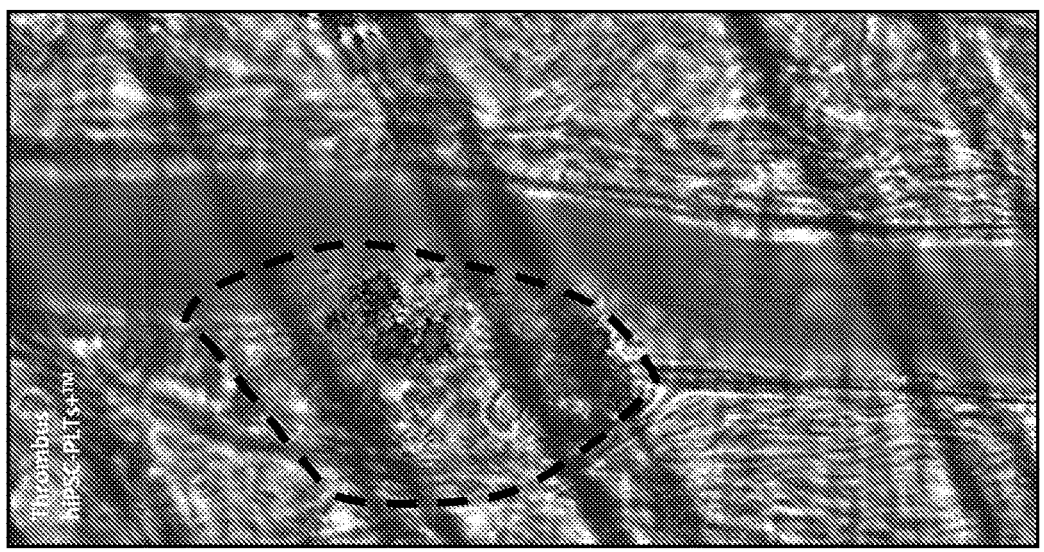
FIG. 48A and FIG. 48B are in vivo micrographs demonstrating that platelets from human iPSCs are incorporated into thrombi using a laser injury model for clot formation in a mouse cremaster arteriole.

In some embodiments, platelets are 2-5 µm in diameter (e.g., 3 µm in diameter) and preplatelets are greater than 5 µm in diameter (FIG. 43A) as determined, in this example, by flow cytometry using calibration beads of known size. These platelets are observed to stain negative for DRAQ, a DNA intercalating dye that detects genomic material, positive for CD61, a platelet specific surface receptor, and have varying degrees of viable cells (Calcein AM) and CD42a expression within the DRAQ-CD61+ gate. DRAQ-CD61+ cells from human iPSC derived platelets also stain negative for CD62p, a marker of platelet activation, suggesting that they are appropriately in a resting, quiescent state when harvested from culture (FIG. 45). In some iterations, PLTs differentiated from iPSC-derived megakaryocytes lack GPVI, a receptor that binds to collagen, as assessed in relation to human donor platelets (FIG. 46C) by antibody staining and subsequent flow cytometry. Additionally, PLTs differentiated from iPSC-derived megakaryocytes are efficient at generating thrombin when stimulated by tissue factor, with reduced lag time and a greater quantity of thrombin than what is observed in platelets from peripheral blood plasma in a thrombin generation assay (FIG. 47). Thrombin generation is quantified by the enzymatic conversion of a thrombin substrate to a fluorogenic molecule that can be detected by standard methods. The graph shows a rapid generation of thrombin as well as a rapid decrease in signal in the hiPSC-derived platelet sample. This effect is in stark contrast to the thrombin generation observed from peripheral blood isolated platelets over the course of 90 minutes Human iPSC derived platelets described herein are distinguished from primary, human donor derived platelets with respect to their lack of GPVI expression and greater thrombin generation over a more acute timeframe (FIGS. 46C-47). They behave similarly to human donor derived platelets in a murine, in vivo laser injury model of thrombus formation in the cremaster arteriole, in which both donor platelets (FIG. 48A) and human iPSC-derived platelets described herein (FIG. 48B) incorporate into a developing thrombus after infusion to proximal sites in the injured blood vessel. This data demonstrates unique features of the human iPSC-derived platelets that do not inhibit their quiescence when harvested from culture and their ability to contribute to thrombi in vivo (FIG. 48B). These data demonstrate a similar readout of platelet functionality with respect to hemostasis and thrombosis between primary platelets and human iPSC-derived platelets.

Additional methods for producing platelets are contemplated herein. For example, platelets can be produced using the methods disclosed in U.S. Pat. No. 9,763,984, the contents of which are incorporated herein by reference in their entirety. Briefly, the megakaryocytes of Stage 3 may be contacted by one or more of the following: thrombopoietin or hematopoietic expansion medium that comprises at least one reagent selected from: Stem Cell Factor (SCF), thrombopoietin (TPO), interleukin-11, at least one ROCK inhibitor, and heparin. In some embodiments, culture mediums and growth factors similar to those of Stage 3 can be used. The platelets produced by the instant methods can be loaded with a therapeutic agent or genetically modified to comprise an agent of interest.

3D Systems
Packed Bed Bioreactor

In some embodiments, a 3D scalable packed-bed bioreactor may be used for the production of one or more of preMKs, megakaryocytes, platelets, or megakaryocytes and platelets. In some embodiments, the packed bed bioreactor can be used for the Stage 1 and Stage 2 culture (FIG. 4). For example, the packed-bed reactor can be used for differentiation of PSCs to hemogenic endothelium cells, followed by the production of preMKs. The packed-bed reactor carriers may be either micro-sized or macro-sized and can be formed from biocompatible plastics, metals, glass, or natural materials, such as alginate. In some embodiments, the carriers are formed from PTFE in the shape of Raschig rings, for example 1 mm Raschig rings. In some embodiments, the carriers can be coated with a matrix as described above. In some embodiments, the carriers may be coated with Laminin, such as a recombinant human protein Laminin 521. In some embodiments, pluripotent cells can be seeded as clumps onto the carriers. In some embodiments, media can be removed and replaced with Stage 1 media, with daily media exchanges. In some embodiments, during Stage 1, the pluripotent cells can exhibit growth areas on the inside of the carriers in the packed bed reactor. In some embodiments, initial differentiation of pluripotent cells to hemogenic endothelium (i.e. Stage 1 of directed differentiation), as well as the further differentiation and release of preMKs (i.e. Stage 2 of directed differentiation) can occur in the same vessel. For example, a packed-bed bioreactor can comprise Laminin-521 coated macrocarriers seeded with pluripotent cells, for example iPSCs. The packed-bed can then be exposed to a continuous flow of media to enable Stage 1 differentiation to hemogenic endothelium. After percolating through the packed-bed, the media can be circulated through a conditioning chamber, where fresh media components can be added, and oxygen/CO2 concentrations can be adjusted via sparging or other means before the media can be recirculated to the cells.

At the completion of Stage 1, the media can be switched to allow Stage 2 differentiation and production and release of preMKs. Appropriately sized and shaped carriers such as the 1 mm Raschig rings can enable sufficient media flow and channel width to enable the released cells to percolate through the packed bed and out of the reactor for collection and cryostorage. In some embodiments, this design can decrease the shear forces experienced by the cells, can allow for efficient media usage due to its perfusion based design, and can enable the continuous collection of preMKs as they are released.

Self Aggregating Spheroids in Stir Tank Bioreactor

In some embodiments, certain process steps may be carried out using a scalable 3D solution, which can involve performing differentiations using self-aggregating spheroids suspended in stirred or shaken vessels. (FIG. 3). In some embodiments, such vessels can include low-adherent surfaces or non-adherent surfaces, that is, surfaces coated with hydrophilic or neutrally charged coatings to inhibit specific and nonspecific cell immobilization on the surface, forcing cells into a suspended state. Pluripotent cells can be dissociated into single cells and resuspended in pluripotent stem cell culture medium, for example, but not limited to, Essential 8 medium (ThermoFisher), StemFlex medium (Thermofisher), or NutriStem medium (Biological Industries). In some embodiments, the maintenance medium can be supplemented with a Rock Inhibitor, such as, for example, but not limited to, Y27632, H1152, or combination thereof. In some embodiments, the medium may include an epidermal growth family member, for example, Heregulin-beta-1. In some embodiments, the medium may include soluble Laminin, for example, recombinant Laminin 521. In some embodiments, the use of Heregulin-beta-1 is restricted to less than 24 hours (e.g., 18-22 hours). The pluripotent cells can then be incubated in a low adherent or non-adherent vessel and subjected to agitation in standard culture conditions (for example, 37C, 5% CO2, 20% O2). In some embodiments to provide agitation, the incubation vessel can be placed on an orbital shaker, or a shaker flask or spinner flask with constant agitation, or a controlled stir tank bioreactor can be used. Within 24 hours, the pluripotent cells can self-aggregate to form spheroids approximately 50-150 um in diameter. As agitation is paused, the spheroids can settle to the bottom of the vessel.

Media can then be partially or completely exchanged with Stage 1 differentiation media to promote the differentiation towards hemogenic endothelium, and agitation can be resumed, with incubation in hypoxic conditions (for example, 37° C., 5% CO2, 5% O2). Partial or complete media exchanges can be performed on a regular basis (for example, daily) during which time the spheroids can grow larger and develop characteristic structure and shape. For example, as shown in FIG. 22A, the spheroids can be cultured for a total of 6 days (4 days in 37° C., 5% CO2, 5% $O_2$, followed by 2 days in 37° C., 5% CO2, 20% O2). As shown in FIG. 29A, at day 6 the spheroids are larger, darker and have an irregular surface.

To transition to Stage 2, agitation can be paused and the spheroids can be allowed settle to the bottom of the vessel. Media can then be partially or completely exchanged with Stage 2 differentiation media to promote the differentiation and subsequent release of preMK-containing suspension cells. On a regular basis thereafter (for example, daily), suspension cells can be collected and a partial media exchange can be performed. The released Stage 2 cells can be harvested by pausing agitation, allowing the aggregates to settle to the bottom of the vessel, and collecting the medium along with the released suspension cells. Thereafter, a half-media change can be initiated by adding half the original volume of fresh Stage 2 medium on top of the adherent cell layer or 3D aggregates. An aliquot of the collected cells in medium can be removed for viable cell enumeration and biomarker analysis by flow cytometry. The remainder of the cells can then be concentrated by centrifugation, counter-centrifugal elutriation, acoustic separation, or other related technology. Following concentration, the half-media change can be completed by adding back half the original volume of conditioned media to the adherent cell layer or 3D aggregates. In some embodiments, additional volumes of fresh media can be added with the net effect of increasing the total volume of the culture. In some embodiments, specific media components can be spiked into the culture in lieu of replacement or addition of fresh Stage 2 media. The remainder of the supernatant can be discarded and the preMK-containing cell pellet can be stored or transitioned directly into Stage 3. In some embodiments, the preMK-containing cells can be collected over a 2- to 7-day period (e.g. 3 days) and additionally cultured in Stage 2 medium or other medium in a separate vessel. Once the final harvest is complete, the preMK-containing cells can be pooled together and stored or transitioned directly into Stage 3. In some embodiments, the preMKs can cryopreserved for storage. For example, the preMKs can be stored at at −180° C. in Cryostor 10 cryopreservation media.

Upon transition to static Stage 3 cultures, preMKs from 3D self-aggregating spheroid cultures can generate similar MK purities as preMKs from 2D culture systems. Furthermore, Stage 3 differentiation cultures generated from 3D self-aggregating spheroid cultures can contain cells that increased dramatically in size and are able to generate proplatelets, consistent with their identity as bona fide megakaryocytes.

Stage 5. Drug Loading in preMK, MK, Preplatelets, and Platelets

Figure 5:
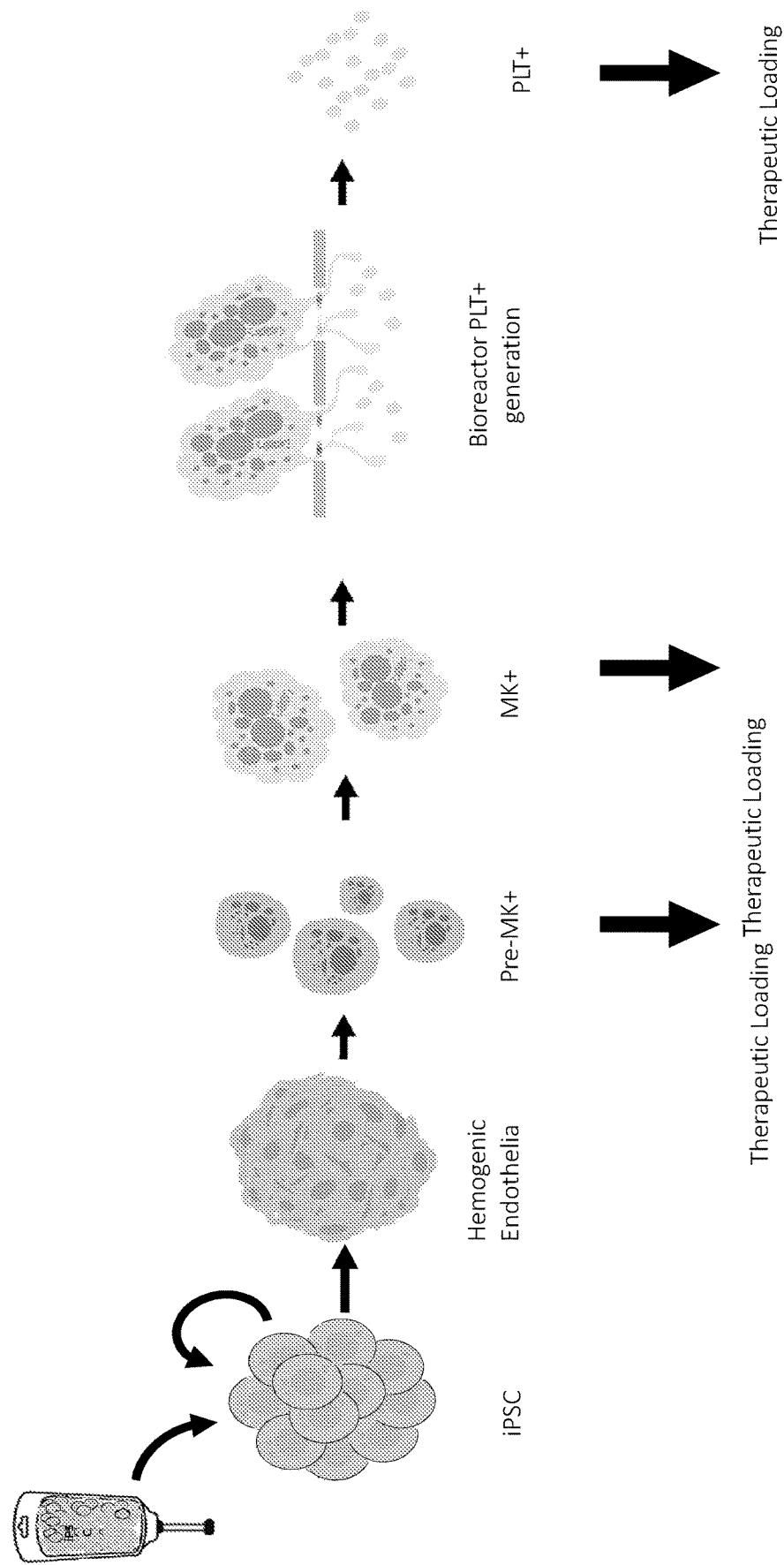
FIG. 5 depicts the process of iPSC directed differentiation to megakaryocytes and platelets from hiPSCs. The cells can be loaded with small molecules, biologics, nucleotides, and other types of drug molecules in the Pre-MK, MK, and PLT stages of differentiation.
Figure 6:
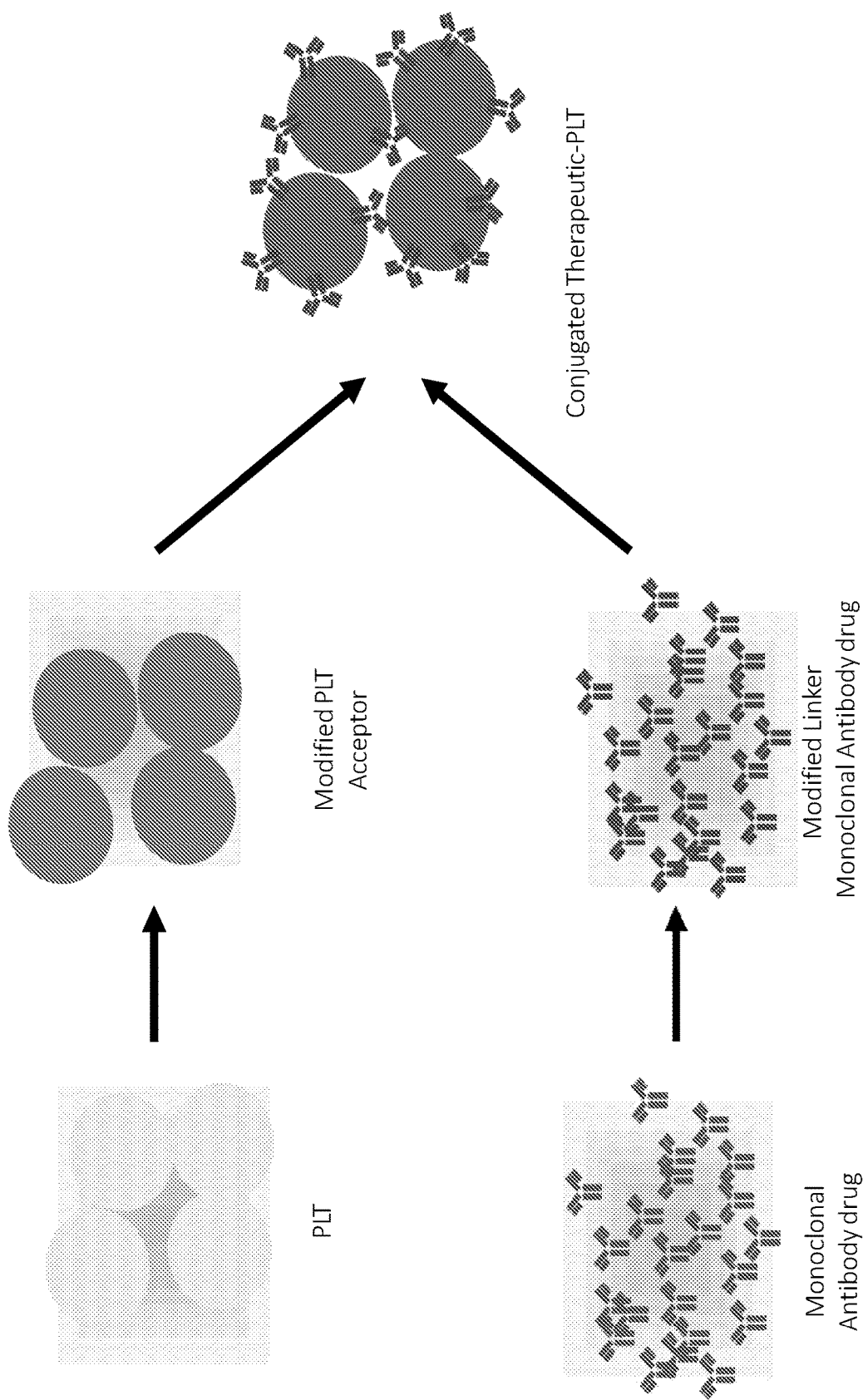
FIG. 6 is a schematic representation of a process for modifying platelets by covalent linkage of antibodies, in some embodiments, for therapeutic effect.
Figure 7:
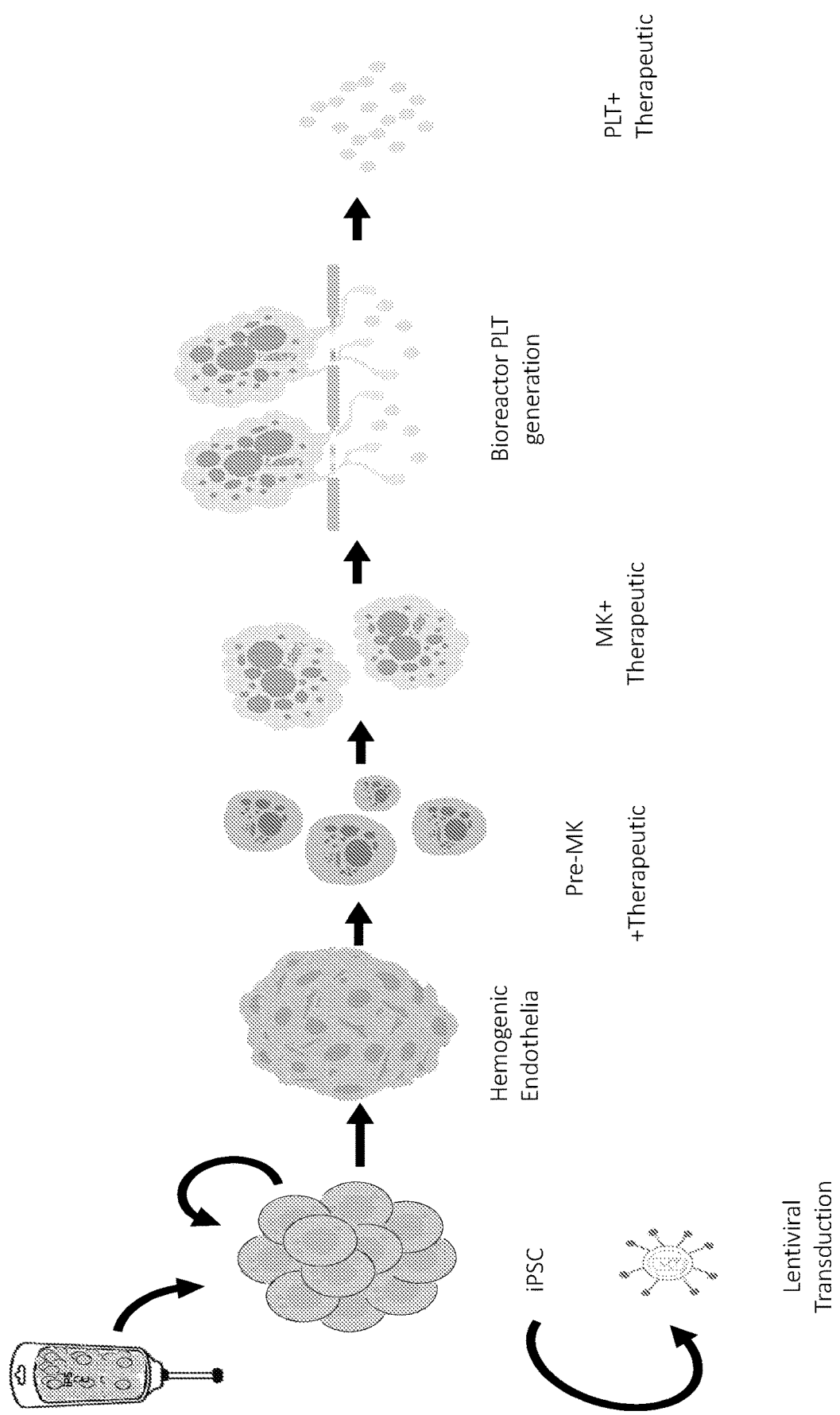
FIG. 7 depicts the process of iPSC genetic engineering to express a transgene for the production of biologic drugs, followed by directed differentiation to megakaryocytes and platelets from hiPSCs. Viral transduction and other methods for transgene delivery to hiPSCs can be used to cause stable expression of biologics that can be used as drugs with efficient transcription and translation in pre-MK, MK, and PLT.
Figure 9A:
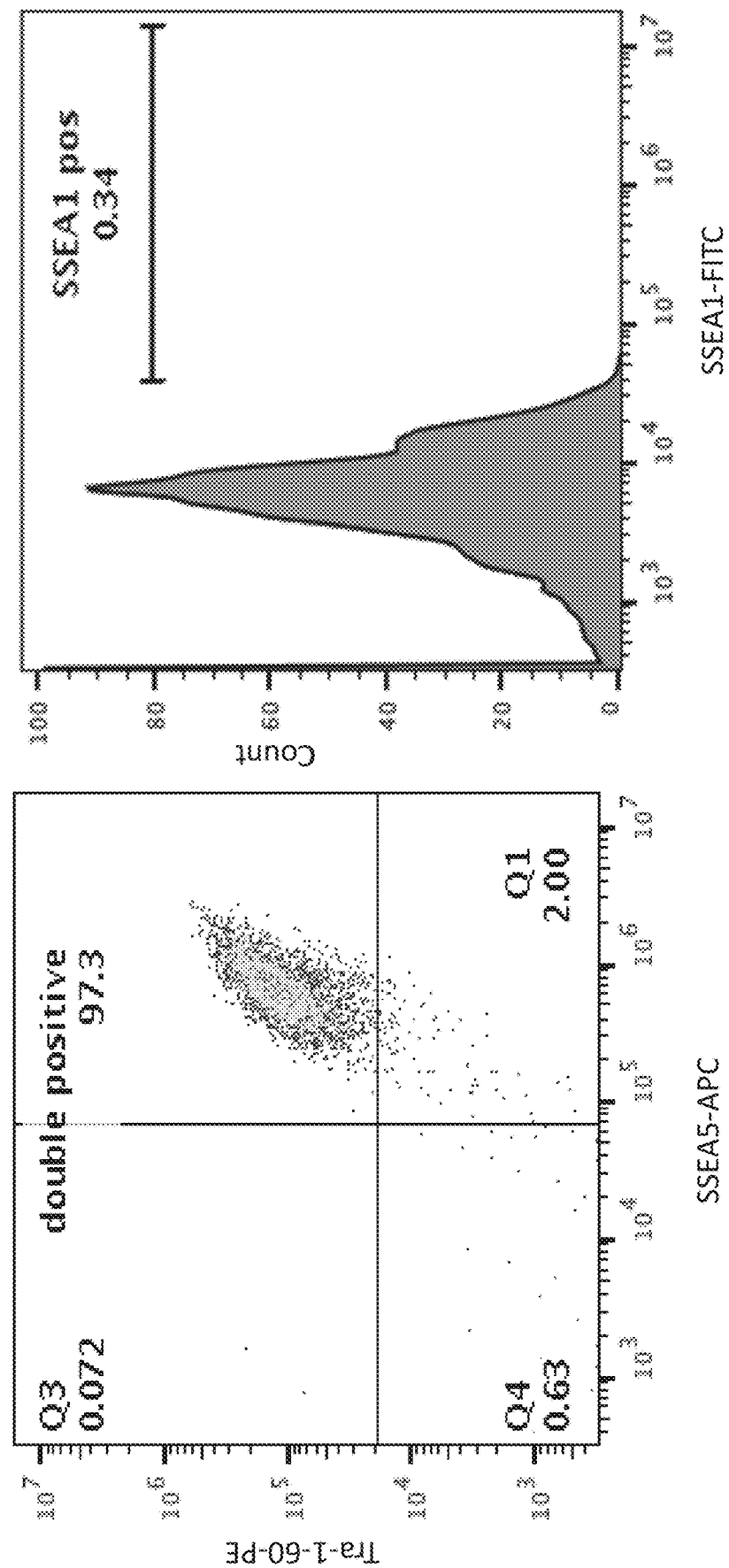
FIGS. 9A-9C depict flow cytometry data assessing expression of the pluripotency markers Tra-1-60, SSEA5, and the differentiation marker SSEA1 on iPSCs expanded on recombinant vitronectin using various growth medias.
Figure 9B:
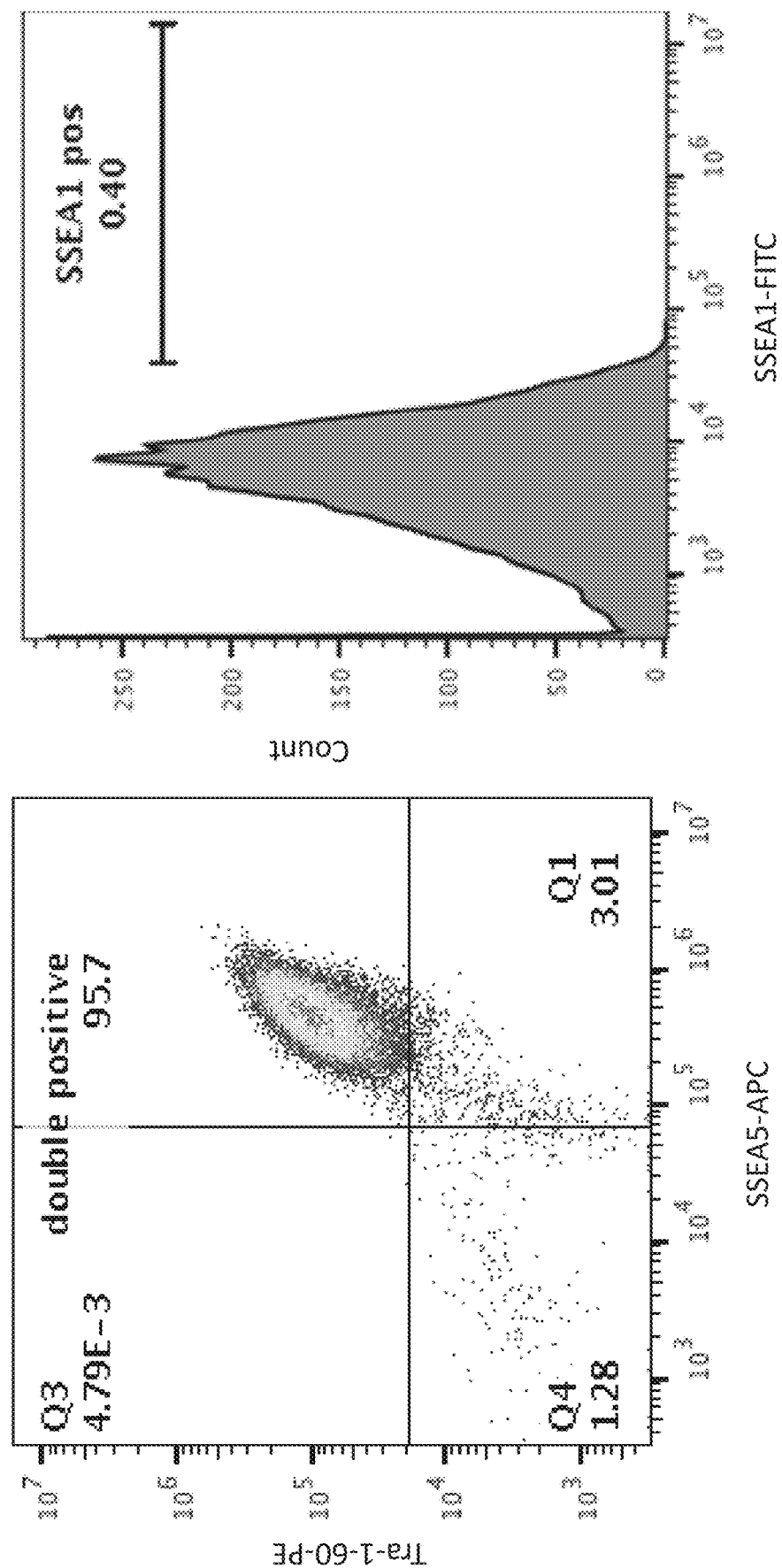
Figure 9C:
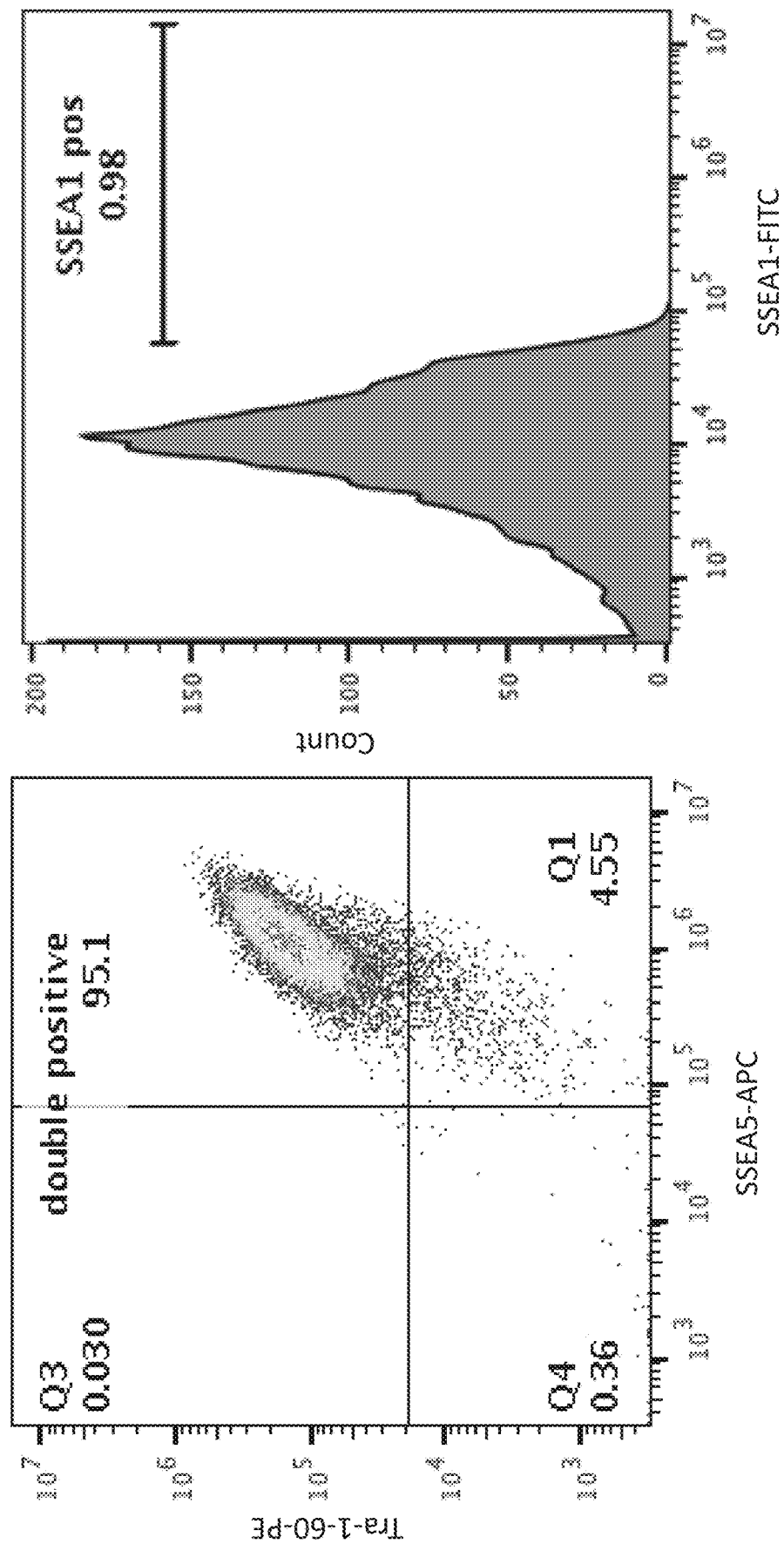

In reference to FIGS. 5-7, defined cell types (e.g., megakaryocyte progenitors from Stage 2, mature megakaryocytes from Stage 3, preplatelets from Stage 4, and platelets from Stage 4) can modified to carry or express a therapeutic composition. In some embodiments, these cell types are harvested for purposes of encapsulation and/or surface conjugation (among other methods) of a therapeutic composition. In some embodiments, the therapeutic composition comprises a small molecule, biologic, nucleic acid, or any other form of therapeutic, including those described below. Therapeutics of interest loaded into or onto any of the cell types can be used for various indications including (but not limited to) cancer, hematological diseases, liver diseases, lung diseases, and others.

In some embodiments, a target cell may be loaded with a therapeutic composition by incubating the therapeutic composition with a cellular suspension. The therapeutic, in some embodiments, is actively taken up by the cell (e.g., receptor dependent uptake), while in other embodiments, the therapeutic is passively taken up by the cell (e.g., receptor independent endocytosis, such as by embedding within the open canalicular system of the platelets and/or by passive diffusion). In some embodiments, the present methods do not require physical or chemical deformation of the cell for efficient uptake of therapeutic composition. Therapeutics taken up by the cells are stored within the cell, for example, in the cell's secretory granules.

In some embodiments, a therapeutic composition is conjugated to the surface of a cell (i.e., megakaryocyte progenitor, mature megakaryocyte, preplatelet, and platelet). Conjugation, in some embodiments, requires functionalization of the surface of the cell using techniques known to those of skill in the art. In some embodiments, the therapeutic composition will comprise a reactive moiety that is able to bind or otherwise interact with the surface of the cell or a functional group on the surface of the cell.

In some embodiments, the iPSCs may be genetically engineered to express a transgene for the production of a therapeutic polynucleotide or polypeptide, followed by directed differentiation to megakaryocytes and platelets from iPSCs. Viral transduction and other methods for transgene delivery to iPSCs can be used to cause stable expression of biologics that can be used as drugs with efficient transcription and translation in pre-MK, MK, and PLT.

Megakaryocytes and Platelets

In some embodiments, the present disclosure provides a megakaryocytic progenitor, a megakaryocyte, preplatelet, proplatelet or a platelet derived in vitro from a PSC cell or cell line. According to aspects of the present disclosure, the megakaryocytic progenitor, a megakaryocyte, preplatelet, proplatelets or a platelet derived from a PSC cell or cell line are produced using the method of U.S. Pat. No. 9,763,984 or the bioreactor as disclosed in International Application No. PCT/US2018/021354, which are incorporated herein by reference in their entireties.

In some embodiments, the present disclosure provides an isolated population of cells comprising the megakaryocyte or megakaryocytic progenitor.

In some embodiments, the present disclosure provides a composition containing a megakaryocyte or megakaryocytic. In some embodiments of the present disclosure, the composition comprising megakaryocyte, megakaryocytic progenitor or products thereof is disclosed.

According to some embodiments of the present disclosure, the megakaryocyte, megakaryocytic progenitor or products thereof are homogenous in shape, size and/or phenotype. It should be appreciated that the megakaryocyte, megakaryocytic progenitor or products thereof of the present disclosure may comprise a variability in biomarker expression, size, ploidy, number and purity that is characteristically different than the variability in corresponding human cells. In some embodiments, such variability can be significantly lower. In some embodiments, the cell populations may be created to have a desired variability, which may be lower or higher than that of the naturally-occurring cells.

In some embodiments, megakaryocytic progenitors (pre-MKs) are characterized by the expression of the markers CD43 and CD41, and the lack of CD14 (i.e. $CD14^-$, $CD41^+$, $CD43^+$). Additional expression of CD42b may indicate that the megakaryocytic progenitor is in the process of final maturation towards mature megakaryocytes. In certain embodiments, megakaryocytic progenitors generated in differentiation cultures are non-adherent and may float freely in the culture medium.

In some embodiments, the instant megakaryocytes are one or more of $CD42a^+$, $CD42b^+$, $CD41^+$, $CD61^+$, GPVI+, and $DNA^+$. In some embodiments, the instant megakaryocytes are one or more $CD42a^+$, $CD42b^+$, $CD41^+$, $CD61^+$, and $DNA^+$. In some embodiments, the instant megakaryocytes are one or more of $CD42b^+$, $CD61^+$, and $DNA^+$. In some embodiments, the instant megakaryocytes are one or more of $CD42a^+$, $CD61^+$, and $DNA^+$. In some embodiments, the instant megakaryocytes are one or more of $CD42a^+$, $CD41^+$, and $DNA^+$. In some embodiments, the instant megakaryocytes are one or more of $CD42b^+$, $CD41^+$, $CD61^+$, and $DNA^+$. In some embodiments, the instant megakaryocytes are one or more of $CD42b^+$, $CD42a^+$, $CD61^+$, and $DNA^+$. In some embodiments, the instant megakaryocytes are one or more of $CD42b^+$, $CD42a^+$, $CD41^+$, and $DNA^+$. In some embodiments, the megakaryocyte is $CD41^+CD61^+CD42b^+GPVI^+$. In some embodiments, the megakaryocyte is $CD41^+CD61^+CD42a^+GPVI+$.

In some embodiments, the instant megakaryocyte is $CD61^+$ and $DNA^+$ and has a diameter of about 10-50 µm. In some embodiments, the megakaryocytes produced by the methods described herein have an average size between 10 and 20 µm, between 11 and 19 µm, between 12 and 18 µm, between 13 and 17 µm, between 14 and 16 µm, between 14 and 15 µm. In some embodiments, the megakaryocytes produced by the methods described herein have an average size of 14.5 µm. In some embodiments, the instant megakaryocyte has a diameter of about 10-20 µm. In some embodiments, the instant megakaryocyte has a diameter of about 10-30 µm. In some embodiments, the instant megakaryocyte has a diameter of about 10-40 µm. In some embodiments, the instant megakaryocyte has a diameter of about 10-50 µm. In some embodiments, the instant megakaryocyte has a diameter of about 20-40 µm. In some embodiments, the instant megakaryocyte has a diameter of about 25-40 µm.

In some embodiments, the instant megakaryocytes produced by the methods described herein have a ploidy of 2N-16N. In some embodiments, the instant megakaryocyte has a ploidy of at least 4N, 8N, or 16N. In some embodiments, instant megakaryocytes have ploidy 4N-16N. In some embodiments, the instant megakaryocytes produced by the methods described herein are 16%+/−11.4% of CD61+ cells at 72 hours of Stage 3 culture with higher than 4N DNA.

In some embodiments, at least 50% of the megakaryocyte population produced by the methods described herein is $CD61^+$ and $DNA^+$, and has a ploidy of 2N to 16N. For example, the megakaryocytes (i.e. beta-1-tubulin positive Stage 3 cells) from a representative iPSCs differentiation culture ranged in size from about 9 µm to about 27 µm, with a median of 15 µm (FIG. 40B). This average size compares similarly with 'normal' megakaryocytes from various bone marrow sources (FIG. 40C). In some embodiments, the isolated population of cells or the composition contains at least 50% of $CD42b^+CD61^+DNA^+$ cells. In some embodiments, the isolated population of cells or the composition contains at least 55% of $CD42b^+CD61^+DNA^+$ cells. In some embodiments, the isolated population of cells or the composition contains at least 65% of $CD42b^+CD61^+DNA^+$ cells. In some embodiments, the isolated population of cells or the composition contains at least 60% of $CD42b^+CD61^+DNA^+$ cells. In some embodiments, the isolated population of cells or the composition contains at least 70% of $CD42b^+CD61^+DNA^+$ cells. In some embodiments, the isolated population of cells or the composition contains at least 75% of $CD42b^+CD61^+DNA^+$ cells. In some embodiments, the isolated population of cells or the composition contains at least 80% of $CD42b^+CD61^+DNA^+$ cells.

In some embodiments, the isolated population of cells or the composition contains at least 85% of $CD42b^+CD61^+DNA^+$ cells. In some embodiments, the isolated population of cells or the composition contains at least 90% of $CD42b^+CD61^+DNA^+$ cells. In some embodiments, the isolated population of cells or the composition contains at least 95% of $CD42b^+CD61^+DNA^+$ cells. In some embodiments, the isolated population of cells or the composition contains at least 98% of $CD42b^+CD61^+DNA^+$ cells.

In some embodiments, the isolated population of cells or the composition contains at least 50% of $CD42b^+CD41^+CD61^+DNA^+$ cells. In some embodiments, the isolated population of cells or the composition contains at least 55% of $CD42b^+CD41^+CD61+DNA^+$ cells. In some embodiments, the isolated population of cells or the composition contains at least 65% of $CD42b^+CD41^+CD61^+DNA^+$ cells. In some embodiments, the isolated population of cells or the composition contains at least 60% of $CD42b^+CD41+CD61^+DNA^+$ cells. In some embodiments, the isolated population of cells or the composition contains at least 70% of $CD42b^+CD41^+CD61^+DNA^+$ cells. In some embodiments, the isolated population of cells or the composition contains at least 75% of $CD42b^+CD41^+CD61^+$ cells. In some embodiments, the isolated population of cells or the composition contains at least 80% of $CD42b^+CD41^+CD61^+DNA^+$ cells. In some embodiments, the isolated population of cells or the composition contains at least 85% of $CD42b^+CD41^+CD61^+DNA^+$ cells. In some embodiments, the isolated population of cells or the composition contains at least 90% of CD42b$^+$CD41$^+$CD61$^+$DNA$^+$ cells. In some embodiments, the isolated population of cells or the composition contains at least 95% of CD42b$^+$CD41$^+$CD61$^+$DNA$^+$ cells. In some embodiments, the isolated population of cells or the composition contains at least 98% of CD42b$^+$CD41$^+$CD61$^+$DNA$^+$ cells.

In some embodiments, the isolated population of cells or the composition contains at least 50% of CD42b$^+$CD42a$^+$CD61$^+$DNA$^+$ cells. In some embodiments, the isolated population of cells or the composition contains at least 55% of CD42b$^+$CD42a$^+$CD61+DNA$^+$ cells. In some embodiments, the isolated population of cells or the composition contains at least 65% of CD42b$^+$CD42a$^+$CD61$^+$DNA$^+$ cells. In some embodiments, the isolated population of cells or the composition contains at least 60% of CD42b$^+$CD42a+ CD61$^+$DNA$^+$ cells. In some embodiments, the isolated population of cells or the composition contains at least 70% of CD42b$^+$CD42a$^+$CD61$^+$DNA$^+$ cells. In some embodiments, the isolated population of cells or the composition contains at least 75% of CD42b$^+$CD42a$^+$CD61$^+$DNA$^+$ cells. In some embodiments, the isolated population of cells or the composition contains at least 80% of CD42b$^+$CD42a$^+$CD61$^+$DNA$^+$ cells. In some embodiments, the isolated population of cells or the composition contains at least 85% of CD42b$^+$CD42a$^+$CD61$^+$DNA$^+$ cells. In some embodiments, the isolated population of cells or the composition contains at least 90% of CD42b$^+$CD42a$^+$CD61$^+$DNA$^+$ cells. In some embodiments, the isolated population of cells or the composition contains at least 95% of CD42b$^+$CD42a$^+$CD61$^+$DNA$^+$ cells. In some embodiments, the isolated population of cells or the composition contains at least 98% of CD42b$^+$CD41$^+$CD61$^+$DNA$^+$ cells.

In some embodiments, the isolated population of cells or the composition contains at least 50% megakaryocytes having ploidy of 4N or greater. In some embodiments, at least 50% megakaryocytes have ploidy 4N-16N. In some embodiments, at least 60% megakaryocytes have ploidy 4N-16N. In some embodiments, at least 70% megakaryocytes have ploidy 4N-16N. In some embodiments, at least 80% megakaryocytes have ploidy 4N-16N. In some embodiments, at least 90% megakaryocytes have ploidy 4N-16N. In some embodiments, the isolated population of cells or composition contains megakaryocytes having a mean ploidy of 4N.

In some embodiments, the isolated population of cells or the composition contains a proplatelet, preplatelet or platelet generated from a megakaryocyte of the present disclosure. In some embodiments, the proplatelet, preplatelet or platelet is a CD42b+CD61$^+$DNA$^-$ cell. In some embodiments, the megakaryocyte is produced in vitro by differentiation of hiPSC cell or cell line.

In some embodiments, the megakaryocytes produced by the methods described herein comprise one or more of the following: (a) content of MK granules by immunofluorescence microscopy: PF4 and VFW for alpha-granules, LAMP-1 and serotonin for dense-granules; (b) gene expression data: Oct4−, Nanog−, Sox2−, Zfp42−, Zfpm1+, Nfe2+, Runx1+, Meis1+, Gata1+; (c) have low/no fibrinogen, serotonin, and LDL, and (d) can uptake fibrinogen, serotonin, and LDL when incubated with plasma.

Figure 42:
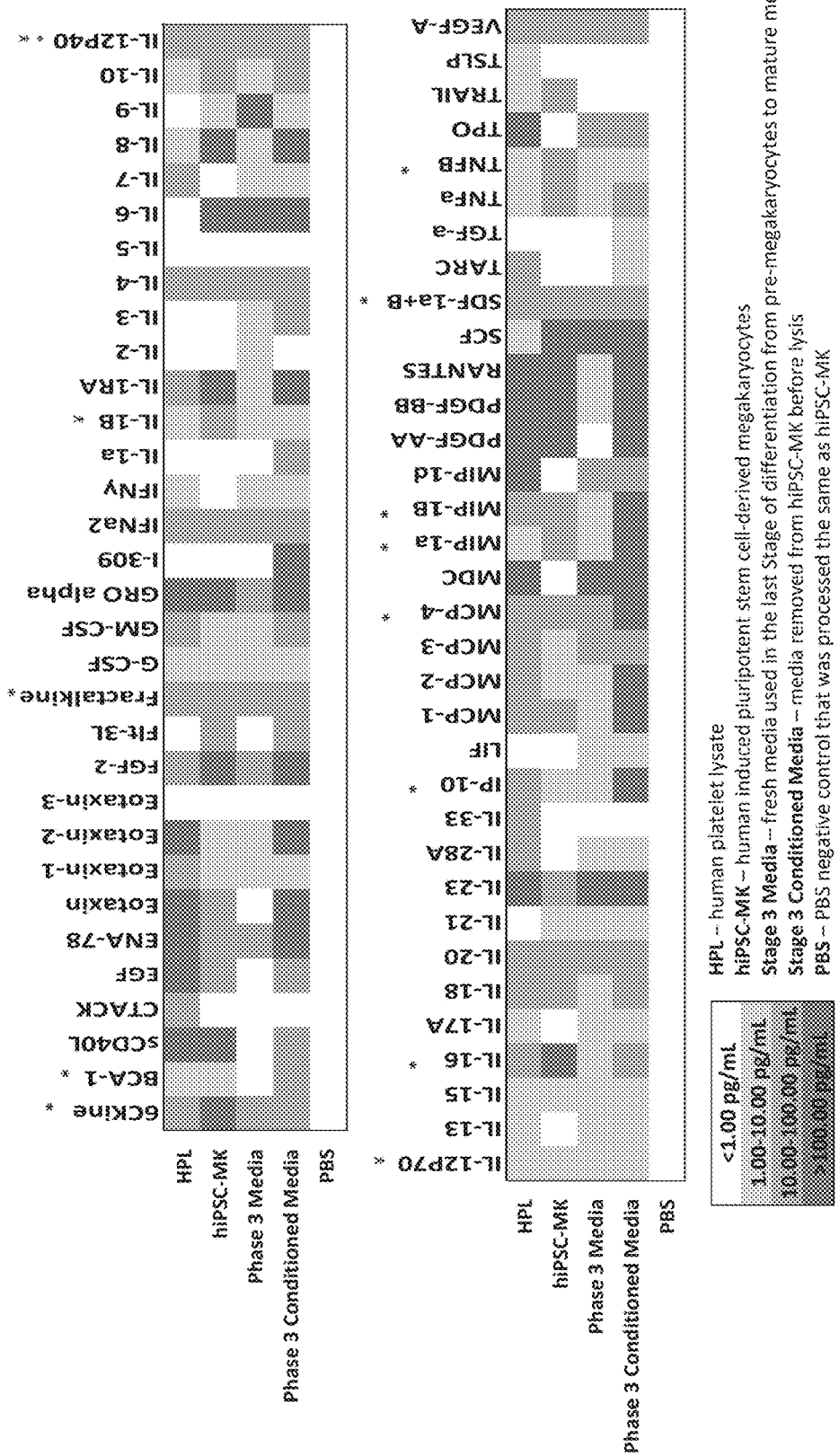
FIG. 42 provides a comparison of presence or absence and concentration range of various factors in hiPSC-MK lysate of megakaryocytes derived by a method of the present disclosure and certain controls. "*" denotes proteins measured in hiPSC-MK that were not previously described in megakaryocytes or platelets; "Ψ" denotes inflammatory cytokines.

In some embodiments, the megakaryocytes produced by the methods described herein have a characteristic expression profile of growth factors, cytokines, chemokines, and related factors (FIG. 42). In some embodiments, the present disclosure provides a composition or pharmaceutical composition comprising the instant megakaryocytes that can include factors such as platelet derived growth factor isoforms PDGF-AA or PDGF-BB, vascular endothelial growth factor (VEGF), epidermal growth factor (EGF), basic fibroblast growth factor (FGF-2), hematopoietic growth factors Flt3L, G-CSF, GM-CSF, interleukins (IL-1RA, IL-8, or IL-16), CXC chemokine family members CXCL1 (GRO alpha) or CXCL12 (SDF-1), TNF superfamily members sCD40L or TRAIL, or CC chemokine family members CCL5 (RANTES), CCL11 (Eotaxin-1), CCL21 (6CKine) or CCL24 (Eotaxin-2). In some embodiments, the present disclosure provides a composition or pharmaceutical composition comprising a lysate of instant megakaryocytes. Such lysates can be prepared by any methods known in the art, such as by breaking down of the membrane of preMKs or MKs by viral, enzymic, or osmnotic mechanisms that compromise its integrity. The lysates, in some embodiments, may include additional agents or be prepared in different compositions (liquid, paste etc.) depending on the needs of specific applications. In some embodiments, such compositions can include factors such as platelet derived growth factor isoforms PDGF-AA or PDGF-BB, vascular endothelial growth factor (VEGF), epidermal growth factor (EGF), basic fibroblast growth factor (FGF-2), hematopoietic growth factors Flt3L, G-CSF, GM-CSF, interleukins (IL-1RA, IL-8, or IL-16), CXC chemokine family members CXCL1 (GRO alpha) or CXCL12 (SDF-1), TNF superfamily members sCD40L or TRAIL, or CC chemokine family members CCL5 (RANTES), CCL11 (Eotaxin-1), CCL21 (6CKine) or CCL24 (Eotaxin-2).

In some embodiments, the instant platelets are one or more of CD61+, DRAQ−, Calcein AM+, CD42a+, and CD62P− (in resting state). In some embodiments, the instant platelets are of CD61+, DRAQ−, Calcein AM+, and CD62P−. In some embodiments, the instant platelets are one or more of CD61+, DRAQ−, Calcein AM+, CD42a+, and CD62P+(in activated state). In some embodiments, the instant platelets are CD61+, DRAQ−, Calcein AM+, and CD62P+ In some embodiments, the instant platelets are distinct from donor platelets in that they do not express GPVI on the cell surface, but are still one or more of CD61+, DRAQ−, Calcein AM+, CD42a+, and CD62P− (in resting state) and/or one or more of CD61+, DRAQ−, Calcein AM+, CD42a+, and CD62P+(in activated state). In some embodiments, the instant platelets are distinct from donor platelets in that they do not express GPVI on the cell surface, but are still CD61+, DRAQ−, Calcein AM+, CD42a+, and CD62P− (in resting state) and/or CD61+, DRAQ−, Calcein AM+, CD42a+, and CD62P+(in activated state). In some embodiments, the instant platelets are distinct from donor platelets in that they do not express GPVI on the cell surface, but are still CD61 and CD62P+. In some embodiments, the instant platelets have a diameter of about 1 μm. In some embodiments, the instant platelets have a diameter of about 2 μm. In some embodiments, the instant platelets have a diameter of about 3 μm. In some embodiments, the instant platelets have a diameter of about 4 μm. In some embodiments, the instant platelets have a diameter of about 5 μm. In some embodiments, instant proplatelets are 5 μm or greater. In some embodiments, instant platelets contain secretory granules, the open canalicular system, and the dense tubular system (FIG. 44A). In some embodiments, instant platelets contain characteristic β1-tubulin rings (FIG. 44B). In some embodiments, instant platelets activate on glass surfaces and display filopodia and lamellipodia (FIG. 44B). In some embodiments, the instant platelets are distinct from donor platelets in that they preferentially generate thrombin in a more acute time window upon stimulation from procoagulants (FIG. 47). In some embodiments, the instant platelets behave similarly to donor platelets with respect to incorporation into thrombi in injured cremaster arterioles in mice (FIG. 48).

In some aspects, compositions are provided that comprise platelets that are one or more of CD61+, DRAQ−, Calcein AM+, CD42a+, and CD62P− (in resting state). In some embodiments, the instant platelets are one or more of CD61+, DRAQ−, Calcein AM+, CD42a+, and CD62P+(in activated state). In some embodiments, the compositions comprise platelets that do not express GPVI.

Megakaryocytic Progenitors, Megakaryocytes, Proplatelet, Preplatelets and Platelets as Drug Delivery Vehicles Platelets circulate in the bloodstream and touch every organ in the body, providing them with the potential to serve as part of a versatile, customizable, and targetable drug delivery system. Moreover, because of their immunomodulatory and angiogenic functions, platelets are actively recruited by tumors to aid in immune evasion and support their growth and metastasis. According to some aspects of the present disclosure, the ex vivo PSC-derived megakaryocytic progenitors, megakaryocytes, proplatelets, preplatelets, or platelets described herein can be used as vehicles for delivering a therapeutic composition, such as a drug, small molecule, biologic (such as a protein) or a similar therapeutic agent. The benefits of this type of drug delivery include, but are not limited to, the ability to deliver molecules to tissues that are traditionally hard to target due to limitations imposed by permeability or retention of the drug; localization and concentration of the drug to the targeted tissue; a reduced need to treat a patient systemically by hiding the drug in megakaryocyte/preplatelet/platelet secretory granules until selective release at therapeutic target; and to avoid unwanted toxicity or immunogenicity. In some embodiments, this type of drug delivery may also lower the dosage needed to achieve a desired therapeutic outcome, and to decrease systemic toxicity.

The terms "therapeutic composition," "drug," "therapeutic," and "agent," are used interchangeably and refer to any small molecule chemical compound, antibody, nucleic acid molecule, polypeptide, or any other biologic or fragments thereof. In some embodiments, the therapeutic composition can be an agent that binds a target of interest, an antibody against a target of interest, an agonist or antagonist of a target of interest, a peptidomimetic of a target of interest, a small RNA directed against or a mimic of a target of interest, and the like. In some embodiments, therapeutic composition can modulate the expression and/or activity of target of interest.

In some embodiments, the therapeutic composition is a polypeptide or a small molecule. For example, the polypeptide can be atezolizumab, a fully humanized monoclonal antibody. Additional polypeptides can be ipilimumab, bevacizumab, cetuximab, or trastuzumab. Small molecule examples include, without limitation, aripiprazole, esomeprazole, or rosuvastatin.

In some embodiments, the therapeutic composition comprises an anti-angiogenic agent or chemotherapeutic agent suitable to treat, inhibit, and/or prevent cancer. Examples of anti-angiogenic agents include, without limitation, doxorubicin, a DNA damaging agent. Additional examples include vincristine, irinotecan, and paclitaxel.

In some embodiments, the therapeutic composition comprises a growth factor, including, but not limited to VWF, keratinocyte growth factor, coagulation factors (e.g. FVII, FVIII, FIX) epidermal growth factor, or hair growth factor. FVIIa is an activated clotting factor which has shown benefit in patients with uncontrollable bleeding. To achieve this effect, FVIIa is be administered systemically at high concentration which has cost implications and has been shown to lead to thrombotic complications in some patients. Megakaryocytic progenitors, megakaryocytes, preplatelets, or platelets generated according to the process of the present disclosure supercharged with FVIIa may markedly improve hemostasis and survival in the acute period following injury. Factor VIII participates in blood coagulation; it is a cofactor for Factor IXa which, in the presence of Ca2+ and phospholipids, forms a complex that converts factor X to the activated factor Xa. In humans, factor VIII is encoded by the F8 gene. Defects in this gene result in hemophilia A, a recessive X-linked coagulation disorder. In response to injury, coagulation factor VIII is activated and separates from von Willebrand factor to become FVIIIa. Factor IX is a serine protease in the coagulation system. Deficiency of this protein causes hemophilia B. Factor IX is produced as a zymogen, an inactive precursor. It is processed to remove the signal peptide, glycosylated and then cleaved by factor XIa (of the contact pathway) or factor VIIa (of the tissue factor pathway) to produce a two-chain form where the chains are linked by a disulfide bridge. When activated into factor IXa, in the presence of Ca2+, membrane phospholipids, and a Factor VIII cofactor, it hydrolyses one argininre-isoleucine bond in factor X to form factor Xa.

In some embodiments, the therapeutic composition is a chemokine or growth factor, such as platelet derived growth factor isoforms (PDGF-AA, -AB and -BB), transforming growth factor-b (TGF-b), insulin-like growth factor-1 (IGF-1), brain derived neurotrophic factor (BDNF), vascular endothelial growth factor (VEGF), epidermal growth factor (EGF), basic fibroblast growth factor (bFGF or FGF-2), hepatocyte growth factor (HGF), connective tissue growth factor (CTGF) and bone morphogenetic protein 2, -4 and -6 (BMP-2, -4, -6).

In some embodiments, the therapeutic composition is a protein. In some embodiments, the protein is a cytokine, such as, for example, Interleukin 1-beta, Interleukin 2, or Interleukin 12. In some embodiments, the protein is an antibody protein. In some embodiments, the antibody is Atezolizumab or Ipilimumab.

Proplatelets, preplatelets and platelets store bioactive factors in secretory granules, which they acquire from megakaryocytes. In some embodiments, the proplatelets, preplatelets and platelets of the present disclosure can be modified to store, or otherwise carry, a therapeutic composition.

In some embodiments, platelets can be engineered to express proteins on their surface, or otherwise tagged with proteins on their surface, or engineered to express or cultured to 'take-up' various antibodies or molecules into their secretory granules. Such engineered platelets can be used to transport a therapeutic composition and directed to to the desired tissue (or therapeutic target). In some embodiments, genetic engineering can occur at the PSC level or at the megakaryocytic progenitor level, and expression conditionally regulated to become expressed at the megakaryocytic progenitor, megakaryocytes, proplatelets, preplatelets, or platelets.

Some aspects of the present disclosure relate to modified megakaryocytes, proplatelets, preplatelets or platelets expressing desired characteristics for targeted applications. These tools can be leveraged to generate the specialized outcomes that personalized medicine approaches promise, without the drawbacks that have prevented their commercial implementation (high cost, time intensive, and inability to scale products). Rather than generating custom hPSC lines from individual donors, it is preferential to develop a platform that utilizes cGMP-compliant hPSC lines that are optimized for therapeutic product manufacture. Genetic control of the hPSC lines can then be applied to generate designer products for targeted therapeutics and recipients.

In some embodiments, the modified megakaryocytic progenitors, megakaryocytes, proplatelets, preplatelets, or platelets express a protein (including a polypeptide, peptide) of interest. In some embodiments, the modified megakaryocytic progenitors, megakaryocytes, proplatelets, preplatelets, or platelets express high level of a protein (including a polypeptide, or peptide) of interest. In some embodiments, the instant megakaryocytic progenitors, megakaryocytes, proplatelets, preplatelets, or platelets are genetically modified to reduce expression or suppress the expression of a protein (including a polypeptide or peptide) of interest. In some embodiments, the instant megakaryocytic progenitors, megakaryocytes, proplatelets, preplatelets, or platelets are genetically modified to express or overexpress a protein (including a polypeptide or peptide) of interest, to reduce expression or suppress the expression of a protein (including a polypeptide or peptide) of interest or any combinations of the foregoing. For example, in some embodiments, the modified megakaryocytic progenitors, megakaryocytes, proplatelets preplatelets, or platelets express high levels of clotting factors, e.g. Factor VIIa, VIII, IX, or VWF, in their granules, thereby enhancing clot formation at the site of damage without risk of systemic hypercoagulation. In some embodiments, the modified megakaryocytic progenitors, megakaryocytes, proplatelets, preplatelets, or platelets are targeted for trauma, increasing the effectiveness of platelet transfusion during the first "Golden Hour" following severe traumatic injury. Another potential application for engineered instant megakaryocytic progenitors, megakaryocytes, preplatelets, or platelets is in the treatment of fetal and neonatal alloimmune thrombocytopenia (FNAIT). In this condition, fetal platelets expressing a human platelet antigen (HPA) that their mother does not express are targeted by the mother's immune system, leading to fetal thrombocytopenia and serious potential complications (including fetal intracranial hemorrhage). In some embodiments, this condition is treated using the instant megakaryocytic progenitors, megakaryocytes, proplatelets, preplatelets, or platelets that have been engineered with a single base pair change, such that HPA (negative) platelets or microparticles are administered to a HPA positive child after delivery by HPA-negative women, preventing the HPA-associated clearance.

In some embodiments, the modified megakaryocytic progenitors, megakaryocytes, proplatelets, preplatelets, or platelets deliver growth factors. In some embodiments, the modified megakaryocytic progenitors, megakaryocytes, proplatelets, preplatelets, or platelets loaded or expressing growth factors are used for cell culture, tissue regeneration, wound healing, cosmeceuticals, and hemostatic bandages.

In some embodiments, the instant megakaryocytic progenitors, megakaryocytes, proplatelets, preplatelets, or platelets are modified to deliver immune-checkpoint inhibitor drugs such as, but not limited to, anti-PDL1, anti-PD1, anti-VEGF, anti-CD20 and anti-CTLA4, or anti-cancer drugs like anti-CCR4, or anti-PI3K. In some embodiments, the instant megakaryocytic progenitors, megakaryocytes, proplatelets, preplatelets, or platelets are modified to deliver cytokines such as, but not limited to, interleukin 1 beta, Interleukin 2 or Interleukin 12.

Loading of iPSC-Derived Megakaryocytic Progenitors, Megakaryocytes, Proplatelets, Preplatelets or Platelets with Therapeutic Composition In reference to FIG. 5 and FIG. 6, in some embodiments, a therapeutic composition can be loaded into or onto megakaryocytic progenitors, megakaryocytes, proplatelets, preplatelets or platelets derived from an iPSC according to the present disclosure.

In some embodiments, as shown in FIG. 5, the instant megakaryocytic progenitors, megakaryocytes, proplatelets, preplatelets, or platelets can be loaded with a therapeutic composition. For example, a small molecule can be loaded into these cells by co-incubating the small molecule with the cells in aqueous solution (FIG. 5). In some embodiments, the therapeutic composition is present in the solution or dialysis cassette at a 1-200 μM concentration (e.g., 100 μM) along with a cellular suspension comprising $10^5$ to $10^7$ cells, for example $10^6$ cells. The therapeutic composition and cellular suspension combination is incubated at room temperature or at 37° C. for 30 minutes to 24 hours, for example 4 hours. In some embodiments, loading a therapeutic composition into the cells in the cellular suspension is aided by constant agitation in a dialysis cassette (i.e., slide-a-lyzer dialysis devices from Thermo Fisher Scientific), allowing for platelets to remain "quiescent" throughout the loading process.

In some embodiments, therapeutics compositions, such as those described above, can be loaded into iPSC-derived platelets, megakaryocytes, megakaryocyte progenitors, and preplatelets by passive loading (also known as "sponge loading"). In some embodiments, passive loading is achieved by adding the therapeutic composition to cellular suspensions of MKs, MK progenitors, preplatelets, and/or platelets in aqueous buffer for 1 to 5 hours, for example 2 hours, at room temperature or 37° C. In some embodiments, the cellular suspensions are washed of excess therapeutic by diluting the cellular suspensions 2 to 10-fold, for example 5-fold. The diluted cellular suspension are then centrifuged suspensions, removing the supernatant, and resuspending the therapeutic loaded cellular suspension into fresh media.

Without being bound to the theory, incubation of the instant megakaryocytic progenitors, megakaryocytes, preplatelets, or platelets with the therapeutic composition results in the sequestration of the therapeutic composition into secretory granules (e.g. alpha-granules, dense granules) of the cell. In some embodiments, the instant megakaryocytic progenitors, megakaryocytes, preplatelets, or platelets loaded with the therapeutic composition can be used to locally deliver the therapeutic composition at a target site, such as sites of inflammation, vascular damage, tissue regeneration, lymphoangiogenesis, cancer development, progression and metastasis.

Figure 54A:
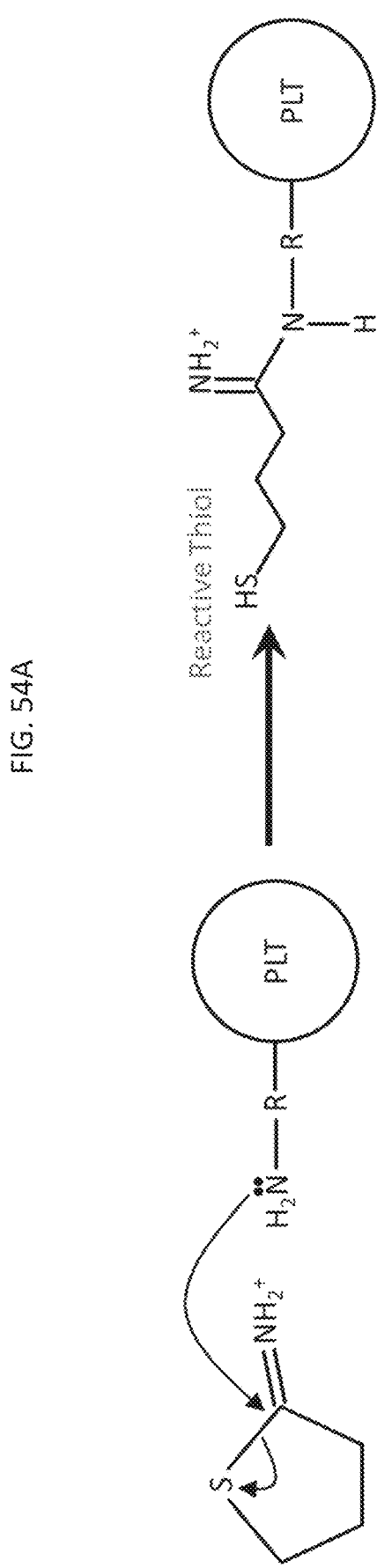
Figure 54B:
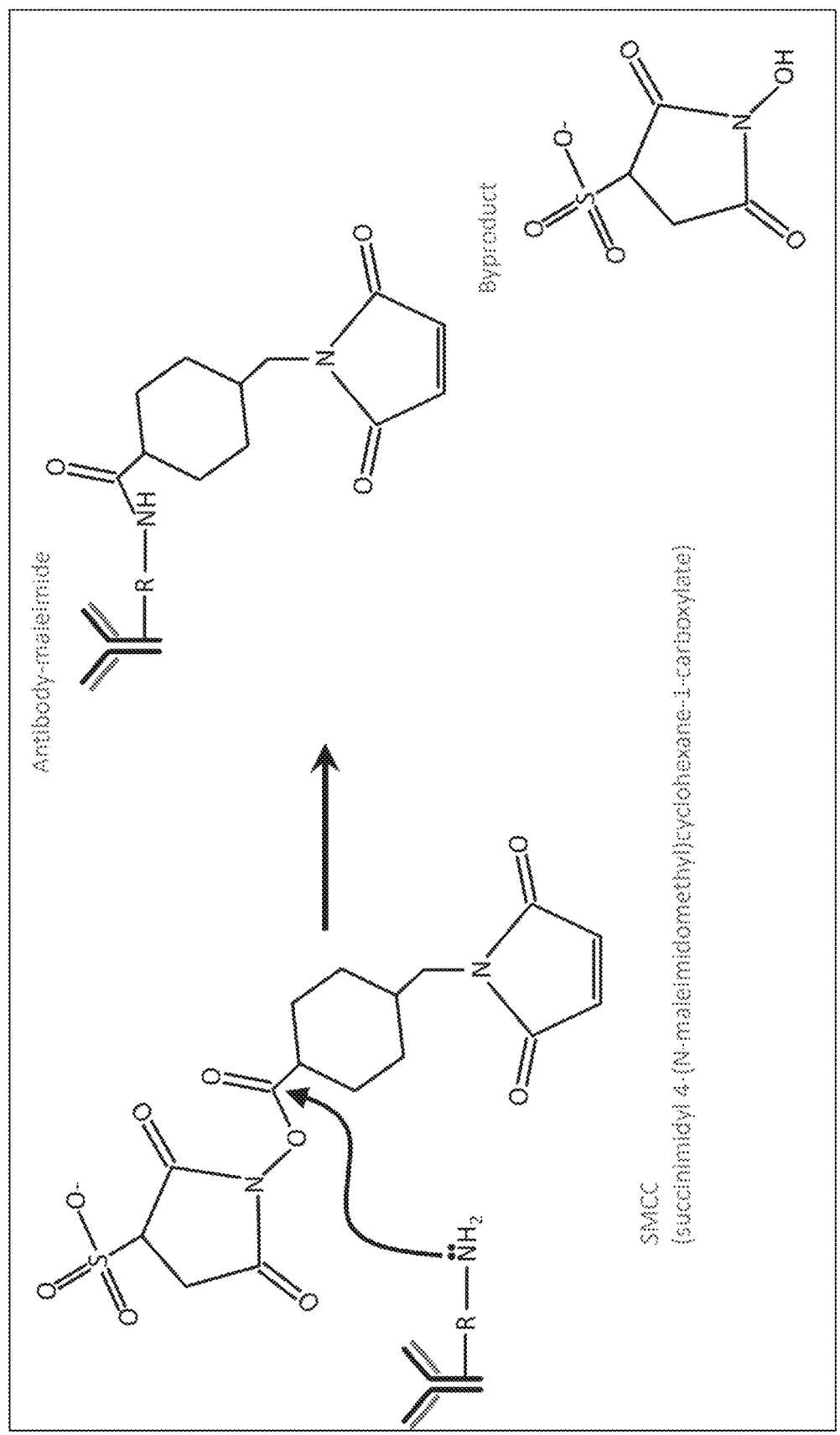
Figure 54C:
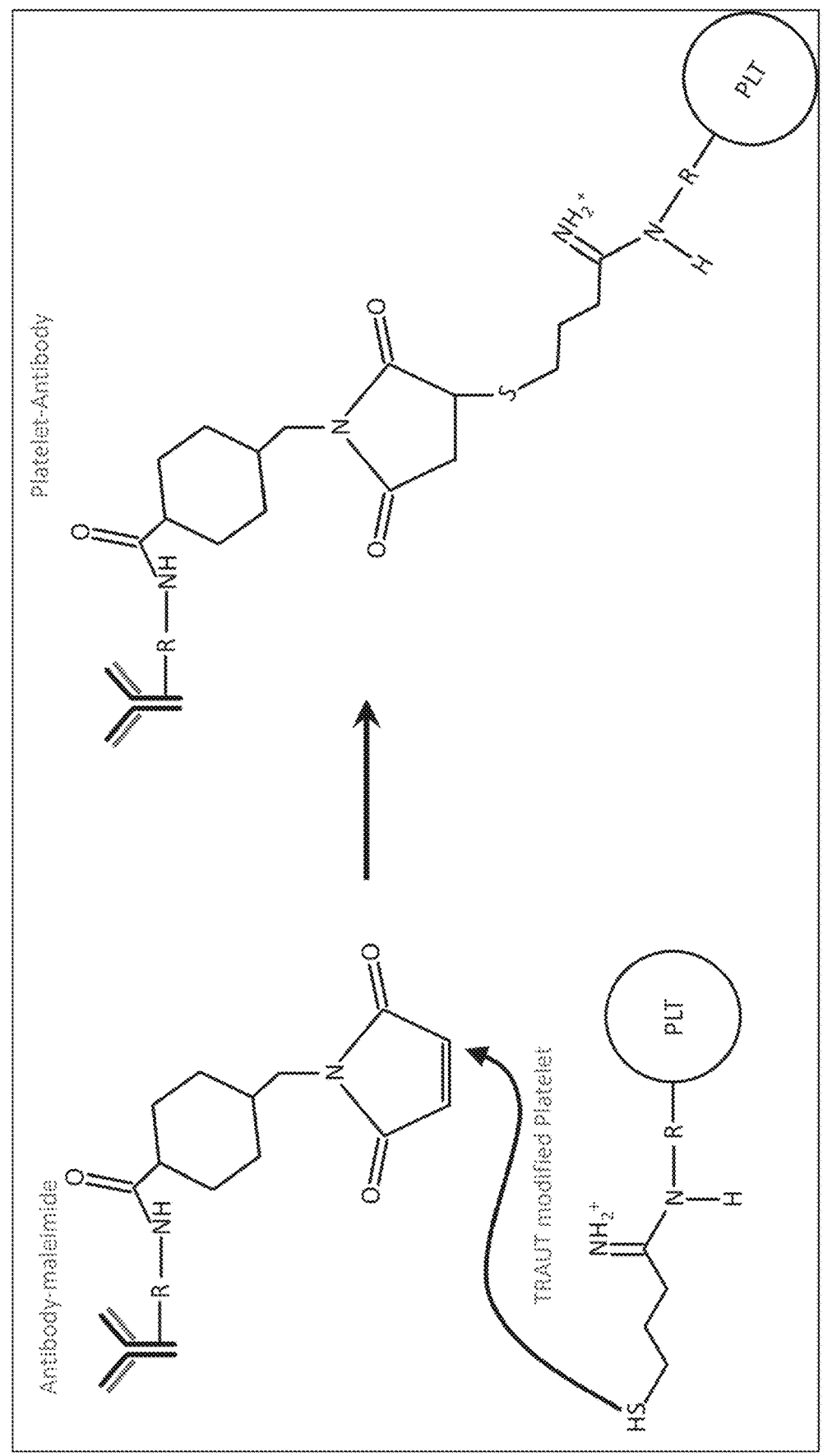

In reference to FIG. 6, iPSC-derived platelets, megakaryocytes, megakaryocyte progenitors, and preplatelets can also be loaded with therapeutic compositions by covalent conjugation of the therapeutic composition to the cell membrane, among other organelles, subcellular compartments, and cellular structures. Covalent conjugation can be achieved using various bioconjugation techniques including (but not limited to) thiolation of membrane proteins and sulfhydryl-reactive crosslinkers (FIG. 54) alkyne reactive azides, high affinity binders, including biotin with avidin (and avidin analogues), antibody docking to membrane bound epitopes, and other methods. In some embodiments, covalent conjugation of a therapeutic composition is achieved by reacting amines present in amino acids in the therapeutic agent with succinimidyl 4-(N-maleimidomethyl) cyclohexane-1-carboxylate (SMCC) (FIG. 54B) for 1 to 4 hours, for example 2 hours (FIG. 54B). In some embodiments, platelets (and other cell types) are functionalized with a reactive thiol group by conversion from a primary amine using 2-iminothiolane, also known as Traut's Reagent (Sigma) (FIG. 54A). In some embodiments, the therapeutic reacted with SMCC and the cell suspension treated with Traut's Reagent are co-incubated in order to complete the chemical conjugation of the therapeutic composition to the membrane of the cells (FIG. 54C).

Genetic Engineering of iPSC-Derived Megakaryocytic Progenitors, Megakaryocytes, Proplatelets, Preplatelets or Platelets to Express a Therapeutic Composition In reference to FIG. 7, in some aspects of the present disclosure, the megakaryocytic progenitors, megakaryocytes, proplatelets, preplatelets or platelets derived from an iPSC can be modified to express a protein of interest (including polypeptide or peptide of interest). Such modifications can take place at a stem cell level, or any other level during the platelet generation process of the present disclosure. For example, the present disclosure provides modified megakaryocytes or megakaryocytic progenitors differentiated from an engineered hPSC cell or cell line, wherein the modified megakaryocyte or megakaryocytic progenitor express a protein of interest (including polypeptide or peptide of interest). In some embodiments, the proplatelets, preplatelets or platelets derived from the modified megakaryocyte or megakaryocytic progenitor can also express the protein of interest, and can be used to deliver the protein of interest to a target site.

In some aspects of the present disclosure, the PSC-derived megakaryocytes are engineered to express at least one peptide, polypeptide or proteins of interest. Yet in other aspects of the present disclosure, the PSC are engineered to express at least one peptide, polypeptide or proteins of interest and megakaryocytes expressing the at least one peptide, polypeptide or proteins of interest or preplatelets or platelets comprising the at least one peptide, polypeptide or proteins of interest can be produced using the methods of U.S. Pat. No. 9,763,984 or the bioreactor as disclosed in International application No. PCT/US2018/021354, which are incorporated herein by reference in their entireties.

In some aspects of the present disclosure, the PSC-derived megakaryocytes are engineered to comprise a DNA or RNA of interest. Yet in other aspects of the present disclosure, the PSC are engineered to comprise a DNA or RNA of interest. In some embodiments, the preplatelets or platelets derived from the modified megakaryocyte or megakaryocytic progenitor comprising the DNA or RNA of interest can deliver the DNA or RNA of interest.

Some embodiments relate to compositions or isolated populations comprising engineered PSCs engineered to express the at least one peptide, polypeptide or protein of interest. In some embodiments, the protein is a cytokine, a chemokine or a growth factor. Some embodiments relate to compositions or isolated populations comprising megakaryocytes engineered to express the at least one peptide, polypeptide or proteins of interest. In some embodiments, the protein is a cytokine, a chemokine or a growth factor. Some embodiments, relate to compositions comprising platelets produced ex vivo from megakaryocytes engineered to express the at least one peptide, polypeptide or proteins of interest. In some embodiments, the protein is a cytokine, a chemokine or a growth factor. Preplatelets or platelets produced by modified megakaryocytes expressing at least one peptide, polypeptide or proteins of interest can be used as a delivery vehicle to deliver the at least one peptide, polypeptide or proteins of interest at site of interest. In some embodiments, the protein is a cytokine, a chemokine or a growth factor.

Some embodiments relate to compositions or isolated populations comprising engineered PSCs engineered to comprise a DNA or RNA of interest. Some embodiments relate to compositions or isolated populations comprising megakaryocytes engineered to comprise a DNA or RNA of interest. Some embodiments relate to compositions comprising platelets produced ex vivo from megakaryocytes engineered to comprise a DNA or RNA of interest of interest. Proplatelets, preplatelets or platelets produced by modified megakaryocytes comprising the DNA or RNA of interest can be used as a delivery vehicle to deliver the DNA or RNA of interest at a target site of interest.

It should be appreciated that modified megakaryocytes (or products thereof) expressing at least one peptide, polypeptide or proteins of interest or comprising a DNA or RNA of interest can be used for the treatment of different diseases.

In some aspects of the present disclosure, the DNA or RNA of interest or the RNA or DNA encoding the protein of interest can be any gene that the skilled practitioner desires to have integrated and/or expressed. In some embodiments, at least one peptide, polypeptide or protein of interest can be expressed in the megakaryocytes by delivering one or more nucleic acid molecules (i.e. gene of interest) encoding at least one peptide, polypeptide or protein of interest to the megakaryocyte or a precursor cell such as an iPSC cell. In some embodiments, the one or more nucleic acid molecules encoding at least one peptide, polypeptide or protein of interest may be contained within an expression vector. In some embodiments, the vector comprises one or more synthetic nucleotides (e.g., locked nucleic acids, peptide nucleic acids, etc.) or nucleoside linkages (e.g., phosphorothioate linkages). The vector may be single-stranded, double-stranded, or contain regions of both single-strandedness and double-strandedness. Exemplary vectors include, but are not limited to, plasmids, retroviral vectors, lentiviral vectors, adenovirus vectors, adeno-associated virus (AAV) vectors, a herpes simplex virus vectors, poxvirus vectors, and baculovirus vectors. In some embodiments, the nucleic acid molecule encoding the peptide, polypeptide or protein of interest may be expressed using a megakaryocyte-specific promoter. In some embodiments, the vector comprises a nucleic acid sequence that encodes a therapeutic polypeptide or fragment thereof. In some embodiments, the vector comprises a nucleic sequence that encodes an mRNA. In some embodiments, the vector comprises a therapeutic gene nucleic acid sequence including the promoter, or a fragment thereof. The vector comprising the nucleic acid molecule of interest may be delivered to the cell (e.g., iPS cell, megakaryocytic progenitor, or megakaryocyte) via any method known in the art, including but not limited to transduction, transfection, infection, and electroporation.

Targeted Delivery of Therapeutics Encapsulated in Memakaryocytes and Platelets

In some embodiments, the megakaryocytic progenitors, megakaryocytes, proplatelets, preplatelets, or platelets of the present disclosure are loaded with therapeutics that would be shielded from circulation upon transfusion of the cellular drug product in vivo. Platelets naturally home to cancerous lesions, solid tumors, and circulating tumor cells, in some examples, by receptor interactions with exposed collagen and other extracellular matrix components, in others by receptors that are surface exposed upon platelet activation. Platelets are known to aggregate in response to tumor cells (also known as tumor cell-induced platelet aggregation) as a result of these interactions. Platelets are "activated" by these interactions and will secrete the contents of their secretory granules, including small-molecule and biologic therapeutics that have been loaded into these cells by passive drug loading or by genetic modification of iPSCs, megakaryocytic progenitors, megakaryocytes, and any other cell that produces a "designer" platelet. They will also shed their membranes as part of an exocytotic process that produces microvesicles. In some embodiments, platelets with small molecule and biologic drugs covalently conjugated to the plasma membrane will remain stably bound during microvesicle formation and selectively delivered to cancer as a result of tumor cell-induced platelet aggregation. In some embodiments, genetically modified human iPSCs, megakaryocyte progenitors, or megakaryocytes can be engineered to express recombinant biologic drugs that are fused to a membrane anchoring domain from surface receptors, in some examples CD3 and DAF, and deliver them specifically to the cell surface. Recombinant biologic drugs anchored to the plasma membrane can also be delivered to sites of disease pathology by being incorporated into microvesicles as a result of platelet activation. Recombinant biologic drugs anchored to the plasma membrane can also include a protease cleavage site to allow for enzymes, in some examples matrix metalloproteases, that are abundant at sites of disease pathology, including a solid tumor, cancerous lesion, or a site of vascular injury or angiogenesis, to cleave the recombinant biologic drug in a separate example of targeted drug delivery.

The practice of the present disclosure may employ, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the present disclosure and, as such, may be considered in making and practicing the present disclosure. Particularly useful techniques for particular embodiments will be discussed in the sections that follow.

Methods of Use

As discussed above, in some embodiments, the megakaryocytic progenitors, megakaryocytes, proplatelets, preplatelets, or platelets of the present disclosure can be modified to include a therapeutic composition for targeted delivery of such therapeutic composition. In particular, the megakaryocytic progenitors, megakaryocytes, proplatelets, preplatelets, or platelets of the present disclosure can be loaded (such as by, passive absorption or covalent conjugation) with or genetically engineered to express a therapeutic composition, either on the surface or within their granules.

In some embodiments, the megakaryocytic progenitors, megakaryocytes, proplatelets, preplatelets, or platelets of the present disclosure can be used in combination with other nanoparticle materials for drug delivery. For example, in some embodiments, a membrane of the megakaryocytic progenitors, megakaryocytes, proplatelets, preplatelets, or platelets of the present disclosure can be used as an outer shell for a drug delivery system that comprises one or more materials compatible with interacting with and transporting therapeutic compositions. For example, an outer shell platelet rembrane can include platelet proteins capable of interacting with cancer cells. In some embodiments, such drug delivery vehicles can be prepared by lysing the megakaryocytic progenitors, megakaryocytes, proplatelets, preplatelets, or platelets of the present disclosure and filling the outer membrane of the lysed cells with a drug delivery system comprising a therapeutic composition.

In some embodiments, the megakaryocytic progenitors, megakaryocytes, proplatelets, preplatelets, or platelets of the present disclosure can be a source of growth factors, such as human growth factors. In some embodiments, such growth factor can be used for cell culture, tissue regeneration, wound healing, bone regeneration, cosmeceuticals, and hemostatic bandages. In some embodiments, the megakaryocytic progenitors, megakaryocytes, proplatelets, preplatelets, or platelets of the present disclosure or their lysate or compositions thereof can be used in cell culture. In some embodiments, the megakaryocytic progenitors, megakaryocytes, proplatelets, preplatelets, or platelets of the present disclosure or their lysate or compositions thereof can be used as a cosmeceutical.

For example, platelets store bioactive factors in secretory granules, which they acquire from megakaryocytes. Contents include various chemokines and growth factors, such as platelet derived growth factor isoforms (PDGF-AA, -AB and -BB), transforming growth factor-b (TGF-b), insulin-like growth factor-1 (IGF-1), brain derived neurotrophic factor (BDNF), vascular endothelial growth factor (VEGF), epidermal growth factor (EGF), basic fibroblast growth factor (bFGF or FGF-2), hepatocyte growth factor (HGF), connective tissue growth factor (CTGF) and bone morphogenetic protein 2, -4 and -6 (BMP-2, -4, -6). Human platelet lysate dramatically increases the expansion of cells ex vivo, improves bone marrow regeneration in vivo, and increases the survival rates of animals in radiation studies. In some embodiments, the present disclosure provides a composition or pharmaceutical composition comprising a lysate of a proplatelet, preplatelet or platelet generated from the instant megakaryocytes, wherein such compositions can include factors such as platelet derived growth factor isoforms PDGF-AA or PDGF-BB, vascular endothelial growth factor (VEGF), epidermal growth factor (EGF), basic fibroblast growth factor (FGF-2), hematopoietic growth factors Flt3L, G-CSF, GM-CSF, interleukins (IL-1RA, IL-8, or IL-16), CXC chemokine family members CXCL1 (GRO alpha) or CXCL12 (SDF-1), TNF superfamily members sCD40L or TRAIL, or CC chemokine family members CCL5 (RANTES), CCL11 (Eotaxin-1), CCL21 (6CKine) or CCL24 (Eotaxin-2).

Administration

Aspects of the present disclosure relate to pharmaceutical compositions comprising instant megakaryocytic progenitors, megakaryocytes, proplatelets, preplatelets, or platelets according to embodiments of the present disclosure. In some embodiments, pharmaceutical composition comprises instant megakaryocytic progenitors, megakaryocytes, proplatelets, preplatelets, or platelets according to embodiments of the present disclosure with a pharmaceutically acceptable carrier. For example, the carrier can be a diluent, an adjuvant, a preservative, an anti-oxidant, a solubilizer, an emulsifier, a buffer, water, an aqueous solution, oil, an excipient, an auxiliary agent or vehicle or combinations thereof. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington. In some embodiments, the carrier may be suitable for intravenous administration.

Aspects of the present disclosure relate to methods of treating a subject in need thereof, the method comprising administering compositions of the instant megakaryocytic progenitors, megakaryocytes, proplatelets, preplatelets, or platelets to a subject in need thereof.

Administration of suitable dose and dosage regimen of the compositions comprising instant megakaryocytic progenitors, megakaryocytes, proplatelets, preplatelets, or platelets according to embodiments of the present disclosure to a subject in need thereof may be determined based on the subject's age, sex, weight, general medical condition, and the specific condition for which the composition is being administered.

Megakaryocytic progenitors, megakaryocytes, proplatelets, preplatelets, or platelets according to embodiments of the present disclosure may be administered by any method. In some embodiments, the instant megakaryocytic progenitors, megakaryocytes, proplatelets, preplatelets, or platelets can be administered by direct injection, for example intravenous injection. Pharmaceutical preparations for injection may be prepared and delivered as known in the art.

Pharmaceutical Compositions

The present disclosure features methods for treating or preventing disease or infection in a subject. The present invention also features methods for treating wounds. The methods include administering to a subject in need thereof a therapeutically effective amount of a composition comprising an induced pluripotent stem cell (iPSC)-derived platelet comprising a therapeutic agent. In an embodiment, the composition is used in a pharmaceutical composition.

In some embodiments, the pharmaceutical compositions described herein comprise a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions ensuring sterility, pH, isotonicity, and stability is affected according to protocols established in the art. Generally, a carrier or excipient is selected to minimize allergic and other undesirable effects, and to suit the particular route of administration, e.g., subcutaneous, intramuscular, intranasal, and the like.

Administration of the pharmaceutical compositions contemplated herein may be carried out using conventional techniques including, but not limited to, infusion, transfusion, or parenterally. In some embodiments, parenteral administration includes infusing or injecting intravascularly, intravenously, intramuscularly, intraarterially, intrathecally, intratumorally, intradermally, intraperitoneally, transtracheally, subcutaneously, subcuticularly, intraarticularly, subcapsularly, subarachnoidly and intrasternally.

Kits

The disclosure provides kits comprising a megakaryocyte or differentiated cell of the disclosure. In one embodiment, the kit includes a composition comprising an isolated megakaryocyte. In particular embodiments, the disclosure provides kits for differentiating, culturing, and/or isolating a megakaryocyte of the disclosure or precursor thereof. In certain embodiments, the disclosure provides kits for producing platelets.

In some embodiments, the kit comprises a sterile container which contains a cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit is provided together with instructions for generating the megakaryocyte. The instructions will generally include information about the conditions and factors required differentiating, culturing, and/or isolating megakaryocytes or precursors thereof. In some embodiments, instructions for producing platelets are included. The instructions may be printed directly on the container (when present), or as a label applied to the container, or as a separate sheet, pamphlet, card, or folder supplied in or with the container.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the disclosure, and, as such, may be considered in making and practicing the disclosure. Particularly useful techniques for particular embodiments will be discussed in the sections that follow.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

EXAMPLES

Example 1: Expansion of Clinical Grade hiPSCs

Prior to differentiation, hiPSC expansion is required to produce the large number of cells for use in appropriately sized master and working cell banks, as well as generate sufficient cell numbers to initiate differentiation at an appropriate scale for clinical production. A clinical grade hiPSC cell line was obtained from the NINDS Human Cell and Data Repository (NHCDR) depository at NINDS (National Institute of Neurological Disorders and Stroke)/NIH(National Institutes of Health). This cell line (NINDS ID: LiPSC-Gr1.1), which was derived from male $CD34^+$ cord blood (Lonza), could be maintained and expanded in 2D cultures using recombinant vitronectin (VTN), plus cGMP compatible reagents such as Essential 8, NutriStem, or StemFlex (FIGS. 8A-8C). Characteristic colony growth and maintenance of pluripotency markers were observed for all three growth conditions (FIGS. 8A-8C, FIGS. 9A-9C).

Figure 10A:
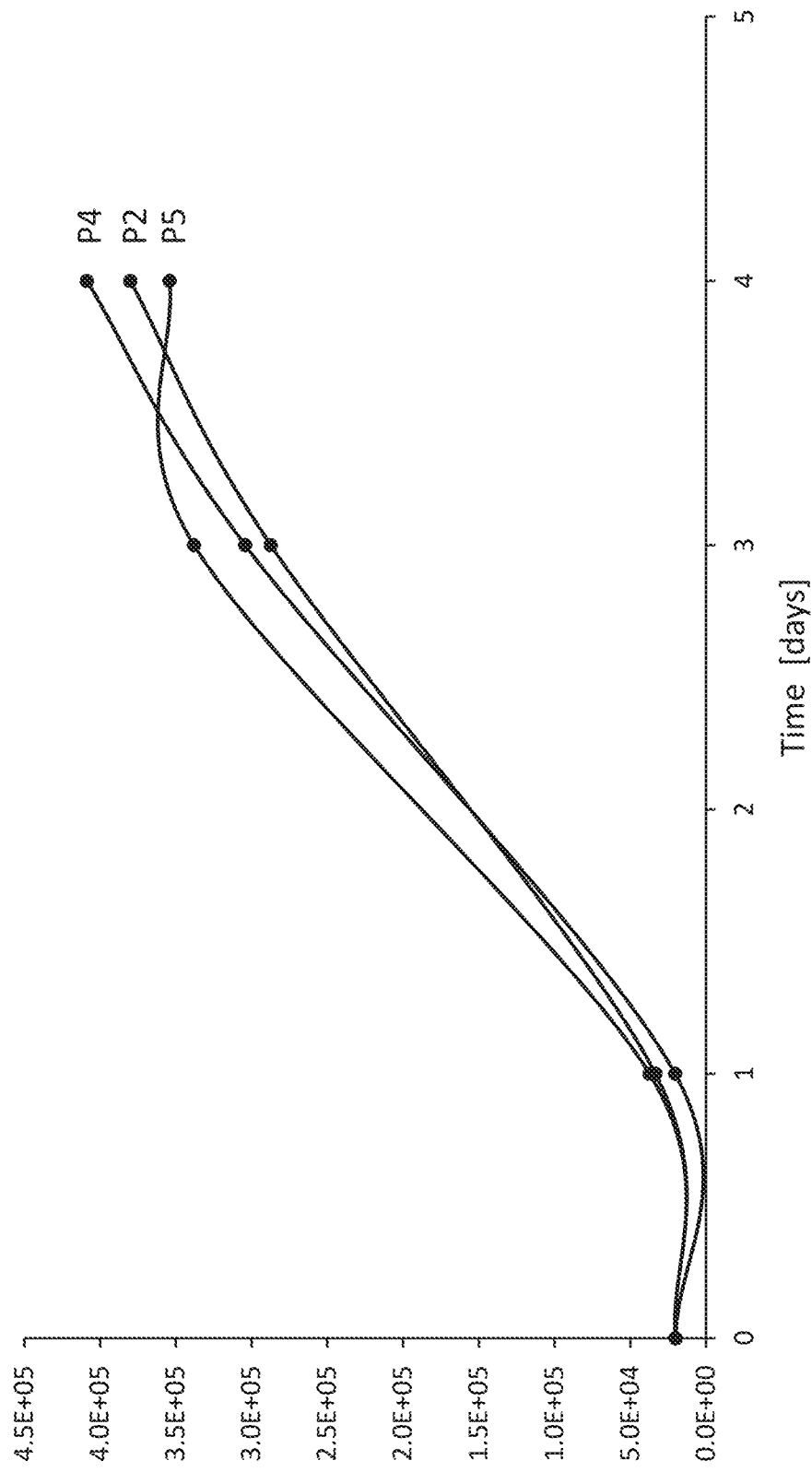
FIGS. 10A-10C depict results of a high-efficiency single cell passaging technique.
Figure 10C:
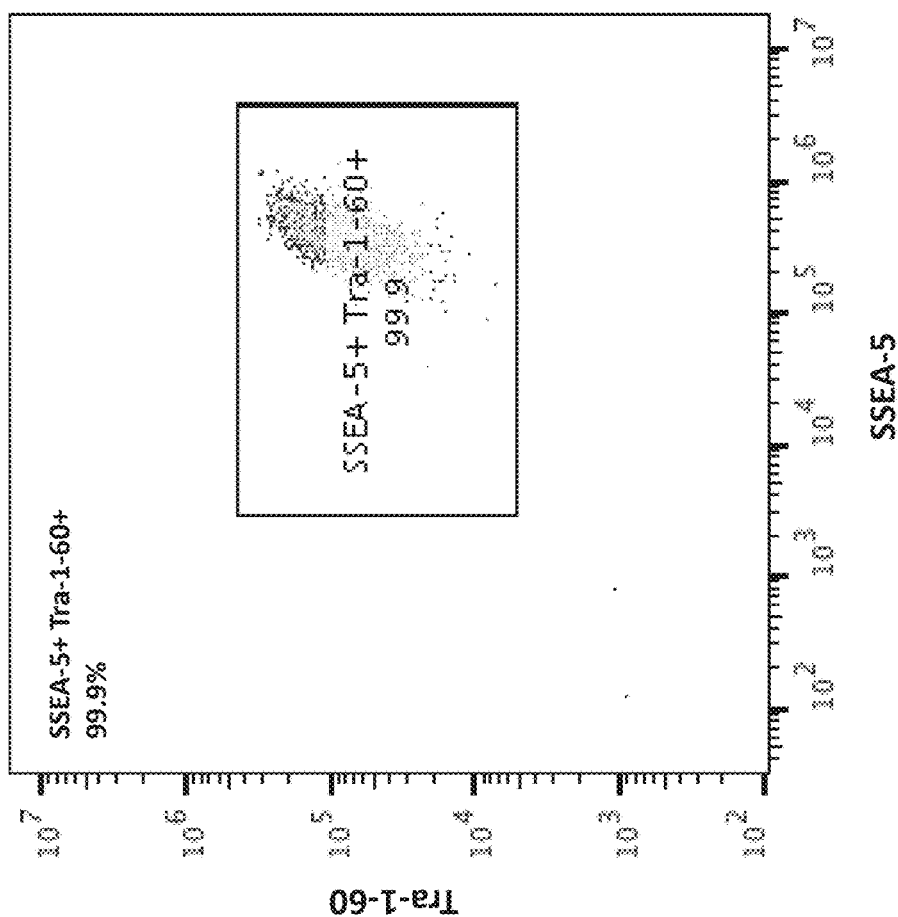
Figure 10B:
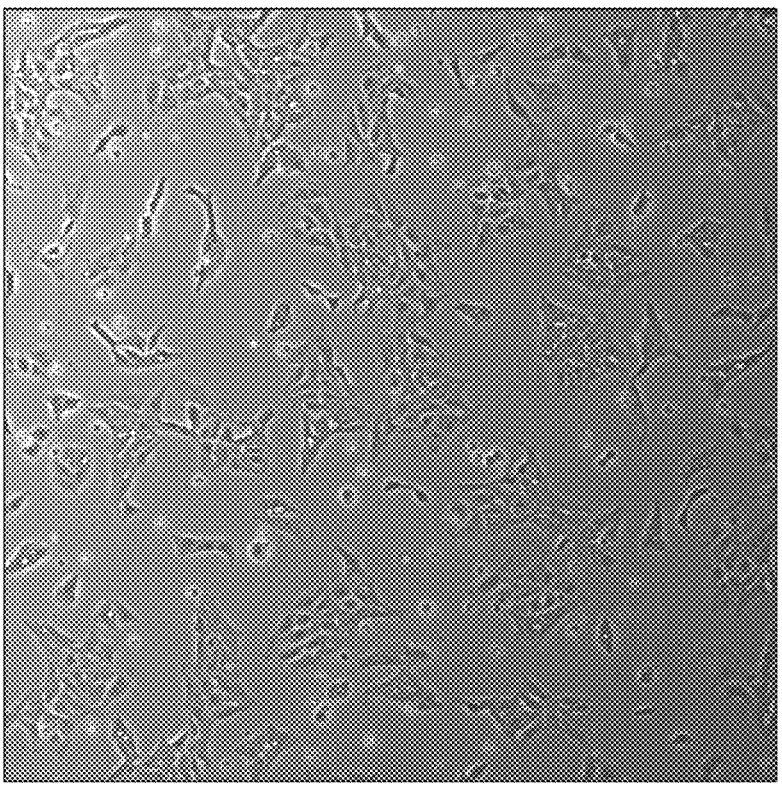
Figure 13A:
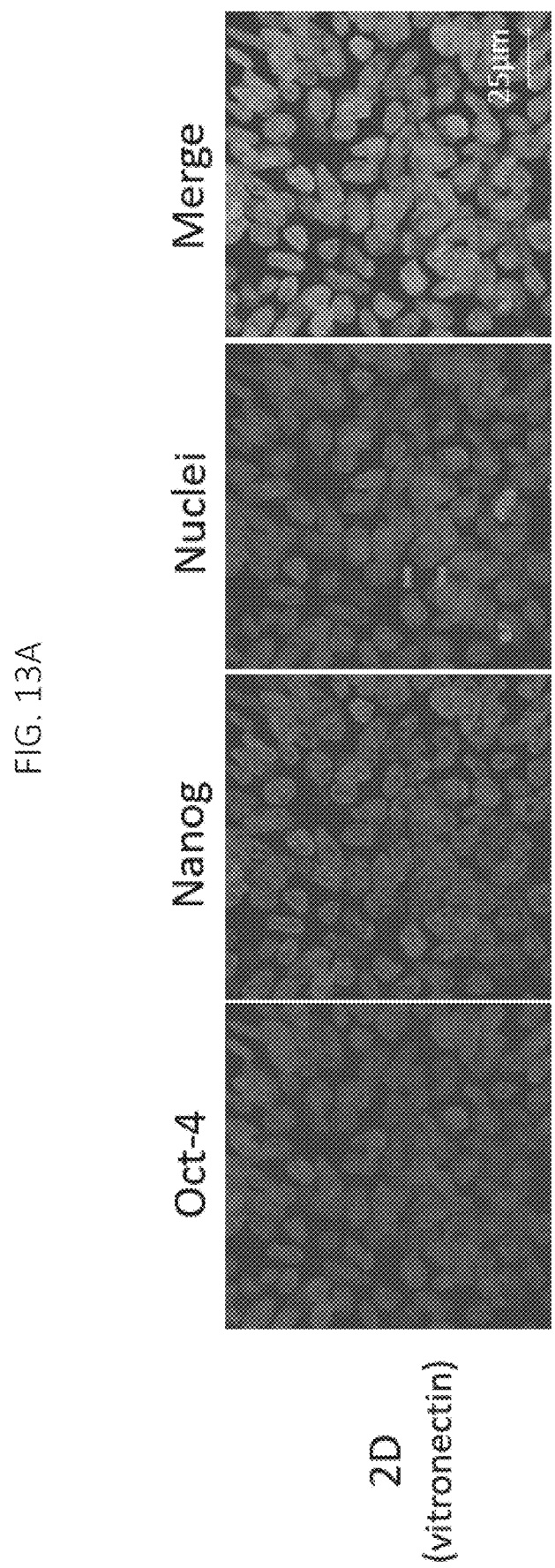
FIG. 13A and FIG. 13B depict iPSCs immunostained for the pluripotency factors Oct 4 and Nanog, and counterstained with a nuclear dye.

A high-efficiency single cell passaging technique was also developed to support scaled expansion of undifferentiated hiPSC cultures. The same methodology is intended for cell banking and scaled hiPSC seed-trains leading to large scale differentiations for clinical manufacturing. The approach provides rapid expansion for overall manufacturing capacity, undifferentiated pluripotent cultures with capacity to produce pre-MK, and uniformity of harvest yields and culture performance in a system compatible with cGMP manufacturing and clinical entry. In this example, LiPSC-Gr1.1 cultures were dissociated to a single cell suspension using TrypLE (Thermo Fisher), followed by plating at a defined density in NutriStem hPSC XF (Biological Industries) containing 0.5 µM H1152 (Tocris) and 10 ng/mL heregulin β1 (Peprotech). Cultures were plated at a density of $1\times10^4$ cells/cm$^2$ for a 4-day culture interval, and $2\times10^4$ cells/cm$^2$ for a 3-day culture interval. Cell attachment to untreated TC-flasks was mediated by 0.5% human AB serum (Valley Biomedical). On the following day 18-22 hours post-plating, cultures were fed with NutriStem hPSC XF without supplementation. Cultures were passaged at 3- or 4-day intervals, achieving predictable and consistent harvest yields over multiple passages (FIG. 10A). The single cell passaging format also supported efficient cryopreservation in 10% DMSO (BloodStor100, STEMCELL Technologies), with cultures exhibiting a high thaw viability (>85%) and plating efficiency (>100% attached/surviving/proliferating cells, as counted one day post-plating) (FIG. 10B). Thawed cultures exhibited >99% co-expression of the SSEA-5 and TRA-1-60 cell surface markers of pluripotent cells (FIG. 10C) and stained positively for Oct4 and Nanog (FIG. 13A), confirming lack of spontaneous differentiation.

Figure 11B:
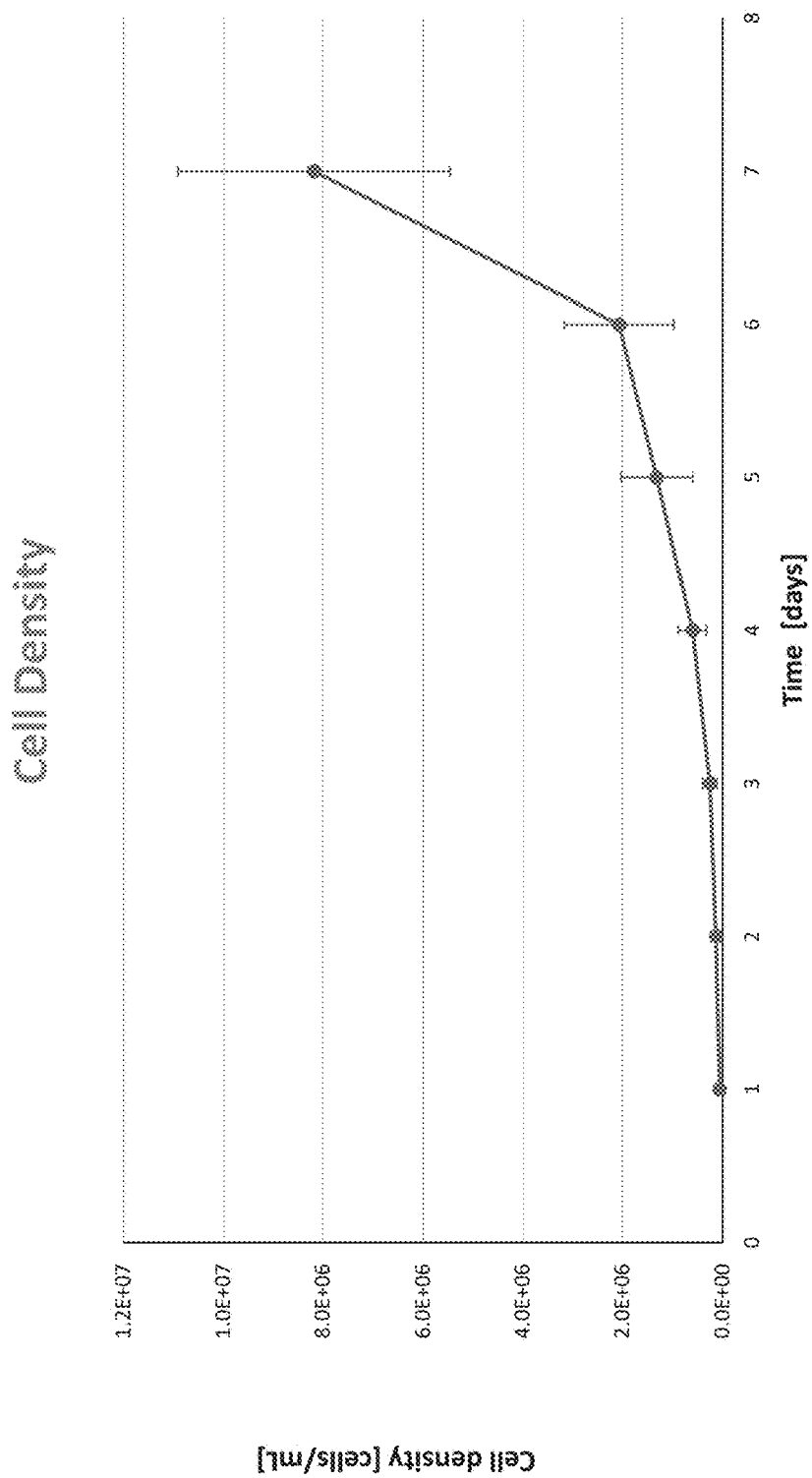
Figure 11C:
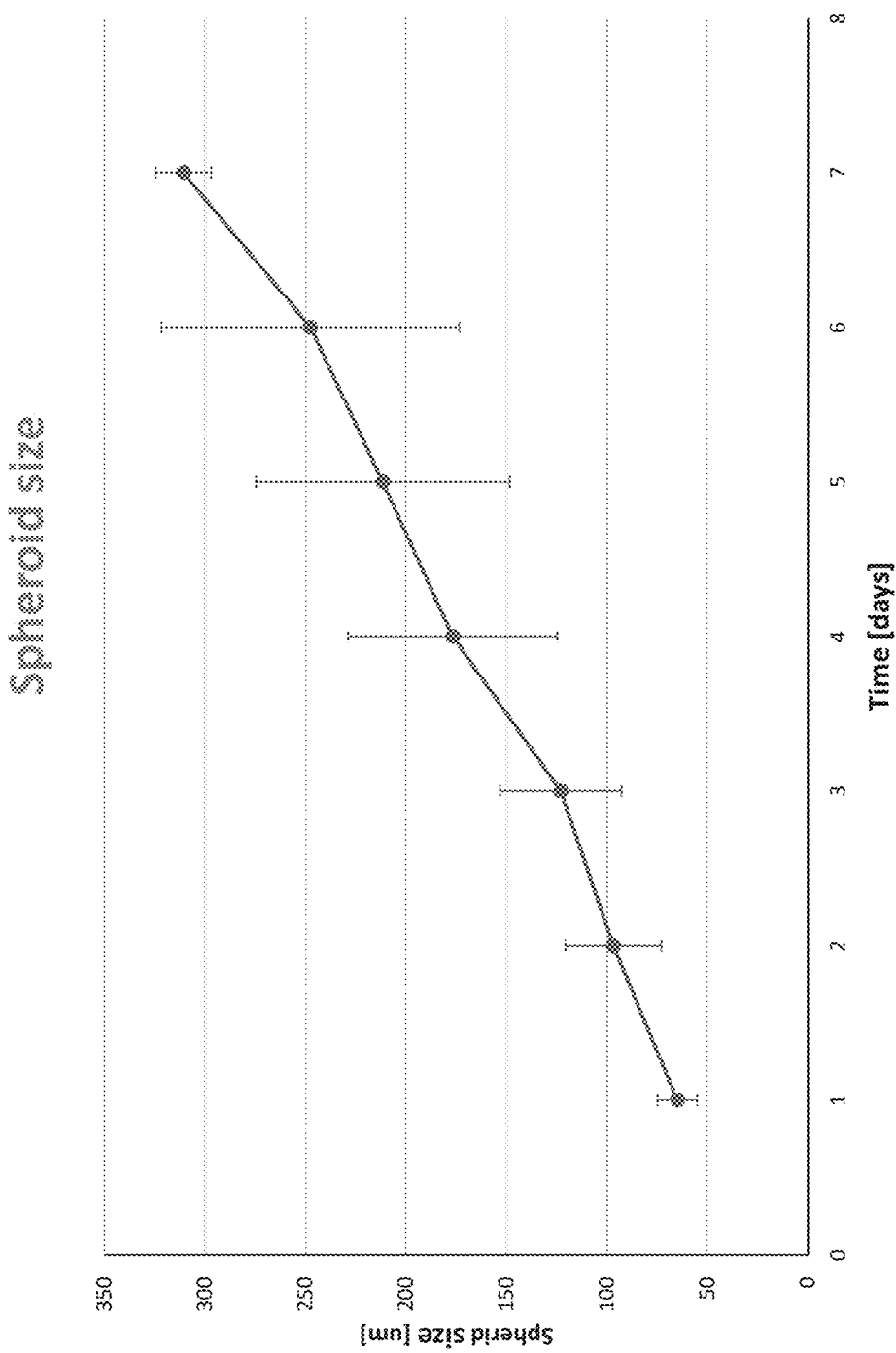
Figure 12A:
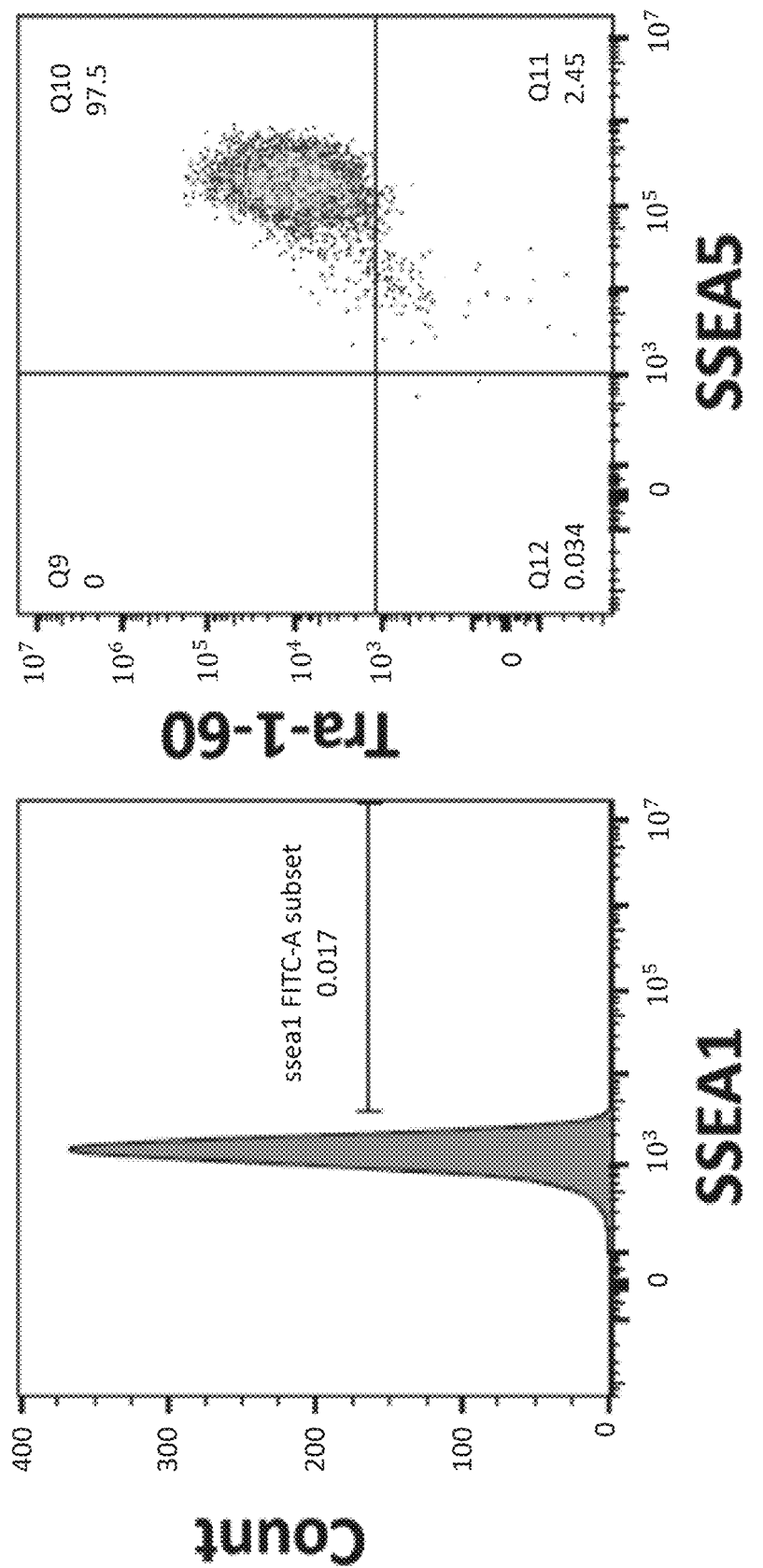
FIG. 12A and FIG. 12B depict flow cytometry data assessing expression of the pluripotency markers Tra-1-60, SSEA5, and the differentiation marker SSEA1 on iPSCs expanded in self-aggregating spheroid cultures in a 3D stir tank (matrix free).
Figure 12B:
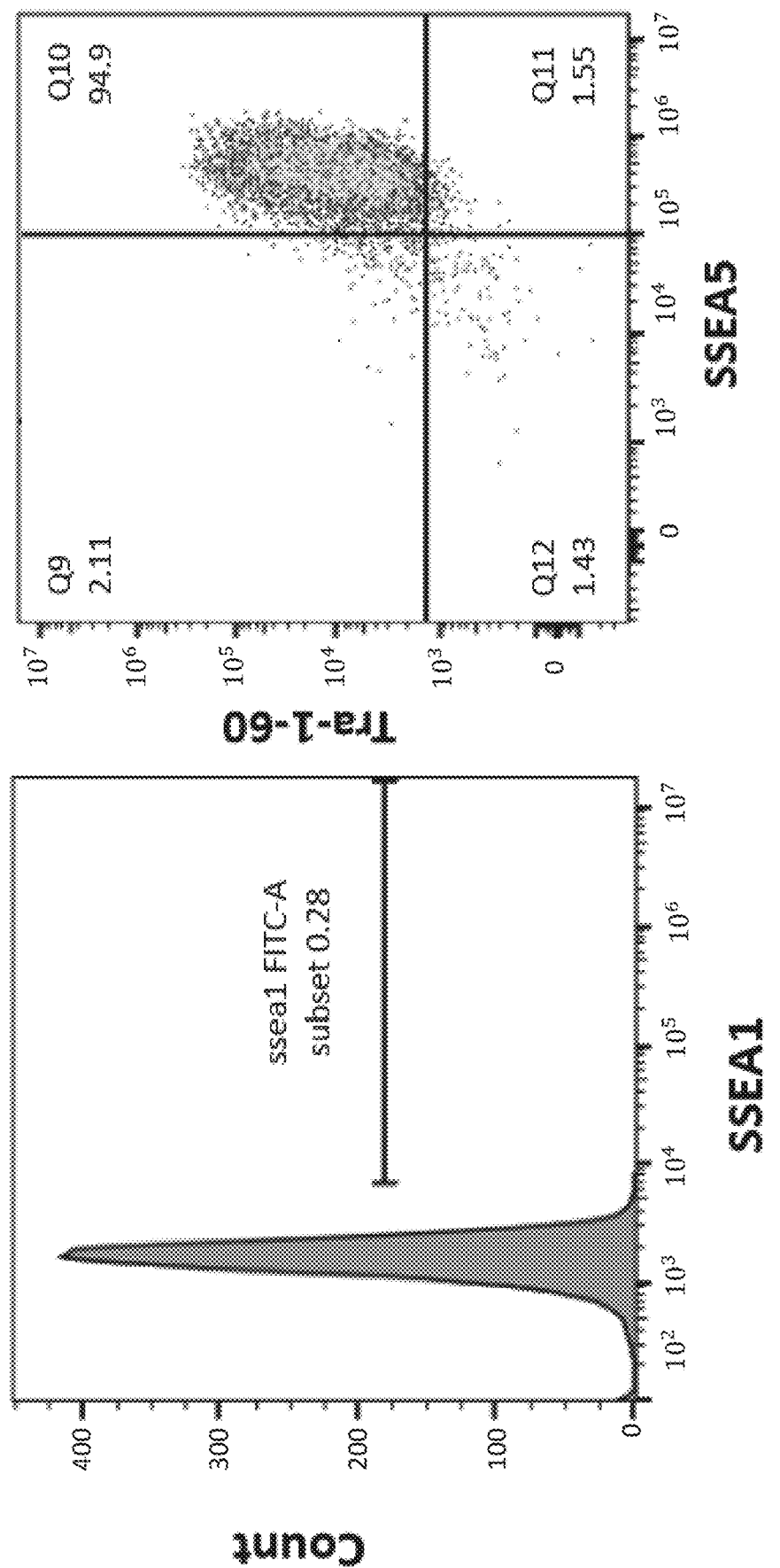
Figure 13B:
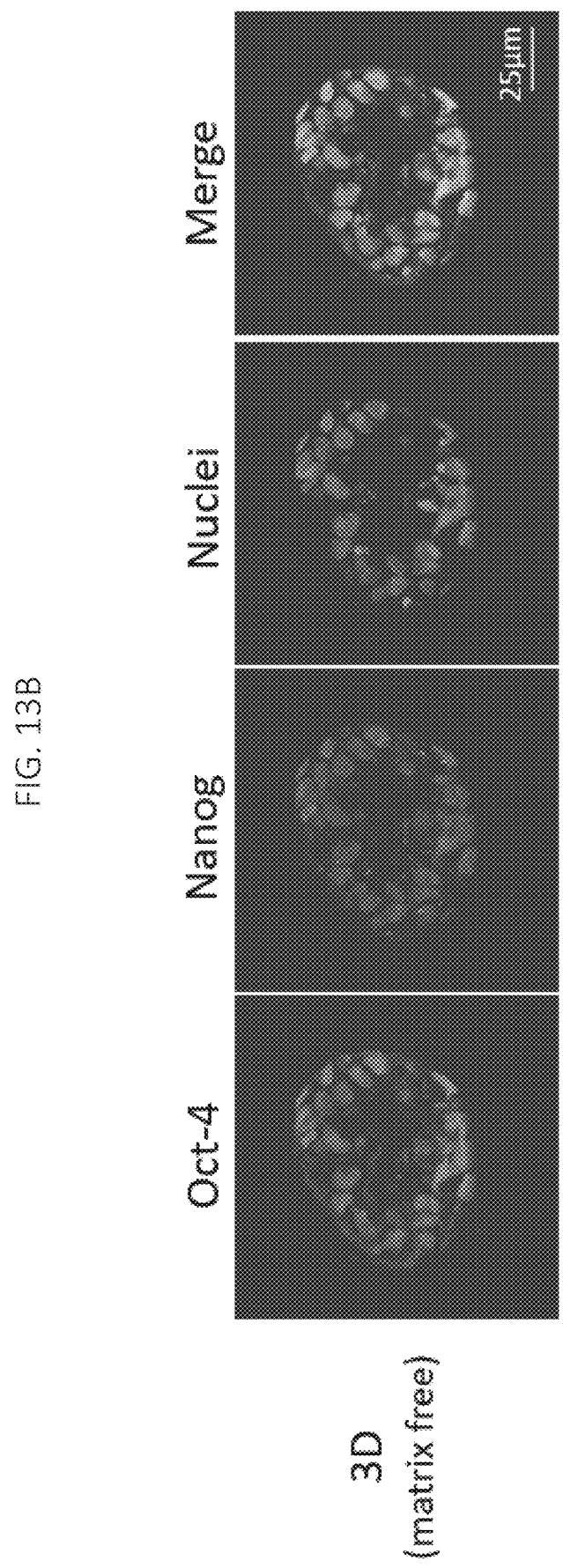
Figure 14:
FIG. 14 depicts karyotype analysis of a metaphase chromosome spread from iPSCs grown for 4 consecutive 6-7 days expansions in a 3D stir tank, demonstrating normal karyotype after 4 rounds of 3D passaging.

To enable large-scale expansion, LiPSC-Gr1.1 cells were harvested from 2D cultures as single cells using TrypLE and allowed to self-aggregate in stirred 3D vessels, in this case a 300 ml DasBOX mini bioreactor system. For the first 24 hours, ROCK inhibitor such as Y27632 was added to the cells to promote cell survival during initial aggregation Over 6-7 days in a stir tank, the resulting spheroids increased their diameter from 50 to 250 microns and the overall cell density increased up to 40-fold within that period of time (FIGS. 11A-11C). hiPSCs grown in this manner could be passaged repeatedly, and maintained their pluripotency for at least 4 consecutive rounds of expansion (FIGS. 12A-12B, FIG. 13B), and maintained a normal karyotype (FIG. 14).

Example 2: Directed Differentiation of hiPSCs to preMKs and MKs Using Collagen IV Matrix in 2D Culture Vessels The LiPSC-Gr1.1 hiPSC line was differentiated into megakaryocytes using the 2D matrix-dependent directed differentiation protocol summarized in FIG. 2, a schematic showing the time course of differentiation of pluripotent stem cells into megakaryocytes. In the timeline schematic, each stage of differentiation (Stage 0, 1, 2, 3) is indicated, with corresponding cell types and cell markers depicted above the timeline, and media composition, matrix, temperature and gas conditions shown below the timeline.

Figure 16B:
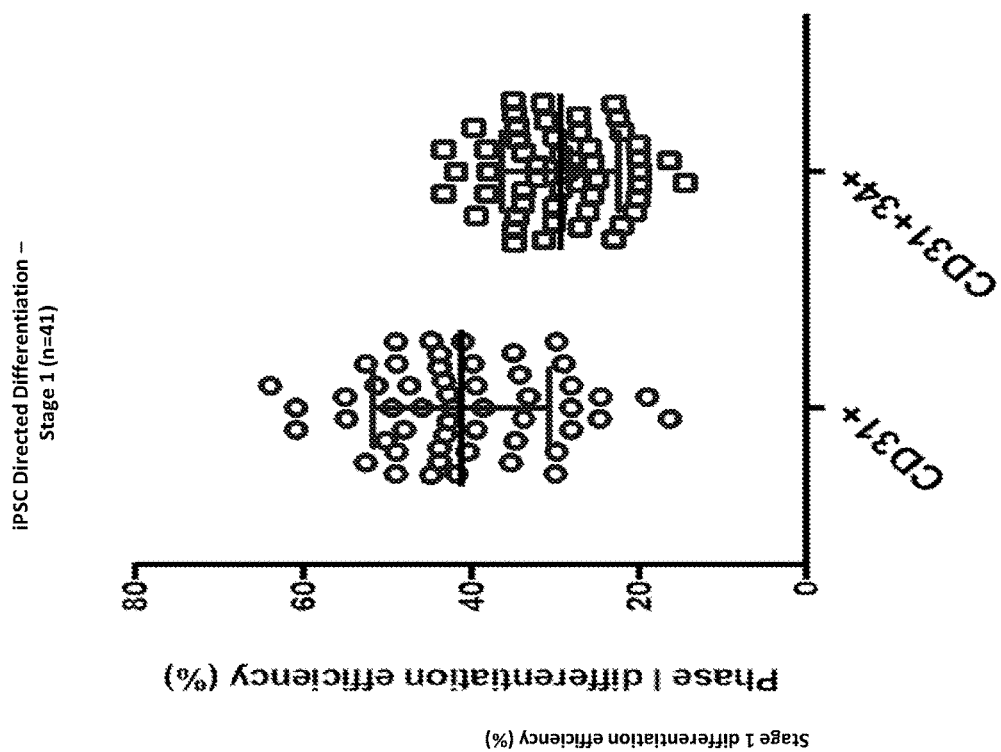
FIG. 16A and FIG. 16B depict representative Stage 1 differentiation data for iPSC-derived cells.
Figure 16A:
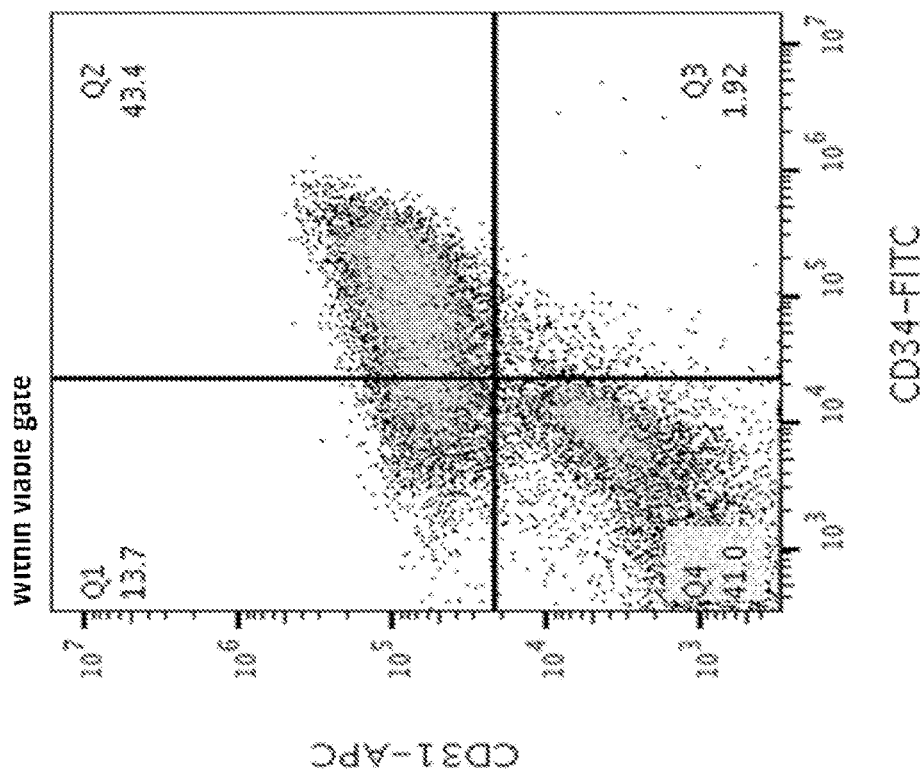

When harvested with 0.5 mM EDTA and plated as small clumps onto 4.2 ug/cm$^2$ human Collagen IV, PSCs exhibit a characteristic set of morphological changes through the course of 6 days of Stage 1 differentiation (FIG. 15). At the end of Stage 1, a representative well is harvested as single cells using Accutase and assessed by flow cytometry for the hemogenic endothelial markers CD31 and CD34 (FIG. 16A). Over multiple independent iPSC differentiations (n=41), the average day 6 differentiation efficiency was determined to be approximately 40% CD31+(range: ~20-60%) and approximately 30% CD31+CD34+(range ~15%-45%) (FIG. 16B).

Figure 18B:
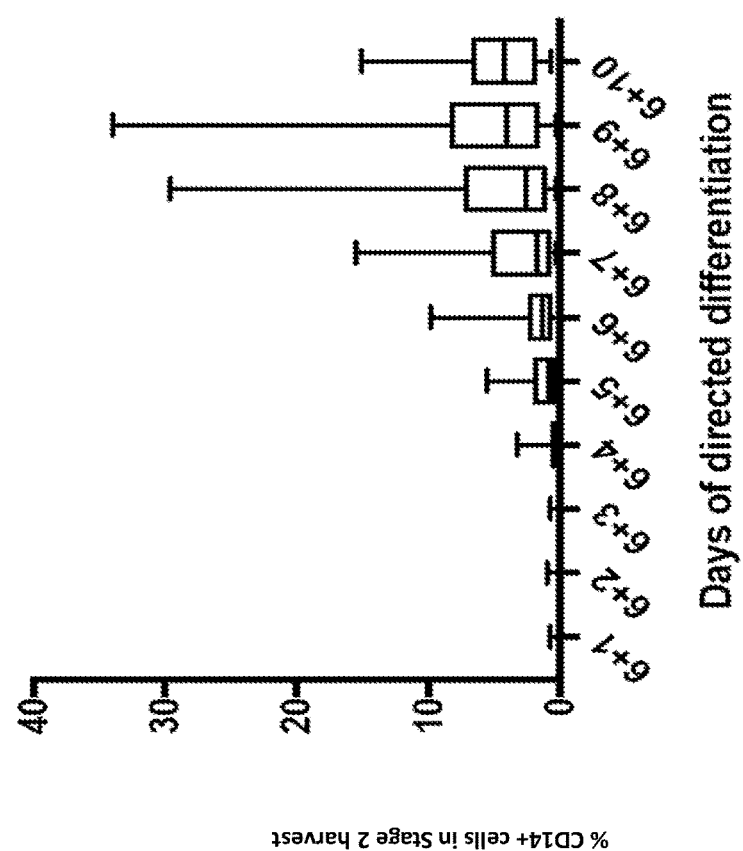
FIG. 18A and FIG. 18B depict average composition characteristics of Stage 2 suspension cells.
Figure 18A:
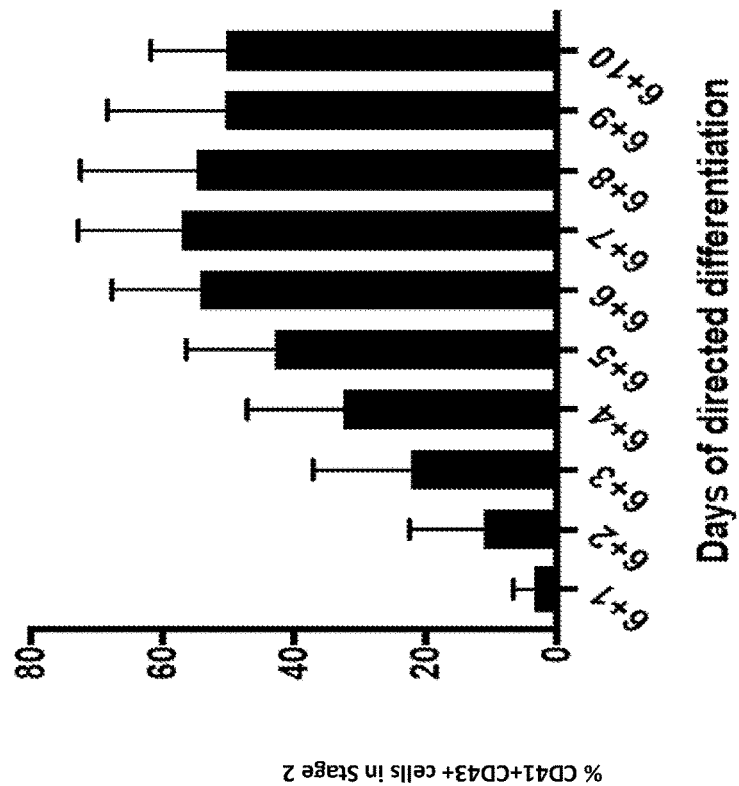
Figure 19B:
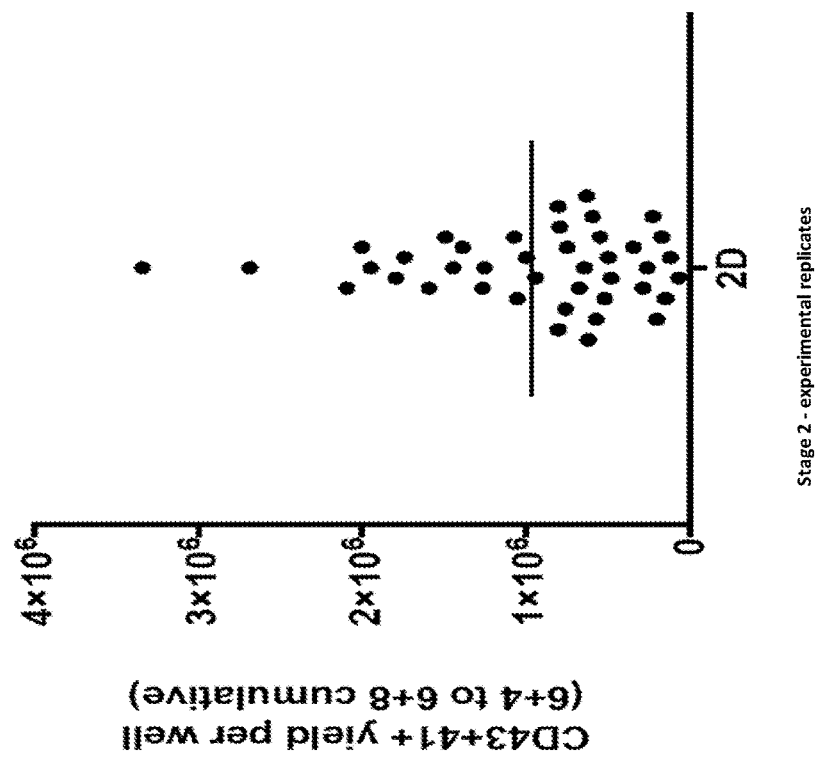
FIG. 19A and FIG. 19B depict yields of released preMKs.
Figure 19A:
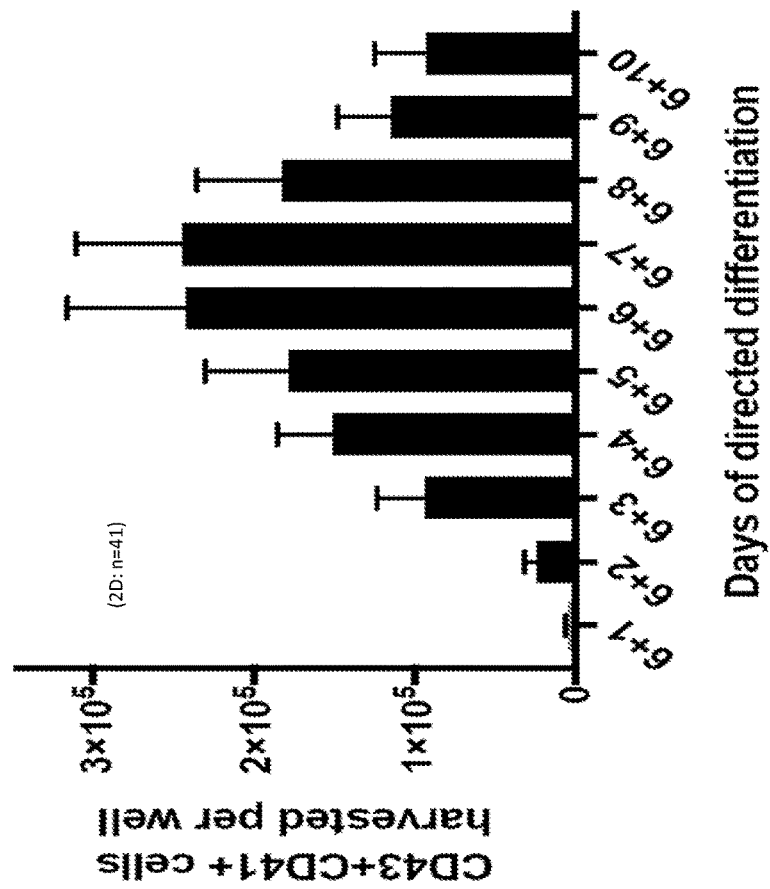

Within 2-3 days after initiation of Stage 2 (i.e. day 6+2 to 6+3), small, round, refractile cells appear within the adherent hemogenic endothelial cells and are eventually released into the supernatant above the adherent hemogenic endothelial monolayer (FIG. 17A). These released cells contain preMKs, as defined by cell surface expression of CD43 and CD41 and lacking expression of CD14 (FIG. 17B, 17C). These floating and weakly attached Stage 2 cells that appear on top of the adherent cell layer are harvested daily by gentle rinsing and collection of the medium into conical tubes, and are analyzed daily for expression of CD43, CD41, and CD14. The purity of the released cells is low for the first several days of Stage 2 and plateaus thereafter, with an average peak preMK purity of 50-60% by day 6+6 (FIG. 18A). CD14$^+$ myeloid cells are not major contaminants in iPSC directed differentiation cultures for the first 6-7 days of Stage 2, although there is some variability thereafter (FIG. 18B). The kinetics of preMK production peaks at day 6+6 and 6+7, on average, and decreases thereafter (FIG. 19A). Over multiple independent iPSC differentiations (n=41), the average cumulative preMK (CD43$^+$CD41$^+$CD14−) yield was determined to be approximately 1 million per well (range: 0.1 to 3.3 million) (FIG. 19B).

Figure 21A:
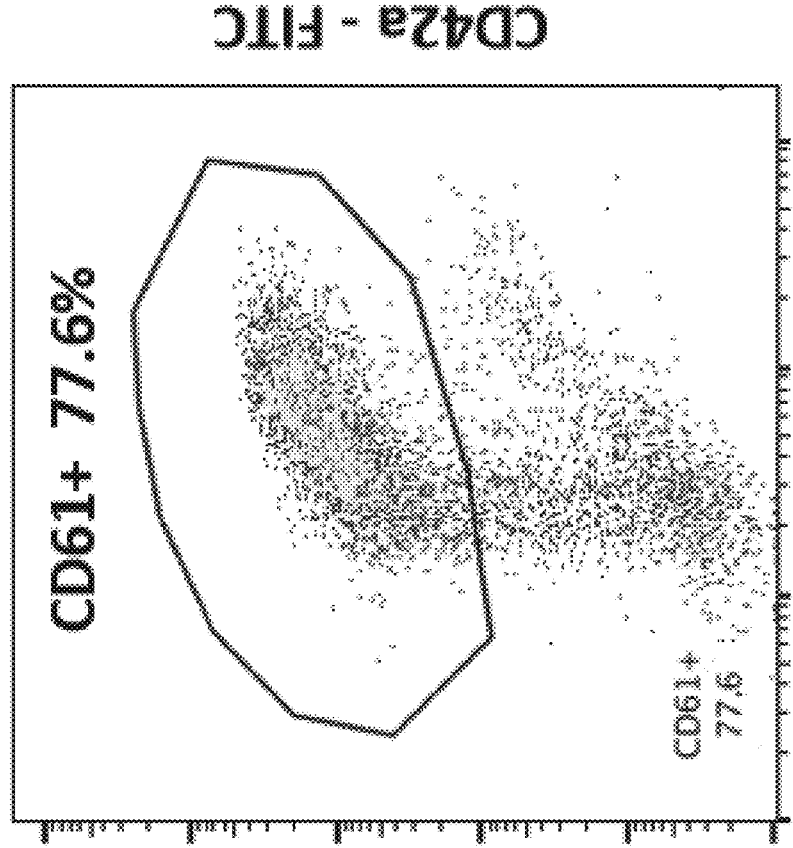
Figure 21C:
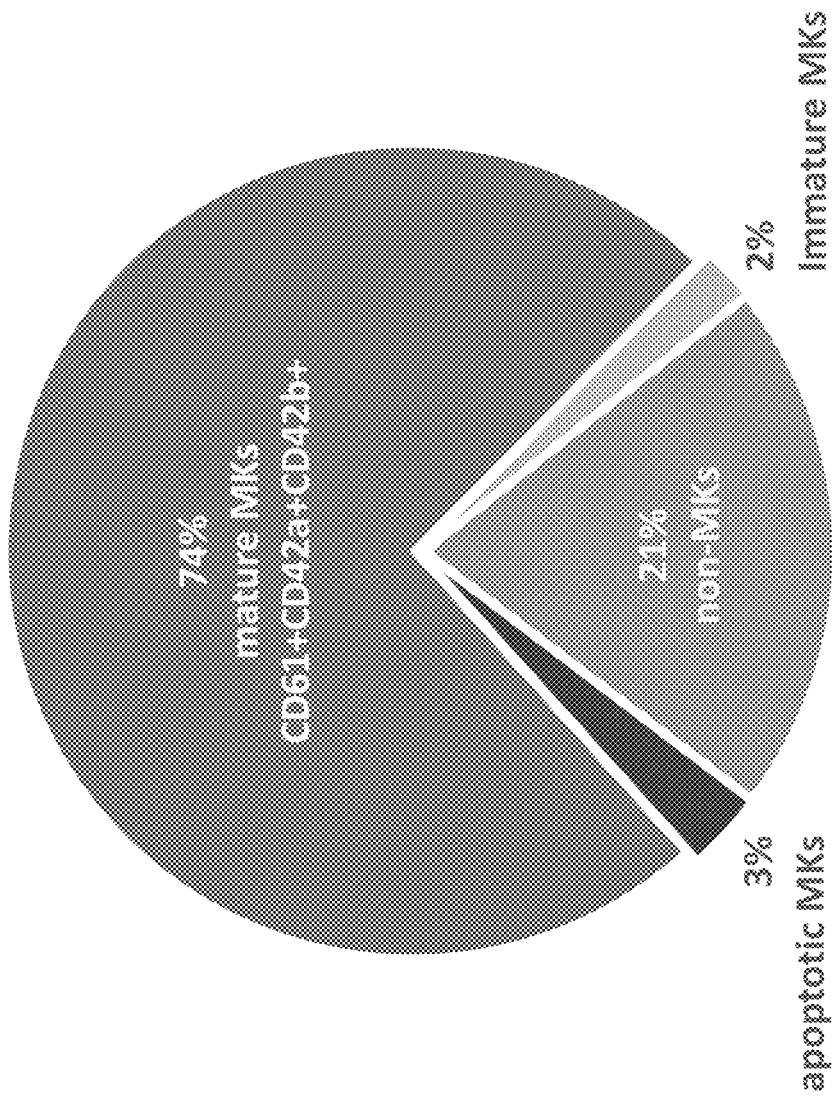

When preMKs from these cultures are transferred to Stage 3 conditions, they differentiate into mature MKs within several days. Cells that are initially uniformly small, round, and refractile (FIG. 20A) begin to increase in size by day 2-4 (FIG. 20B and FIG. 20C). Simultaneously, proplatelet-producing MKs can be readily observed (FIG. 20C and FIG. 20D). By 3-4 days of Stage 3, the proportion of CD61$^+$ (megakaryocytic lineage) cells co-expressing the mature MK markers CD42a and CD42b are determined by FACS (FIG. 21A and FIG. 21B) and the purity of mature MKs (CD61+CD42a+CD42b+ cells) can reach levels as high as 70-90% of all nucleated cells in the culture (FIG. 21C).

Example 3: Directed Differentiation in Matrix-Independent 3D Cultures

Figure 22B:
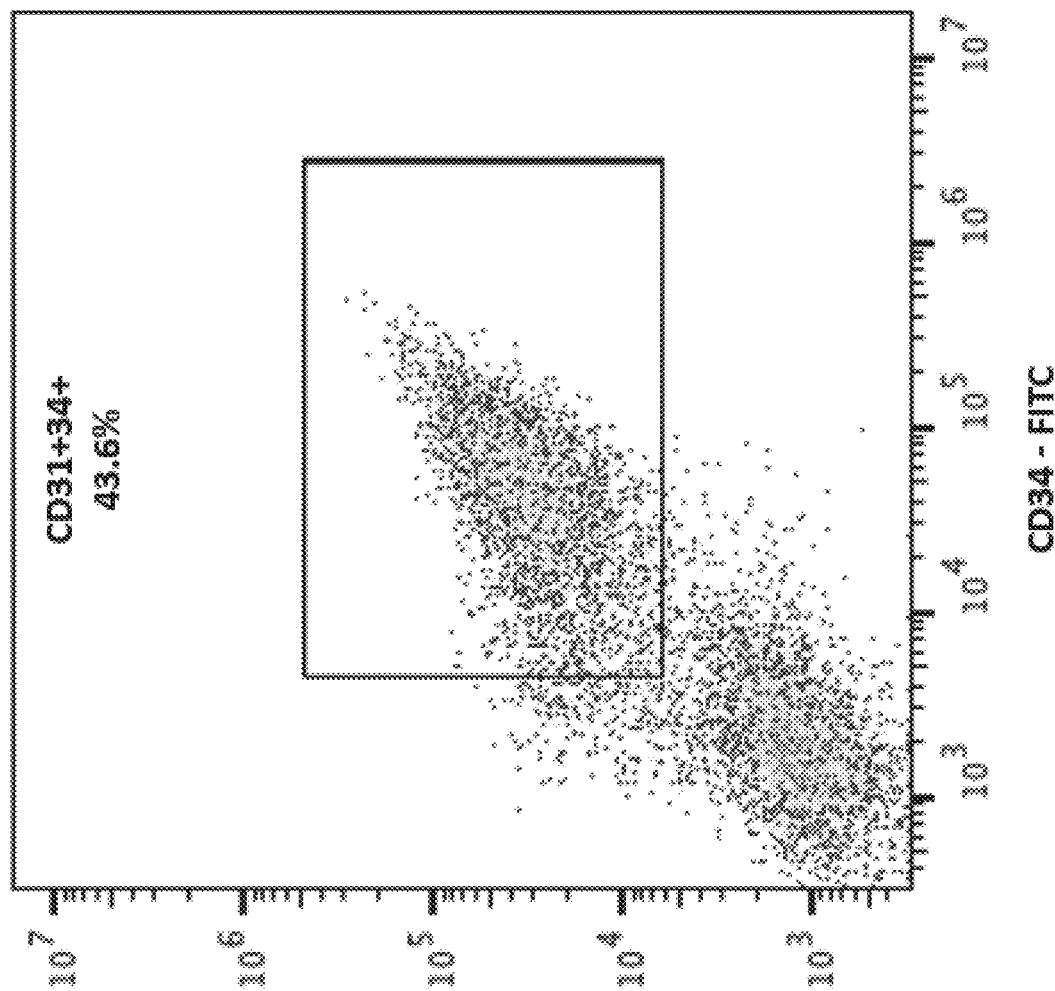
Figure 24C:
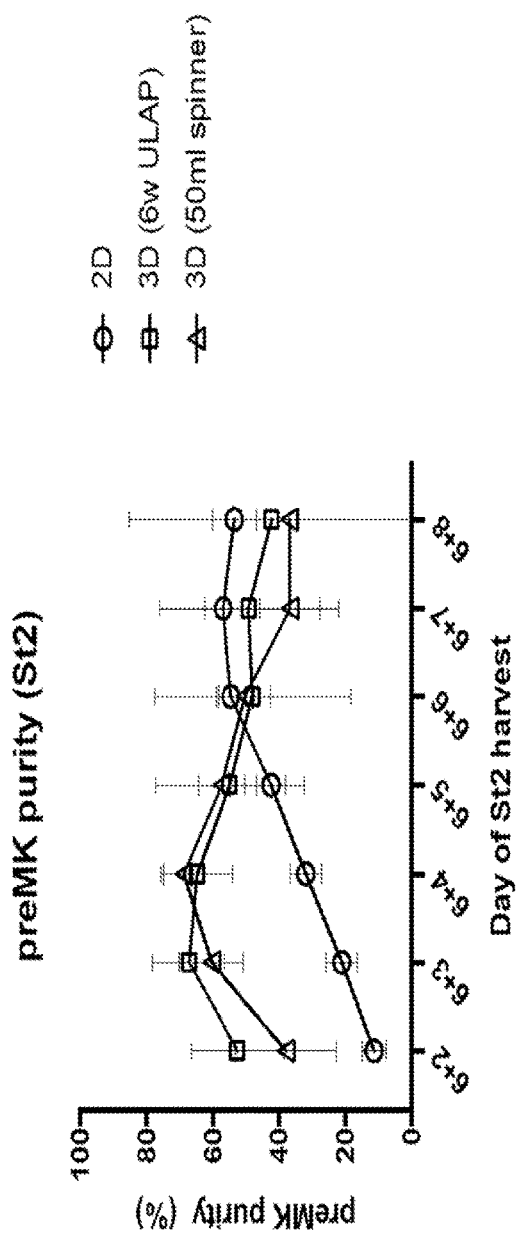
Figure 24D:
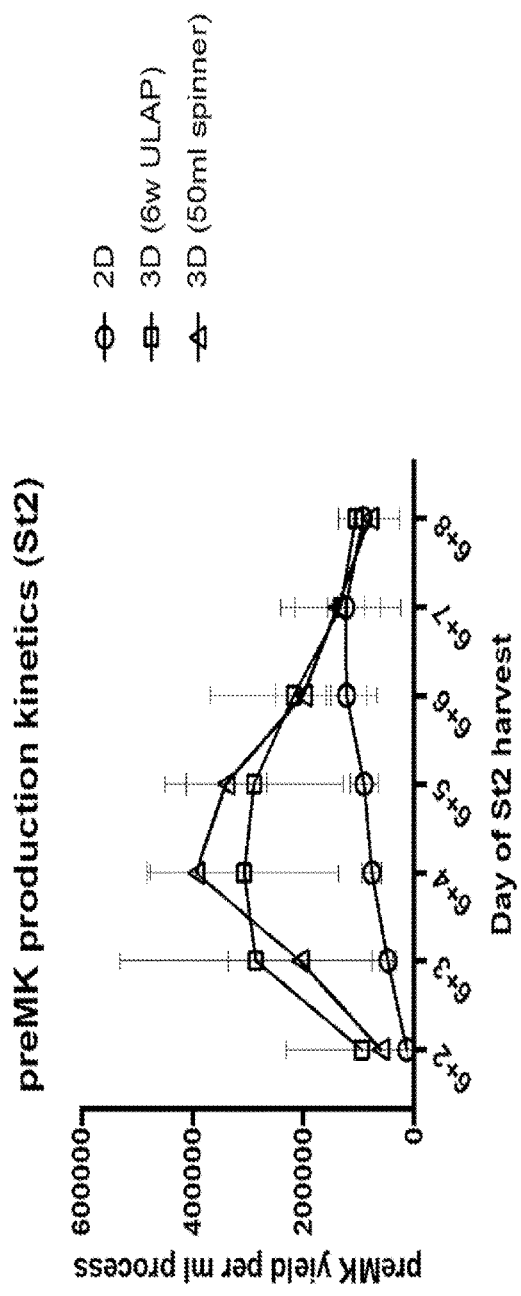

To enable yields required for clinical production of megakaryocytes and platelets, it is crucial to transition the entire differentiation process from small-scale tissue culture plasticware (2D, matrix dependent) to a 3D scalable solution. An example of a scalable 3D solution involves performing differentiations using self-aggregating spheroids suspended in stirred or shaken ultra-low-adherent vessels (FIG. 3). In this example, LiPSC-Gr1.1 hiPSCs were dissociated into single cells using TrypLE, resuspended at 0.5-1 million cells/ml in pluripotency maintenance media (such as Essential 8, Nutristem, StemFlex, other similar media, or combinations thereof) plus H1152 or other ROCK inhibitor, and incubated at 37 C, 5% CO2, 20%O2 in a 6-well ultra-low adherent plate on an orbital shaker at 90 rpm, or a spinner flask with constant agitation (90 rpm for 50 ml volume in a 125 ml spinner flask). Within 24 hours in either system, the hiPSCs self-aggregated to form spheroids approximately 50-150 um in diameter (FIG. 22A, also see FIG. 23A and FIG. 11A for similar examples in different vessels). Agitation was then paused, and the spheroids were allowed to settle to the bottom of the vessel (approximately 5 minutes). 50%-100% of the media was then exchanged with Stage 1 differentiation media to promote the differentiation towards hemogenic endothelium, and agitation was resumed, with incubation in hypoxic conditions (37 C, 5% CO2, 5% O2). Media exchanges were similarly performed on a daily basis for a total of 6 days (4 days in 37° C., 5% CO2, 5% $O_2$, followed by 2 days in 37 C, 5% CO2, 20% O2), during which time the spheroids grew larger and developed characteristic structure and shape by day 6 (FIG. 22A). When a sample of these spheroids at day 6 were dissociated and assessed by flow cytometry, ~44% of the cells were found to express the hemogenic endothelial markers CD31 and CD34 (FIG. 22B), a purity that compared favorably to 2D matrix-dependent cultures (FIG. 16B). To transition to Stage 2, agitation was paused and the spheroids were allowed to settle to the bottom of the vessel (approximately 5 minutes). 50-100% of the media was then exchanged with Stage 2 differentiation media to promote the differentiation and release of suspension cells (FIG. 24A). On a daily basis thereafter, suspension cells were collected and a partial media exchange was performed. To do this, agitation was paused and the hemogenic endothelial spheroids were allowed to settle to the bottom of the vessel (approximately 5 minutes). Approximately 80% of the media (together with the suspension cells) was collected, and centrifuged. Half the working volume of fresh Stage 2 differentiation media was added to the spheroids, along with a sufficient volume of conditioned media (i.e. supernatant post-centrifugation) to restore the original working volume. The remaining supernatant was then discarded, with a portion of the cell pellet used for FACS analysis (FIG. 24B), and the remainder cryopreserved or transferred to Stage 3 for maturation to mature MKs. Flow cytometric analysis of the suspension cells revealed that the self-aggregated spheroids that were differentiated in a 6-well ultra-low adherent plate on an orbital shaker, and self-aggregated spheroids that were differentiated in a 50 ml spinner flask, showed similar preMK production kinetics, both purity and yield over time. Compared to the 2D Collagen IV differentiation cultures, these 3D cultures produced more preMKs, at a higher purity, and earlier in Stage 2 (FIG. 24C, 24D).

Cultures expanded and harvested with single cell passaging (FIGS. 10A-10C) could also be aggregated to 3D spheroids and differentiated effectively to pre-MK cells using the 6-well suspension differentiation methodology just described (FIG. 23A). pre-MK yields were comparable to historical 6-well plate cultures, as were purities as assessed by co-staining of CD41/CD43 (FIG. 23B). These data demonstrate effective control of hiPSC self-renewal in single-cell passaging conditions supporting stable expansion and scalability whilst retaining differentiation potential to pre-MK cells.

Figure 25A:
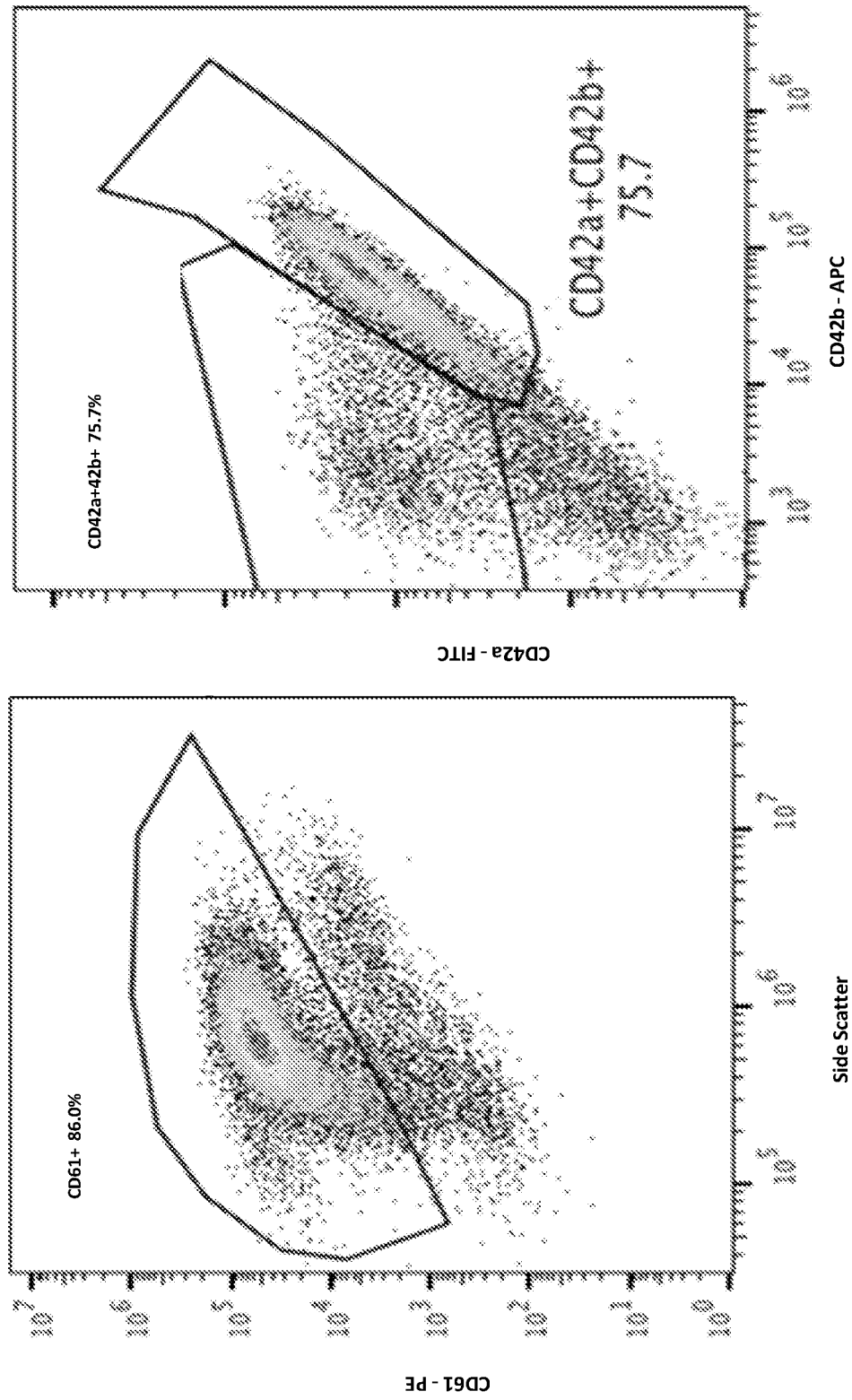
FIGS. 25A-25C depict Stage 3 MK differentiation from 3D, matrix-independent cultures initiated from self-aggregating spheroids of iPSCs.
Figure 25B:
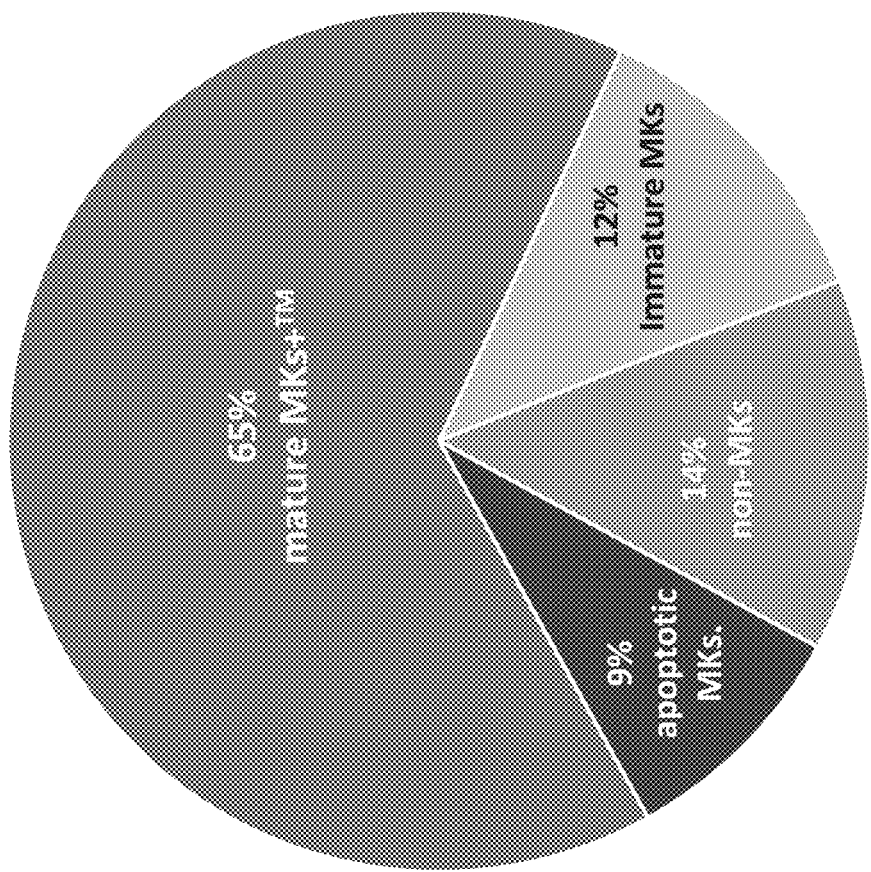
Figure 25C:
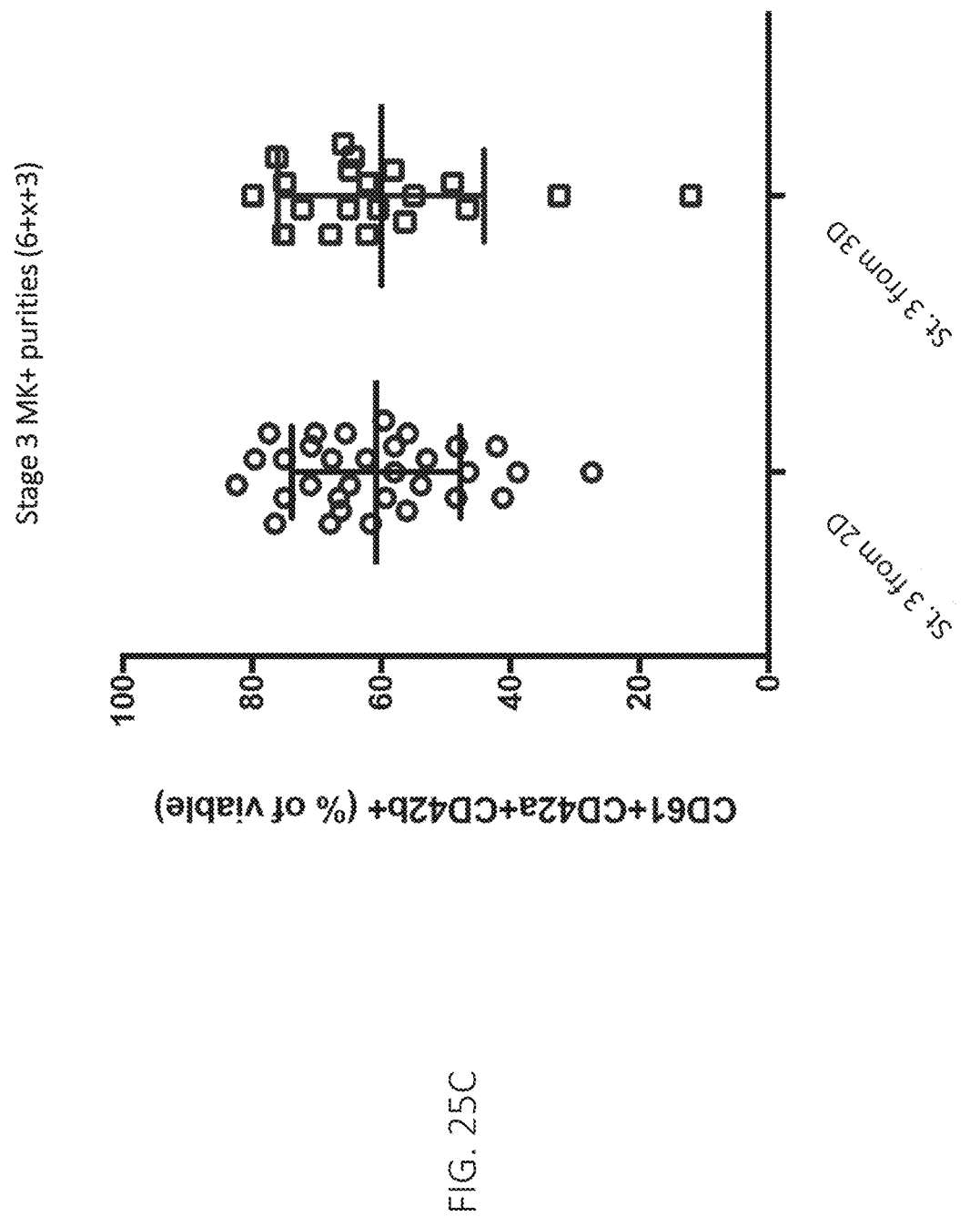
Figure 26:
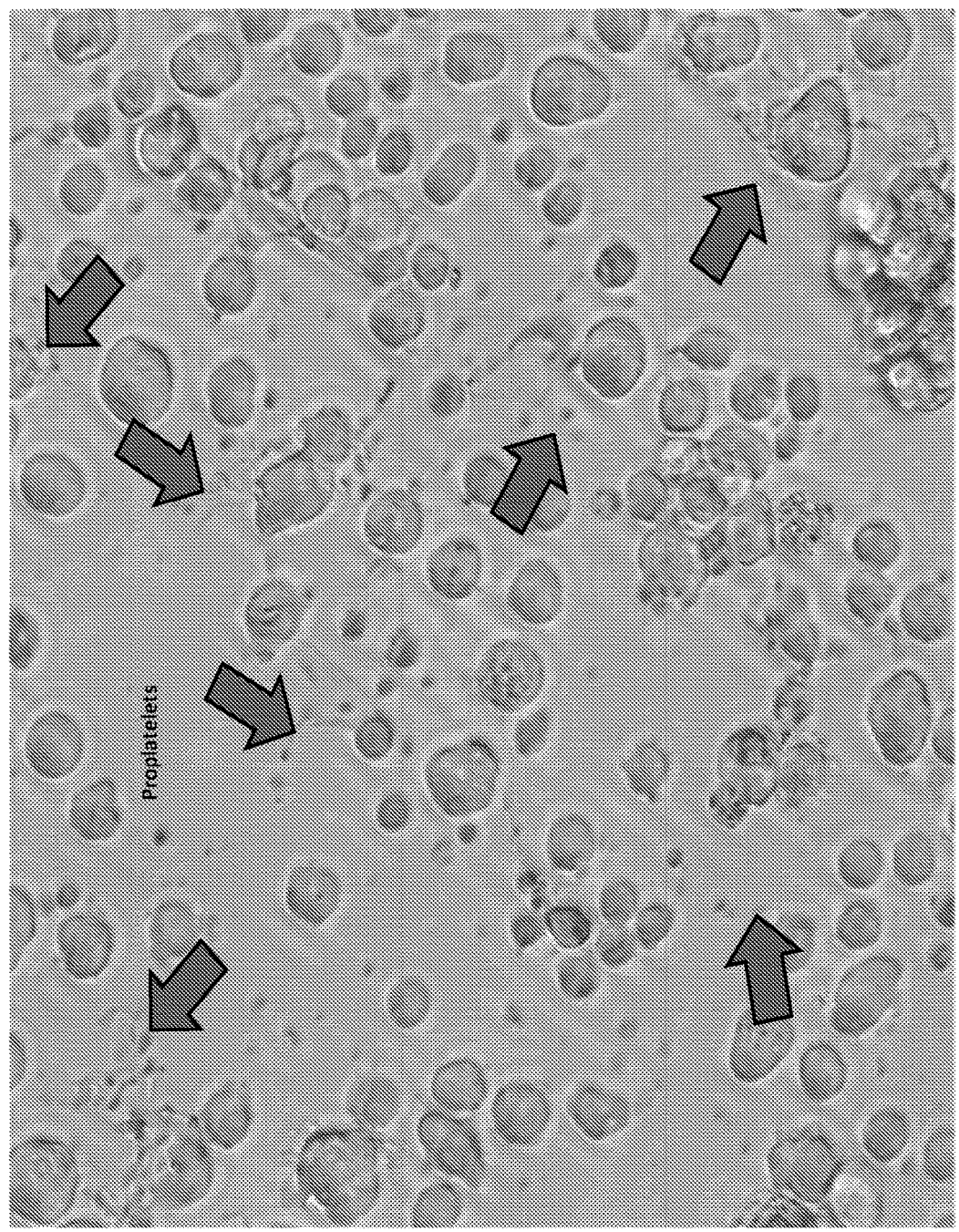
FIG. 26 depicts proplatelet extensions of mature MK harvested from 3D self-aggregating spheroid differentiation cultures. Examples of proplatelet extensions are indicated with arrows.

Upon transition to static Stage 3 cultures, preMKs from 3D self-aggregating spheroid cultures generated similar MK purities as preMKs from 2D culture systems (FIGS. 25A-25C). Furthermore, Stage 3 differentiation cultures generated from 3D self-aggregating spheroid cultures contained cells that increased dramatically in size and were able to generate proplatelets (FIG. 26), consistent with their identity as bona fide megakaryocytes.

Example 4: Addition of Soluble Laminin 521 During iPSC Aggregation or at Stage 1-2 Transition Improves Stage 2 preMK Yields in Two Different 3D Differentiation Formats Addition of Laminin 521 during the initial iPSC aggregation step 24 hours prior to initiation of differentiation (day −1) or at the time of transition between Stage 1 and Stage 2 (day 6) resulted in increased preMK yields in two different 3D differentiation formats. 5000 single-cell dissociated iPSCs were seeded per well of a 96-well U-bottom ultra-low adherent plate containing StemFlex and the Rock inhibitor H1152 (control media), with or without soluble recombinant Laminin 521. 24 hours later, the media was replaced with Stage 1 media and media exchanges were performed for 6 days. Media was then exchanged with Stage 2 media, with or without soluble Laminin 521. 24 hours later, daily half media exchanges were performed for up to 6 additional days. Comparing the preMK yields in Stage 2 revealed that the addition of Laminin 521 at Day −1 or Day 6 of the differentiation process increased the preMK yields compared to control cultures without Laminin 521 addition (FIG. 27 A, 27B). To determine if the effect of Laminin 521 could also be observed in agitated 3D cultures, iPSCs were dissociated as single cells and 1.5 million cells were seeded into each well of a 6-well ultra-low adherent plate containing StemFlex and the Rock inhibitor H1152 (control media), with or without soluble recombinant Laminin 521, and placed on an orbital shaker. 24 hours later, the media was replaced with Stage 1 media and media exchanges were performed for 6 days. Media was then exchanged with Stage 2 media, with or without soluble Laminin 521. 24 hours later, daily half media exchanges were performed for up to 6 additional days. Comparing the preMK yields in Stage 2 revealed that the addition of Laminin 521 at Day −1 or Day 6 of the differentiation process increased the preMK yields compared to control cultures without Laminin 521 addition (FIG. 27C). When iPSCs derived from the high-efficiency single cell passaging technique described in Example 1 were similarly allowed to self-aggregate in NutriStem in a 6-well plate on an orbital shaker, the Laminin 521 effect was amplified (FIG. 27D).

Figure 28A:
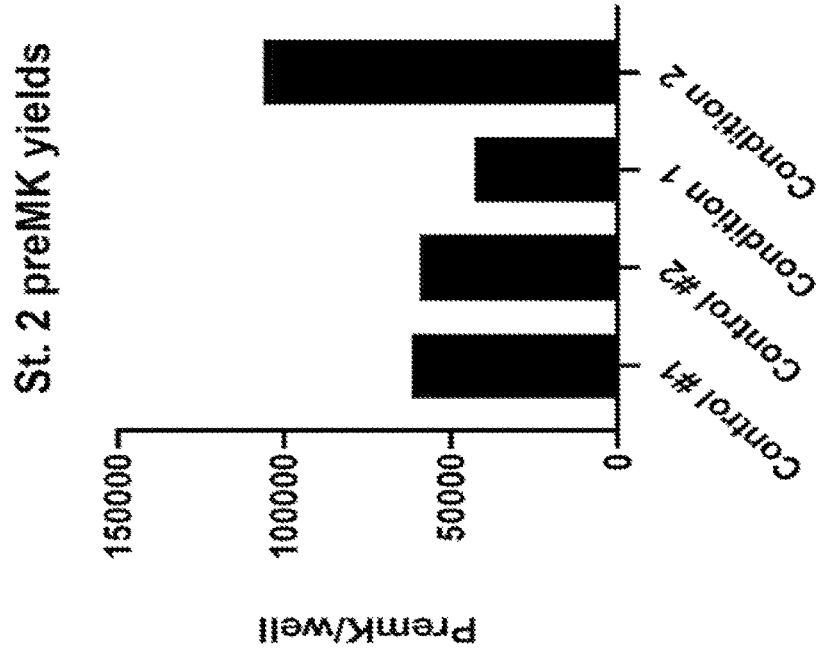
Figure 28B:
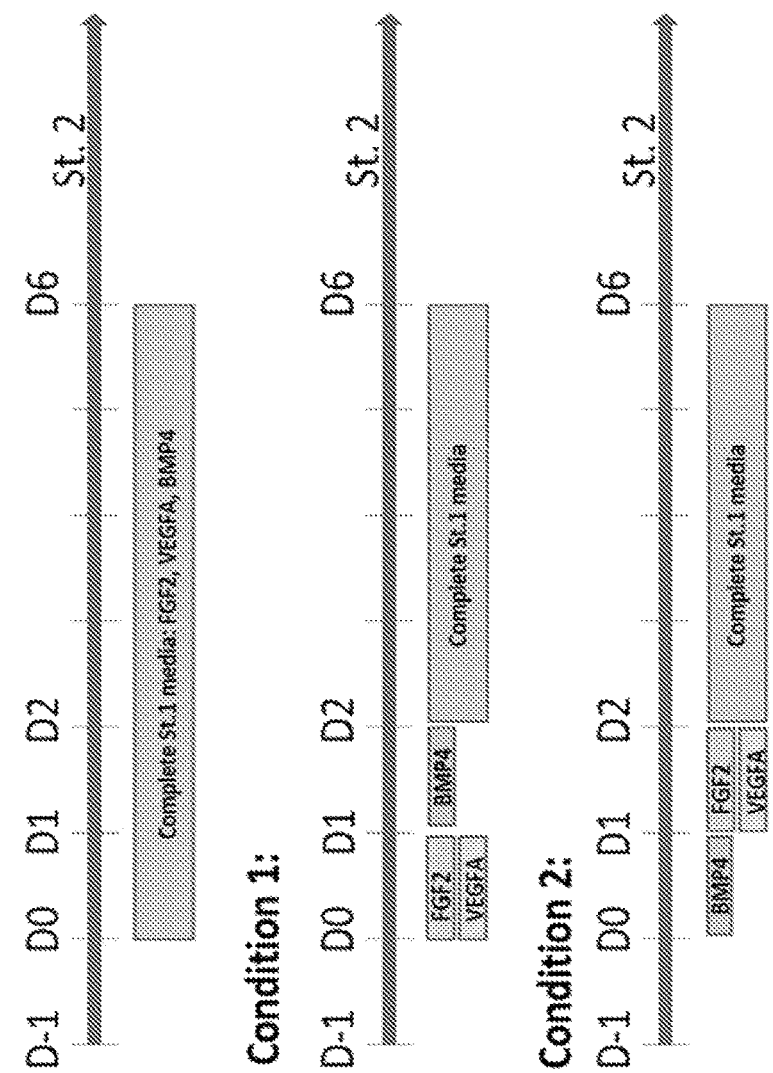

Example 5: Adjustment of Order and Timing of Growth Factor Addition During Stage 1 Increases Differentiation Efficiency and Decreases Overall Growth Factor Usage The initial specification events that occur during Stage 1 of differentiation are complex and require a unique order and timing of cell signaling events. Therefore, adjusting the order and timing of addition of the Stage 1 media factors BMP4, bFGF and VEGFA could improve the efficiency of the differentiation process and reduce growth factor usage compared to the standard complete St1 media conditions, where all three growth factors are included for the entirety of Stage 1. The first experiment (Experiment A) (FIG. 28A) tested the order and timing of addition. When BMP4 alone was added for the first 24 hours, followed by VEGFA and bFGF (without BMP4) for the next 24 hours, followed by 4 days of complete St1 media, the number of preMKs produced in Stage 2 was markedly higher than control cultures that received complete St1 media throughout Stage 1 (FIG. 28B). Performing the same order for 48 hours did not have the same effect. The second experiment (Experiment B) (FIG. 28C) demonstrated that BMP4 was dispensable beyond 24 hours in this system, while FGF2 and VEGFA are critical for differentiation to proceed effectively (FIG. 28D). This example demonstrates that Stage 1 of differentiation can proceed effectively using BMP4 alone for 24 hours, followed by bFGF and VEGFA for 5 days, before transitioning to Stage 2 of differentiation.

Example 6: WNT Modulators can Affect Stage 1 and Stage 2 Differentiation Efficiency WNT signaling is important during development. The GSK3 kinase inhibitors CHIR98014 and CHIR99021 act as WNT agonists. When the Stage 1 differentiation conditions described herein were augmented with 0.6 μM CHIR98014 or 6 μM CHIR99021 for the first 48 hours of differentiation only, a dramatic increase in Stage 1 differentiation efficiency was observed at day 6, as determined by immunofluorescence staining of CD31 and CD34 (FIGS. 29A-29C). The control and CHIR98014 cultures were then transitioned to Stage 2, where the production and release of preMKs were tracked by immunofluorescence staining of CD41 and CD43. Visual estimation of the number of CD41+ cells suggests that the higher Stage 1 efficiency engendered by WNT modulators in the first 48 hours can correspond to a higher output during Stage 2 (FIGS. 30A-30B). Therefore, a short period of addition of WNT modulators can impact differentiation efficiency throughout subsequent differentiation stages.

Example 7: Packed Bed Bioreactor with Laminin 521-Coated Macrocarriers

Figure 32:
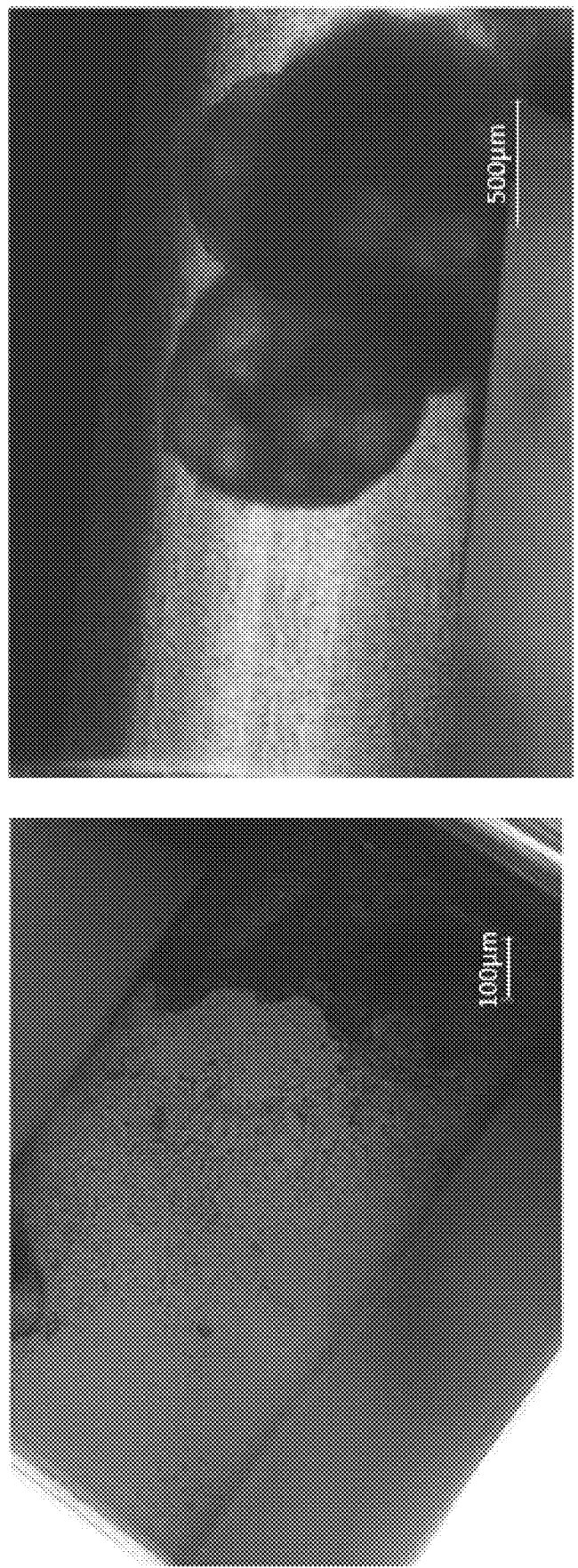
FIG. 32 depicts Stage 2 differentiation of iPSCs on Laminin521 coated Rachig rings at day 6+0 (100 µm scale bar) and day 6+4 (500 µm scale bar).
Figure 33B:
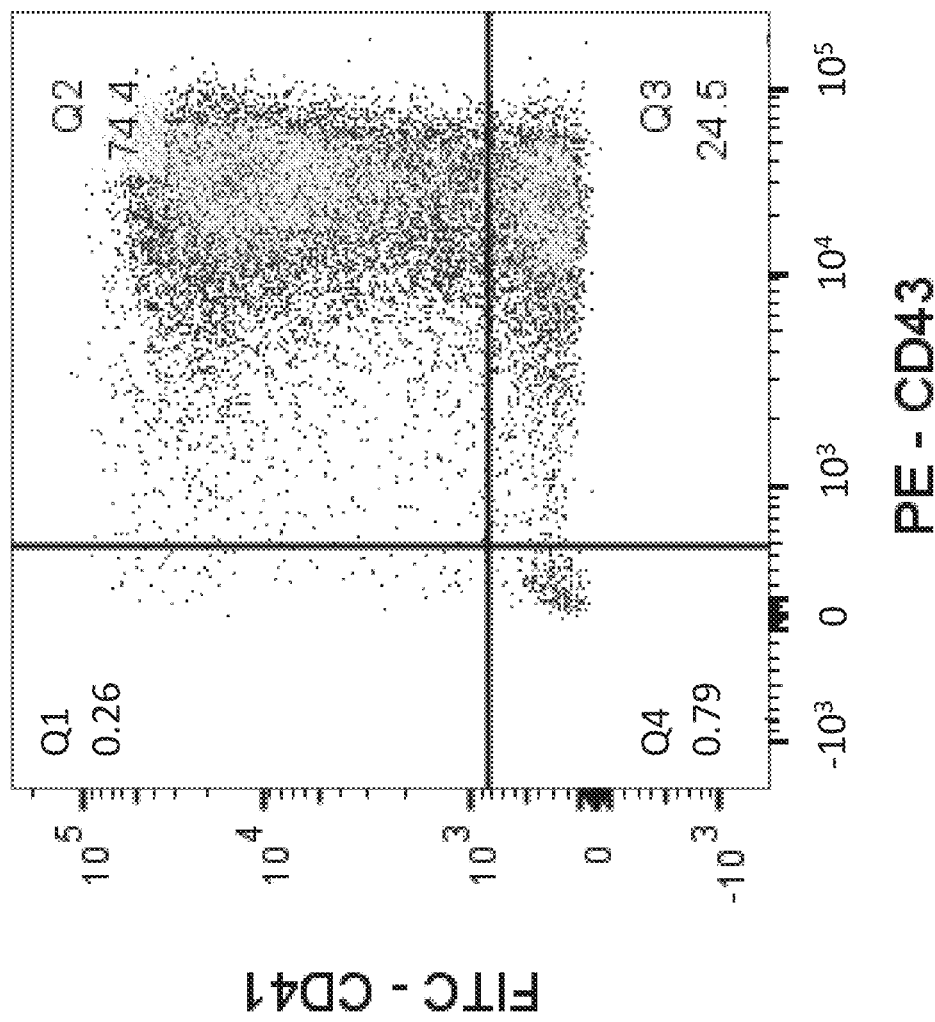
Figure 33C:
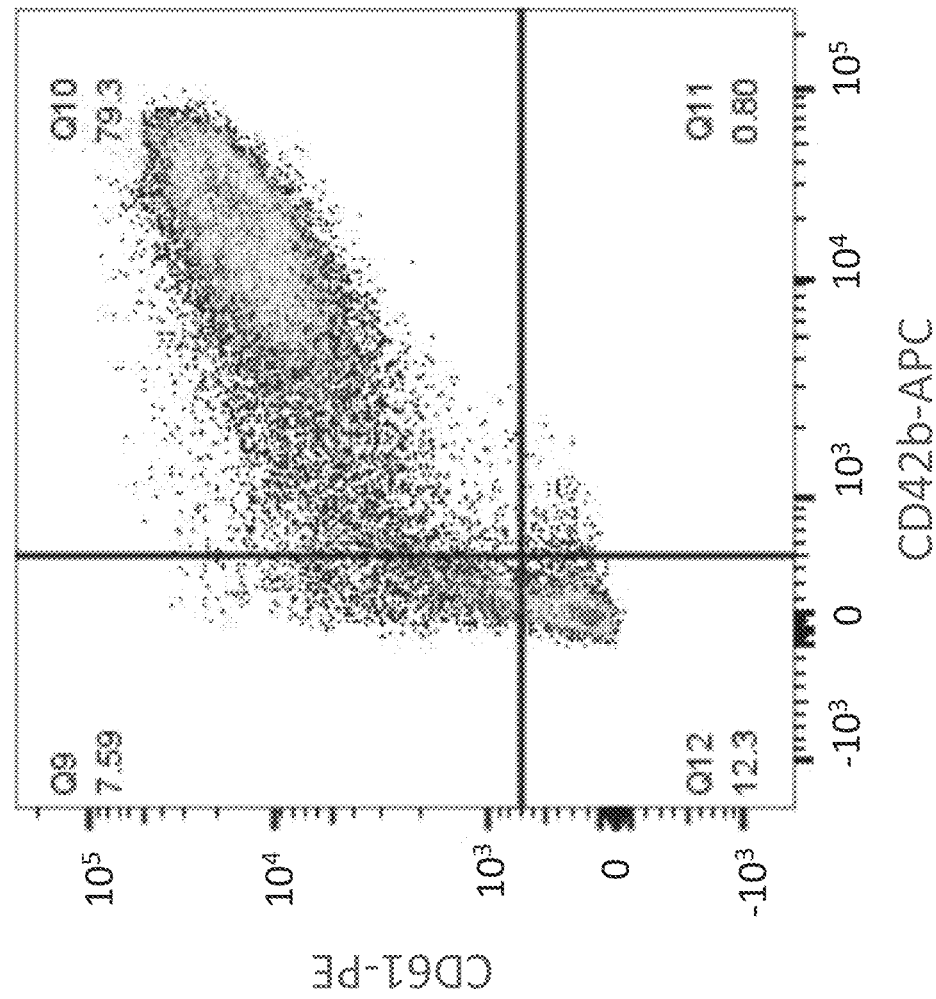
Figure 36F:
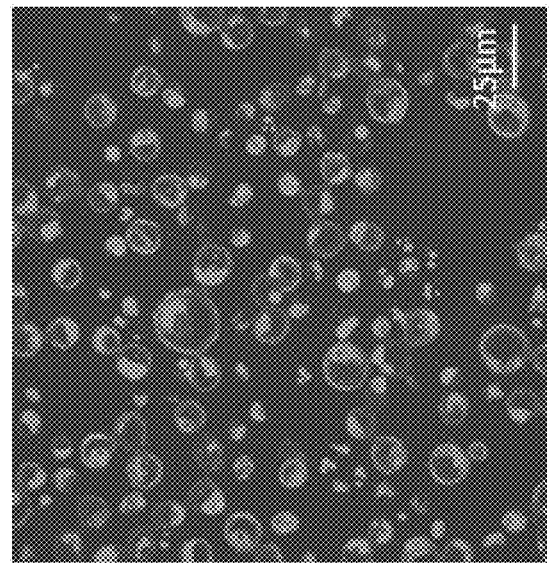
Figure 36E:
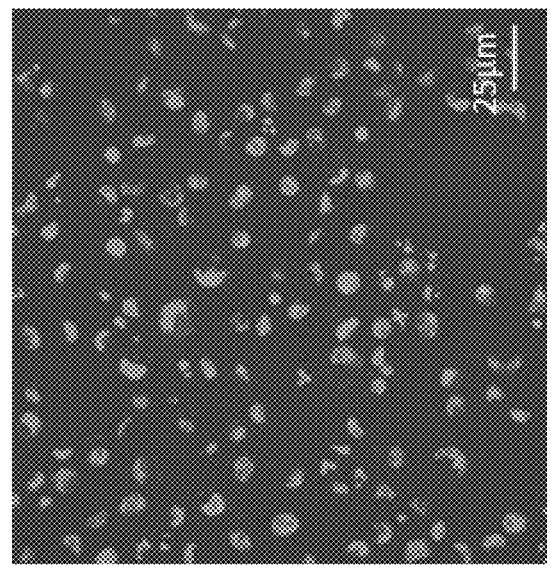
Figure 36D:
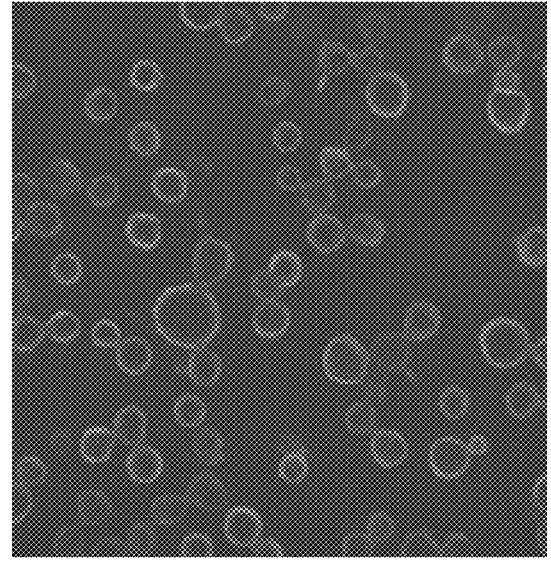
Figure 37B:
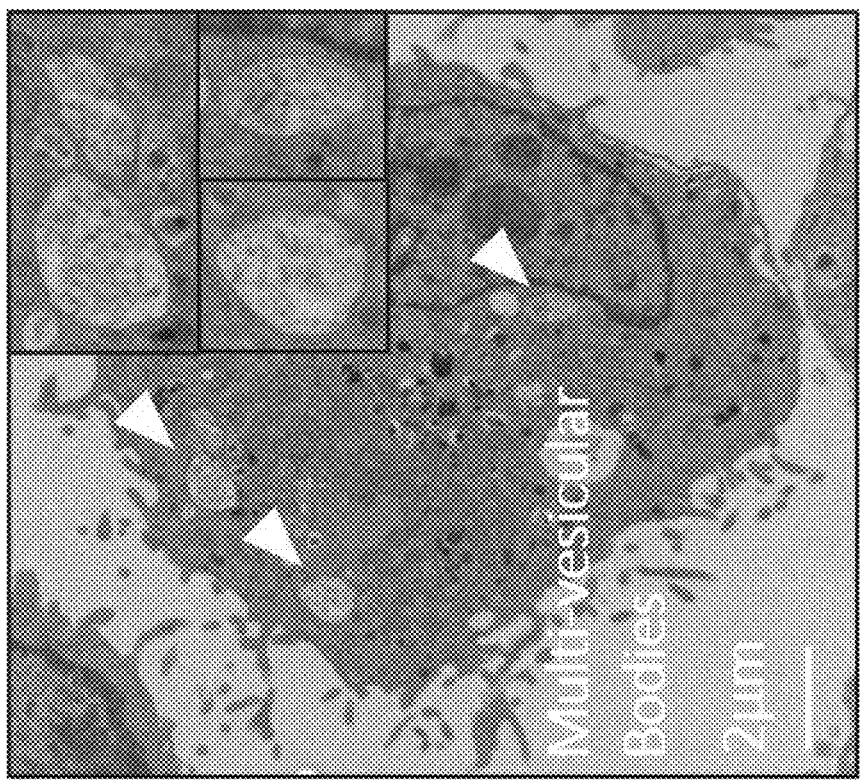
FIGS. 37A-37D are electron microscopy images showing a iPSC-derived megakaryocyte.
Figure 37A:
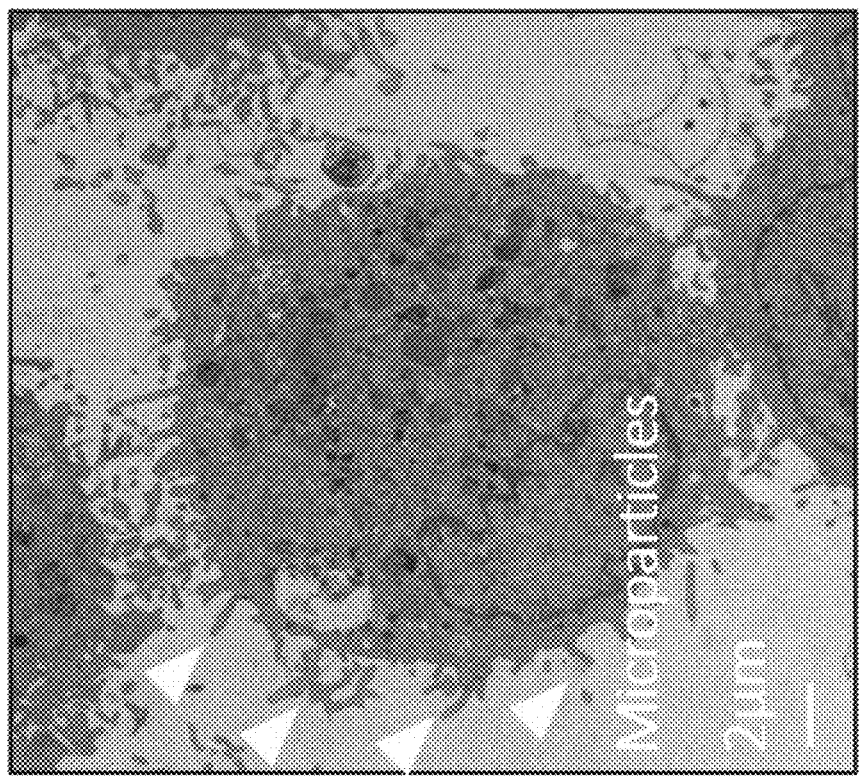
Figure 37D:
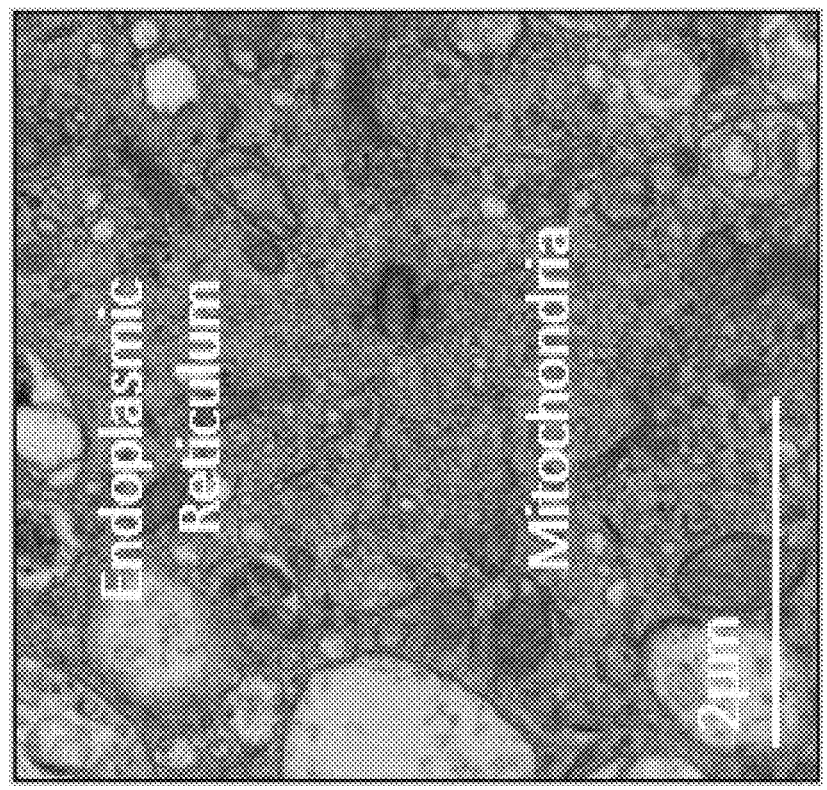
Figure 37C:
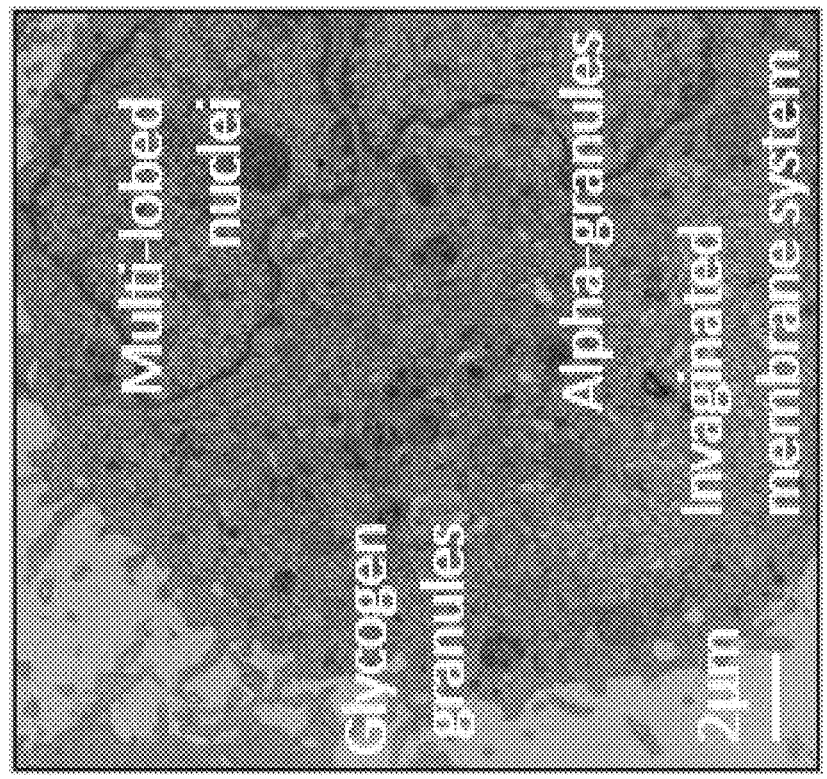

Here, evidence is provided demonstrating that a Laminin 521-coated PTFE macrocarrier in the shape of a 1 mm Raschig ring can provide support for the differentiation of iPSCs and that this macrocarrier material would be amenable for use in a packed bed bioreactor, as illustrated in the schematic shown in FIG. 4. PTFE rings were first incubated overnight on a rocker at 4° C. with 1.25 ug/ml Laminin-521. Before use, the PTFE rings were equilibrated in a 6-well plate with Essential 8 media plus H1152, a ROCK inhibitor. Pluripotent iPSCs were harvested using 0.5 mM EDTA, resuspended Essential 8 media plus H1152, and seeded as clumps onto the PTFE rings. Every 10 minutes, the plate was run for 30 seconds at 75 rpm on an orbital shaker. After 1 hour, the plate was shaken continuously at 75 rpm overnight. 24 hours later, 90% of the media was removed and replaced with Stage 1 media, with daily media exchanges. During Stage 1, the iPSCs exhibited growth areas on the inside of the Raschig rings (FIG. 31), and the growth areas developed similar morphological characteristics to those seen in 2D cultures (FIG. 22). Flow cytometric analysis of these cells indicated a high proportion of hemogenic endothelial cells, with ~80% of the cells expressing CD31, with more than half of those cells double positive for CD34+ (FIG. 33A). Upon switching to Stage 2 media and initiating half daily media exchanges, the morphology changed from a generally flat colony to a 3D spheroid-type structure, although it should be noted these structures were still attached to the Laminin 521 coating on the inside of the ring-shaped macrocarrier (FIG. 32). Cells that were released during Stage 2 had a high preMK content even as early as Day 6+2, with ~75% of the cells co-expressing CD43 and CD41 (FIG. 33B), a purity that compares favorably to 2D matrix-dependent cultures (FIG. 18A). Cells released at day 6+3 were collected and cultured for an additional 3 days in Stage 3 media in an ultra-low-adherent plate, and ~80% of these cells co-expressed CD61 and CD42b (FIG. 33C), indicating that efficient MK differentiation had occurred. Such macrocarriers are amenable for use as material for a packed bed bioreactor in which initial differentiation of iPSCs to hemogenic endothelium (i.e. Stage 1 of directed differentiation), as well as the further differentiation and release of preMKs (i.e. Stage 2 of directed differentiation) could occur in the same vessel (FIG. 4). In this design, a packed bed bioreactor is set up with Laminin-521 coated macrocarriers freshly seeded with pluripotent iPSCs. The packed bed is then exposed to a continuous flow of media to enable Stage 1 differentiation to hemogenic endothelium. After percolating through the packed bed, the media would be circulated through a conditioning chamber, where fresh media components would be added, and oxygen/CO2 concentrations would be adjusted via sparging or other means before the media would be recirculated to the cells. At the completion of Stage 1, the media would be switched to allow Stage 2 differentiation and production and release of preMKs. Appropriately sized and shaped macrocarrier substrates such as the 1 mm Raschig rings would enable sufficient media flow and channel width to enable the released cells to percolate through the packed bed and out of the reactor for collection and cryostorage. This design decreases the shear forces experienced by the cells, allows for efficient media usage due to its perfusion based design, and enables the continuous collection of preMKs as they are released.

Example 8: Detailed Characterization of iPSC-Derived Megakaryocytes

Figure 38B:
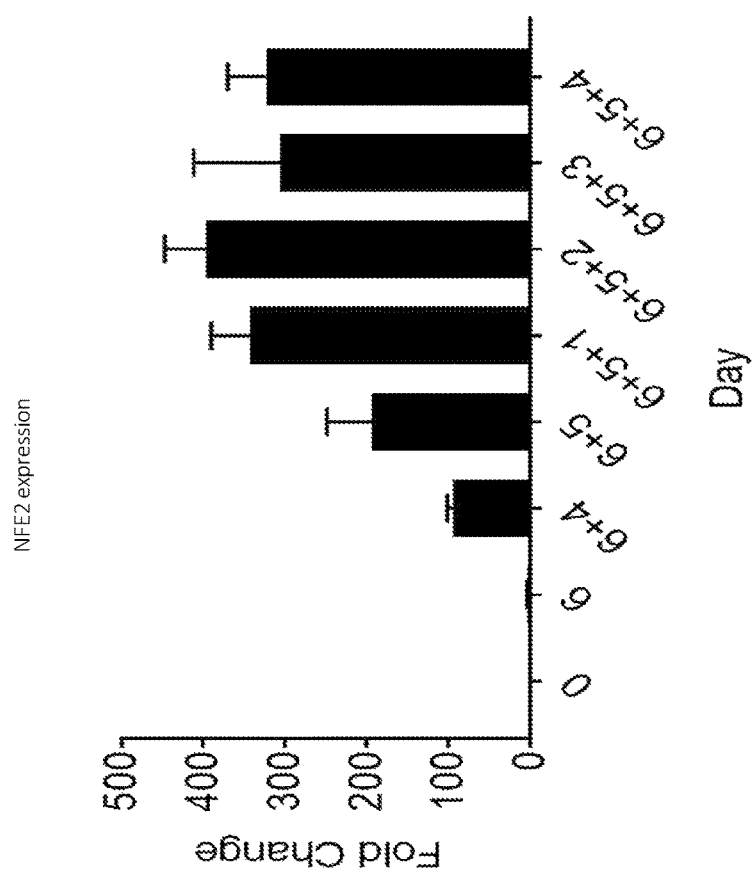
FIG. 38A and FIG. 38B illustrate characteristic gene expression changes that occur through the course of iPSC directed differentiation to megakaryocytes. For all expression analyses, the expression in the iPSCs was set at 1, and all other expression values are presented in relative terms.
Figure 38A:
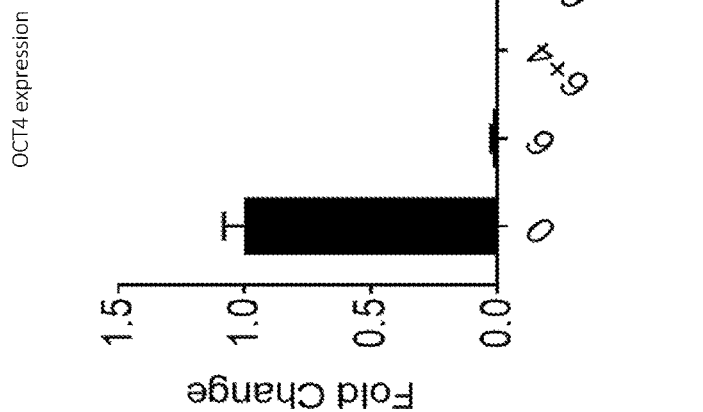
Figure 39:
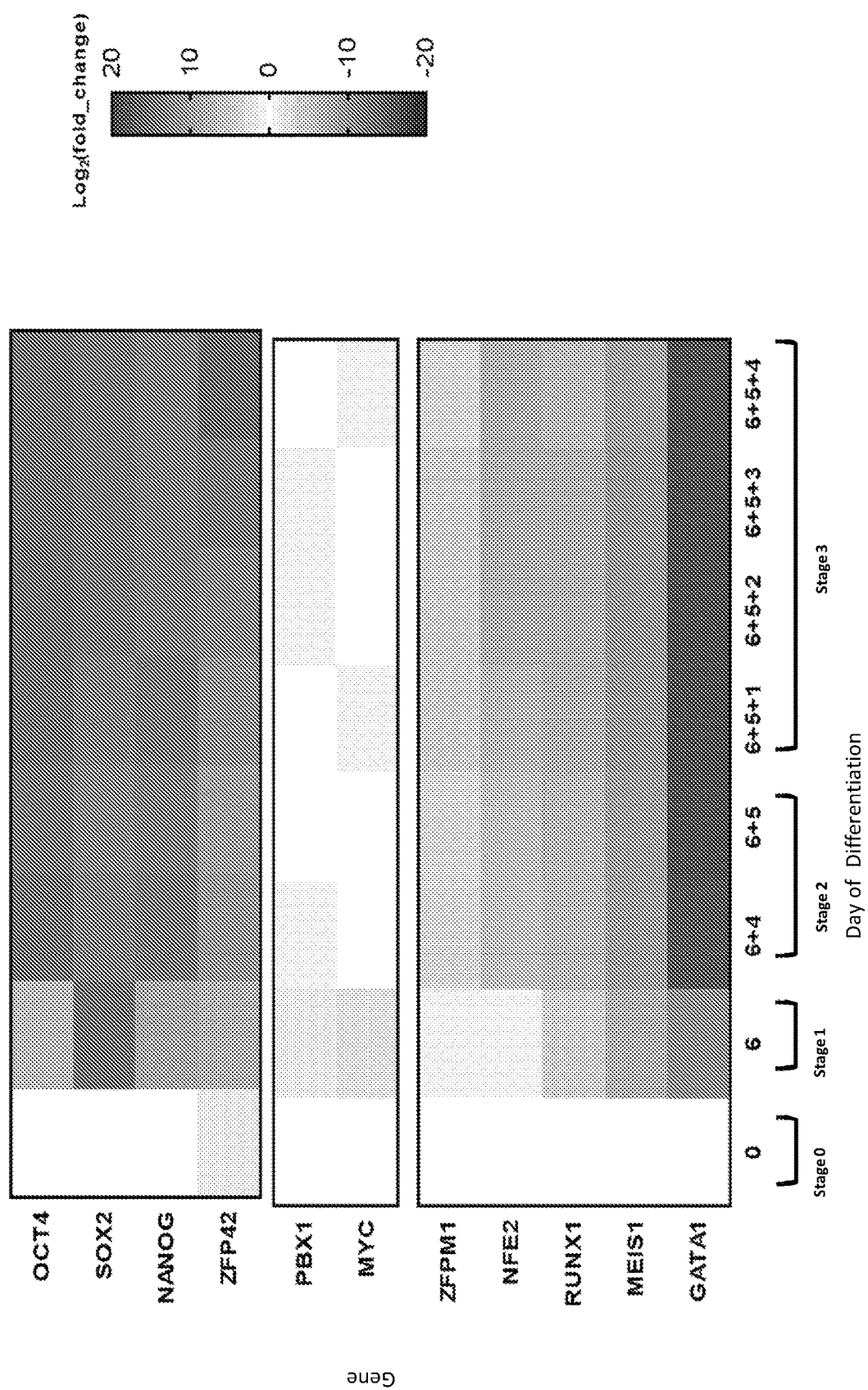
FIG. 39 is a heat map showing OCT4, SOX2, NANOG, and ZFP42 being downregulated during differentiation, ZFPM1, NFE2, RUNX1, MEIS1, and GATA1 being upregulated during differentiation, and PBX1 and MYC remaining at a substantially consistent level.
Figure 41B:
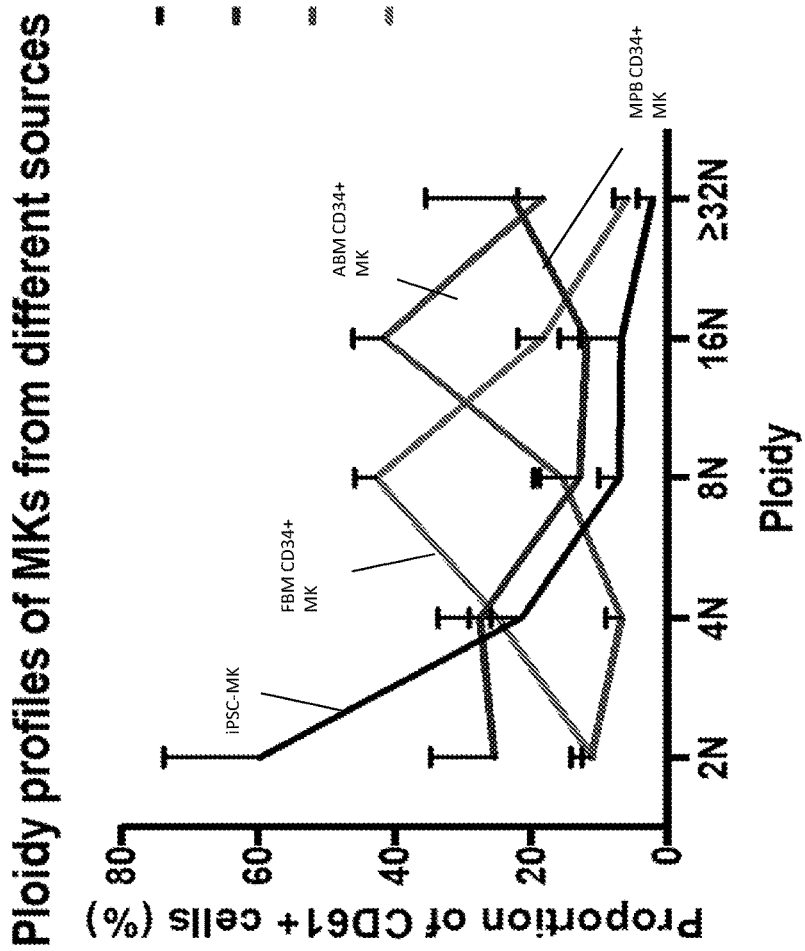
FIG. 41A and FIG. 41B provide ploidy measurements on iPSC derived megakaryocytes.
Figure 41A:
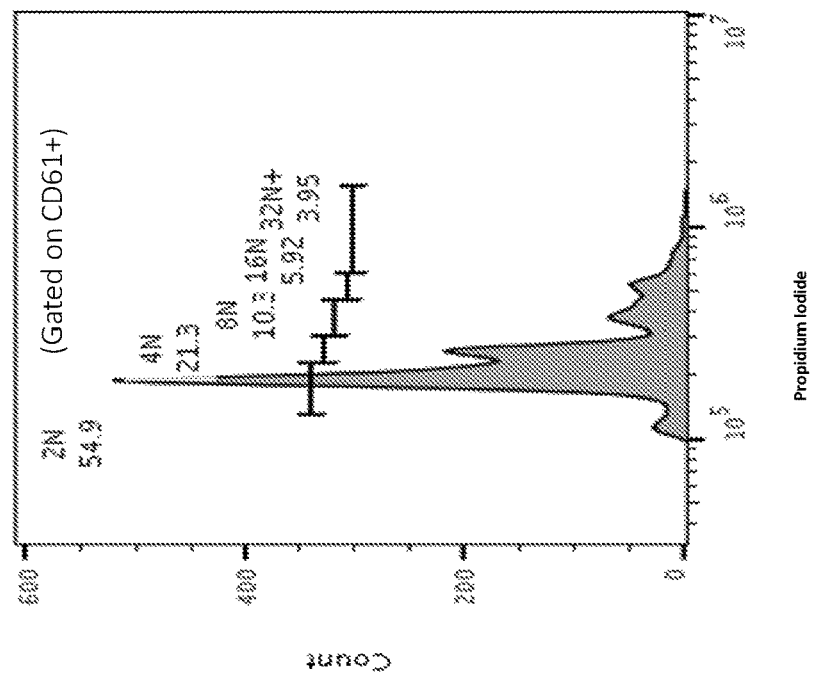

Megakaryocytes generated using the methods described herein demonstrate many features associated with functional mature MKs, including when imaged by immunofluorescence microscopy for the MK-specific protein beta-1-tubulin (FIG. 34), as well as proteins associated with alpha-granules (PF4 and VWF, FIGS. 35A-35F) and dense granules (LAMP1 and serotonin, FIGS. 36A-36F). Electron microscopy images of iPSCs derived MKs reveal characteristic ultrastructural features, including multivesicular bodies, glycogen granules, and an invaginated membrane system (FIGS. 37A-37D). Gene expression analysis revealed the downregulation of pluripotency genes such as OCT4 (FIG. 38A) and upregulation of megakaryocyte lineage genes, such as NFE2 (FIG. 38B). Similar analyses were performed on a panel of relevant genes, and the results of this analysis are consistent with the loss of a pluripotent stem cell signature and the acquisition of a megakaryocyte signature (FIG. 39).

When compared to primary megakaryocytes (natural product) derived from bone marrow CD34+, peripheral blood CD34+, or cord-blood CD34+ cells, iPSCS-derived MKs, it was found that iPSC-derived MKs had a similar average size (FIGS. 40A-40C), yet a characteristic lower ploidy distribution (FIGS. 41A-41B), compared to primary megakaryocytes (natural product) derived from CD34+ bone marrow, peripheral blood, or cord-blood stem cells (FIG. 40C, FIG. 41B). iPSCs derived megakaryocytes also had a characteristic growth factor, cytokine, and chemokine expression profile of factors similar to that present in human platelets, including the presence of multiple factors not previously reported in megakaryocytes (FIG. 42). To prepare the data, hiPSC-MK at 25 million/mL in 1×PBS were lysed by freezing the cells at −80° C. overnight and then thawed at 37° C. This freeze/thaw cycle was repeated 4 times. The resulting suspension was filtered using a 0.22 μm syringe filter. Lysates were tested for a select panel of growth factors, cytokines, and chemokines using multiplexing laser bead technology (Eve Technologies). Data was corrected for background (PBS, which was processed similarly as hiPSC-MK), then compared to commercially available human platelet lysate (HPL), fresh MK differentiation media (used in the final stage of differentiation), and Conditioned Media, i.e. MK differentiation media removed from hiPSC-MK before lysis. While a strong overlap was observed between hiPSC-MK and HPL, there were also several proteins measured in hiPSC-MK that were not previously described in megakaryocytes or platelets (FIG. 42).

The results described herein demonstrate a robust process for generating clinical grade human iPSC-derived megakaryocytes. Human iPSC-derived megakaryocytes can be isolated and concentrated for further characterization or use in downstream applications, such as the generation of human platelets.

Example 9: Detailed Characterization of Human iPSC-Derived Platelets

Figure 43A:
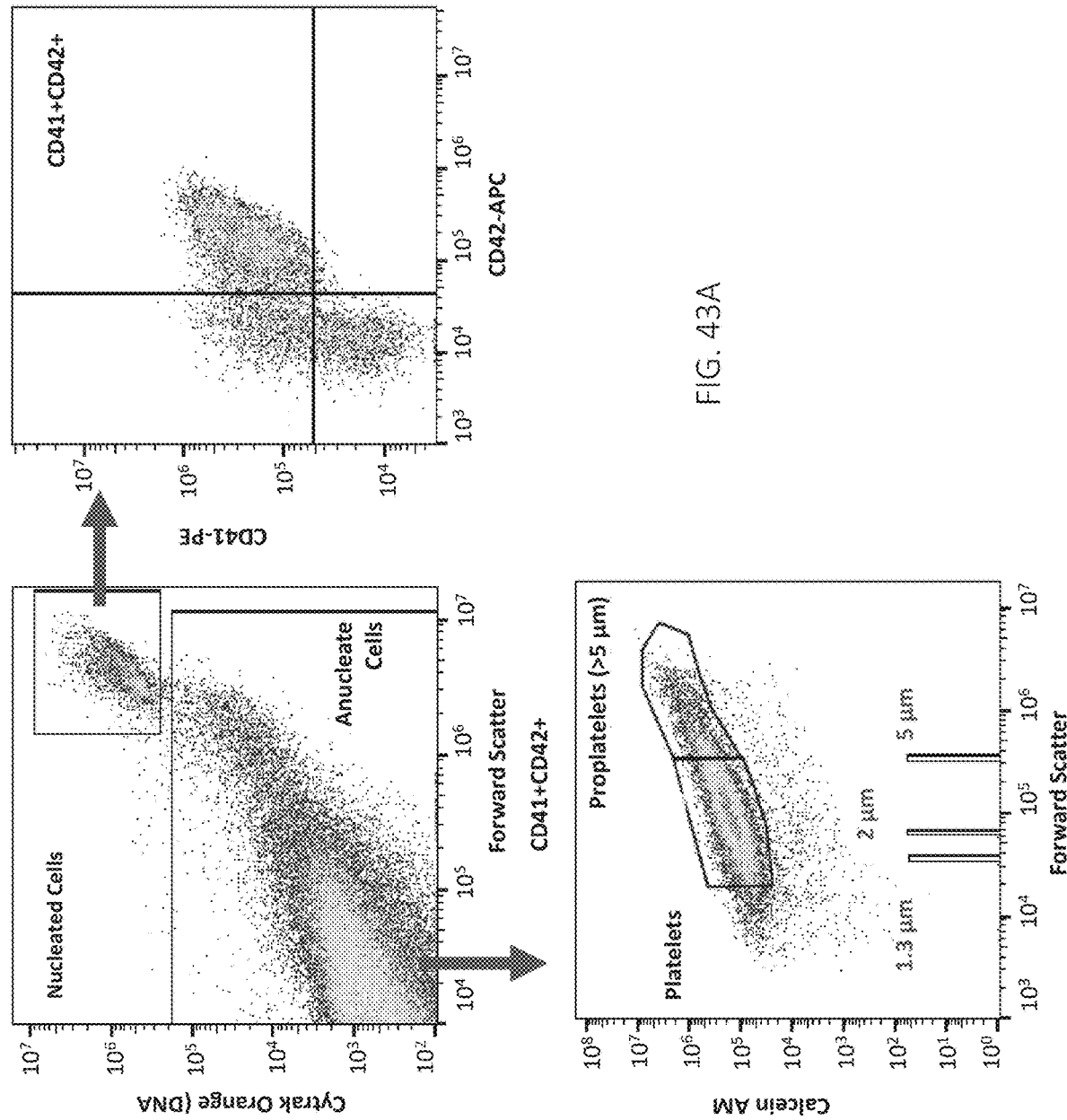
FIG. 43A and FIG. 43B depict hiPSC platelet production.
Figure 43B:
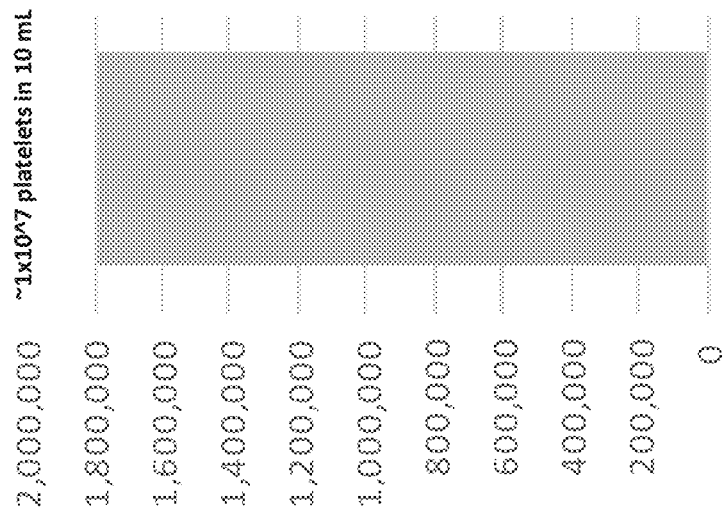

Platelets are generated from mature MKs derived from human iPSCs using the culture methods and harvesting techniques described in this filing. The platelets can be collected in static culture (FIGS. 43A, 43B) or produced by feeding a millifluidic bioreactor (referred to in U.S. Pat. No. 9,795,965; US2017/0183616; US2018/0334652; WO2018165308) with mature MKs at the culmination of Stage 3 of the directed differentiation process. Platelets derived from the directed differentiation process stain negative for DNA intercalating dyes and fall within a size distribution of 2-5 m; preplatelets are also observed in this culture at a diameter of 5 m and greater (FIG. 43A). Human iPSC-derived platelets have a resting phenotype, as indicated by micrographs showing distinct β1-tubulin rings, and an absence of the activation marker CD62p (FIGS. 44B and 45A). They can be experimentally activated using a glass spreading technique that reveals cytoskeletal changes indicative of filopodia and lamellipodia formation and spreading (FIGS. 44A and 44B).

Figure 48A:
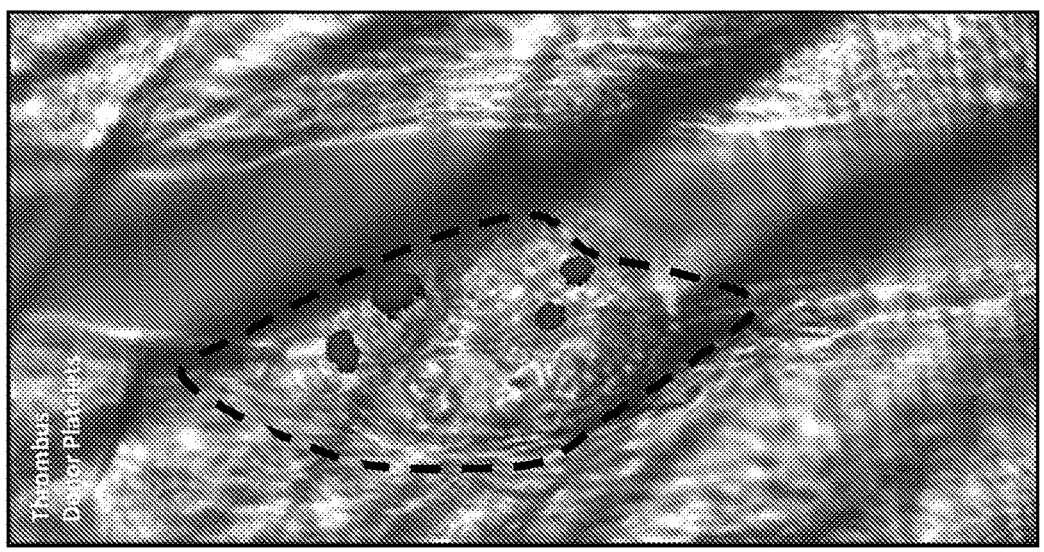

Human iPSC-derived platelets have some features that distinguish them from primary, donor-derived, human platelets. They lack a surface receptor, glycoprotein VI, that is abundantly expressed on human platelets (FIGS. 46A-46C). They also generate thrombin in greater abundance than platelets in plasma and do so over a shorter timeframe after being exposed to recombinant human tissue factor, a key initiator of the clotting cascade (FIG. 47). Despite these differences, human iPSC-derived platelets retain all indices of functionality (FIGS. 43A-43B, 44A-44B, 45, 46A-46C, and 47) including incorporation into thrombi that form in the cremaster arteriole as part of a mouse model of laser-induced injury (FIGS. 48A-48C).

Example 10: Human iPSC-Derived Platelets Take Up Recombinant Biologic Drugs by Passive Drug Loading Platelets produced by the methods described herein have characteristics akin to platelets that are extracted from whole peripheral blood as well as platelets that are differentiated from a human CD34+ mobilized peripheral blood cell source.

The drawing in FIG. 6 provides a schematic by which drugs, herein referring to any biologic, small molecule, or other form of therapeutic particle, can be loaded by various methods in and on preMKs, MKs, and PLTs. In some forms, a millifluidic bioreactor (referred to in U.S. Pat. No. 9,795, 965; US2017/0183616; US2018/0334652; WO2018165308) is used to induce PLT production from MKs. The drawing in FIG. 7 provides a schematic by which a genetically modified version of a stem cell, in some forms an iPS, ES, hematopoietic stem cell, or others, is produced by lentiviral transduction of genetic material that integrates into the genome. In some embodiments, integrating genetic material into stem cells is achieved by using various nuclease-based approaches, homologous recombination, or other viral and non-viral methods. The integration of genetic material into the genome could happen in hemogenic endothelia, preMKs, and MKs.

In one example, human IgG was loaded into and/or on donor-derived, human washed platelets. Human IgG was conjugated to NHS-ester Cy5.5 fluorophore according to manufacturer instructions and at 8-fold molar excess. Conjugated preparations were passed through a 40 k molecular weight cut-off (mwco) zeba desalting column and quantified by pierce 660 kit. Preps were kept at 4 degrees Celsius until further use. For drug loading experiments, Cy5.5 conjugated human IgG was brought to room temperature and centrifuged at 15,000 rcf for 1 minute to remove aggregates. The antibody was then added to 1×10e7 platelets in 1 mL of reaction volume for 1 hour at 37 degrees Celsius. PGE1 was added at 1 ug/ml final concentration to inhibit platelet activation and the cells were centrifuged at 1250 rcf for 17 minutes with no brake. In platelet preparations that were gated on CD61 expression (FIG. 49A and FIG. 49B), this wash step was performed a second time and the relative drug uptake after wash was assessed (FIGS. 49C and 49D) Drug uptake was visualized in the cell pellet (FIG. 49E). A dose titer of human IgG was performed, showing that increasing the input concentration led to a concomitant increase in detectable human IgG by flow cytometry (FIG. 49F). The mean fluorescence intensity was plotted as a function of human IgG dosage (FIG. 49G) and the amount of human IgG retained in washed platelets was quantified (FIG. 49H).

Figure 50A:
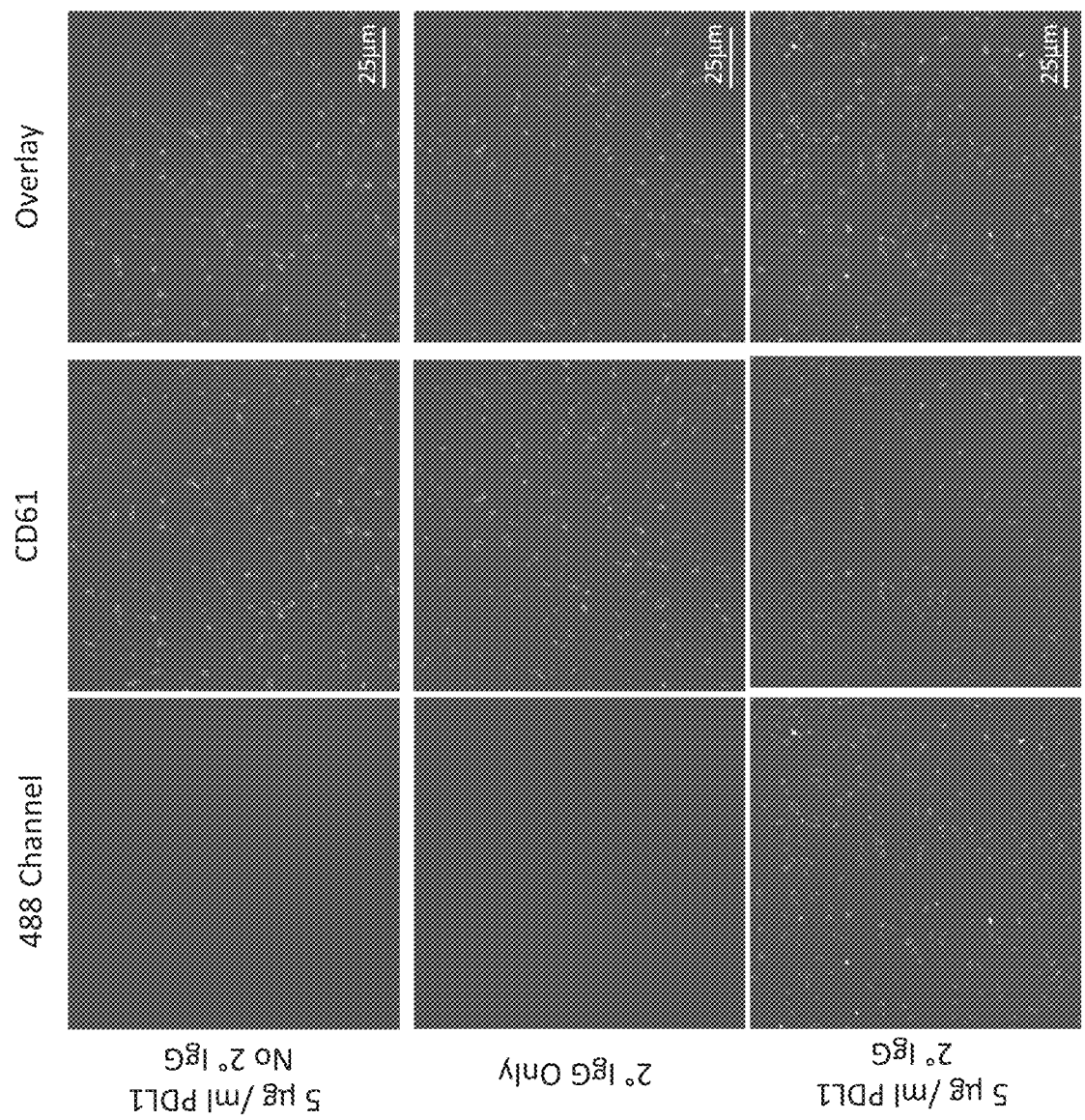
FIG. 50A and FIG. 50B demonstrate direct loading of human washed PLTs with Atezolizumab.
Figure 50B:
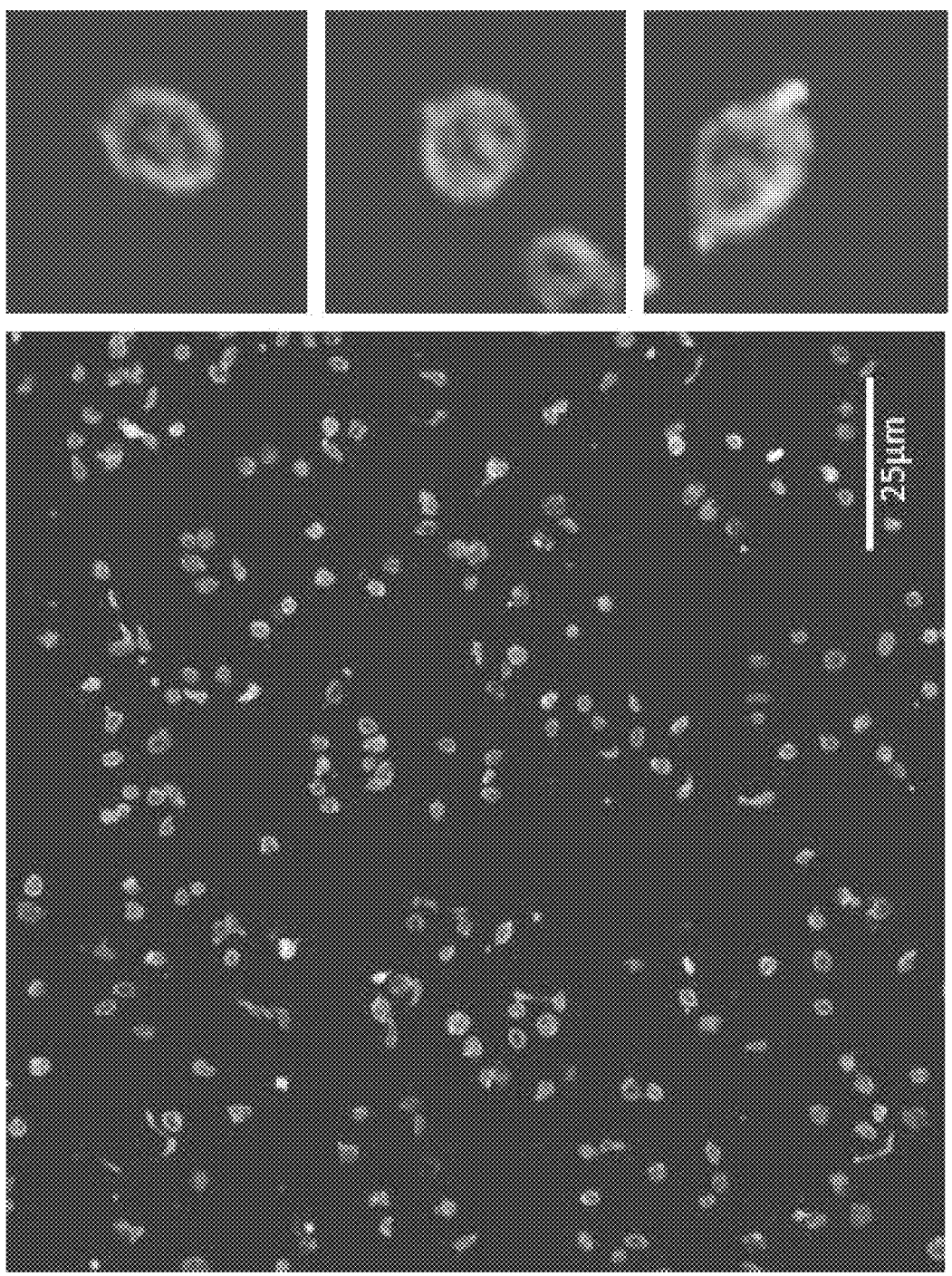

Human donor platelets were able to uptake concentrations up to 200 μg of labeled anti-PD-L1 antibody (atezolizumab) in a subsequent experiment (FIG. 49I). 200 μg represents a therapeutic dose of atezolizumab. This experiment was designed to determine a maximal dose of uptake. However, the platelets did not exhibit a plateau or maximum dose of uptake. To demonstrate that uptake was not antibody specific, human IgG was labeled with CF55 (Biotium) as directed by the manufacturer. To prevent further uptake during analysis, cells were fixed with 4% paraformaldehyde prior to measuring fluorescent intensity. Uptake of human IgG was observed in a dose dependent manner by measuring fluorescent intensity. These results do not represent maximum tolerated concentrations. Following fixation, some of the platelet prep was washed and adhered to poly-1-lysine coated glass coverslips by centrifugation. Platelets were then permeabilized with 0.5% Triton-X in PBS and blocked overnight in immunofluorescence blocking buffer (IFBB) (5 ml goat serum, 1% BSA in 50 ml PBS). Atezolizumab was visualized by incubation with AlexaFluor 488 anti-human secondary IgG. Background fluorescence was monitored in samples that were exposed to atezolizumab or secondary antibody alone. For additional specificity, cells were labeled with CD61-APC (Biolegend). Coverslips were mounted onto glass slides using Aqua-Poly/Mount (Fisher Scientific). Samples were imaged using a Zeiss Meta 880 confocal scanning microscope with Zen Black software for image acquisition (FIG. 50A). Image processing and analysis was completed using ImageJ software (Fiji/NIH). FIG. 50B is a high magnification of dual labeled platelets demonstrating sub-cellular localization within the platelets.

Figure 51A:
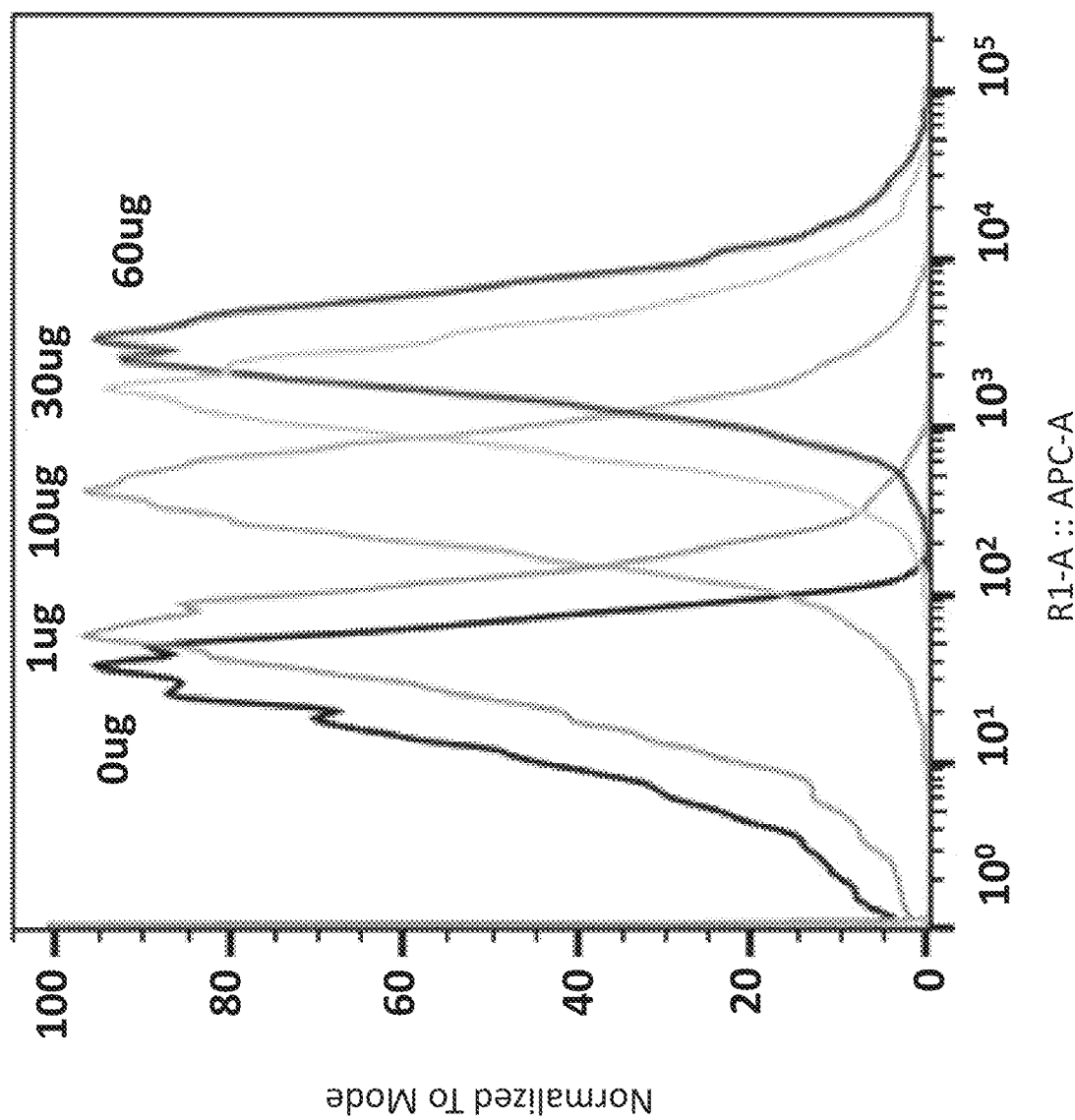
FIG. 51A and FIG. 51B demonstrate passive loading of Ipilimumab in human iPSC-derived platelets.
Figure 51B:
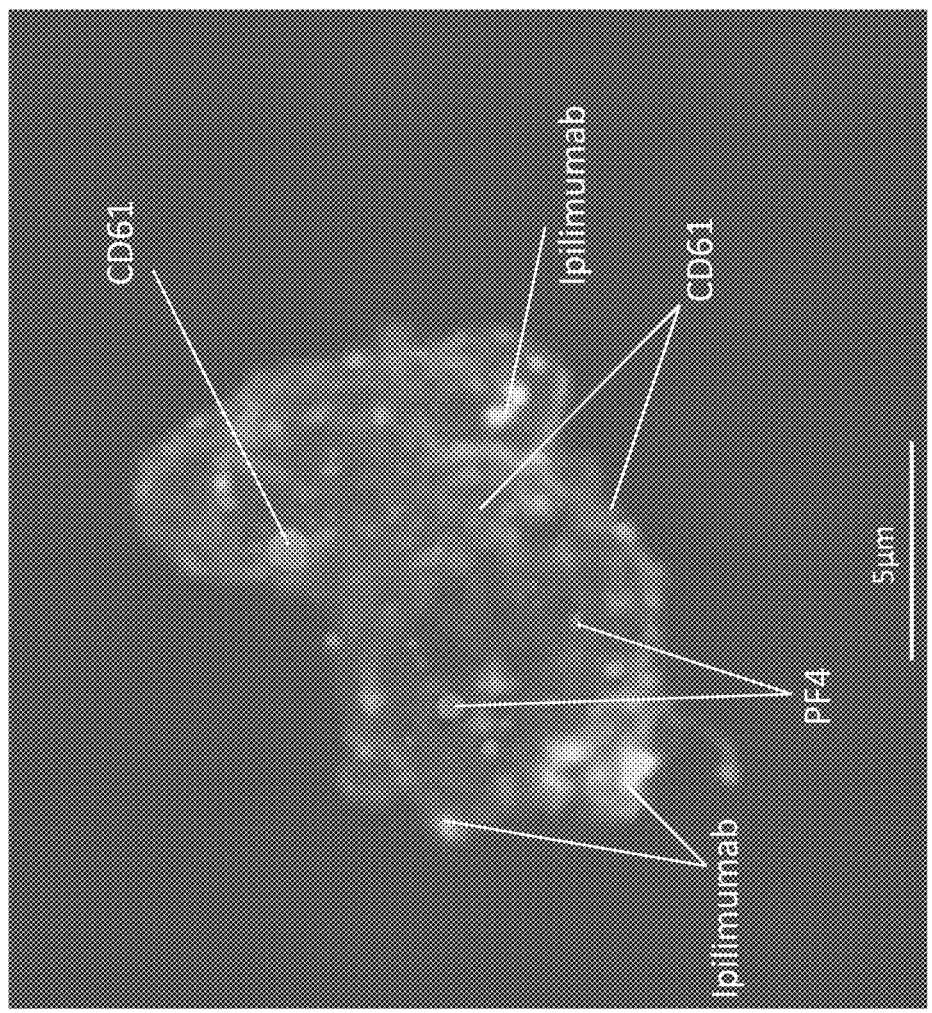

Human iPSC-derived platelets, produced using the methods described herein, were loaded with the anti-CTLA4 antibody drug, Ipilimumab, by co-incubation in aqueous buffer. Ipilimumab was loaded at varying concentrations, resulting in flow cytometry histogram plots that reveal a dose-dependent increase in encapsulated dose. Ipilimumab was conjugated to NHS-ester Cy5.5 fluorophore according to manufacturer instructions and at 8-fold molar excess. Conjugated preparations were passed through a 40 k molecular weight cut-off (mwco) zeba desalting column and quantified by pierce 660 kit. Preps were kept at 4 degrees Celsius until further use. For drug loading experiments, Cy5.5 conjugated Ipilimumab was brought to room temperature and centrifuged at 15,000 rcf for 1 minute to remove aggregates. Ipilimumab was added to 1e6 human iPSC-derived platelets in 100 microliter volume. In one example, 1, 10, 30, and 60 μg of Ipilimumab was added per sample, incubated at 37° C. for 1 hour, and washed and centrifuged to remove non-specifically bound drug. A flow cytometry based histogram plot was generated showing a dose-dependent increase in Ipilimumab encapsulation in the human iPSC-derived platelets (FIG. 51A). In a separate experiment, Ipilimumab that was not conjugated to Cy5.5 was loaded into human iPSC-derived platelets at 100 μg/ml final concentration using the same techniques, fixed with 4% paraformaldehyde, and centrifuged onto poly-1-lysine coated coverslips for immunofluorescence imaging experiments. Platelets were then permeabilized with 0.5% Triton-X in PBS and blocked overnight in immunofluorescence blocking buffer (IFBB) (5 ml goat serum, 1% BSA in 50 ml PBS). Platelets were stained with granule (PF4) and surface (CD61) markers and drug signal was found to be punctate within the cell. The resulting micrograph demonstrates Ipilimumab loading in a CD61+ human iPSC-derived platelet with evidence of Ipilimumab localization on the cell surface and within select alpha granules as delineated by PF4 staining (FIG. 51B).

Figure 52A:
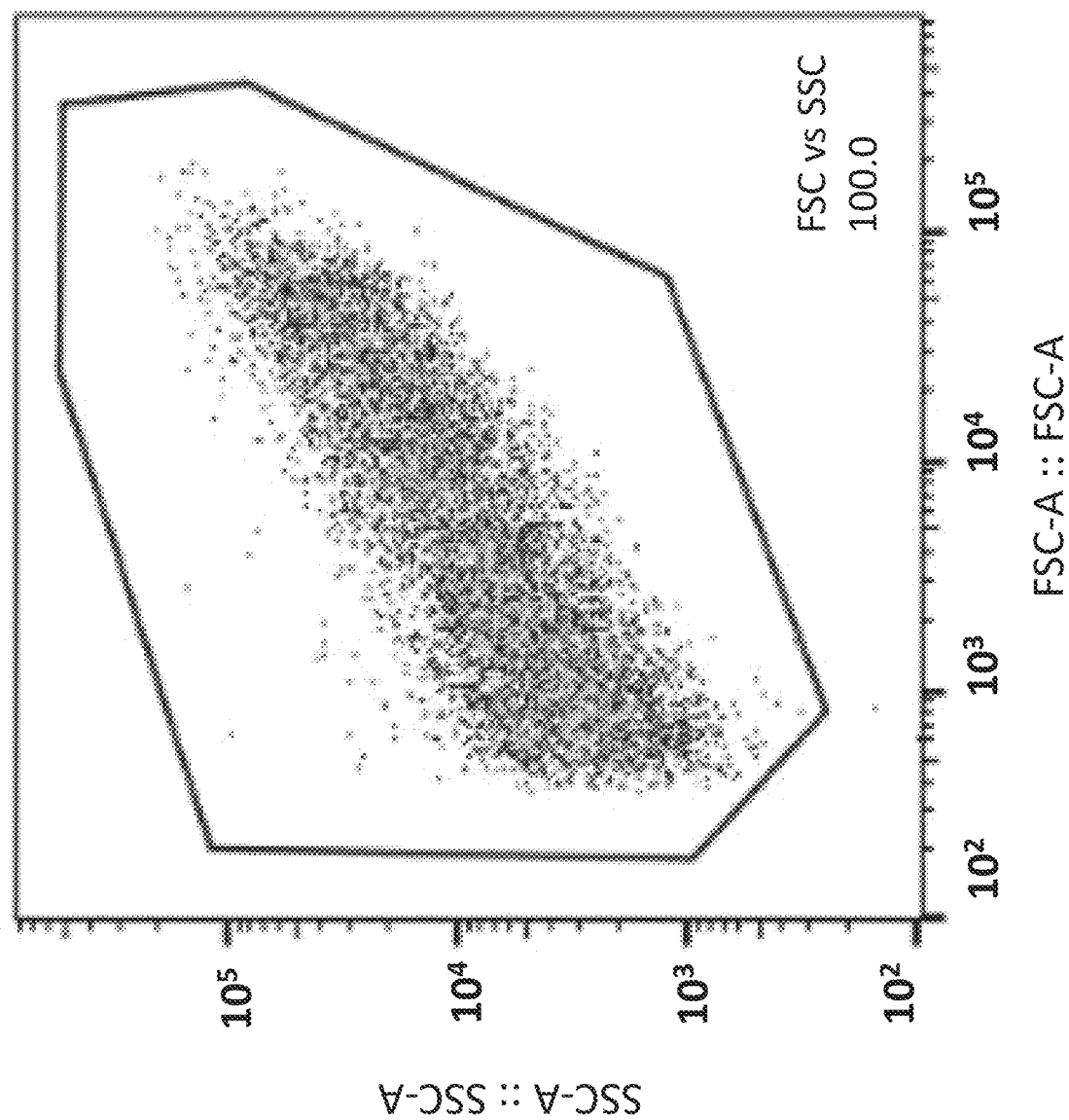
Figure 52B:
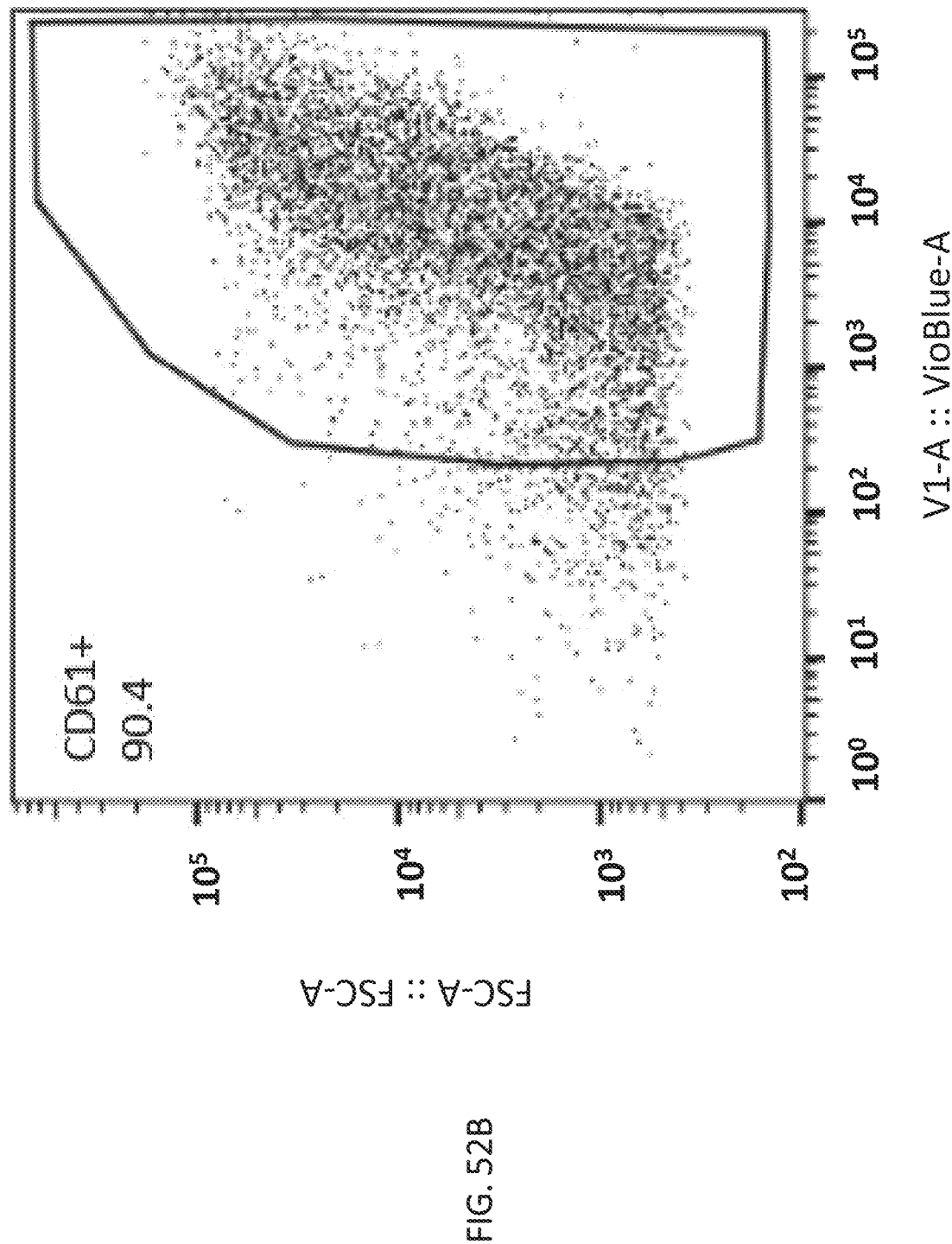
Figure 52D:
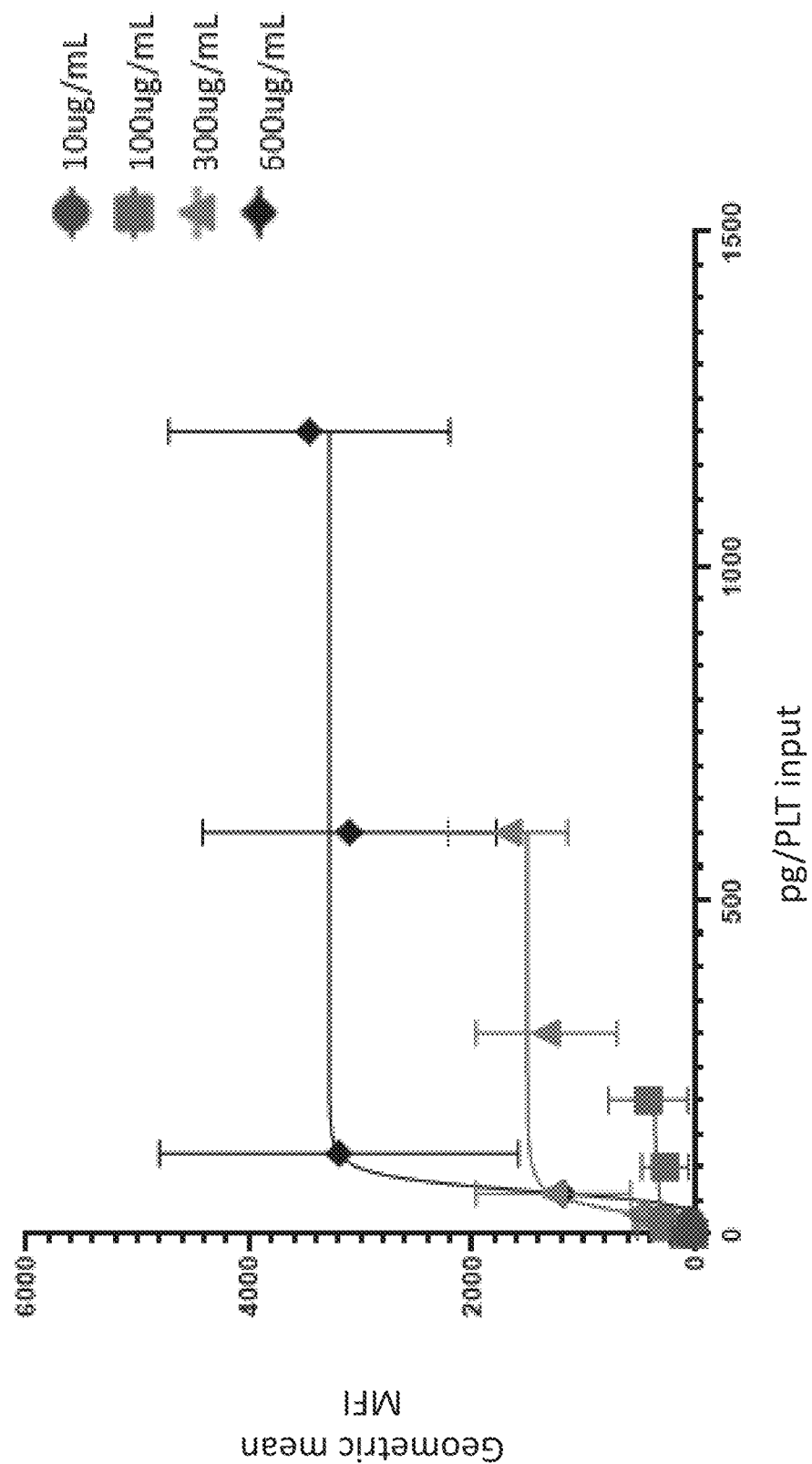
Figure 52E:
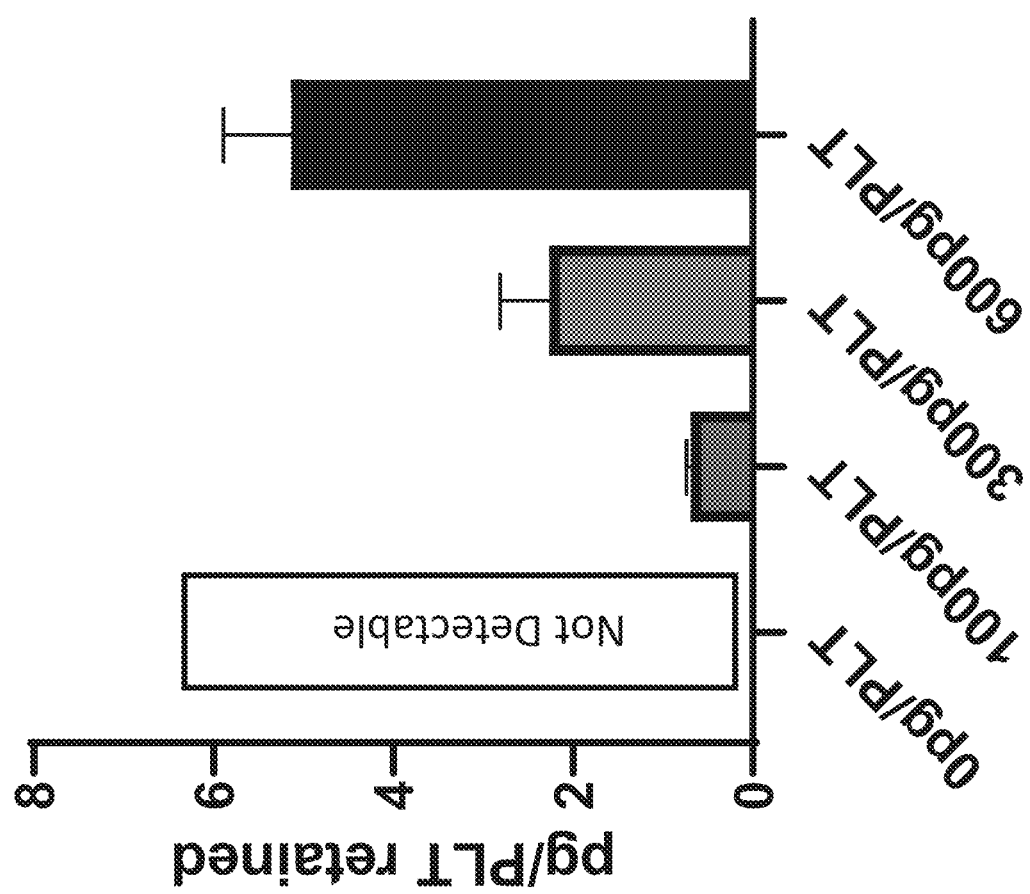
Figure 52F:
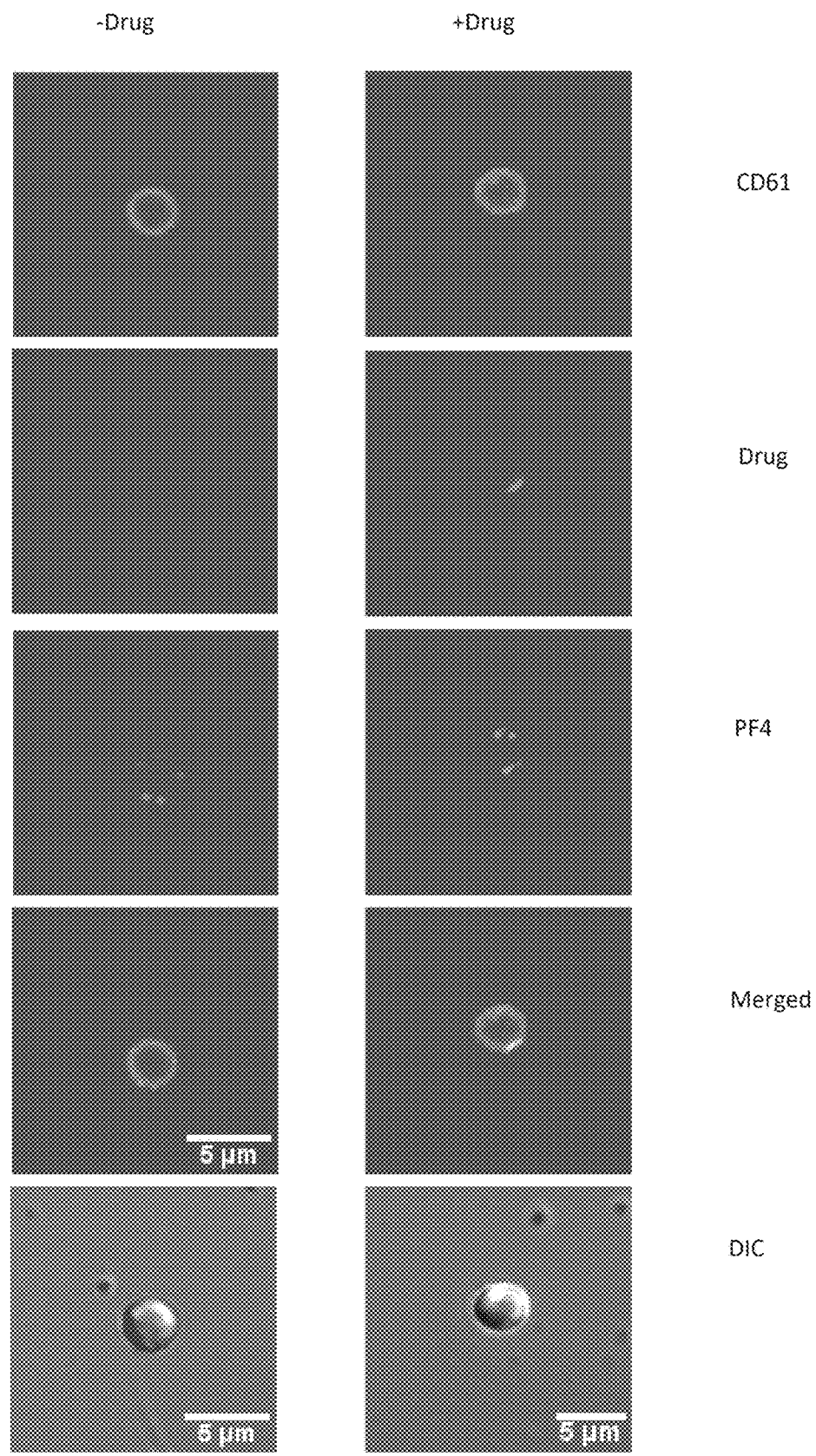

A further example of recombinant protein loading in platelets was performed in CD34+ derived material using Ipilimumab conjugated to the fluorophore Cy5.5 using the methods described herein. CD34+ derived platelets were analyzed for size and granularity (FIG. 52A) and CD61 expression (FIG. 52B) to confirm a platelet phenotype. Ipilimumab was incubated with the platelet preparation for 1 hour at 37 degrees Celsius at varying concentrations without a maximal signal established at 600 μg/ml Ipilimumab (FIG. 52C). Converting measurements to pg of Ipilimumab per platelet in the reaction vessel, an input ratio of roughly 100-300 pg/plt was sufficient to see a maximal signal by flow cytometry (FIG. 52D), and the final concentration of retained Ipilimumab per platelet was found to be between 1 and 6 pg/platelet, depending upon treatment dose (FIG. 52E). Following fixation, some of the platelet prep was washed and adhered to poly-1-lysine coated glass coverslips by centrifugation. Platelets were then permeabilized with 0.5% Triton-X in PBS and blocked overnight in immunofluorescence blocking buffer (IFBB) (5 ml goat serum, 1% BSA in 50 ml PBS). Platelets were stained with granule (PF4) and surface (CD61) markers and drug signal was found to be punctate within the cell (FIG. 52F).

To determine whether donor-derived human platelets take up atezolizumab (FIG. 53A) or ipilimumab (FIG. 53B) and remain functional, platelets were incubated with 15 μg of Dylight-488-labeled antibody for 30 minutes. Identical samples were then exposed to human thrombin (1 unit/ml) for the last ten minutes of the 30-minute incubation. Cells were immediately fixed with 4% paraformaldehyde to prevent further uptake during analysis and the mean fluorescent intensity was analyzed by FACS and compared to samples loaded with drug alone (unconjugated). As observed in FIGS. 53A and 53B, activation of platelets reduced the fluorescence intensity as seen in the shift of the labeled drug histograms to the left (closer to the drug alone). FIG. 53C is a resting loaded platelet with fluorescent PDL1 (similar to that in 13A). FIG. 53D is an activated platelet that was loaded with PDL1, but upon glass activation, it no longer contains the fluorescent PDL1. These data suggest that platelet activation with thrombin results in the release of the antibody demonstrating that the drug loaded platelets remain functional and are capable of release upon agonist stimulation.

Example 11: Covalent Conjugation of Recombinant Proteins in Human iPSC-Derived Platelets There are many strategies to create covalent linkages of recombinant proteins on the cell membrane (FIG. 6). For iPSC-derived platelets described herein, 2-iminothiolane (Traut's Reagent, Thermofisher #26101) was incubated at varying concentrations with 1e6 platelets in 500 ul of buffer at 37 degrees Celsius for 1 hour to convert primary amines to sulfhydryls (depicted in FIG. 54A). Concomitantly, succinimidyl 4-(N-maleimidomethyl)cyclohexane-1-carboxylate (SMCC, Thermofisher #22360) was incubated with human IgG for 2 hours at 4C (depicted in FIG. 54B). The Traut reagent treated platelets were then incubated with the SMCC linkered IgG for 1 hour at 37 degrees Celsius (FIG. 54C). A dose-titer of Traut was performed on washed, donor platelets with a static concentration of SMCC-linkered IgG (vs. IgG without SMCC). The signal was significantly greater by flow cytometry with the SMCC-linkered IgG at increasing doses of Traut reagent, with maximal efficiency observed at 0.4 mg/ml of the traut reagent (FIG. 54D). Without the SMCC linker, the IgG signal did not increase by flow cytometry (FIG. 54E), suggesting that the conjugation reaction was efficient in promoting conjugation of IgG to the surface of washed platelets.

Figure 55A:
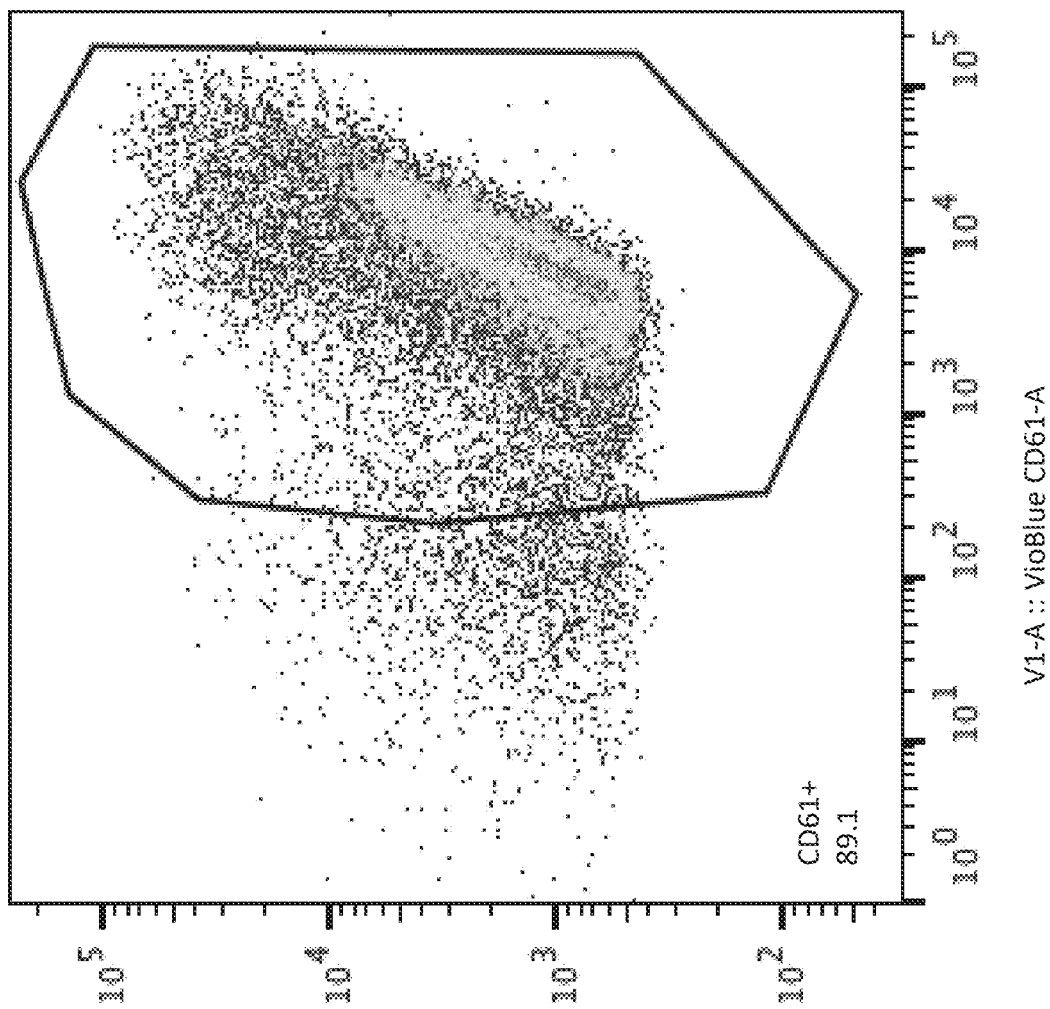
FIGS. 55A-55C provide an example of using, in one iteration, the covalent conjugation strategy outlined in FIG. 53 to conjugate a molecule, in this example the antibody drug Ipilimumab, to human iPSC-derived platelets.
Figure 55B:
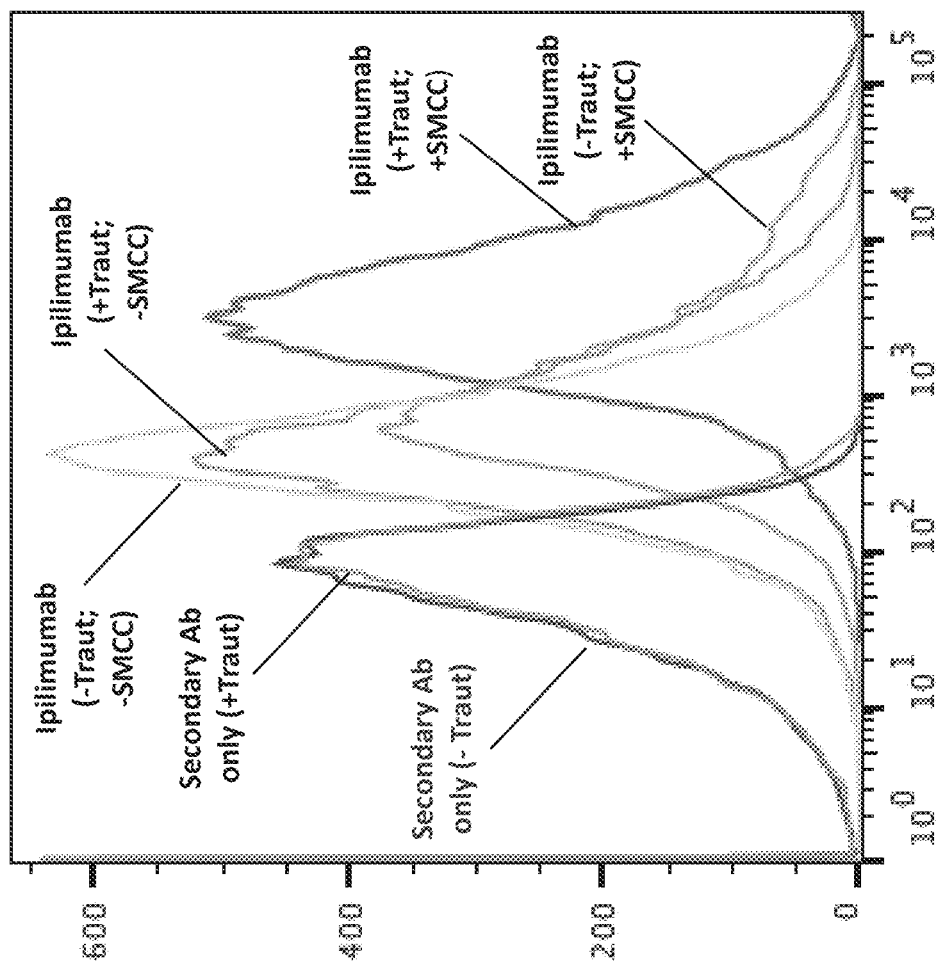
Figure 55C:
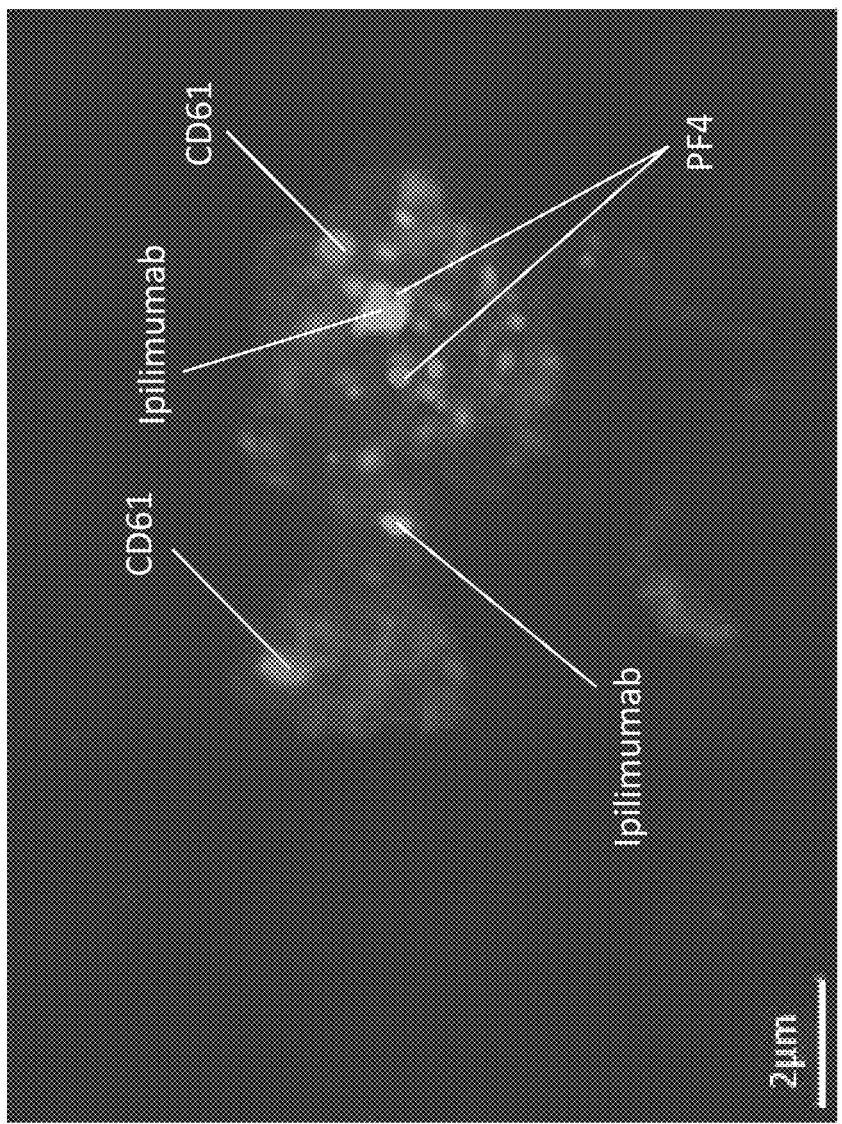

The protocol described in FIGS. 54A-54C was then used in human iPSC-derived platelets using the anti-CTLA4, commercially available antibody Ipilimumab (Selleckchem #A2001). Ipilimumab-conjugated platelets retained CD61 expression (FIG. 55A) and weren't activated by the procedure, as assessed by CD62p expression (data not shown). Ipilimumab was observed in greatest abundance by flow cytometry (gated on CD61 expression) with traut reagent treated platelets and using SMCC-linkered Ipilimumab (FIG. 55B, denoted by arrow). The same cells were fixed in 4% PFA and immobilized on poly-1-lysine coated coverslips and subsequently stained for CD61 and PF4 using the methods described herein. Ipilimumab was observed to be conjugated mostly on the cell surface (FIG. 55C).

Figure 56A:
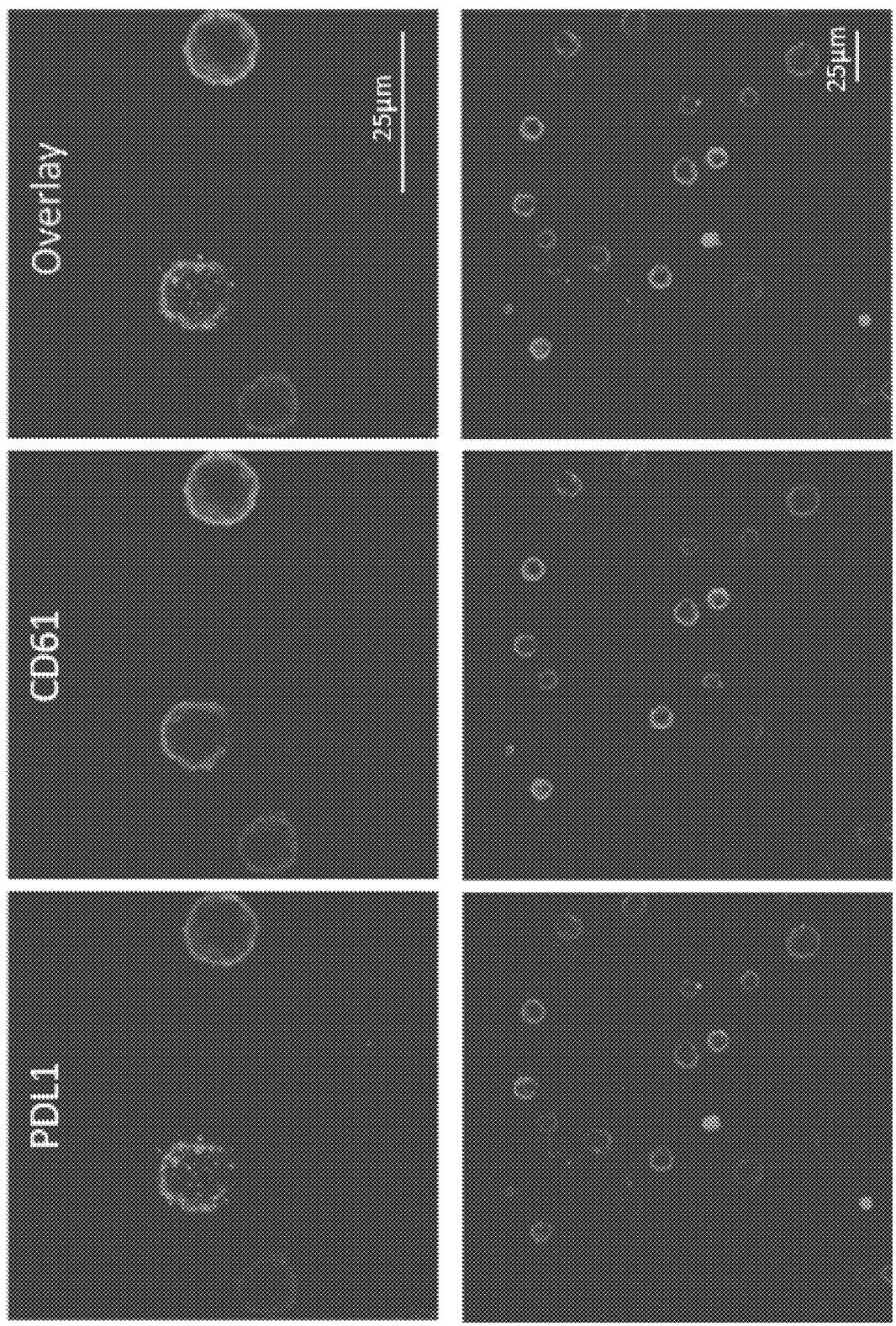

Example 12: Passive Loading of Recombinant Drug Biologics in Human iPSC-Derived preMK's and MK's Induced pluripotent stem cells were differentiated into mature megakaryocytes using the methods described herein. Cells were incubated for 30 minutes with Dylight 488-labeled Atezolizumab and fixed with 4% paraformaldehyde and centrifuged onto prepared poly-1-lysine coated glass coverslips. To confirm mature megakaryocytes within the culture, cells were additionally stained for CD61. CD61 was visualized using a preconjugated CD61-APC antibody. Samples were washed and mounted onto glass coverslips with Aqua-poly/mount (Fisher Scientific). Images were captured using a Zeiss Meta 880 confocal scanning microscope and analyzed using Fiji ImageJ software (FIGS. 56A-56C). These data suggest that megakaryocytes and their static generated platelets of the present disclosure are capable of uptake of atezolizumab. Atezolizumab is demonstrated to colocalize with the alpha granule stain PF4 (FIG. 56C) and is also shown on the cell surface. This provides evidence that passive loading (as opposed to covalent conjugation to the cellular membrane) may facilitate alpha granule localization in the MKs that produce platelets and may be retained in the granules upon platelet differentiation.

Megakaryocyte progenitors, or preMKs, were loaded with an unconjugated version of the anti-CTLA4 antibody Ipilimumab using 1e6 cells in 1 ml and with 100 ug of Ipilimumab. PreMKs were immobilized to poly-1-lysine coated coverslips and stained with fibrinogen (alpha granule stain) and CD61 (surface marker) (FIG. 57). Ipilimumab was observed to colocalize with both CD61 and fibrinogen, suggesting that preMKs can be loaded with antibody drugs that potentially can retain drug in granules throughout the differentiation process to MKs and platelets.

Example 13: Covalent Conjugation of Recombinant Drug Biologics in Human iPSC-Derived preMK's and MK's The ability to conjugate recombinant drug biologics to the cellular membrane of megakaryocyte progenitors (preMKs) and mature megakaryocytes (MKs) derived from human iPSCs is demonstrated herein. PreMKs were harvested from Stage 2 cultures and immunophenotyped for CD41 and CD43 co-expression (FIGS. 58A and 58B). The iPSC-derived preMKs were treated with Traut's Reagent at 0.4 mg/ml with 1e6 cells in 500 ul of buffer at 37° C. for 1 hour to convert primary amines to sulfhydryls. Concomitantly, SMCC was incubated with Ipilimumab for 2 hours at 4° C. The Traut reagent treated preMKs were then incubated with the SMCC linkered Ipilimumab at 100 µg/ml for 1 hour at 37° C. A secondary antibody against human IgG and conjugated to alexafluor 647 was used to detect the conjugated Ipilimumab. In the absence of drug treatment, there was no detectable drug in the CD41 and CD43 double positive cells (FIG. 58C). For drug treated sample, all observable CD41 and CD43 dual positive preMKs had detectable Ipilimumab (FIG. 58D). Mature megakaryocytes were harvested in Stage 3 of the directed differentiation protocol from human iPSCs and immunophenotyped for CD61 (FIG. 59A) and CD42a (FIG. 59B). MKs were treated with Traut's reagent at 0.4 mg/ml with 1e6 cells in 500 µl of buffer at 37° C. for 1 hour to convert primary amines to sulfhydryls. Concomitantly, SMCC was incubated with Ipilimumab for 2 hours at 4° C. The SMCC linkered Ipilimumab was reacted with the traut treated MKs for 1 hour at 37° C. A secondary antibody against human IgG and conjugated to alexafluor 647 was used to detect the conjugated Ipilimumab. In the absence of drug treatment, there was no detectable drug in the CD61 and CD42a dual positive cells (FIG. 59C). For drug treated sample, all observable CD61 and CD42a dual positive MKs had detectable Ipilimumab (FIG. 59D).

This data demonstrates covalent conjugation of recombinant protein biologic drugs to megakaryocyte progenitors (preMKs) and mature megakaryocytes (MKs) derived from human induced pluripotent stem cells (iPSCs).

Figure 60B:
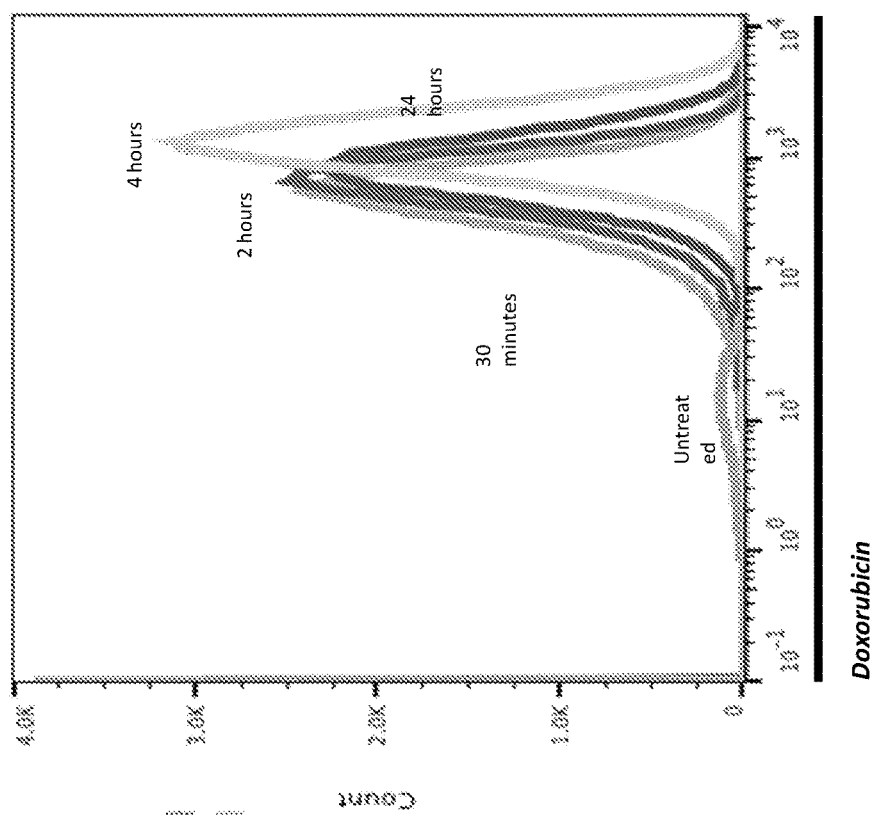
FIG. 60A and FIG. 60B show efficient loading of donor-derived, human washed platelets with the small molecule chemotherapeutic drug, doxorubicin.
Figure 60A:
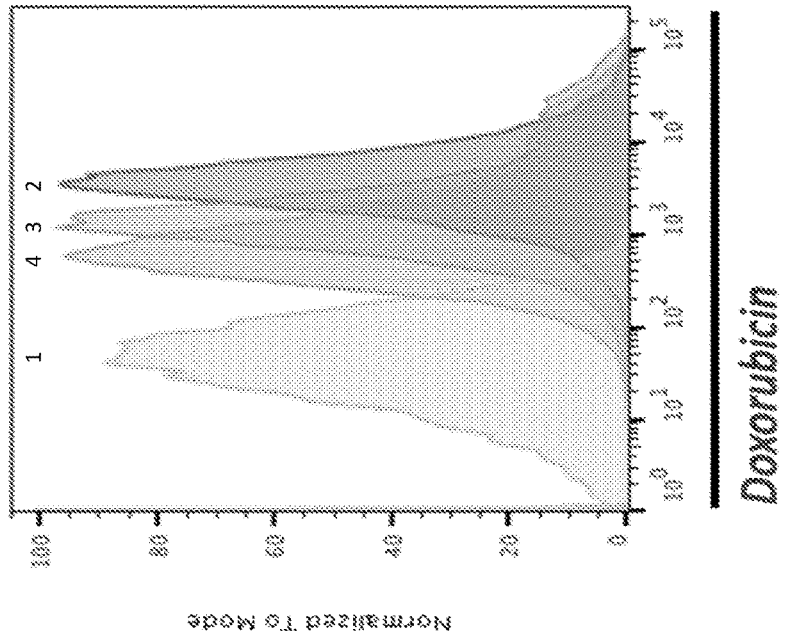

Example 14: Small-molecule loading of human washed platelets by passive diffusion To demonstrate small-molecule loading and retention in a platelet product from human iPSCs, human washed platelets were co-incubated with the DNA intercalating chemotherapeutic, Doxorubicin hydrochloride (Sigma #D1515). As an anucleate cell type, platelets do not contain genomic material that would typically sequester this drug within the cell as a result of co-incubation with a platelet preparation and entry into the cell by passive diffusion. 100 µM of Doxorubicin was used with a preparation of 1e7 platelets in 1 ml of buffer and incubated at ambient temperature for 30, 120, 240, and 1440 minutes under constant agitation on an orbital shaker in a dialysis cassette (Thermofisher #88400). Doxorubicin has intrinsic fluorescent properties that can be detected by flow cytometry (Ex 427 nm/Em 585 nm), and it was found that multiple wash steps could be performed on the platelet preparation and the drug cargo would still be retained after loss of non-specifically bound molecules (FIG. 60A). A kinetic study was employed to understand the minimum and maximum amount of time necessary for doxorubicin encapsulation in the washed platelets. It was observed that 30 minutes was sufficient to see detectable doxorubicin expression in sampled platelets, with the signal retained after 1440 minutes (FIG. 60B). This data suggests that small-molecule drugs can be efficiently captured in platelets.

Example 15: Generating platelets from genetically modified premegakaryoctyes

Platelets expressing a therapeutic transgene would represent a significant advancement in treating injuries, illness, and disease. To generate platelets that express a transgene, premegakaryocytes were transduced with a lentiviral vector comprising nucleic acid cassette encoding a reporter protein. Specifically, the cassette encoded an EF1alpha promoter and a ZsGreen fluorescent protein. 42 hours post infection with the lentiviral vector, fluorescence was detected in premegakaryocytes transduced but not in the untransduced (mock) controls (FIG. 61), indicating that the premegakaryocytes were successfully transduced.

Figure 62A:
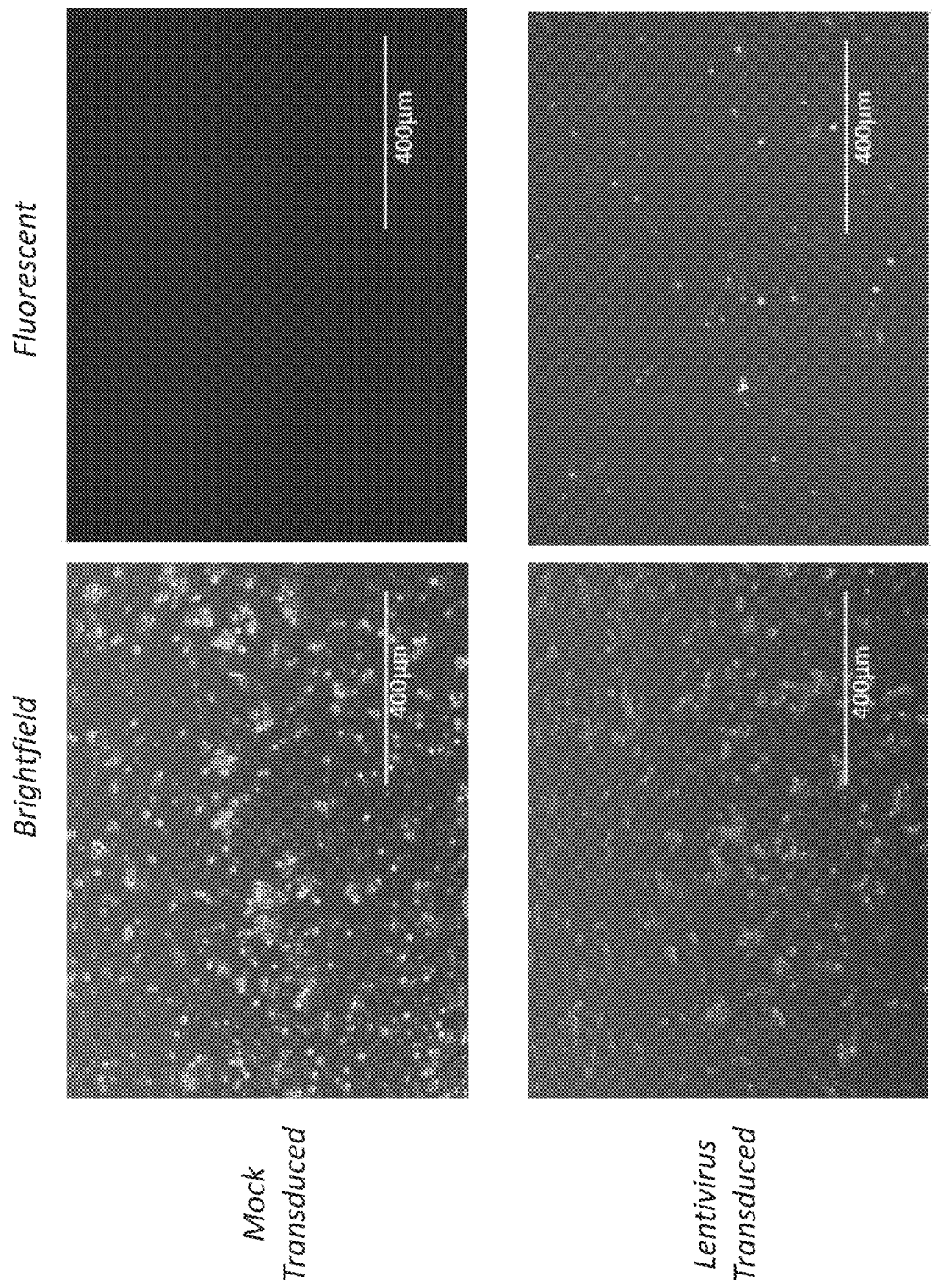
FIGS. 62A-62C show retention of genetic modification introduced into premegakaryoctyes via lentiviral transduction.
Figure 62B:
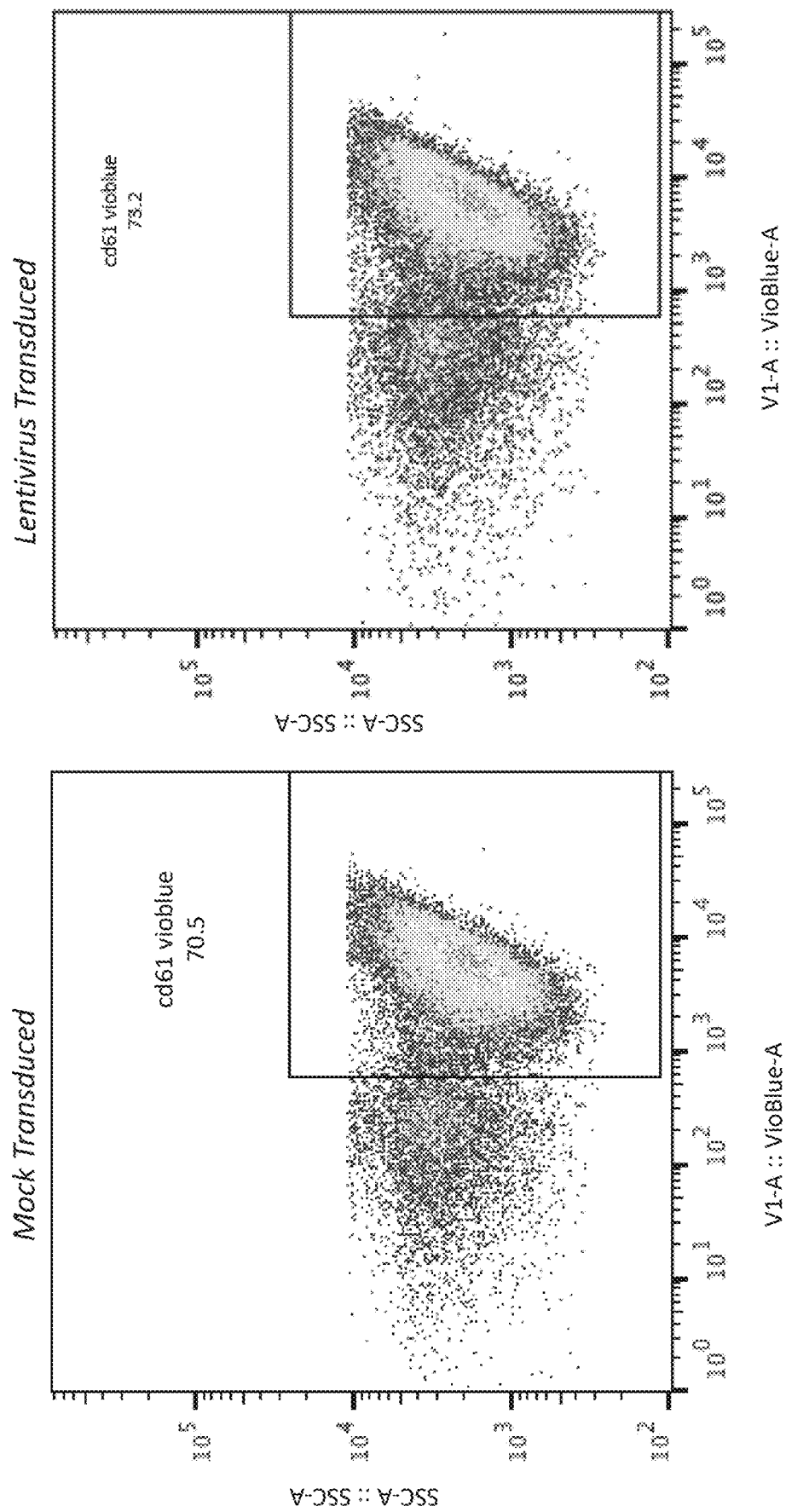
Figure 62C:
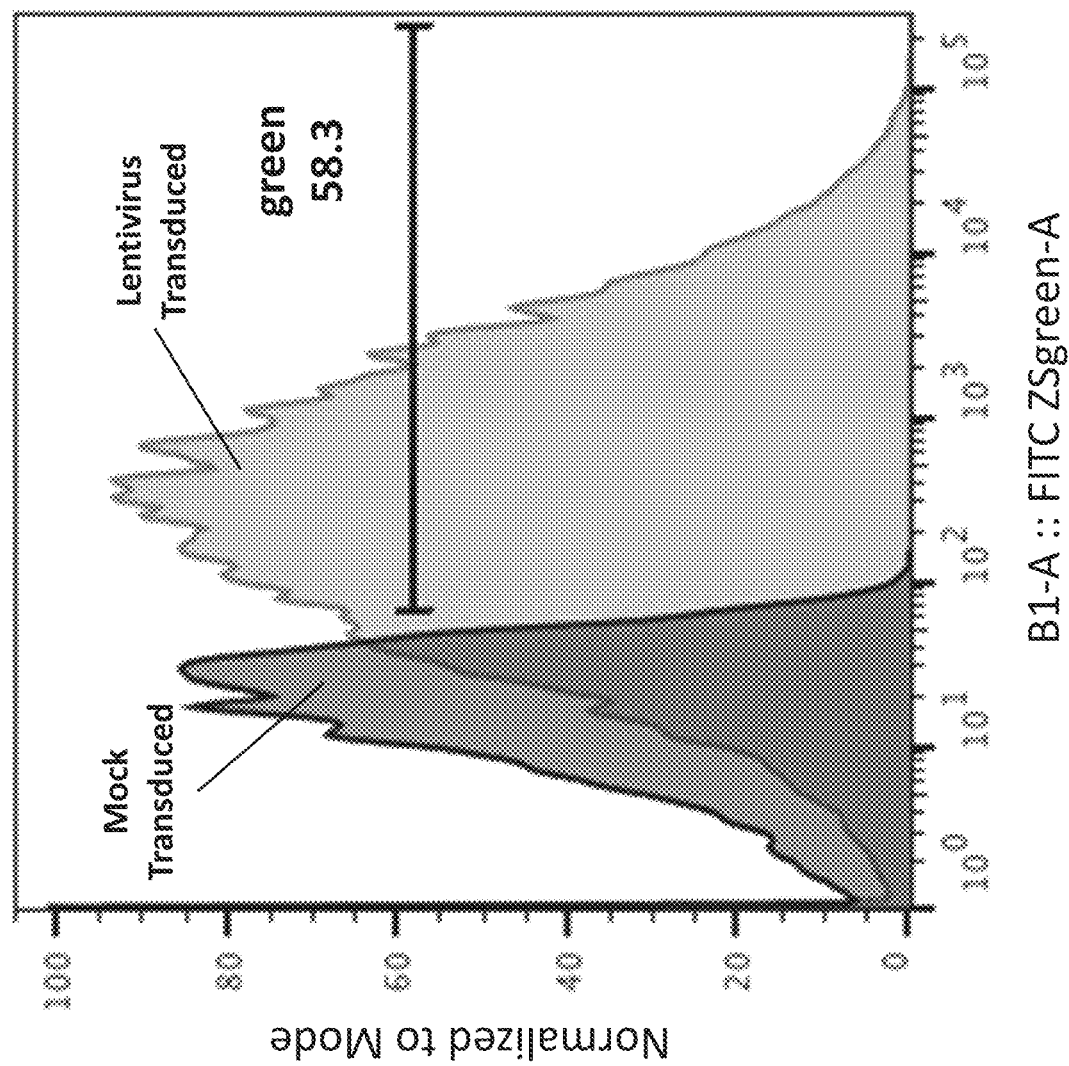

The premegakaryoctyes carrying the transgene were cultured according to the methods described herein to produce platelets. Referring to FIG. 62A, CD61+ cells derived from transduced premegakaryocytes (i.e., platelets) exhibited expression of the reporter protein, whereas no fluorescence was visible in the CD61 cells derived from mock transduced premegakaryocytes, which indicates that the nucleic acid cassette was successfully inherited from the transduced premegakaryoctye. To validate that the fluorescent signal was produced by platelets, the platelets derived from the mock and the lentivirally transduced megakaryoctyes were sorted using a CD61 gating strategy (FIG. 62B). The fluorescent histogram shown in FIG. 62C demonstrates that the fluorescent signal was detected in CD61+ platelets.

Example 16: Manufacturing platelets using a Bioreactor Ssytem

Figure 63D:
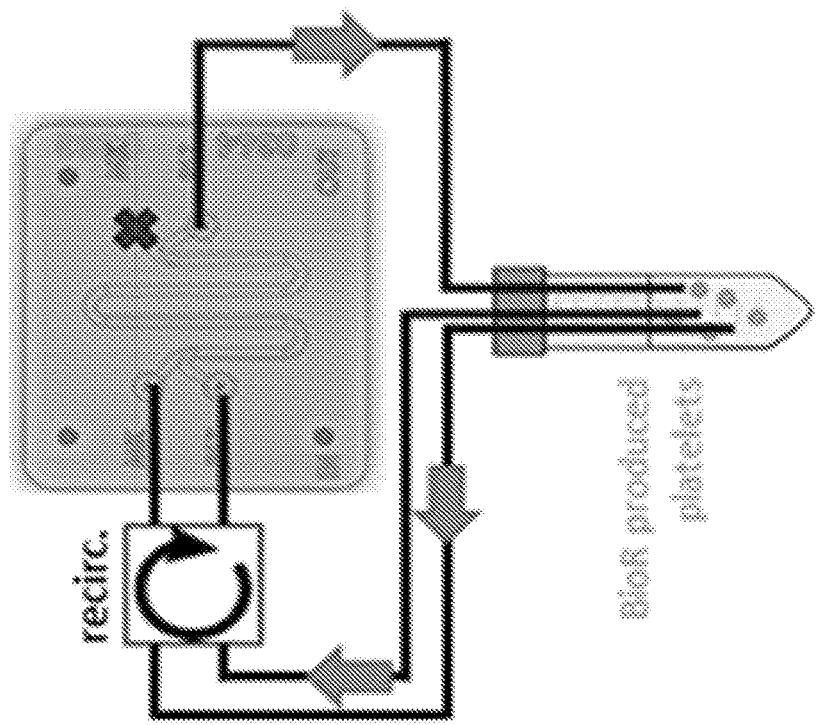
FIGS. 63A-63D describe a bioreactor for platelet production.
Figure 63A:
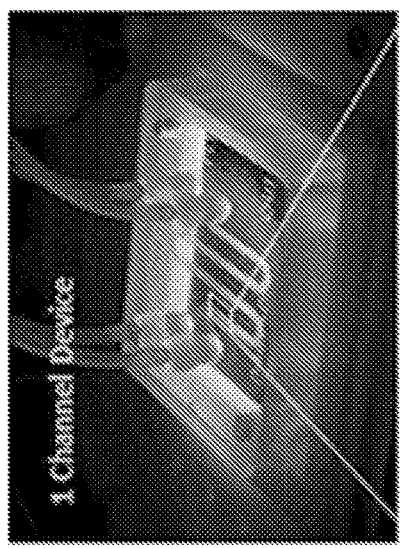
Figure 63B:
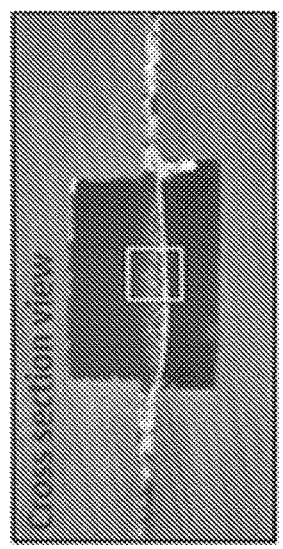
Figure 63C:
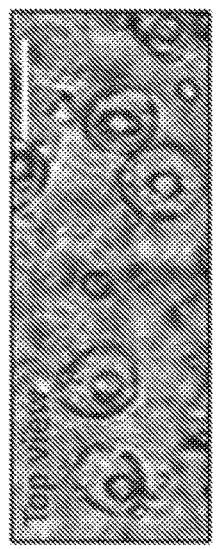
Figure 64:
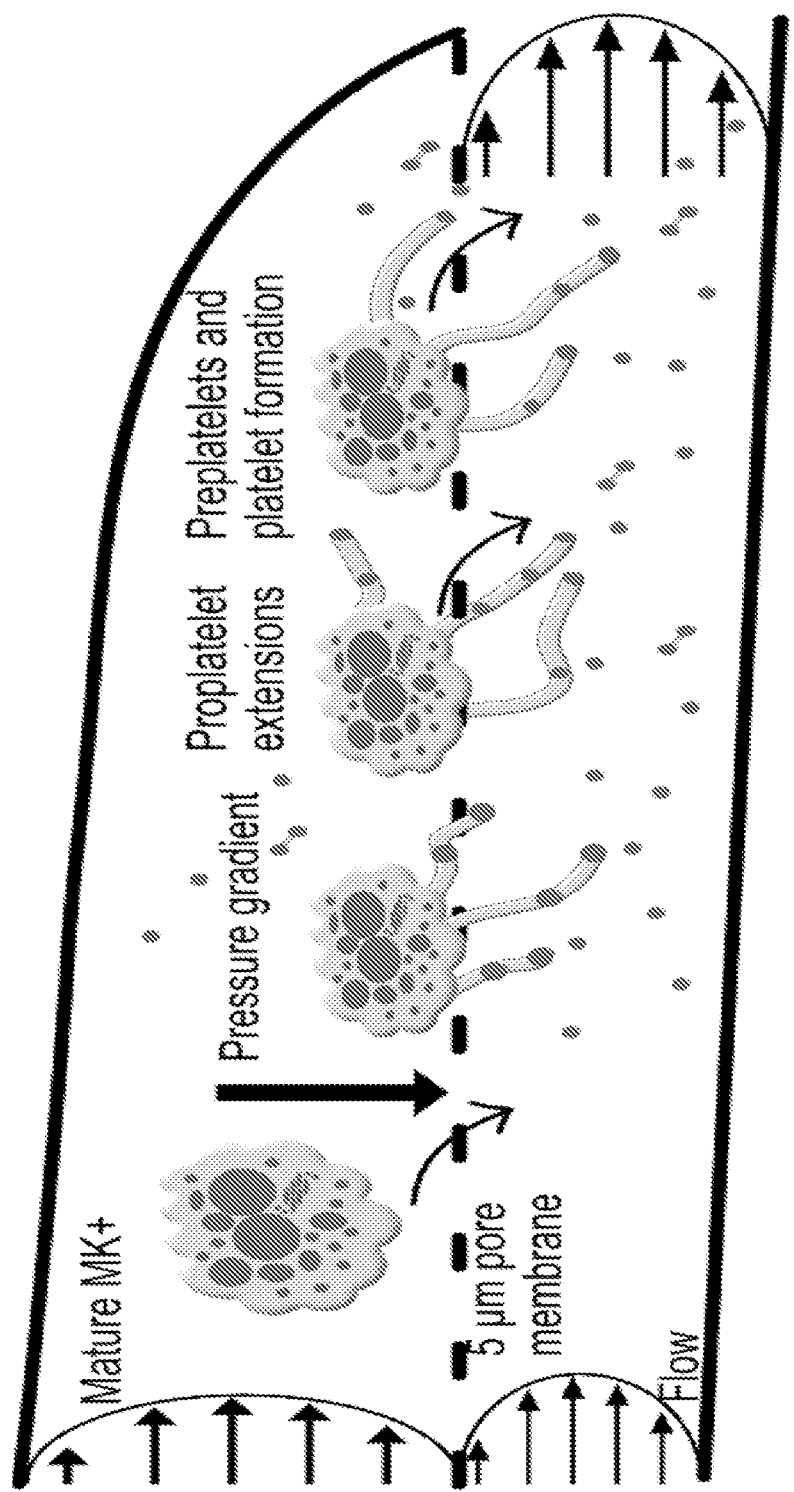
FIG. 64 is a side view schematic of a bioreactor for platelet production having an upper channel and a lower channel separated by a pourous membrane (dashed line). Megakaryocytes captured on the porous membrane in the first channel are subject to shear stresses and extend processes that release platelets (dark circles) into the lower channel. Straight arrows indicate fluid flow.
Figure 65:
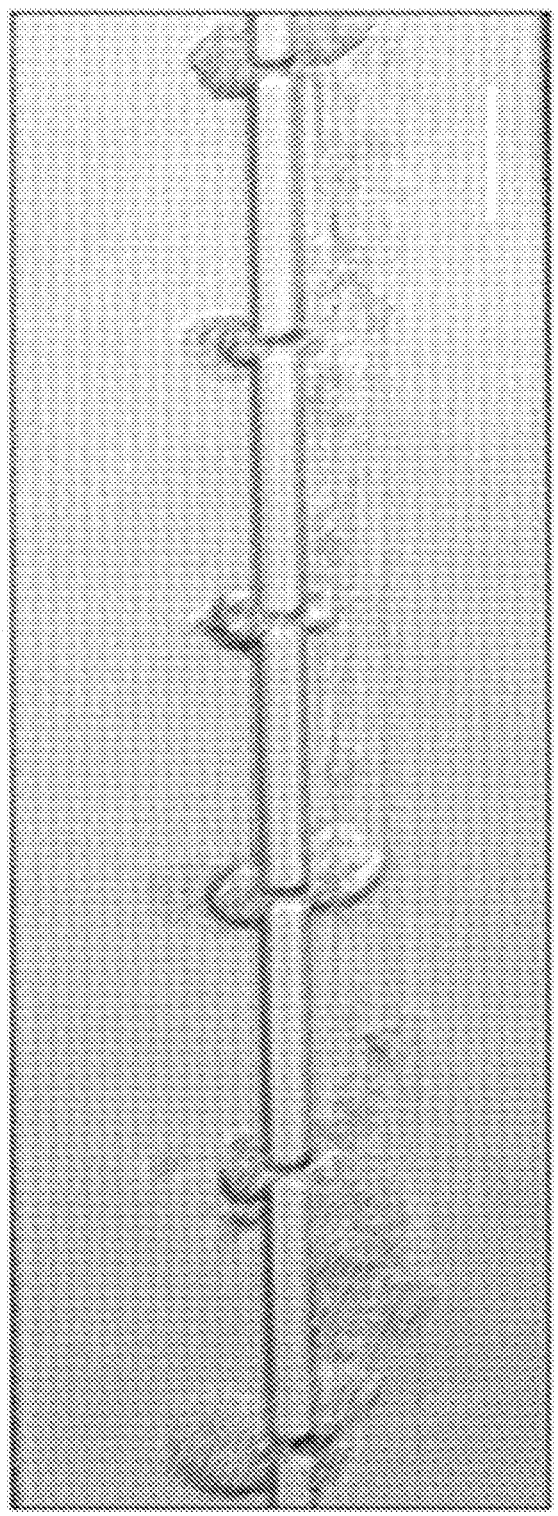
FIG. 65 is a microscopy image of MKs under physiological shear illustrating the production of proplatelets upon being captured on a porous membrane.

Platelets were produced using a bioreactor and conditions suitable for loading with therapeutic agents or genetic modification. To produce the platelets, megakaryocytes were seeded into a platelet bioreactor (FIG. 63A). The bioreactor consisted of two contiguous channels (FIGS. 63B, 63C) separated by a porous membrane (5 µm pores) (FIG. 64). The megakaryocytes are immobilized onto the porous membrane with high efficiency (>99% retention, as demonstrated by flow cytometry analysis), and media flowing in the channels exerts physiologically relevant shear forces onto the megakaryocytes (FIG. 64). The flow rates in the first channel and the second channel are independentiy adjusted to selectively capture the megakaryocytes on the membrane and to create a differential between the channels configured to generate physiological shear rates along the second channel on the captured megakaryocytes to produce the platelets.

Megakaryocytes immobilized on the porous membrane extend processes into the second chamber from which the megakaryocytes release platelets (FIGS. 64 and 65), which release the platelets into the second channel. (FIG. 64). Because the bioreactor replicates the physiologic conditions during platelet formation (for example, shearing forces of the bone marrow environment), the platelets produced in the bioreactor are functional and provide replacements for human platelets. The blood platelets produced using the bioreactor methods described herein can be used for infusion and drug delivery.

OTHER EMBODIMENTS

From the foregoing description, it will be apparent that variations and modifications may be made to the disclosure described herein to adopt it to various usages and conditions. Such embodiments are also within the scope of the following claims. In particular, various variations useful in the methods and compositions of the present disclosure are described in commonly-owned PCT/US2019/012437, filed on Jan. 5, 2019, as well as U.S. Pat. Nos. 9,763,984, 9,795,965; US2017/0183616; US2018/0334652; WO2018165308, all of which are incorporated herein by reference in their entireties.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for differentiating induced pluripotent stem cells (iPSC) to prepare a composition, the method comprising:
    expanding induced pluripotent cells in a matrix independent culture using single cell passaging;
    dissociating the expanded pluripotent cells into a single cell suspension;
    differentiating the dissociated pluripotent cells in a first culture medium into hemogenic endothelial cells;
    differentiating the hemogenic endothelial cells in a second culture medium into megakaryocytic progenitors;
    differentiating the megakaryocytic progenitors in a third culture medium into megakaryocytes; and
    lysing the megakaryocytes so as to obtain a lysate composition comprising one or more of Interleukin 1-beta, Interleukin 16, Interleukin 12P40, TNF-beta, BCA-1, IP-30, Fractalkine, GCkine, MCP-4, MIP-1alpha, MIP-1beta, SDF-1alpha, SDF-1beta, or a combination thereof.

2. The method of claim 1, wherein the megakaryocytes are $CD42b^+$, $CD61^+$, and $DNA^+$.

3. The method of claim 1, wherein the first culture medium comprises one or more of Bone morphogenic protein 4 (BMP4), Basic fibroblast growth factor (bFGF), and Vascular endothelial growth factor (VEGF).

4. The method of claim 1, wherein the first culture medium comprises BMP4 for a first time period, and for a second time period bFGF and VEGF are added to the first culture medium.

5. The method of claim 4, wherein for the first time period, the first culture medium comprises BMP4 without bFGF and VEGF.

6. The method of claim 1, wherein the second culture medium comprises one or more of Stem cell factor (SCF), Thrombopoietin (TPO), Fms-related tyrosine kinase 3 ligand (Flt3-L), Interleukin-3 (IL-3), Interleukin-6 (IL-6) and Heparin.

7. The method of claim 1, wherein the third culture medium comprises one or more of Stem cell factor (SCF), Thrombopoietin (TPO), Interleukin-6 (IL-6), Interleukin-9 (IL-9) and Heparin.

8. The method of claim 1, wherein one or more of the dissociated pluripotent cells, the hemogenic endothelial cells or the megakaryocytic progenitors are differentiated under continuous agitation in a matrix independent culture.

9. The method of claim 1, wherein the dissociated pluripotent cells are cultured so as to form self-aggregating pluripotent cell spheroids in a matrix independent culture.

10. The method of claim 9, wherein the self-aggregating pluripotent cell spheroids are differentiated so as to form hemogenic endothelial cell spheroids.

11. The method of claim 10, wherein the hemogenic endothelial cell spheroids are differentiated so as to produce the megakaryocytic progenitors, causing the hemogenic endothelial cell spheroids to release the megakaryocytic progenitors into suspension while maintaining the hemogenic endothelial cell spheroids for subsequent production and release of the megakaryocytic progenitors.

12. A method for differentiating induced pluripotent stem cells (iPSC) to prepare a composition, the method comprising:
    differentiating induced pluripotent cells in a first culture medium into hemogenic endothelial cells, the first culture medium comprising BMP4 for a first time period and bFGF and VEGF for a second time period after the first time period;
    differentiating the hemogenic endothelial cells in a second culture medium into megakaryocytic progenitors;
    differentiating the megakaryocytic progenitors in a third culture medium into megakaryocytes; and
    lysing the megakaryocytes so as to obtain a lysate composition comprising one or more of Interleukin 1-beta, Interleukin 16, Interleukin 12P40, TNF-beta, BCA-1, IP-30, Fractalkine, GCkine, MCP-4, MIP-1alpha, MIP-1beta, SDF-1alpha, SDF-1beta, or a combination thereof.

13. The method of claim 12, wherein for the first time period, the first culture medium comprises BMP4 without bFGF and VEGF.

14. The method of claim 12, wherein the second culture medium comprises one or more of Stem cell factor (SCF), Thrombopoietin (TPO), Fms-related tyrosine kinase 3 ligand (Flt3-L), Interleukin-3 (IL-3), Interleukin-6 (IL-6) and Heparin.

15. The method of claim 12, wherein the third culture medium comprises one or more of Stem cell factor (SCF), Thrombopoietin (TPO), Interleukin-6 (IL-6), Interleukin-9 (IL-9) and Heparin.

16. The method of claim 12, wherein differentiating the induced pluripotent cells comprises expanding induced pluripotent cells in a matrix independent culture using single cell passaging and dissociating the expanded pluripotent cells into a single cell suspension.

17. The method of claim 12, wherein one or more of the induced pluripotent cells, the hemogenic endothelial cells or the megakaryocytic progenitors are differentiated under continuous agitation.

18. The method of claim 12, wherein the induced pluripotent cells are cultured so as to form self-aggregating pluripotent cell spheroids.

19. The method of claim 18, wherein the self-aggregating pluripotent cell spheroids are differentiated so as to form hemogenic endothelial cell spheroids.

20. The method of claim 19, wherein the hemogenic endothelial cell spheroids are differentiated so as to produce the megakaryocytic progenitors, causing the hemogenic endothelial cell spheroids to release the megakaryocytic progenitors into suspension while maintaining the hemogenic endothelial cell spheroids for subsequent production and release of the megakaryocytic progenitors.

* * * * *